United States Patent
Liu et al.

(10) Patent No.: US 12,325,755 B2
(45) Date of Patent: *Jun. 10, 2025

(54) MACROPINOCYTOSING HUMAN ANTI-CD46 ANTIBODIES AND TARGETED CANCER THERAPEUTICS

(71) Applicant: The Regents of the University of California, Oakland, CA (US)

(72) Inventors: Bin Liu, San Francisco, CA (US); Yang Su, South San Francisco, CA (US); Scott Bidlingmaier, San Francisco, CA (US); Christopher R. Behrens, San Francisco, CA (US); Namkyung Lee, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1112 days.

This patent is subject to a terminal disclaimer.

(21) Appl. No.: 16/691,417

(22) Filed: Nov. 21, 2019

(65) Prior Publication Data

US 2020/0199245 A1   Jun. 25, 2020

Related U.S. Application Data

(63) Continuation of application No. 15/508,059, filed as application No. PCT/US2015/049492 on Sep. 10, 2015, now Pat. No. 10,533,056.

(60) Provisional application No. 62/049,973, filed on Sep. 12, 2014.

(51) Int. Cl.
| | | |
|---|---|---|
| C07K 16/28 | (2006.01) | |
| A61K 31/7088 | (2006.01) | |
| A61K 39/00 | (2006.01) | |
| A61K 47/68 | (2017.01) | |
| A61K 51/10 | (2006.01) | |
| C07K 16/30 | (2006.01) | |
| G01N 33/574 | (2006.01) | |

(52) U.S. Cl.
CPC ...... *C07K 16/2896* (2013.01); *A61K 31/7088* (2013.01); *A61K 47/6811* (2017.08); *A61K 47/6817* (2017.08); *A61K 47/6849* (2017.08); *A61K 47/6869* (2017.08); *A61K 51/1027* (2013.01); *C07K 16/30* (2013.01); *C07K 16/3069* (2013.01); *G01N 33/57492* (2013.01); *A61K 2039/505* (2013.01); *C07K 2317/21* (2013.01); *C07K 2317/30* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/77* (2013.01); *G01N 2333/70596* (2013.01); *Y02A 50/30* (2018.01)

(58) Field of Classification Search
CPC ............ A61K 47/6811; A61K 47/6817; A61K 47/6849; C07K 16/2896; C07K 2317/77; C07K 2317/21; C07K 16/30; C07K 16/3069

See application file for complete search history.

(56) References Cited

U.S. PATENT DOCUMENTS

| | | |
|---|---|---|
| 9,567,402 B2 | 2/2017 | Liu |
| 10,400,045 B2 | 9/2019 | Liu |
| 10,533,056 B2 | 1/2020 | Liu et al. |
| 11,208,493 B2 | 12/2021 | Liu |
| 11,434,301 B2 | 9/2022 | Liu et al. |
| 2002/0115065 A1* | 8/2002 | Logtenberg ........ C07K 16/2896 435/7.1 |
| 2003/0108966 A1 | 6/2003 | Mather |
| 2017/0362330 A1 | 12/2017 | Liu et al. |

FOREIGN PATENT DOCUMENTS

| | | | |
|---|---|---|---|
| CN | 108290949 A | 7/2018 | |
| EP | 1184458 A1 | 3/2002 | |
| JP | 2005-511525 A | 4/2005 | |
| JP | 2017513709 A | 6/2017 | |
| JP | 6730260 B2 | 7/2020 | |
| WO | WO 03/032814 A2 | 4/2003 | |
| WO | WO 2009/039192 A2 | 3/2009 | |
| WO | WO-2012/031273 A2 | 3/2012 | |
| WO | WO-2012/031273 A3 | 3/2012 | |
| WO | WO-2012/031273 A9 | 3/2012 | |
| WO | WO-2014174316 A1 * | 10/2014 | ......... A61K 31/5365 |
| WO | WO-2020/160020 A1 | 8/2020 | |
| WO | WO-2022150512 A1 | 7/2022 | |
| WO | WO-2022150514 A1 | 7/2022 | |
| WO | WO-2022150517 A1 | 7/2022 | |

OTHER PUBLICATIONS

Krall et al (Angewandte Chem. Int. Ed., 2013, vol. 52, pp. 1384-1402) (Year: 2013).*
Badescu et al (Bioconjugate Chemistry, Jun. 2014, vol. 25, pp. 1124-1136) (Year: 2014).*
Junutula et al (Nature Biotechnology, 2008, vol. 26, pp. 925-932) (Year: 2008).*
Acchione et al (mAbs, 2012, vol. 4, pp. 362-372) (Year: 2012).*
Francisco et al (Blood, 2003, vol. 102, pp. 1458-1465) (Year: 2003).*
Dorman et al (Blood, 2009, vol. 114, pp. 2721-2729) (Year: 2009).*
Chari et al (Angewandte Chemie Int Ed, e-pub Feb. 20, 2014, vol. 53, pp. 3796-3827) (Year: 2014).*
Chinese Office Action dated Jun. 22, 2020 issued in CN 201580061138.5.

(Continued)

*Primary Examiner* — Karen A. Canella
(74) *Attorney, Agent, or Firm* — Mintz Levin Cohn Ferris Glovsky and Popeo, P.C.

(57) ABSTRACT

In various embodiments human anti-CD46 antibodies that are internalizing and enter tumor cells via the macropinocytosis pathway are provided, as well as antibody-drug conjugates (ADCs) developed from these antibodies for diagnostic and/or therapeutic targeting of CD46-overexpressing tumors.

43 Claims, 34 Drawing Sheets

Specification includes a Sequence Listing.

(56) References Cited

OTHER PUBLICATIONS

Eurasian Office Action dated Jul. 13, 2020 issued in EU Application No. 201790404.
EP Office Action dated May 8, 2020 issued in EP 15839357.9.
He et al. (2010) "Targeting Prostate Cancer Cells In Vivo Using a Rapidly Internalizing Novel Human Single-Chain Antibody Fragment" *The Journal of Nuclear Medicine*, 51(3): 427-432.
PCT International Search Report and Written Opinion dated Nov. 17, 2015 issued in PCT/US2015/049492.
PCT International Preliminary Report on Patentability and Written Opinion dated Mar. 23, 2017 issued in PCT/US2015/049492.
EP Extended Search Report dated Apr. 26, 2018 issued in EP 15839357.9.
Eurasian Office Action dated Oct. 30, 2018 issued in EU Application No. 201790404.
Eurasian Office Action dated Jul. 9, 2019 issued in EU Application No. 201790404.
Israel Office Action dated Dec. 11, 2019 issued in IL Application No. 251045.
JP Office Action dated Aug. 5, 2019 issued in JP Application No. 2017-513709.
US Office Action dated Sep. 7, 2018 issued in U.S. Appl. No. 15/5080,059.
US Final Office Action dated May 30, 2019 issued in U.S. Appl. No. 15/5080,059.
US Notice of Allowance dated Sep. 3, 2019 issued in U.S. Appl. No. 15/5080,059.
Crimeen-Irwin et al. (2003) "Ligand Binding Determines Whether CD46 Is Internalized by Clathrin-coated Pits or Macropinocytosis" *The Journal of Biological Chemistry*, 278(47): 46927-46937.
Dejong et al. (2008) "Drug delivery and nanoparticles: Applications and hazards" *International Journal of Nanomedicine*, 3: 133-149.
Geuijen et al. (2005) "Affinity ranking of antibodies using flow cytometry: application in antibody phage display-based target discovery" *Journal of Immunological Methods*, 302(1): 68-77.
Haraldsdottir and Bekaii-Saab, (2013) "Integrating anti-EGFR therapies in metastatic colorectal cancer" *Journal of Gastrointestinal Oncology*, 4(3): 285-298.
Mantaj et al. (2016) "Covalent Bonding of Pyrrolobenzodiazepines (PBDs) to Terminal Guanine Residues within Duplex and Hairpin DNA Fragments" *PLOS One*, 11(4): e0152303 (26 pages).
Ni Choileain et al. (Jan. 2011) "The dynamic processing of CD46 intracellular domains provides a molecular rheostat for T cell activation" *PLoS One*, 6(1): e16287 (15 pages) doi:10.1371/journal.pone.0016287.
Schweiser et al. (2014) "Controlled release of therapeutic antibody formats" *European Journal of Pharmaceutics and Biopharmaceutics*, 88(2): 291-309.
Sherbenou et al. (Dec. 2016) "Antibody-drug conjugate targeting CD46 eliminates multiple myeloma cells" *Journal of Clinical Investigation*, 126(12): 4640-4653.
Su et al. (2018) "ATargeting CD46 for both adenocarcinoma and neuroendocrine prostate cancer" *JCI Insight.*, 3(17): e121497 (20 pages) https://doi.org/10.1172/jci.insight.121497.
Australian Office Action dated Aug. 25, 2020 issued in AU 2015315006.
Brazilian Office Action dated Sep. 23, 2020 issued in BR 1120170050021.
Chinese 2nd Office Action dated Mar. 1, 2021 issued in CN 201580061138.5.
Eurasian Office Action dated Feb. 17, 2021 issued in EU Application No. 201790404.
Canadian Office Action dated Oct. 6, 2021 issued in CA 2,960,282.
IL Office action dated Oct. 31, 2021, in IL Application No. IL282077.
Indian Office Action dated Jul. 14, 2021 issued in IN 201717007927.
Japanese Office Action dated Aug. 2, 2021 issued in JP Application No. 2020-113065.
JP Office Action dated Apr. 13, 2022, in Application No. JP20200113065 with translation.
KR Office Action dated May 23, 2022, in Application No. KR20177009569.
Mexican Office Action mailed Dec. 8, 2021 in Application No. MX/a/2017/003246 with English translation.
AU Office action dated Apr. 30, 2023, in AU Application No. AU2021211989.
Canadian Office Action dated Oct. 14, 2022 Application No. CA2960282.
KR Office Action dated Dec. 26, 2022 in Application No. KR10-2017-7009569 with English translation.
U.S. Appl. No. 17/815,514, inventors Liu et al., filed Jul. 27, 2022.
BR Office Action dated Sep. 25, 2023, in Application No. BR1120170050021.
CA Office Action dated Aug. 31, 2023, in Application No. CA2960282.
U.S. Appl. No. 18/271,205, inventors Lui B, et al., filed Jan. 6, 2022.
Neri, D. et al. (Dec. 1996). "Biophysical methods for the determination of antibody-antigen affinities," *TIBTECH* 14:465-470.
Extended European Search Report mailed on Feb. 28, 2025, for EP Patent Application No. 22737129.1, 9 pages.

\* cited by examiner

| VH | Frame 1 | CDR 1 | Frame 2 | CD R2 | Frame 3 | CDR3 | Frame 4 |
|---|---|---|---|---|---|---|---|
| YS5 | QVQLVQSGGG VVQPGRSLRL ACAAS (SEQ ID NO: 79) | GLTVNNYA (SEQ ID NO: 80) | MHWVRQAPG KGLEWVAV (SEQ ID NO: 81) | ISYDGNN K (SEQ ID NO: 82) | YYADSVKGRFTI SRDNSKNTLYLQ MNSLRAEDTAVY YC (SEQ ID NO: 83) | AKGGGYFD L (SEQ ID NO: 84) | WGRGTL VTVSS (SEQ ID NO: 85) |
| YS5F | QVQLVQSGGG VVQPGRSLRL ACAAS (SEQ ID NO: 86) | GFTVNNYA (SEQ ID NO: 87) | MHWVRQAPG KGLEWVAV (SEQ ID NO: 88) | ISYDGNN K (SEQ ID NO: 89) | YYADSVKGRFTI SRDNSKNTLYLQ MNSLRAEDTAVY YC (SEQ ID NO: 90) | AKGGGYFD L (SEQ ID NO: 91) | WGRGTL VTVSS (SEQ ID NO: 92) |
| YS5vID | QVQLVQSGGG VVQPGRSLRL ACAAS (SEQ ID NO: 93) | GFTVNNYA (SEQ ID NO: 94) | MHWVRQAPG KGLEWVAV (SEQ ID NO: 95) | ISYDGNN K (SEQ ID NO: 96) | YYADSVKGRFTI SRDNSKNTLYLQ MNSLRAEDTAVY YC (SEQ ID NO: 97) | AKGGGYFD L (SEQ ID NO: 98) | WGRGTL VTVSS (SEQ ID NO: 99) |
| SB1HG NY | QVQLQQSGGG VVQPGRSLRL SCAAS (SEQ ID NO: 100) | GFTFSSYA (SEQ ID NO: 101) | MHWVRQAPG KGLEWVAF (SEQ ID NO: 102) | IRSDGSK K (SEQ ID NO: 103) | YYADSVKGRFTI SRDNSKNTLYLQ MNSLRAEDTAVY YC (SEQ ID NO: 104) | ARHGNYFD S (SEQ ID NO: 105) | WGQGTL VTVSS (SEQ ID NO: 106) |
| YS12 | QVQLVESGGG VVQPGR SLRLSCAAS (SEQ ID NO: 107) | GFTFSTYG (SEQ ID NO: 108) | MHWVRQAPG KGLEW LSF (SEQ ID NO: 109) | ISYDGDE K (SEQ ID NO: 110) | YYADSVKGRFTI SRDNSKNT LYLQMNSLRA EDTAVYWC (SEQ ID NO: 111) | AKASGYG MGILDY (SEQ ID NO: 112) | WGQGTL VTVSS (SEQ ID NO: 113) |
| 3G7RY aka 3G8 | EVQLVESGGG LVQPGGSLRL SCAAS (SEQ ID NO: 114) | GFTFSDYY (SEQ ID NO: 115) | MSWIRQAPG KGLEWVSY (SEQ ID NO: 116) | ISSSGS TI (SEQ ID NO: 117) | YYADSVKGRF TISRDNSKNT LYLQMNSLRA EDTAVYYC (SEQ ID NO: 118) | ARDYGRIA AAGRRY (SEQ ID NO: 119) | WGQGTL VTVSS (SEQ ID NO: 120) |
| YS6 | QVQLQESG GGVVRPGG SLRLSCAAS (SEQ ID NO: 121) | GFTFSDYY (SEQ ID NO: 122) | MSWIRQA PGKGLEW VSY (SEQ ID NO: 123) | ISSSGS TI (SEQ ID NO: 124) | YYADSVKGRF TISRDNSKNTLY LQMNSLRAEDTA VYYC (SEQ ID NO: 125) | ARDYGRIA AAGRHY (SEQ ID NO: 126) | WGQGTL VTVSS (SEQ ID NO: 127) |
| YS1 | EVQLVESGGG LVQPGGSLRL SCAAS (SEQ ID NO: 128) | GFTFSDYY (SEQ ID NO: 129) | MSWIRQAPG KGLEWVSY (SEQ ID NO: 130) | ISSSGST I (SEQ ID NO: 131) | YYADSVKGRFTI SRDNSKNTLYLQ MNSLRAEDTAVY YC (SEQ ID NO: 132) | ARDYGRIA AAGRHY (SEQ ID NO: 133) | WGQGTL VTVSS (SEQ ID NO: 134) |

*Fig. 1A*

| VH | Frame 1 | CDR 1 | Frame 2 | CD R2 | Frame 3 | CDR3 | Frame 4 |
|---|---|---|---|---|---|---|---|
| YS3 | QVQLQESGGGL VQPGGSLRLSC AAS (SEQ ID NO: 135) | GFTFSSYW (SEQ ID NO: 136) | MSWVRQA PGKGLEW VAD (SEQ ID NO: 137) | IKQDGSE K (SEQ ID NO: 138) | YYVDSVKGRFTI SGDNAKNSLYLQ MNSLRAEDTAVY YC (SEQ ID NO: 139) | AKDVGSTAI NYVRAYTWF DP (SEQ ID NO: 140) | WGQGTLV TVSS (SEQ ID NO: 141) |
| YS4 | QVQLQESGGGL VQPGGSLRLSC AAS (SEQ ID NO: 142) | GFTFSNYA (SEQ ID NO: 143) | MSWVRQA PGKGLEW VST (SEQ ID NO: 144) | ISGSGSS T (SEQ ID NO: 145) | FYVDSVKGRFTI SRDNSKNTLYLQ MNSLRAEDTAVY YC (SEQ ID NO: 146) | AQGLYSSGW ANWFD P (SEQ ID NO: 147) | RGQGTLV TVSS (SEQ ID NO: 148) |
| YS8 | QVQLQESGGGV VQPGRSLRLSC AAS (SEQ ID NO: 149) | GFTFSSYG (SEQ ID NO: 150) | MHWVRQA PGKGLEW VAV (SEQ ID NO: 151) | ISYDGSN K (SEQ ID NO: 152) | YYADSVKGRFTI SRDNSKNT LYLQMNSLRAED TAVYYC (SEQ ID NO: 153) | AKVMGLAAA GLDAFDI (SEQ ID NO: 154) | WGQGTTV TVSS (SEQ ID NO: 155) |
| YS7 | QVQLVQSGGGV VQPGRSLRLSC AAS (SEQ ID NO: 156) | GFTFSSYA (SEQ ID NO: 157) | MHWVRQA PGKGLEW VAV (SEQ ID NO: 158) | ISYDGSN K (SEQ ID NO: 159) | YYADSVKGRFTI SRDTSTNTLYLQ MNSLRADDTAVY YC (SEQ ID NO: 160) | GRESSGS PGV (SEQ ID NO: 161) | WGQGTTV TVSS (SEQ ID NO: 162) |
| YS9 | QVQLVESGGGL IQPGGSLRLSC AAS (SEQ ID NO: 163) | GFTVSSNY (SEQ ID NO: 164) | MSWVRQA PGKGLEW VSV (SEQ ID NO: 165) | IYTDGST (SEQ ID NO: 166) | YYADSVKGRFTI SRDNSKNTLYLQ MNSLRAEDTAIY YC (SEQ ID NO: 167) | ARDRGTSGY DWAWF DL (SEQ ID NO: 168) | WGQGTLV TVSS (SEQ ID NO: 169) |
| YS10 | QVQLQESGGGL VQPGGSLRLSC AAS (SEQ ID NO: 170) | GFTFSSYA (SEQ ID NO: 171) | MSWVRQA PGKGLEW VSA (SEQ ID NO: 172) | ISGSGGS T (SEQ ID NO: 173) | YYADSVKGRFTI SRDNSKNTLYMQ MNSLRAEDTAVY YC (SEQ ID NO: 174) | AKDRYYY GSGKDAF DI (SEQ ID NO: 175) | WGRGTMV TVSS (SEQ ID NO: 176) |
| YS11 | QVQLVESGGGL VQPGGSLGLSC AAS (SEQ ID NO: 177) | GFTFSNYW (SEQ ID NO: 178) | MSWVRQA PGKGLEW VAN (SEQ ID NO: 179) | VRQDGGQ K (SEQ ID NO: 180) | YYVDSVKGRF TISRDNAKNS LYLQMNSLRT EDTAVYFC (SEQ ID NO: 181) | VSQRNSG EHDY (SEQ ID NO: 182) | WGQGTLV TVSS (SEQ ID NO: 183) |

*Fig. 1A, cont'd.*

| VH | Frame 1 | CDR 1 | Frame 2 | CD R2 | Frame 3 | CDR3 | Frame 4 |
|---|---|---|---|---|---|---|---|
| 3G7HY | EVQLVESGGGL VQPGGSLRLSC AAS (SEQ ID NO: 184) | GFTFSDYY (SEQ ID NO: 185) | MSWIRQA PGKGLEW VSY (SEQ ID NO: 186) | ISSSGST I (SEQ ID NO: 187) | YYADSVKGRF TISRDNSKNTLY LQMNSLRAEDTA VYYC (SEQ ID NO: 188) | ARDYGRI AAAGRHY (SEQ ID NO: 189) | WGQGTLV TVSS (SEQ ID NO: 190) |
| 3G7NY | EVQLVESGGGL VQPGGSLRLSC AAS (SEQ ID NO: 191) | GFTFSDYY (SEQ ID NO: 192) | MSWIRQA PGKGLEW VSY (SEQ ID NO: 193) | ISSSGS TI (SEQ ID NO: 194) | YYADSVKGRF TISRDNSKNTLY LQMNSLRAEDTA VYYC (SEQ ID NO: 195) | ARDYGRIAA AGRNY (SEQ ID NO: 196) | WGQGTLV TVSS (SEQ ID NO: 197) |
| 3G7 | QVQLQESGGGV VRPGGSLRLSC AAS (SEQ ID NO: 198) | GFTFSDYY (SEQ ID NO: 199) | MSWIRQA PGKGLEW VSY (SEQ ID NO: 200) | ISSSGST I (SEQ ID NO: 201) | YYADSVKGRF TISRDNSKNT LYLQMNSLRA EDTAVYYC (SEQ ID NO: 202) | ARDYGRI AAAGRHY (SEQ ID NO: 203) | WGQGTLV TVSS (SEQ ID NO: 204) |
| SB2 | EVQLVESGGGL VKPGGSLRLSC AAS (SEQ ID NO: 205) | GFTFSDYY (SEQ ID NO: 206) | MSWIRQA PGKGLEW VSY (SEQ ID NO: 207) | ISSSGS SI (SEQ ID NO: 208) | YYADSVKGRF TISRDNAKNS LYLQMNSLKA EDTAVYYC (SEQ ID NO: 209) | ARDITDVVG VSFDY (SEQ ID NO: 210) | WGQGTLV TVSS (SEQ ID NO: 211) |
| 2C8 | EVQLVESGGGV VQPGRSLRLSC AAS (SEQ ID NO: 212) | GFTFSSYG (SEQ ID NO: 213) | MHWVRQA PGKGLEW VAV (SEQ ID NO: 214) | ISYDGS NK (SEQ ID NO: 215) | YYADSVKGRF TISRDNSKNT LYLQMNSLRA EDTAEYYC (SEQ ID NO: 216) | AKVMGLAAA GLDAFDI (SEQ ID NO: 217) | WGQGTLV TVSS (SEQ ID NO: 218) |
| UA8kap pa | EVQLVESGGGV VQPGRSLRLSC AAS (SEQ ID NO: 219) | GFTFSSFG (SEQ ID NO: 220) | MHWVRRA PGKGLEW VAV (SEQ ID NO: 221) | ISYDGSN Q (SEQ ID NO: 222) | YYADSVKGRF TISRDNSKNTLY LQMNSLRAEDTA VYYC (SEQ ID NO: 223) | GSRPGGG YASGSTVAY (SEQ ID NO: 224) | WGQGTLV TVSS (SEQ ID NO: 225) |

*Fig. 1A, cont'd.*

| VL | Frame 1 | CDR 1 | Frame 2 | CD R2 | Frame 3 | CDR3 | Frame 4 |
|---|---|---|---|---|---|---|---|
| YS5 | QSVLTQPPSV SGAPGQRVTI SCTGS (SEQ ID NO: 226) | SSNIGAGYD (SEQ ID NO: 227) | VHWYQQLPG TAPKLLIY (SEQ ID NO: 228) | GNN (SEQ ID NO: 229) | NRPSGVPDRFSG SKSGTSASLAIT GLQAEDEADYYC (SEQ ID NO: 230) | SSYTSGTW L (SEQ ID NO: 231) | FGGGTKL TVL (SEQ ID NO: 232) |
| YS5F | QSVLTQPPSV SGAPGQRVTI SCTGS (SEQ ID NO: 233) | SSNIGAGYD (SEQ ID NO: 234) | VHWYQQLPG TAPKLLIY (SEQ ID NO: 235) | GNN (SEQ ID NO: 236) | NRPSGVPDRFSG SKSGTSASLAIT GLQAEDEADYYC (SEQ ID NO: 237) | SSYTSGTW L (SEQ ID NO: 238) | FGGGTKL TVL (SEQ ID NO: 239) |
| YS5vID | QSVLTQPPSV SGAPGQRVTI SCTGS (SEQ ID NO: 240) | SSNIGAGYD (SEQ ID NO: 241) | VHWYQQLPG TAPKLLIY (SEQ ID NO: 242) | GDN (SEQ ID NO: 243) | NRPSGVPDRFSG SKSGTSASLAIT GLQAEDEADYYC (SEQ ID NO: 244) | SSYTSGTW L (SEQ ID NO: 245) | FGGGTKL TVL (SEQ ID NO: 246) |
| SB1HG NY | DIQMTQSPSF LSASVGDRVT ITCRAS (SEQ ID NO: 247) | QGISSY (SEQ ID NO: 248) | LAWYQQKPG KAPKLLIY (SEQ ID NO: 249) | AAS (SEQ ID NO: 250) | TLQSGVPSSFSG SGSGTEFTLTIS SLQPEDFATYYC (SEQ ID NO: 251) | QQLASYPL T (SEQ ID NO: 252) | FGGGTKV DIK (SEQ ID NO: 253) |
| YS12 | SSELTQDPAV SVALGQTVRI TCQGD (SEQ ID NO: 254) | SLRSYY (SEQ ID NO: 255) | VSWFQQKPG QAPVFVMY (SEQ ID NO: 256) | GQN (SEQ ID NO: 257) | NRPSGISERFSG SSSGNTASLIIT GAQAEDEADYYC (SEQ ID NO: 258) | HSRDSSGT HLRV (SEQ ID NO: 259) | FGGGTKL TVL (SEQ ID NO: 260) |
| 3G7RY aka 3G8 | QSALTQPPSA SATPGQRVTI SCSGR (SEQ ID NO: 261) | TSNIGSNH (SEQ ID NO: 262) | VYWYQQLPG TAPKLLIY (SEQ ID NO: 263) | RNN (SEQ ID NO: 264) | QRPSGVPDRFSG SKSGTSASLAIS GLRSEDEADYYC (SEQ ID NO: 265) | ATWDDSLS GEV (SEQ ID NO: 266) | FGGGTKL TVL (SEQ ID NO: 267) |
| YS6 | SSELTQDPAV SVALGQTVRI TCQGD (SEQ ID NO: 268) | SLRSYY (SEQ ID NO: 269) | ASWYQQKPG QAPVLVIY (SEQ ID NO: 270) | GKN (SEQ ID NO: 271) | NRPSGIPDRFSG SSSGNTASLTIT GAQAEDEADYYC (SEQ ID NO: 272) | NSRDSSGT HLEV (SEQ ID NO: 273) | FGGGTKV TVL (SEQ ID NO: 274) |
| YS1 | SSELTQDPAV SVALGQTVRI TCQGD (SEQ ID NO: 275) | TLSTYY (SEQ ID NO: 276) | ANWYQQK PGQAPVL VIY (SEQ ID NO: 277) | GKN (SEQ ID NO: 278) | NRPSGIPDRFSG SSSGNTASLTIT GAQAEDEADYYC (SEQ ID NO: 279) | HSRDISGN YL (SEQ ID NO: 280) | FASGTKL TVL (SEQ ID NO: 281) |

*Fig. 1B*

| VL | Frame 1 | CDR 1 | Frame 2 | CDR2 | Frame 3 | CDR3 | Frame 4 |
|---|---|---|---|---|---|---|---|
| YS3 | QSVLTQPPSASGTPGQRVTISCSGS (SEQ ID NO: 282) | SSNIGSNT (SEQ ID NO: 283) | VNWSRQLPGTAPKLLIY (SEQ ID NO: 284) | SNN (SEQ ID NO: 285) | QRPSGVPDRFSGSKSGTSASLAISGLQSEDEADYYC (SEQ ID NO: 286) | AAWDDSLNVYV (SEQ ID NO: 287) | FGTGTKVTVL (SEQ ID NO: 288) |
| YS4 | KIVLTQSPSSLSASVGDTVTIACRAS (SEQ ID NO: 289) | RDIRND (SEQ ID NO: 290) | LAWYQQKPGKAPKLLIY (SEQ ID NO: 291) | GAS (SEQ ID NO: 292) | SLQSGVPSRFSGSGSGTEFILTISSLQPEDFATYYC (SEQ ID NO: 293) | HRLNSYPLTFGGGTKVDIK (SEQ ID NO: 294) | |
| YS8 | NFMLTQPASLSGSPGQSITISCTGT (SEQ ID NO: 295) | SSDVGGYNY (SEQ ID NO: 296) | VSWYQQHPGYAPKLMIY (SEQ ID NO: 297) | DVS (SEQ ID NO: 298) | NRPSGVSNRFSGSKSGNTASLTISGLQAEDEADYYC (SEQ ID NO: 299) | SSYTSSSTPWV (SEQ ID NO: 300) | FGGGTKLTVL (SEQ ID NO: 301) |
| YS7 | SYVLTQDPAVSVALGQTVRITCQGD (SEQ ID NO: 302) | SLRSYY (SEQ ID NO: 303) | ASWYQQKPGQAPVLVIY (SEQ ID NO: 304) | GKN (SEQ ID NO: 305) | NRPSGIPDRFSGSSSGNTASLTITGAQAEDEADYYC (SEQ ID NO: 306) | NSRDSSGNQ (SEQ ID NO: 307) | FGGGTKLTVL (SEQ ID NO: 308) |
| YS9 | SSELTQDPAVSVALGQTVRITCQGD (SEQ ID NO: 309) | SLRTYY (SEQ ID NO: 310) | ASWYQQRPGQAPILVLY (SEQ ID NO: 311) | GKN (SEQ ID NO: 312) | NRPSGIPDRFSGSSSGNTASLTITGAQAEDEADYYC (SEQ ID NO: 313) | NSRDSSGNHVV (SEQ ID NO: 314) | FGGGTKLTVL (SEQ ID NO: 315) |
| YS10 | QSVLTQPASVSGSPGQSITISCTGT (SEQ ID NO: 316) | GSDVGSYNY (SEQ ID NO: 317) | VSWYQQNPGKAPKLMIY (SEQ ID NO: 318) | EVS (SEQ ID NO: 319) | NRPSGVSNRFSGSKSGNTASLTISGLQAEDEADYYC (SEQ ID NO: 320) | SSYTTSSTLV (SEQ ID NO: 321) | FGGGTKVTVL (SEQ ID NO: 322) |
| YS11 | SELTQDPAVSVALGQTVRITCQGD (SEQ ID NO: 323) | SLRSYY (SEQ ID NO: 324) | ASWYQQKPGQAPVLVIY (SEQ ID NO: 325) | GEN (SEQ ID NO: 326) | SRPSGIPDRFSGSSSGNTASLTITGAQAEDEADYYC (SEQ ID NO: 327) | NSWDSSGNHVV (SEQ ID NO: 328) | FGGGTKLTVL (SEQ ID NO: 329) |
| 3G7HY | AIRMTQSPSSLSASVGDRVTITCRAS (SEQ ID NO: 330) | QSISSY (SEQ ID NO: 331) | LNWYQQKPGKAPKLLIY (SEQ ID NO: 332) | AAS (SEQ ID NO: 333) | SLQSGVPSRFSGSGSGTDFTLTISSLQPEDFATYYC (SEQ ID NO: 334) | QQSYSTPRT (SEQ ID NO: 335) | FGQGTKLEIK (SEQ ID NO: 336) |

*Fig. 1B, cont'd.*

| VL | Frame 1 | CDR 1 | Frame 2 | CDR2 | Frame 3 | CDR3 | Frame 4 |
|---|---|---|---|---|---|---|---|
| 3G7NY | DIVMTQSPLSLPVTPGEPASISCRSS (SEQ ID NO: 337) | QSLLHSNGYDY (SEQ ID NO: 338) | LDWYLQKPGQSPQLLIY (SEQ ID NO: 339) | LGS (SEQ ID NO: 340) | NRASGVPDRFSGSGSGTDFTLKISRVETEDVGIYYC (SEQ ID NO: 341) | MQGLQTPS (SEQ ID NO: 342) | FGQGTKLEIK (SEQ ID NO: 343) |
| 3G7 | SSELTQDPAVSVALGQTVRITCQGD (SEQ ID NO: 344) | SLRSYY (SEQ ID NO: 345) | ASWYQQKPGQAPVPVIY (SEQ ID NO: 346) | GKN (SEQ ID NO: 347) | NRPSGIPDRFSGSSSGNTASLTITGAQAEDEADYYC (SEQ ID NO: 348) | NSRDSSSTHRGV (SEQ ID NO: 349) | FGGGTKLTVL (SEQ ID NO: 350) |
| SB2 | DIQLTQSPSSLSASVGDRVTITCRAS (SEQ ID NO: 351) | RSISTY (SEQ ID NO: 352) | LSWYQQKPGKAPKLLIY (SEQ ID NO: 353) | DAS (SEQ ID NO: 354) | RLQNGVPSRFSGSGSDTDFTLTISSLQPEDFATYFC (SEQ ID NO: 355) | QQSYNPPWT (SEQ ID NO: 356) | FGQGTKLEIK (SEQ ID NO: 357) |
| 2C8 | QSALTQPASVSGSPGQSITISCTGT (SEQ ID NO: 358) | SSDVGGYNY (SEQ ID NO: 359) | VSWYQQHPGKAPKLMIY (SEQ ID NO: 360) | DVS (SEQ ID NO: 361) | NRPSGVSNRFSGSKSGNTASLTISGLQAEDEAYYYC (SEQ ID NO: 362) | SSYTSSSDPWV (SEQ ID NO: 363) | FGGGTQLTVL (SEQ ID NO: 364) |
| UA8kappa | NIQMTQSPSSLSASVGDRVTITCRAG (SEQ ID NO: 365) | QPISTY (SEQ ID NO: 366) | VNWYQHKPGKAPKLLIY (SEQ ID NO: 367) | GAS (SEQ ID NO: 368) | NLQSGVPSRFSGGGSATDFTLTISSLQPEDFATYYC (SEQ ID NO: 369) | QQSYSSLLTFGDGTKVEIK (SEQ ID NO: 370) | |

*Fig. 1B, cont'd.*

| organ | type | Staining |
|---|---|---|
| Lymph node | Normal | |
| Lymph node | Normal | |
| Lymph node | Normal | |
| Skeletal muscle | Normal | |
| Skeletal muscle | Normal | |
| Skeletal muscle | Normal | |
| Prostate | Normal | |
| Prostate | Normal | ▓▓▓ |
| Prostate | Normal | ▓▓▓ |
| Kidney | Normal | |
| Kidney | Normal | |
| Kidney | Normal | |
| Liver | Normal | ░░░ |
| Liver | Normal | ░░░ |
| Liver | Normal | ░░░ |
| Lung | Normal | ░░░ |
| Lung | Normal | ░░░ |
| Lung | Normal | ░░░ |
| Stomach | Normal | ░░░ |
| Stomach | Normal | ░░░ |
| Stomach | Normal | ░░░ |
| Esophagus | Normal | |
| Esophagus | Normal | |
| Esophagus | Normal | |
| Heart | Normal | |
| Heart | Normal | |
| Heart | Normal | |
| Colon | Normal | |
| Colon | Normal | ░░░ |
| Colon | Normal | ░░░ |
| Small intestine | Normal | |
| Small intestine | Normal | ░░░ |
| Small intestine | Normal | |
| Peripheral nerve | Normal | |
| Peripheral nerve | Normal | |
| Peripheral nerve | Normal | |
| Smooth muscle | Normal | |
| Smooth muscle | Normal | |
| Smooth muscle | Normal | |
| Cerebellum | Normal | |
| Cerebellum | Normal | |
| Cerebellum | Normal | |
| cerebrum | Normal | |
| cerebrum | Normal | |
| cerebrum | Normal | |

| organ | type | Staining |
|---|---|---|
| Ovary | Normal | |
| Ovary | Normal | |
| Ovary | Normal | |
| Pancreas | Normal | |
| Pancreas | Normal | |
| Pancreas | Normal | |
| Salivary gland | Normal | |
| Salivary gland | Normal | |
| Salivary gland | Normal | |
| Pituitary gland | Normal | |
| Pituitary gland | Normal | |
| Pituitary gland | Normal | |
| Placenta | Normal | ▓▓▓ |
| Placenta | Normal | ███ |
| Placenta | Normal | ███ |
| Prostate | Normal | ▓▓▓ |
| Prostate | Normal | ▓▓▓ |
| Prostate | Normal | ▓▓▓ |
| Skin | Normal | |
| Skin | Normal | |
| Skin | Normal | |
| Spinal cord | Normal | |
| Spinal cord | Normal | |
| Spinal cord | Normal | |
| Spleen | Normal | |
| Spleen | Normal | |
| Spleen | Normal | |
| Skeletal muscle | Normal | |
| Skeletal muscle | Normal | |
| Skeletal muscle | Normal | |
| Testis | Normal | |
| Testis | Normal | |
| Testis | Normal | |
| Thymus | Normal | |
| Thymus | Normal | |
| Thymus | Normal | |
| Thyroid gland | Normal | |
| Thyroid gland | Normal | |
| Thyroid gland | Normal | |
| Ureter | Normal | |
| Ureter | Normal | |
| Ureter | Normal | |
| Uterine cervix | Normal | |
| Uterine cervix | Normal | |
| Uterine cervix | Normal | |

*Fig. 10*

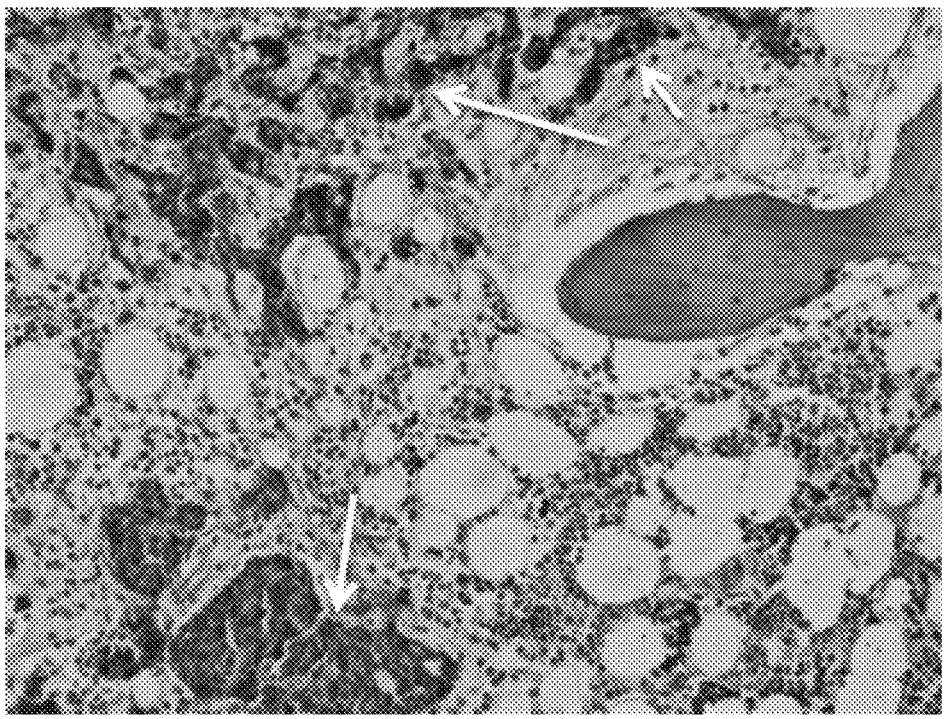
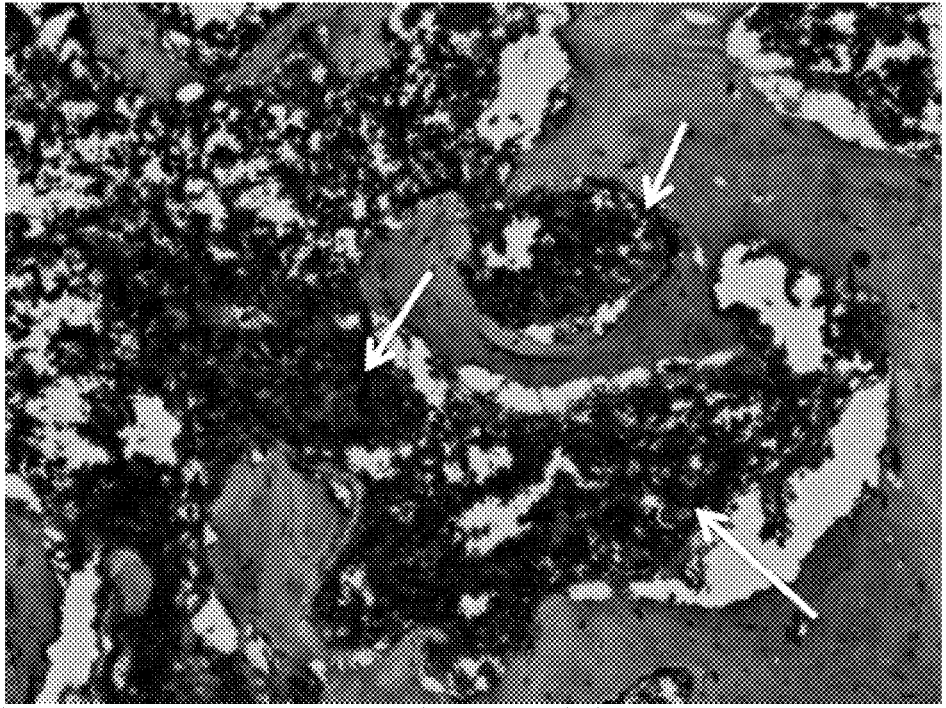
Fig. 34

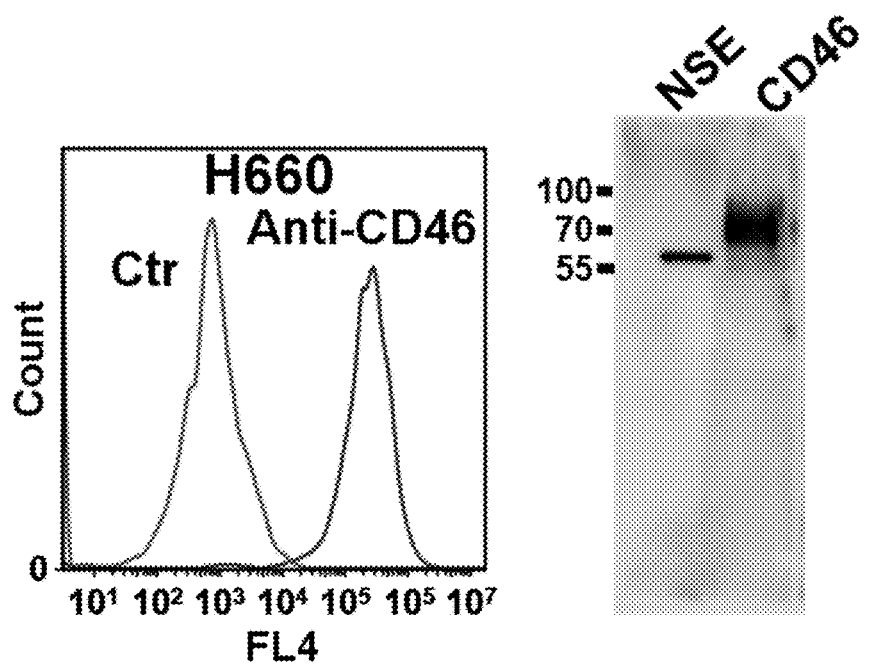
*Fig. 37*
Internalization and lysosomal trafficking
CD46　　　　　LAMP1　　　　　Merge
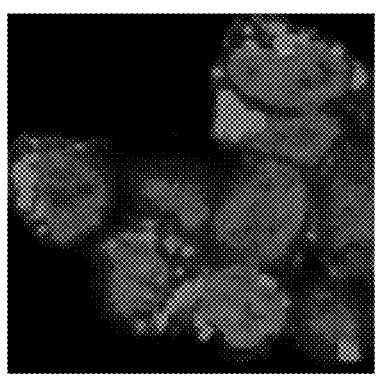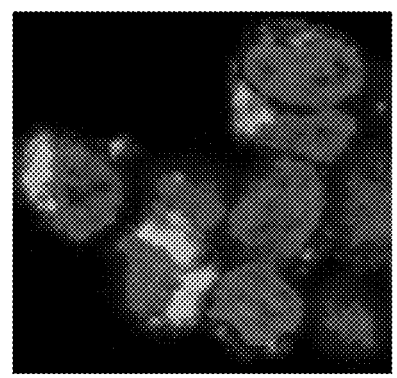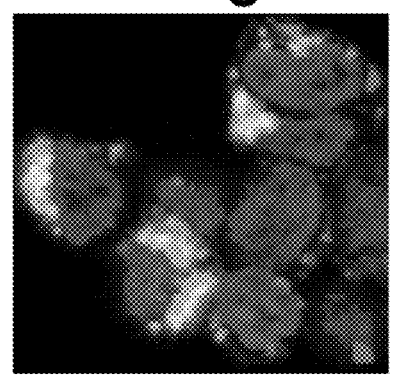
*Fig. 38*

CD46 is highly overexpressed by both primary and metastatic colorectal cancer

Primary colorectal cancer

Lymph node metastasis of colorectal cancer
4x 20x

Bladder metastasis of colorectal cancer
4x 20x

MACROPINOCYTOSING HUMAN ANTI-CD46 ANTIBODIES AND TARGETED CANCER THERAPEUTICS

CROSS-REFERENCE TO RELATED APPLICATIONS

This application is a continuation of U.S. Ser. No. 15/508,059, filed on Mar. 1, 2017, which is a U.S. 371 National Phase of PCT/US2015/049492, filed on Sep. 10, 2015, which claims benefit of and priority to U.S. Ser. No. 62/049,973, filed on Sep. 12, 2014, all of which are incorporated herein by reference in their entirety for all purposes.

INCORPORATION BY REFERENCE OF SEQUENCE LISTING PROVIDED AS A TEXT FILE

Incorporation by Reference of Sequence Listing Provided as a Text File

A Sequence Listing is provided herewith as a text file, "148640-009211-S SL.txt" created on Jun. 14, 2023 and having a size of 184,409 bytes. The contents of the text file are incorporated by reference herein in their entirety.

STATEMENT AS TO RIGHTS TO INVENTIONS MADE UNDER FEDERALLY SPONSORED RESEARCH AND DEVELOPMENT

This invention was made with government support under grant nos. R01 CA118919, R01 CA129491 and R01 CA171315 awarded by the National Institutes of Health. The government has certain rights in the invention.

BACKGROUND

Due to ease of accessibility, tumor cell surface antigens are valuable targets for therapeutic development. The epitope space at the cell surface is highly complex. Relevant antigens may include glycosylated proteins and other post-translationally modified products that may not be readily predicted from studies of genomic copy number or mRNA expression levels (Liu et al. (2004) Cancer Res. 64: 704-710; Kobata and Amano (2005) Immunol. Cell Biol. 83: 429-439; Birkle et al. (2003) Biochimie (Paris) 85: 455-463; Hakomori (2001) Adv. Exp. Med. Biol. 491: 369-402; Hanisch, F. G. (2001) O-Glycosylation of the mucin type. Biol. Chem. 382, 143-149; Ugorski and Laskowska (2002) Acta Biochim. Pol. 49: 303-311).

Identification of tumor cell surface epitopes allows the production of antibodies to achieve specific binding to neoplastic cells, an ability that can be utilized in applications such as induction of antibody-dependent cell cytotoxicity (see, e.g., Clynes et al. (2000) Nat. Med. 6: 443-446), or inhibition of signaling pathways involved in tumor cell migration, growth, and survival (see, e.g., McWhirter et al. (2006) Proc. Natl. Acad. Sci., USA, 103: 1041-1046; Fuh et al. (2006) J. Biol. Chem. 281: 6625-6631). In addition, antibodies targeting internalizing tumor epitopes can be exploited to achieve efficient and specific intracellular delivery of cytotoxins, cytostatic agents, chemotherapeutic drugs and/or other tumor-modulating agents (see, e.g., Liu et al. (2004) Cancer Res. 64: 704-710; Nielsen et al. (2002) Biochim. Biophys. Acta 1591: 109-118; Pirollo et al. (2006) Hum. Gene Ther. 17: 117-124; Song et al. (2005) Nat. Biotechnol. 23:709-717; Liu et al. (2002) J. Mol. Biol. 315: 1063-1073).

Phage antibody display has been widely used to develop cancer-specific antibodies (see, e.g., Liu et al. (2004) Cancer Res. 64: 704-710; Liu and Marks (2000) Anal. Biochem. 286: 119-128; 15. Marks et al. (1992) Biotechnology (N. Y.) 10: 779-783; Marks et al. (1991) J. Mol. Biol. 222: 581-597; Marks et al. (1992) J. Biol. Chem. 267: 16007-16010; Sharon et al. (2005) J. Cell. Biochem. 96: 305-313; Silacci et al. (2005) Proteomics 5: 2340-2350; Gao et al. (2003) J. Immunol. Methods 274: 185-197; Lekkerkerker and Logtenberg (1999) J. Immunol. Meth., 231: 53-63; de Kruif et al. (1995) Proc. Natl. Acad. Sci., USA, 92: 3938-3942; Pini et al. (1998) J. Biol. Chem. 273: 21 769-21 776). A combinatorial phage antibody library serves as a source of random shape repertoire that can be used to probe neoplastic variations on the surface of cancer cells (see, e.g., Liu et al. (2004) Cancer Res. 64: 704-710; Geuijen et al. (2005) Eur. J. Cancer 41: 178-187; Poul et al. (2000) J. Mol. Biol. 301: 1149-1161; Cai and Garen (1995) Proc. Natl. Acad. Sci., USA, 92: 6537-6541). Selecting phage antibody libraries directly on cancer cell lines enables the identification of tumor-targeting antibodies without prior knowledge of target antigens see, e.g., (Liu et al. (2004) Cancer Res. 64: 704-710; Gao et al. (2003) J. Immunol. Methods 274: 185-197; Geuijen et al. (2005) Eur. J. Cancer 41: 178-187; Poul et al. (2000) J. Mol. Biol. 301: 1149-1161).

Although numerous antibodies have been found by this approach, the screening process against cell lines does not provide an ideal picture as to how specific these antibodies will be to actual cancer cells in patient populations. Nor does it necessarily provide an indication of whether or not the antibodies will internalize in vivo.

SUMMARY

In various embodiments human anti-CD46 antibodies that are internalizing and enter tumor cells via the macropinocytosis pathway are provided, as well as antibody-drug conjugates (ADCs) developed from these antibodies for diagnostic and/or therapeutic targeting of CD46-overexpressing tumors.

Various embodiments contemplated herein may include, but need not be limited to, one or more of the following:

Embodiment 1: An isolated human antibody that specifically binds CD46 and is internalized into a cell expressing or overexpressing CD46, wherein: said antibody is an antibody that specifically binds cells that express or overexpress a CD46, wherein said antibody specifically binds an epitope bound by one or more antibodies selected from the group consisting of YS5, YS5F, YS5vlD, SB1HGNY, YS12, 3G7RY, YS6, YS1, YS3, YS4, YS8, YS7, YS9, YS10, YS11, 3G7HY, 3G7NY, 3G7, SB2, 2C8, and/or UA8kappa; and said antibody is internalized into said cell via macropinocytosis.

Embodiment 2: The antibody of embodiment 1, wherein said antibody binds domain 1 and/or domain 2 of CD46.

Embodiment 3: The antibody of embodiments 1 or 2, wherein said antibody does not bind domain 3 and/or domain 4 of CD46.

Embodiment 4: The antibody according to any one of embodiments 1-3, wherein said cells that express or overexpress a CD46 are cancer cells.

Embodiment 5: The antibody according to any one of embodiments 1-4, wherein said cells that express or overexpress a CD46 are prostate cancer cells.

Embodiment 6: The antibody of embodiment 5, wherein said antibody binds cells of a cell line selected from the group consisting of DU145 cells, PC3 cells, and LnCaP cells.

Embodiment 7: The antibody according to any one of embodiments 1-6, wherein said antibody binds to a prostate tumor cell with an affinity ($K_D$) of at least about 5-10 nM when measured on live prostate tumor cells by FACS.

Embodiment 8: The antibody of embodiment 7, wherein said antibody binds to a prostate tumor cell with an affinity ($K_D$) of at least about 3 nM when measured on live prostate tumor cells by FACS.

Embodiment 9: The antibody according to any one of embodiments 1-8, wherein said antibody is a substantially intact immunoglobulin.

Embodiment 10: The antibody of embodiment 9, wherein said antibody comprises an IgA, IgE, or IgG.

Embodiment 11: The antibody of embodiment 9, wherein said antibody comprises an IgG1.

Embodiment 12: The antibody according to any one of embodiments 1-8, wherein said antibody is an antibody fragment that specifically binds cells that express or overexpress a CD46.

Embodiment 13: The antibody of embodiment 12, wherein said antibody is an antibody fragment selected from the group consisting of Fv, Fab, (Fab')$_2$, (Fab')$_3$, IgGΔCH2, and a minibody.

Embodiment 14: The antibody according to any one of embodiments 1-8, wherein said antibody is a single chain antibody.

Embodiment 15: The antibody of embodiment 14, wherein the VL region of said antibody is attached to the VH region of said antibody by an amino acid linker ranging in length from about 3 amino acids up to about 15 amino acids.

Embodiment 16: The antibody of embodiment 14, wherein the VL region of said antibody is attached to the VH region of said antibody by an amino acid linker selected from the group consisting of The antibody of embodiment 14, wherein the VL region of said antibody is attached to the VH region of said antibody by an amino acid linker selected from the group consisting of GGGGS GGGGS GGGGS (SEQ ID NO: 43), GGGGS GGGGS (SEQ ID NO: 67), GGGGS (SEQ ID NO: 68), GS GGGGS GGGGS GGS GGGGS (SEQ ID NO: 69), SGGGGS (SEQ ID NO: 70), GGGS (SEQ ID NO: 71), VPGV (SEQ ID NO: 72), VPGVG (SEQ ID NO: 73), GVPGVG (SEQ ID NO: 74), GVG VP GVG (SEQ ID NO: 75), VP GVG VP GVG (SEQ ID NO: 76), GGSSRSS (SEQ ID NO: 77), and GGSSRSSSSGGGGSGGGG (SEQ ID NO: 78).

Embodiment 17: The antibody according to any one of embodiments 1-16, wherein said antibody competes with YS5 for binding at CD46.

Embodiment 18: The antibody according to any one of embodiments 1-16, wherein said antibody competes with YS5F for binding at CD46.

Embodiment 19: The antibody according to any one of embodiments 1-16, wherein said antibody competes with YS5vlD for binding at CD46.

Embodiment 20: The antibody according to any one of embodiments 1-16, wherein said antibody competes with SB1HGNY for binding at CD46.

Embodiment 21: The antibody according to any one of embodiments 1-16, wherein said antibody competes with YS12 for binding at CD46.

Embodiment 22: The antibody according to any one of embodiments 1-16, wherein said antibody competes with 3G7RY for binding at CD46.

Embodiment 23: The antibody according to any one of embodiments 1-16, wherein said antibody competes with YS6 for binding at CD46.

Embodiment 24: The antibody according to any one of embodiments 1-16, wherein said antibody competes with YS1 for binding at CD46.

Embodiment 25: The antibody according to any one of embodiments 1-16, wherein said antibody competes with YS3 for binding at CD46.

Embodiment 26: The antibody according to any one of embodiments 1-16, wherein said antibody competes with YS4 for binding at CD46.

Embodiment 27: The antibody according to any one of embodiments 1-16, wherein said antibody competes with YS8 for binding at CD46.

Embodiment 28: The antibody according to any one of embodiments 1-16, wherein said antibody competes with YS7 for binding at CD46.

Embodiment 29: The antibody according to any one of embodiments 1-16, wherein said antibody competes with YS9 for binding at CD46.

Embodiment 30: The antibody according to any one of embodiments 1-16, wherein said antibody competes with YS10 for binding at CD46.

Embodiment 31: The antibody according to any one of embodiments 1-16, wherein said antibody competes with YS11 for binding at CD46.

Embodiment 32: The antibody according to any one of embodiments 1-16, wherein said antibody competes with 3G7HY for binding at CD46.

Embodiment 33: The antibody according to any one of embodiments 1-16, wherein said antibody competes with 3G7NY for binding at CD46.

Embodiment 34: The antibody according to any one of embodiments 1-16, wherein said antibody competes with 3G7 for binding at CD46.

Embodiment 35: The antibody according to any one of embodiments 1-16, wherein said antibody competes with SB2 for binding at CD46.

Embodiment 36: The antibody according to any one of embodiments 1-16, wherein said antibody competes with 2C8 for binding at CD46.

Embodiment 37: The antibody according to any one of embodiments 1-16, wherein said antibody competes with UA8kappa for binding at CD46.

Embodiment 38: The antibody according to any one of embodiments 1-16, wherein said antibody comprises VH CDR1, and/or VH CDR2, and/or VH CDR3, and/or VL CDR1, and/or VL CDR2, and/or VL CDR3 of an antibody selected from the group consisting of YS5, YS5F, YS5vlD, SB1HGNY, YS12, 3G7RY, YS6, YS1, YS3, YS4, YS8, YS7, YS9, YS10, YS11, 3G7HY, 3G7NY, 3G7, SB2, 2C8, and UA8kappa.

Embodiment 39: The antibody according to any one of embodiments 1-16, wherein said antibody comprises VH CDR1, and/or VH CDR2, and/or VH CDR3 of the YS5 antibody.

Embodiment 40: The antibody according to any one of embodiments 1-16, wherein said antibody comprises VL CDR1, and/or VL CDR2, and/or VL CDR3 of the YS5 antibody.

Embodiment 41: The antibody according to any one of embodiments 1-16, wherein said antibody comprises VH CDR1, VH CDR2, VH CDR3, VL CDR1, VLCDR2, and VL CDR3 of the YS5 antibody.

Embodiment 42: The antibody according to any one of embodiments 1-16, wherein said antibody comprises the variable light (VL) chain of the YS5 antibody.

Embodiment 43: The antibody according to any one of embodiments 1-16, wherein said antibody comprises the variable heavy (VH) chain of the YS5 antibody.

Embodiment 44: The antibody according to any one of embodiments 1-16, wherein said antibody comprises the variable light (VL) chain of the YS5 antibody and the variable heavy (VH) chain of the YS5 antibody.

Embodiment 45: The antibody of embodiment 1, wherein said antibody is a human YS5 scFv.

Embodiment 46: The antibody of embodiment 1, wherein said antibody is a human YS5 IgG.

Embodiment 47: The antibody according to any one of embodiments 1-16, wherein said antibody comprises VH CDR1, and/or VH CDR2, and/or VH CDR3 of the YS5F antibody.

Embodiment 48: The antibody according to any one of embodiments 1-16, wherein said antibody comprises VL CDR1, and/or VL CDR2, and/or VL CDR3 of the YS5F antibody.

Embodiment 49: The antibody according to any one of embodiments 1-16, wherein said antibody comprises VH CDR1, VH CDR2, VH CDR3, VL CDR1, VLCDR2, and VL CDR3 of the YS5F antibody.

Embodiment 50: The antibody according to any one of embodiments 1-16, wherein said antibody comprises the variable light (VL) chain of the YS5F antibody.

Embodiment 51: The antibody according to any one of embodiments 1-16, wherein said antibody comprises the variable heavy (VH) chain of the YS5F antibody.

Embodiment 52: The antibody according to any one of embodiments 1-16, wherein said antibody comprises the variable light (VL) chain of the YS5F antibody and the variable heavy (VH) chain of the YS5F antibody.

Embodiment 53: The antibody of embodiment 1, wherein said antibody is a human YS5F scFv.

Embodiment 54: The antibody of embodiment 1, wherein said antibody is a human YS5F IgG.

Embodiment 55: The antibody according to any one of embodiments 1-16, wherein said antibody comprises VH CDR1, and/or VH CDR2, and/or VH CDR3 of the YS5F antibody.

Embodiment 56: The antibody according to any one of embodiments 1-16, wherein said antibody comprises VL CDR1, and/or VL CDR2, and/or VL CDR3 of the YS5F antibody.

Embodiment 57: The antibody according to any one of embodiments 1-16, wherein said antibody comprises VH CDR1, VH CDR2, VH CDR3, VL CDR1, VLCDR2, and VL CDR3 of the YS5F antibody.

Embodiment 58: The antibody according to any one of embodiments 1-16, wherein said antibody comprises the variable light (VL) chain of the YS5F antibody.

Embodiment 59: The antibody according to any one of embodiments 1-16, wherein said antibody comprises the variable heavy (VH) chain of the YS5F antibody.

Embodiment 60: The antibody according to any one of embodiments 1-16, wherein said antibody comprises the variable light (VL) chain of the YS5F antibody and the variable heavy (VH) chain of the YS5F antibody.

Embodiment 61: The antibody of embodiment 1, wherein said antibody is a human YS5F scFv.

Embodiment 62: The antibody of embodiment 1, wherein said antibody is a human YS5F IgG.

Embodiment 63: The antibody according to any one of embodiments 1-16, wherein said antibody comprises VH CDR1, and/or VH CDR2, and/or VH CDR3 of the YS5V1D antibody.

Embodiment 64: The antibody according to any one of embodiments 1-16, wherein said antibody comprises VL CDR1, and/or VL CDR2, and/or VL CDR3 of the YS5V1D antibody.

Embodiment 65: The antibody according to any one of embodiments 1-16, wherein said antibody comprises VH CDR1, VH CDR2, VH CDR3, VL CDR1, VLCDR2, and VL CDR3 of the YS5V1D antibody.

Embodiment 66: The antibody according to any one of embodiments 1-16, wherein said antibody comprises the variable light (VL) chain of the YS5V1D antibody.

Embodiment 67: The antibody according to any one of embodiments 1-16, wherein said antibody comprises the variable heavy (VH) chain of the YS5V1D antibody.

Embodiment 68: The antibody according to any one of embodiments 1-16, wherein said antibody comprises the variable light (VL) chain of the YS5V1D antibody and the variable heavy (VH) chain of the YS5V1D antibody.

Embodiment 69: The antibody of embodiment 1, wherein said antibody is a human YS5V1D scFv.

Embodiment 70: The antibody of embodiment 1, wherein said antibody is a human YS5V1D IgG.

Embodiment 71: The antibody according to any one of embodiments 1-16, wherein said antibody comprises VH CDR1, and/or VH CDR2, and/or VH CDR3 of the SB1HGNY antibody.

Embodiment 72: The antibody according to any one of embodiments 1-16, wherein said antibody comprises VL CDR1, and/or VL CDR2, and/or VL CDR3 of the SB1HGNY antibody.

Embodiment 73: The antibody according to any one of embodiments 1-16, wherein said antibody comprises VH CDR1, VH CDR2, VH CDR3, VL CDR1, VLCDR2, and VL CDR3 of the SB1HGNY antibody.

Embodiment 74: The antibody according to any one of embodiments 1-16, wherein said antibody comprises the variable light (VL) chain of the SB1HGNY antibody.

Embodiment 75: The antibody according to any one of embodiments 1-16, wherein said antibody comprises the variable heavy (VH) chain of the SB1HGNY antibody.

Embodiment 76: The antibody according to any one of embodiments 1-16, wherein said antibody comprises the variable light (VL) chain of the SB1HGNY antibody and the variable heavy (VH) chain of the SB1HGNY antibody.

Embodiment 77: The antibody of embodiment 1, wherein said antibody is a human SB1HGNY scFv.

Embodiment 78: The antibody of embodiment 1, wherein said antibody is a human SB1HGNY IgG.

Embodiment 79: The antibody according to any one of embodiments 1-16, wherein said antibody comprises VH CDR1, and/or VH CDR2, and/or VH CDR3 of the YS12 antibody.

Embodiment 80: The antibody according to any one of embodiments 1-16, wherein said antibody comprises VL CDR1, and/or VL CDR2, and/or VL CDR3 of the YS12 antibody.

Embodiment 81: The antibody according to any one of embodiments 1-16, wherein said antibody comprises VH CDR1, VH CDR2, VH CDR3, VL CDR1, VLCDR2, and VL CDR3 of the YS12 antibody.

Embodiment 82: The antibody according to any one of embodiments 1-16, wherein said antibody comprises the variable light (VL) chain of the YS12 antibody.

Embodiment 83: The antibody according to any one of embodiments 1-16, wherein said antibody comprises the variable heavy (VH) chain of the YS12 antibody.

Embodiment 84: The antibody according to any one of embodiments 1-16, wherein said antibody comprises the variable light (VL) chain of the YS12 antibody and the variable heavy (VH) chain of the YS12 antibody.

Embodiment 85: The antibody of embodiment 1, wherein said antibody is a human YS12 scFv.

Embodiment 86: The antibody of embodiment 1, wherein said antibody is a human YS12 IgG.

Embodiment 87: The antibody according to any one of embodiments 1-16, wherein said antibody comprises VH CDR1, and/or VH CDR2, and/or VH CDR3 of the 3G7RY antibody.

Embodiment 88: The antibody according to any one of embodiments 1-16, wherein said antibody comprises VL CDR1, and/or VL CDR2, and/or VL CDR3 of the 3G7RY antibody.

Embodiment 89: The antibody according to any one of embodiments 1-16, wherein said antibody comprises VH CDR1, VH CDR2, VH CDR3, VL CDR1, VLCDR2, and VL CDR3 of the 3G7RY antibody.

Embodiment 90: The antibody according to any one of embodiments 1-16, wherein said antibody comprises the variable light (VL) chain of the 3G7RY antibody.

Embodiment 91: The antibody according to any one of embodiments 1-16, wherein said antibody comprises the variable heavy (VH) chain of the 3G7RY antibody.

Embodiment 92: The antibody according to any one of embodiments 1-16, wherein said antibody comprises the variable light (VL) chain of the 3G7RY antibody and the variable heavy (VH) chain of the 3G7RY antibody.

Embodiment 93: The antibody of embodiment 1, wherein said antibody is a human 3G7RY scFv.

Embodiment 94: The antibody of embodiment 1, wherein said antibody is a human 3G7RY IgG.

Embodiment 95: The antibody according to any one of embodiments 1-16, wherein said antibody comprises VH CDR1, and/or VH CDR2, and/or VH CDR3 of the YS6 antibody.

Embodiment 96: The antibody according to any one of embodiments 1-16, wherein said antibody comprises VL CDR1, and/or VL CDR2, and/or VL CDR3 of the YS6 antibody.

Embodiment 97: The antibody according to any one of embodiments 1-16, wherein said antibody comprises VH CDR1, VH CDR2, VH CDR3, VL CDR1, VLCDR2, and VL CDR3 of the YS6 antibody.

Embodiment 98: The antibody according to any one of embodiments 1-16, wherein said antibody comprises the variable light (VL) chain of the YS6 antibody.

Embodiment 99: The antibody according to any one of embodiments 1-16, wherein said antibody comprises the variable heavy (VH) chain of the YS6 antibody.

Embodiment 100: The antibody according to any one of embodiments 1-16, wherein said antibody comprises the variable light (VL) chain of the YS6 antibody and the variable heavy (VH) chain of the YS6 antibody.

Embodiment 101: The antibody of embodiment 1, wherein said antibody is a human YS6 scFv.

Embodiment 102: The antibody of embodiment 1, wherein said antibody is a human YS6 IgG.

Embodiment 103: The antibody according to any one of embodiments 1-16, wherein said antibody comprises VH CDR1, and/or VH CDR2, and/or VH CDR3 of the YS1 antibody.

Embodiment 104: The antibody according to any one of embodiments 1-16, wherein said antibody comprises VL CDR1, and/or VL CDR2, and/or VL CDR3 of the YS1 antibody.

Embodiment 105: The antibody according to any one of embodiments 1-16, wherein said antibody comprises VH CDR1, VH CDR2, VH CDR3, VL CDR1, VLCDR2, and VL CDR3 of the YS1 antibody.

Embodiment 106: The antibody according to any one of embodiments 1-16, wherein said antibody comprises the variable light (VL) chain of the YS1 antibody.

Embodiment 107: The antibody according to any one of embodiments 1-16, wherein said antibody comprises the variable heavy (VH) chain of the YS1 antibody.

Embodiment 108: The antibody according to any one of embodiments 1-16, wherein said antibody comprises the variable light (VL) chain of the YS1 antibody and the variable heavy (VH) chain of the YS1 antibody.

Embodiment 109: The antibody of embodiment 1, wherein said antibody is a human YS1 scFv.

Embodiment 110: The antibody of embodiment 1, wherein said antibody is a human YS1 IgG.

Embodiment 111: The antibody according to any one of embodiments 1-16, wherein said antibody comprises VH CDR1, and/or VH CDR2, and/or VH CDR3 of the YS3 antibody.

Embodiment 112: The antibody according to any one of embodiments 1-16, wherein said antibody comprises VL CDR1, and/or VL CDR2, and/or VL CDR3 of the YS3 antibody.

Embodiment 113: The antibody according to any one of embodiments 1-16, wherein said antibody comprises VH CDR1, VH CDR2, VH CDR3, VL CDR1, VLCDR2, and VL CDR3 of the YS3 antibody.

Embodiment 114: The antibody according to any one of embodiments 1-16, wherein said antibody comprises the variable light (VL) chain of the YS3 antibody.

Embodiment 115: The antibody according to any one of embodiments 1-16, wherein said antibody comprises the variable heavy (VH) chain of the YS3 antibody.

Embodiment 116: The antibody according to any one of embodiments 1-16, wherein said antibody comprises the variable light (VL) chain of the YS3 antibody and the variable heavy (VH) chain of the YS3 antibody.

Embodiment 117: The antibody of embodiment 1, wherein said antibody is a human YS3 scFv.

Embodiment 118: The antibody of embodiment 1, wherein said antibody is a human YS3 IgG.

Embodiment 119: The antibody according to any one of embodiments 1-16, wherein said antibody comprises VH CDR1, and/or VH CDR2, and/or VH CDR3 of the YS4 antibody.

Embodiment 120: The antibody according to any one of embodiments 1-16, wherein said antibody comprises VL CDR1, and/or VL CDR2, and/or VL CDR3 of the YS4 antibody.

Embodiment 121: The antibody according to any one of embodiments 1-16, wherein said antibody comprises VH CDR1, VH CDR2, VH CDR3, VL CDR1, VLCDR2, and VL CDR3 of the YS4 antibody.

Embodiment 122: The antibody according to any one of embodiments 1-16, wherein said antibody comprises the variable light (VL) chain of the YS4 antibody.

Embodiment 123: The antibody according to any one of embodiments 1-16, wherein said antibody comprises the variable heavy (VH) chain of the YS4 antibody.

Embodiment 124: The antibody according to any one of embodiments 1-16, wherein said antibody comprises the variable light (VL) chain of the YS4 antibody and the variable heavy (VH) chain of the YS4 antibody.

Embodiment 125: The antibody of embodiment 1, wherein said antibody is a human YS4 scFv.

Embodiment 126: The antibody of embodiment 1, wherein said antibody is a human YS4 IgG.

Embodiment 127: The antibody according to any one of embodiments 1-16, wherein said antibody comprises VH CDR1, and/or VH CDR2, and/or VH CDR3 of the YS8 antibody.

Embodiment 128: The antibody according to any one of embodiments 1-16, wherein said antibody comprises VL CDR1, and/or VL CDR2, and/or VL CDR3 of the YS8 antibody.

Embodiment 129: The antibody according to any one of embodiments 1-16, wherein said antibody comprises VH CDR1, VH CDR2, VH CDR3, VL CDR1, VLCDR2, and VL CDR3 of the YS8 antibody.

Embodiment 130: The antibody according to any one of embodiments 1-16, wherein said antibody comprises the variable light (VL) chain of the YS8 antibody.

Embodiment 131: The antibody according to any one of embodiments 1-16, wherein said antibody comprises the variable heavy (VH) chain of the YS8 antibody.

Embodiment 132: The antibody according to any one of embodiments 1-16, wherein said antibody comprises the variable light (VL) chain of the YS8 antibody and the variable heavy (VH) chain of the YS8 antibody.

Embodiment 133: The antibody of embodiment 1, wherein said antibody is a human YS8 scFv.

Embodiment 134: The antibody of embodiment 1, wherein said antibody is a human YS8 IgG.

Embodiment 135: The antibody according to any one of embodiments 1-16, wherein said antibody comprises VH CDR1, and/or VH CDR2, and/or VH CDR3 of the YS7 antibody.

Embodiment 136: The antibody according to any one of embodiments 1-16, wherein said antibody comprises VL CDR1, and/or VL CDR2, and/or VL CDR3 of the YS7 antibody.

Embodiment 137: The antibody according to any one of embodiments 1-16, wherein said antibody comprises VH CDR1, VH CDR2, VH CDR3, VL CDR1, VLCDR2, and VL CDR3 of the YS7 antibody.

Embodiment 138: The antibody according to any one of embodiments 1-16, wherein said antibody comprises the variable light (VL) chain of the YS7 antibody.

Embodiment 139: The antibody according to any one of embodiments 1-16, wherein said antibody comprises the variable heavy (VH) chain of the YS7 antibody.

Embodiment 140: The antibody according to any one of embodiments 1-16, wherein said antibody comprises the variable light (VL) chain of the YS7 antibody and the variable heavy (VH) chain of the YS7 antibody.

Embodiment 141: The antibody of embodiment 1, wherein said antibody is a human YS7 scFv.

Embodiment 142: The antibody of embodiment 1, wherein said antibody is a human YS7 IgG.

Embodiment 143: The antibody according to any one of embodiments 1-16, wherein said antibody comprises VH CDR1, and/or VH CDR2, and/or VH CDR3 of the YS9 antibody.

Embodiment 144: The antibody according to any one of embodiments 1-16, wherein said antibody comprises VL CDR1, and/or VL CDR2, and/or VL CDR3 of the YS9 antibody.

Embodiment 145: The antibody according to any one of embodiments 1-16, wherein said antibody comprises VH CDR1, VH CDR2, VH CDR3, VL CDR1, VLCDR2, and VL CDR3 of the YS9 antibody.

Embodiment 146: The antibody according to any one of embodiments 1-16, wherein said antibody comprises the variable light (VL) chain of the YS9 antibody.

Embodiment 147: The antibody according to any one of embodiments 1-16, wherein said antibody comprises the variable heavy (VH) chain of the YS9 antibody.

Embodiment 148: The antibody according to any one of embodiments 1-16, wherein said antibody comprises the variable light (VL) chain of the YS9 antibody and the variable heavy (VH) chain of the YS9 antibody.

Embodiment 149: The antibody of embodiment 1, wherein said antibody is a human YS9 scFv.

Embodiment 150: The antibody of embodiment 1, wherein said antibody is a human YS9 IgG.

Embodiment 151: The antibody according to any one of embodiments 1-16, wherein said antibody comprises VH CDR1, and/or VH CDR2, and/or VH CDR3 of the YS10 antibody.

Embodiment 152: The antibody according to any one of embodiments 1-16, wherein said antibody comprises VL CDR1, and/or VL CDR2, and/or VL CDR3 of the YS10 antibody.

Embodiment 153: The antibody according to any one of embodiments 1-16, wherein said antibody comprises VH CDR1, VH CDR2, VH CDR3, VL CDR1, VLCDR2, and VL CDR3 of the YS10 antibody.

Embodiment 154: The antibody according to any one of embodiments 1-16, wherein said antibody comprises the variable light (VL) chain of the YS10 antibody.

Embodiment 155: The antibody according to any one of embodiments 1-16, wherein said antibody comprises the variable heavy (VH) chain of the YS10 antibody.

Embodiment 156: The antibody according to any one of embodiments 1-16, wherein said antibody comprises the variable light (VL) chain of the YS10 antibody and the variable heavy (VH) chain of the YS10 antibody.

Embodiment 157: The antibody of embodiment 1, wherein said antibody is a human YS10 scFv.

Embodiment 158: The antibody of embodiment 1, wherein said antibody is a human YS10 IgG.

Embodiment 159: The antibody according to any one of embodiments 1-16, wherein said antibody comprises VH CDR1, and/or VH CDR2, and/or VH CDR3 of the YS11 antibody.

Embodiment 160: The antibody according to any one of embodiments 1-16, wherein said antibody comprises VL CDR1, and/or VL CDR2, and/or VL CDR3 of the YS11 antibody.

Embodiment 161: The antibody according to any one of embodiments 1-16, wherein said antibody comprises VH CDR1, VH CDR2, VH CDR3, VL CDR1, VLCDR2, and VL CDR3 of the YS11 antibody.

Embodiment 162: The antibody according to any one of embodiments 1-16, wherein said antibody comprises the variable light (VL) chain of the YS11 antibody.

Embodiment 163: The antibody according to any one of embodiments 1-16, wherein said antibody comprises the variable heavy (VH) chain of the YS11 antibody.

Embodiment 164: The antibody according to any one of embodiments 1-16, wherein said antibody comprises the variable light (VL) chain of the YS11 antibody and the variable heavy (VH) chain of the YS11 antibody.

Embodiment 165: The antibody of embodiment 1, wherein said antibody is a human YS11 scFv.

Embodiment 166: The antibody of embodiment 1, wherein said antibody is a human YS11 IgG.

Embodiment 167: The antibody according to any one of embodiments 1-16, wherein said antibody comprises VH CDR1, and/or VH CDR2, and/or VH CDR3 of the 3G7HY antibody.

Embodiment 168: The antibody according to any one of embodiments 1-16, wherein said antibody comprises VL CDR1, and/or VL CDR2, and/or VL CDR3 of the 3G7HY antibody.

Embodiment 169: The antibody according to any one of embodiments 1-16, wherein said antibody comprises VH CDR1, VH CDR2, VH CDR3, VL CDR1, VLCDR2, and VL CDR3 of the 3G7HY antibody.

Embodiment 170: The antibody according to any one of embodiments 1-16, wherein said antibody comprises the variable light (VL) chain of the 3G7HY antibody.

Embodiment 171: The antibody according to any one of embodiments 1-16, wherein said antibody comprises the variable heavy (VH) chain of the 3G7HY antibody.

Embodiment 172: The antibody according to any one of embodiments 1-16, wherein said antibody comprises the variable light (VL) chain of the 3G7HY antibody and the variable heavy (VH) chain of the 3G7HY antibody.

Embodiment 173: The antibody of embodiment 1, wherein said antibody is a human 3G7HY scFv.

Embodiment 174: The antibody of embodiment 1, wherein said antibody is a human 3G7HY IgG.

Embodiment 175: The antibody according to any one of embodiments 1-16, wherein said antibody comprises VH CDR1, and/or VH CDR2, and/or VH CDR3 of the 3G7NY antibody.

Embodiment 176: The antibody according to any one of embodiments 1-16, wherein said antibody comprises VL CDR1, and/or VL CDR2, and/or VL CDR3 of the 3G7NY antibody.

Embodiment 177: The antibody according to any one of embodiments 1-16, wherein said antibody comprises VH CDR1, VH CDR2, VH CDR3, VL CDR1, VLCDR2, and VL CDR3 of the 3G7NY antibody.

Embodiment 178: The antibody according to any one of embodiments 1-16, wherein said antibody comprises the variable light (VL) chain of the 3G7NY antibody.

Embodiment 179: The antibody according to any one of embodiments 1-16, wherein said antibody comprises the variable heavy (VH) chain of the 3G7NY antibody.

Embodiment 180: The antibody according to any one of embodiments 1-16, wherein said antibody comprises the variable light (VL) chain of the 3G7NY antibody and the variable heavy (VH) chain of the 3G7NY antibody.

Embodiment 181: The antibody of embodiment 1, wherein said antibody is a human 3G7NY scFv.

Embodiment 182: The antibody of embodiment 1, wherein said antibody is a human 3G7NY IgG.

Embodiment 183: The antibody according to any one of embodiments 1-16, wherein said antibody comprises VH CDR1, and/or VH CDR2, and/or VH CDR3 of the 3G7 antibody.

Embodiment 184: The antibody according to any one of embodiments 1-16, wherein said antibody comprises VL CDR1, and/or VL CDR2, and/or VL CDR3 of the 3G7 antibody.

Embodiment 185: The antibody according to any one of embodiments 1-16, wherein said antibody comprises VH CDR1, VH CDR2, VH CDR3, VL CDR1, VLCDR2, and VL CDR3 of the 3G7 antibody.

Embodiment 186: The antibody according to any one of embodiments 1-16, wherein said antibody comprises the variable light (VL) chain of the 3G7 antibody.

Embodiment 187: The antibody according to any one of embodiments 1-16, wherein said antibody comprises the variable heavy (VH) chain of the 3G7 antibody.

Embodiment 188: The antibody according to any one of embodiments 1-16, wherein said antibody comprises the variable light (VL) chain of the 3G7 antibody and the variable heavy (VH) chain of the 3G7 antibody.

Embodiment 189: The antibody of embodiment 1, wherein said antibody is a human 3G7 scFv.

Embodiment 190: The antibody of embodiment 1, wherein said antibody is a human 3G7 IgG.

Embodiment 191: The antibody according to any one of embodiments 1-16, wherein said antibody comprises VH CDR1, and/or VH CDR2, and/or VH CDR3 of the SB2 antibody.

Embodiment 192: The antibody according to any one of embodiments 1-16, wherein said antibody comprises VL CDR1, and/or VL CDR2, and/or VL CDR3 of the SB2 antibody.

Embodiment 193: The antibody according to any one of embodiments 1-16, wherein said antibody comprises VH CDR1, VH CDR2, VH CDR3, VL CDR1, VLCDR2, and VL CDR3 of the SB2 antibody.

Embodiment 194: The antibody according to any one of embodiments 1-16, wherein said antibody comprises the variable light (VL) chain of the SB2 antibody.

Embodiment 195: The antibody according to any one of embodiments 1-16, wherein said antibody comprises the variable heavy (VH) chain of the SB2 antibody.

Embodiment 196: The antibody according to any one of embodiments 1-16, wherein said antibody comprises the variable light (VL) chain of the SB2 antibody and the variable heavy (VH) chain of the SB2 antibody.

Embodiment 197: The antibody of embodiment 1, wherein said antibody is a human SB2 scFv.

Embodiment 198: The antibody of embodiment 1, wherein said antibody is a human SB2 IgG.

Embodiment 199: The antibody according to any one of embodiments 1-16, wherein said antibody comprises VH CDR1, and/or VH CDR2, and/or VH CDR3 of the 2C8 antibody.

Embodiment 200: The antibody according to any one of embodiments 1-16, wherein said antibody comprises VL CDR1, and/or VL CDR2, and/or VL CDR3 of the 2C8 antibody.

Embodiment 201: The antibody according to any one of embodiments 1-16, wherein said antibody comprises VH CDR1, VH CDR2, VH CDR3, VL CDR1, VLCDR2, and VL CDR3 of the 2C8 antibody.

Embodiment 202: The antibody according to any one of embodiments 1-16, wherein said antibody comprises the variable light (VL) chain of the 2C8 antibody.

Embodiment 203: The antibody according to any one of embodiments 1-16, wherein said antibody comprises the variable heavy (VH) chain of the 2C8 antibody.

Embodiment 204: The antibody according to any one of embodiments 1-16, wherein said antibody comprises the variable light (VL) chain of the 2C8 antibody and the variable heavy (VH) chain of the 2C8 antibody.

Embodiment 205: The antibody of embodiment 1, wherein said antibody is a human 2C8 scFv.

Embodiment 206: The antibody of embodiment 1, wherein said antibody is a human 2C8 IgG.

Embodiment 207: The antibody according to any one of embodiments 1-16, wherein said antibody comprises VH CDR1, and/or VH CDR2, and/or VH CDR3 of the UA8kappa antibody.

Embodiment 208: The antibody according to any one of embodiments 1-16, wherein said antibody comprises VL CDR1, and/or VL CDR2, and/or VL CDR3 of the UA8kappa antibody.

Embodiment 209: The antibody according to any one of embodiments 1-16, wherein said antibody comprises VH CDR1, VH CDR2, VH CDR3, VL CDR1, VLCDR2, and VL CDR3 of the UA8kappa antibody.

Embodiment 210: The antibody according to any one of embodiments 1-16, wherein said antibody comprises the variable light (VL) chain of the UA8kappa antibody.

Embodiment 211: The antibody according to any one of embodiments 1-16, wherein said antibody comprises the variable heavy (VH) chain of the UA8kappa antibody.

Embodiment 212: The antibody according to any one of embodiments 1-16, wherein said antibody comprises the variable light (VL) chain of the UA8kappa antibody and the variable heavy (VH) chain of the UA8kappa antibody.

Embodiment 213: The antibody of embodiment 1, wherein said antibody is a human UA8kappa scFv.

Embodiment 214: The antibody of embodiment 1, wherein said antibody is a human UA8kappa IgG.

Embodiment 215: An immunoconjugate including an antibody according to any one of embodiments 1-214 attached to an effector wherein said effector is selected from the group consisting of a second antibody, a detectable label, a cytotoxin or cytostatic agent, a liposome containing a drug, a radionuclide, a drug, a prodrug, a viral particle, a cytokine, and a chelate.

Embodiment 216: The immunoconjugate of embodiment 215, wherein said antibody is attached to a cytotoxin.

Embodiment 217: The immunoconjugate of embodiment 216, wherein said antibody is attached to a cytotoxin selected from the group consisting of a Diphtheria toxin, a *Pseudomonas* exotoxin, a ricin, an abrin, saporin, and a thymidine kinase.

Embodiment 218: The immunoconjugate of embodiment 215, wherein said antibody is attached to a cytotoxic and/or cytostatic drug.

Embodiment 219: The immunoconjugate of embodiment 216, wherein said antibody is attached directly or through a linker to one or more of the following: said drug a lipid or liposome containing said drug; a polymeric drug carrier including said drug; and a nanoparticle drug carrier including said drug.

Embodiment 220: The immunoconjugate according to any one of embodiments 218-219, wherein said drug is an anti-cancer drug.

Embodiment 221: The immunoconjugate according to any one of embodiments 218-219, wherein said drug is selected from the group consisting of a microtubule inhibitor, a DNA-damaging agents, and a polymerase inhibitor.

Embodiment 222: The immunoconjugate of embodiment 221, wherein the drug comprises a tubulin inhibitor.

Embodiment 223: The immunoconjugate of embodiment 222, wherein the drug comprises a drug selected from the group consisting of an auristatin, Dolastatin-10, synthetic derivatives of the natural product Dolastatin-10, and maytansine or a maytansine derivative.

Embodiment 224: The immunoconjugate of embodiment 222, wherein the drug comprises a drug selected from the group consisting Monomethylauristatin F (MMAF), Auristatin E (AE), Monomethylauristatin E (MMAE), vcMMAE, and vcMMAF.

Embodiment 225: The immunoconjugate of embodiment 222, wherein the drug comprises a maytansine selected from the group consisting of Mertansine (DM1), DM3, and DM4.

Embodiment 226: The immunoconjugate of embodiment 221, wherein the drug comprises a DNA-damaging agent.

Embodiment 227: The immunoconjugate of embodiment 226, wherein the drug comprises a drug selected from the group consisting of a calicheamicin, a duocarmycin, and a pyrrolobenzodiazepines.

Embodiment 228: The immunoconjugate of embodiment 227, wherein the drug comprises a calicheamicin or a calicheamicin analog.

Embodiment 229: The immunoconjugate of embodiment 227, wherein the drug comprises a duocarmycin.

Embodiment 230: The immunoconjugate of embodiment 229, wherein the drug comprises a duocarmycin, selected from the group consisting of duocarmycin A, duocarmycin B1, duocarmycin B2, duocarmycin C1, duocarmycin C2, duocarmycin D, duocarmycin SA, Cyclopropylbenzoindole duocarmycin (CC-1065), Centanamycin, Rachelmycin, Adozelesin, Bizelesin, and Carzelesin.

Embodiment 231: The immunoconjugate of embodiment 227, wherein the drug comprises a pyrrolobenzodiazepine or a pyrrolobenzodiazepine dimer.

Embodiment 232: The immunoconjugate of embodiment 231, wherein the drug comprise a drug selected from the group consisting of Anthramycin (and dimers thereof), Mazethramycin (and dimers thereof), Tomaymycin (and dimers thereof), Prothracarcin (and dimers thereof), Chicamycin (and dimers thereof), Neothramycin A (and dimers thereof), Neothramycin B (and dimers thereof), DC-81 (and dimers thereof), Sibiromycin (and dimers thereof), Porothramycin A (and dimers thereof), Porothramycin B (and dimers thereof), Sibanomycin (and dimers thereof), Abbeymycin (and dimers thereof), SG2000, and SG2285.

Embodiment 233: The immunoconjugate of embodiment 221, wherein the drug comprises a polymerase inhibitor.

Embodiment 234: The immunoconjugate of embodiment 233, wherein said drug comprise a poly(ADP-ribose) polymerase (PARP) inhibitor.

Embodiment 235: The immunoconjugate of embodiment 234, wherein said drug comprise a poly(ADP-ribose) polymerase (PARP) inhibitor selected from the group consisting of Iniparib (BSI 201), Talazoparib (BMN-673), Olaparib (AZD-2281), Olaparib, Rucaparib (AG014699, PF-01367338), Veliparib (ABT-888), CEP 9722, MK 4827, BGB-290, and 3-aminobenzamide.

Embodiment 236: The immunoconjugate according to any one of embodiments 218-219, wherein said drug is selected from the group consisting of auristatin, dolastatin, colchicine, combretastatin, and mTOR/PI3K inhibitors.

Embodiment 237: The immunoconjugate according to any one of embodiments 218-219, wherein said drug is selected from the group consisting of flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitrosourea (BCNU), 1,-(2-chloroethyl)-3-cyclohexyl-lnitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, and vinflunine.

Embodiment 238: The immunoconjugate according to any one of embodiments 218-219, wherein said drug is selected from the group consisting of carboplatin, cisplatin, cyclophosphamide, docetaxel, doxorubicin, erlotinib, etoposide, gemcitabine, imatinib mesylate, irinotecan, methotrexate, sorafinib, sunitinib, topotecan, vinblastine, and vincristine.

Embodiment 239: The immunoconjugate according to any one of embodiments 218-219, wherein said drug is selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, and zoledronic acid.

Embodiment 240: The immunoconjugate of embodiment 215, wherein said antibody is attached to a chelate including an isotope selected from the group consisting of $^{99}$Tc, $^{203}$Pb, $^{67}$Ga, $^{68}$Ga, $^{72}$As, $^{111}$In, $^{113}$In, $^{97}$Ru, $^{62}$Cu, $^{641}$Cu, $^{52}$Fe, $^{52}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Ln, $^{105}$Rh, and $^{111}$Ag.

Embodiment 241: The immunoconjugate of embodiment 215, wherein said antibody is attached to an alpha emitter.

Embodiment 242: The immunoconjugate of embodiment 241, wherein said alpha emitter is bismuth 213.

Embodiment 243: The immunoconjugate of embodiment 215, wherein said antibody is attached to a lipid or a liposome complexed with or containing an anti-cancer drug.

Embodiment 244: The immunoconjugate of embodiment 215, wherein said antibody is attached to a detectable label.

Embodiment 245: The immunoconjugate of embodiment 244, wherein said antibody is attached to a detectable label selected from the group consisting of a radioactive label, a radioopaque label, an MM label, and a PET label.

Embodiment 246: A pharmaceutical formulation said formulation including: a pharmaceutically acceptable excipient and an antibody according to any one of embodiments 1-214; and/or a pharmaceutically acceptable excipient and an immunoconjugate according to any one of embodiments 215-245.

Embodiment 247: The pharmaceutical formulation of embodiment 246, wherein said formulation is a unit dosage formulation.

Embodiment 248: The formulation according to any one of embodiments 246-247, wherein said formulation is formulated for administration via a route selected from the group consisting of oral administration, nasal administration, rectal administration, intraperitoneal injection, intravascular injection, subcutaneous injection, transcutaneous administration, and intramuscular injection.

Embodiment 249: A method of inhibiting the growth and/or proliferation of a cell that expresses or overexpresses CD46, said method including: contacting said cancer cell with an antibody according to any one of embodiments 1-214; and/or contacting said cancer cell with an immunoconjugate including an antibody according to any one of embodiments 1-214 attached to an effector that has cytostatic and/or cytotoxic activity.

Embodiment 250: The method of embodiment 249, wherein said method comprises contacting said cancer cell with an antibody according to any one of embodiments 1-214.

Embodiment 251: The method of embodiment 249, wherein said method comprises contacting said cancer cell with an immunoconjugate including an antibody according to any one of embodiments 1-214 attached to an effector that has cytostatic and/or cytotoxic activity.

Embodiment 252: The method of embodiments 249-251, wherein said cell is a cancer cell.

Embodiment 253: The method of embodiment 252, wherein said cell is a cancer cell that overexpresses CD46.

Embodiment 254: The method of embodiment 252, wherein said cancer cell is selected from the group consisting of ovarian cancer, colorectal cancer, breast cancer, lung cancer, prostate cancer, kidney cancer, pancreatic cancer, mesothelioma, lymphoma, liver cancer, urothelial cancer, stomach cancer, multiple myeloma, glioblastoma multiforme, glioma, neuroblastoma, and cervical cancer.

Embodiment 255: The method of embodiment 252, wherein said cancer cell is a prostate cancer cell.

Embodiment 256: The method of embodiment 255, wherein said cancer cell is a cell of a castration-resistant prostate cancer.

Embodiment 257: The method of embodiment 252, wherein said cancer cell is a cell of a multiple myeloma.

Embodiment 258: The method according to any one of embodiments 252-257, wherein said cell is a metastatic cell.

Embodiment 259: The method of embodiment 258, wherein said metastatic cell is a bone metastasis, a liver metastasis, a bladder metastasis, and/or a lymph node metastasis.

Embodiment 260: The method according to any one of embodiments 252-258, wherein said cell is a solid tumor cell.

Embodiment 261: The method according to any one of embodiments 249, and 251-260, wherein said effector comprises a radionuclide and/or a cytostatic drug.

Embodiment 262: The method of embodiment 261, wherein said effector comprises one or more of the following: a cytotoxic and/or cytostatic drug; a lipid or liposome containing a cytotoxic and/or cytostatic drug; a polymeric drug carrier including a cytotoxic and/or cytostatic drug; and a nanoparticle drug carrier including a cytotoxic and/or cytostatic drug.

Embodiment 263: The method of embodiment 262, wherein said drug is an anti-cancer drug.

Embodiment 264: The method of embodiment 263, wherein said drug is selected from the group consisting of auristatin, dolastatin, colchicine, combretastatin, and mTOR/PI3K inhibitors.

Embodiment 265: The method of embodiment 263, wherein said drug is monomethyl auristatin F.

Embodiment 266: The method of embodiment 263, wherein said drug is selected from the group consisting of flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitosourea (BCNU), 1,-(2-chloroethyl)-3-cyclohexyl-lnitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, and vinflunine.

Embodiment 267: The method of embodiment 263, wherein said drug is selected from the group consisting of carboplatin, cisplatin, cyclophosphamide, docetaxel, doxorubicin, erlotinib, etoposide, gemcitabine, imatinib mesylate, irinotecan, methotrexate, sorafinib, sunitinib, topotecan, vinblastine, and vincristine.

Embodiment 268: The method of embodiment 263, wherein said drug is selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, and zoledronic acid.

Embodiment 269: The method according to any one of embodiments 262-268, wherein said drug is conjugated to said antibody.

Embodiment 270: The method according to any one of embodiments 262-268, wherein said drug is contained in a lipid or liposome attached to said antibody.

Embodiment 271: The method according to any one of embodiments 262-268, wherein said drug is contained in a polymeric and/or nanoparticle carrier attached to said antibody.

Embodiment 272: The method of embodiment 249, and 251-260, wherein said effector comprises a cytotoxin.

Embodiment 273: The method of embodiment 272, wherein said cytotoxin is selected from the group consisting of Diphtheria toxin, *Pseudomonas* exotoxin, ricin, abrin, saporin, and thymidine kinase.

Embodiment 274: The method of embodiment 249, wherein said effector comprises a radionuclide.

Embodiment 275: The method according to any one of embodiments 249-274, wherein said immunoconjugate or antibody is administered in a pharmaceutical composition including a pharmaceutical acceptable carrier.

Embodiment 276: The method according to any one of embodiments 249-275, wherein said administering comprises administering to a human.

Embodiment 277: The method according to any one of embodiments 249-275, wherein said administering comprises administering to a non-human mammal.

Embodiment 278: The method according to any one of embodiments 249-277, wherein said administering comprises administering parenterally.

Embodiment 279: The method according to any one of embodiments 249-277, wherein said administering comprises administering into a tumor or a surgical site.

Embodiment 280: The method according to any one of embodiments 249-279, wherein said immunoconjugate is administered as an adjunct therapy to surgery and/or radiotherapy.

Embodiment 281: The method according to any one of embodiments 249-279, wherein said antibody and/or immunoconjugate is administered in conjunction with another anti-cancer drug and/or a hormone.

Embodiment 282: The method of embodiment 281, wherein said antibody and/or immunoconjugate is administered in conjunction with abiraterone and/or enzalutamide.

Embodiment 283: The method of embodiment 282, wherein said cells comprise prostate cancer cells.

Embodiment 284: The method of embodiment 283, wherein said prostate cancer cells comprise neuroendocrine prostate cancer (NEPC) cells.

Embodiment 285: The method of embodiment 283, wherein said prostate cancer cells comprise metastatic castration resistant prostate cancer (mCRPC) cells resistant to abiraterone (Abi) or enzalutamide (Enz).

Embodiment 286: A method of detecting a cancer cell of a cancer that expresses or overexpresses CD46, said method including: contacting said cancer cell with a immunoconjugate including an antibody according to any one of embodiments 1-214 attached to a detectable label; and detecting the presence and/or location of said detectable label where the presence and/or location is an indicator of the location and/or presence of a cancer cell.

Embodiment 287: The method of embodiment 286, wherein said label comprises a label selected from the group consisting of a radioactive label, a radioopaque label, an Mill label, a PET label, and an SPECT label.

Embodiment 288: The method of embodiment 286, wherein said detectable label is selected from the group consisting of a gamma-emitter, a positron-emitter, an x-ray emitter, an alpha emitter, and a fluorescence-emitter.

Embodiment 289: The method according to any one of embodiments 286-288, wherein said cancer cell is selected from the group consisting of ovarian cancer, colorectal cancer, breast cancer, lung cancer, prostate cancer, kidney cancer, pancreatic cancer, mesothelioma, lymphoma, liver cancer, urothelial cancer, stomach cancer, multiple myeloma, glioma, neuroblastoma, and cervical cancer.

Embodiment 290: The method of embodiment 289, wherein said cancer cell is a prostate cancer cell.

Embodiment 291: The method of embodiment 290, wherein said cancer cell is a cell of a castration-resistant prostate cancer.

Embodiment 292: The method of embodiment 289, wherein said cancer cell is a cell of a multiple myeloma.

Embodiment 293: The method according to any one of embodiments 286-292, wherein said contacting comprises administering said immunoconjugate to a non-human mammal.

Embodiment 294: The method according to any one of embodiments 286-292, wherein said contacting comprises administering said immunoconjugate to a human.

Embodiment 295: The method according to any one of embodiments 286-294, wherein said detecting comprises detecting said label in vivo.

Embodiment 296: The method of embodiment 295, wherein said detecting comprises using a detection method selected from the group consisting of X-ray, PET, SPECT, MRI, and CAT.

Embodiment 297: The method according to any one of embodiments 286-294, wherein said detecting comprises detecting said label ex vivo in a biopsy or a sample derived from a biopsy.

Embodiment 298: A nucleic acid encoding an antibody or a fragment of an antibody according to any of embodiments 1-214.

Embodiment 299: An expression vector including the nucleic acid of embodiment 298.

Embodiment 300: A cell including the expression vector of embodiment 299.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) 1 *Am. Chem. Soc.* 111:2321, O-methylphophoroamidite linkages (see Eckstein, Oligonucleotides and Analogues: A Practical Approach, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, *ASC Symposium Series* 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, *ASC Symposium Series* 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al.

(1988) *Proc. Nat. Acad. Sci. USA,* 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331).

The term "specifically binds", as used herein, when referring to a biomolecule (e.g., protein, nucleic acid, antibody, etc.), refers to a binding reaction that is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The phrase "inhibition of proliferation of a cell expressing CD46" as used herein, refers to the ability of an anti-CD46 antibody or immunoconjugate described herein decrease, preferably to statistically significantly decrease proliferation of a cell expressing CD46 relative to the proliferation in the absence of the antibody or immunoconjugate. In one embodiment, the proliferation of a cell expressing CD46 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof or an immunoconjugate described herein, relative to the proliferation measured in the absence of the antibody or antigen binding portion thereof or immunoconjugate (control). Cellular proliferation can be assayed using art recognized techniques which measure rate of cell division, the fraction of cells within a cell population undergoing cell division, and/or rate of cell loss from a cell population due to terminal differentiation or cell death (e.g., using a cell titer glow assay or thymidine incorporation).

The phrase "inhibition of the migration of cells expressing CD46" as used herein, refers to the ability of an anti-CD46 antibody or an antigen-binding portion thereof or an immunoconjugate described herein to decrease, preferably to statistically significantly decrease the migration of a cell expressing CD46 relative to the migration of the cell in the absence of the antibody. In one embodiment, the migration of a cell expressing CD46 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof or immunoconjugate thereof, relative to cell migration measured in the absence of the antibody or antigen binding portion thereof or immunoconjugate thereof (control). Cell migration can be assayed using art recognized techniques. In various embodiments, it is contemplated that the antibodies and/or the immunoconjugates thereof described herein can inhibit the migration of cells (e.g., cancer cells as described herein) expressing or overexpressing CD46.

The term "antigen-binding portion" of an antibody (or simply "antibody portion"), as used herein, refers to one or more fragments of an antibody that retain the ability to specifically bind to an antigen (e.g., CD46 domain 1 and/or domain 2). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (see, e.g., Ward et al. (1989) *Nature* 341: 544-546), which consists of a $V_H$ domain; (vii) a dAb which consists of a $V_H$ or a $V_L$ domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, can be coded for by separate genes, they can be joined, using recombinant methods, by a synthetic linker that enables them to be made as a single protein chain in which the $V_L$ and V-regions pair to form monovalent molecules (known as single chain Fv (scFv); see e.g., Bird et al. (1988) *Science* 242: 423-426; and Huston et al. (1988) *Proc. Natl. Acad. Sci. USA* 85: 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al. (1975) *Nature,* 256: 495, a transgenic animal, as described by, for example, (see e.g., Lonberg, et al. (1994) *Nature* 368(6474): 856-859), recombinant DNA methods (see, e.g., U.S. Pat. No. 4,816,567), or using phage antibody libraries using the techniques described in, for example, Clackson et al. (1991) *Nature,* 352: 624-628, and Marks et al. (1991) *J. Mol. Biol.,* 222: 581-597. Monoclonal antibodies include chimeric antibodies, human antibodies and humanized antibodies and may occur naturally or be recombinantly produced.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline V- and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue which is not encoded by the human germline immunoglobulin sequence. Typically, the human antibody can have up to twenty positions replaced with amino acid residues which are not part of the human germline immunoglobulin sequence. In a particular embodiment, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

As used herein, a "heterologous antibody" is defined in relation to the transgenic non-human organism or plant producing such an antibody.

An "isolated antibody," as used herein, is intended to refer to an antibody that is substantially free of other antibodies having different antigenic specificities (e.g., an isolated antibody that specifically binds to CD46 is substantially free of antibodies that specifically bind antigens other than CD46). In addition, an isolated antibody is typically substantially free of other cellular material and/or chemicals. In one embodiment, a combination of "isolated" monoclonal antibodies having different CD46 binding specificities are combined in a well defined composition.

As used herein, "isotype" refers to the antibody class (e.g., IgM or IgG1) that is encoded by heavy chain constant region genes. In one embodiment, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, a monoclonal antibody of the invention is of the IgG1 isotype. In other embodiments, a monoclonal antibody of the invention is of the IgG2 isotype.

An "antigen" is an entity (e.g., a proteinaceous entity or peptide) to which an antibody or antigen-binding portion thereof binds. In various embodiments of the present invention, an antigen is CD46, e.g., as presented on a cell (e.g., a CD46 positive cancer cell).

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

Also contemplated herein are antibodies that bind the same or an overlapping epitope as the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibodies described herein. Antibodies that recognize the same epitope can be identified using routine techniques such as an immunoassay, for example, by showing the ability of one antibody to block the binding of another antibody to a target antigen, i.e., a competitive binding assay. Competitive binding is determined in an assay in which the immunoglobulin under test inhibits specific binding of a reference antibody to a common antigen, such as CD46 domain 1 and/or domain 2. Numerous types of competitive binding assays are known, for example: solid phase direct or indirect radioimmunoassay (RIA), solid phase direct or indirect enzyme immunoassay (EIA), sandwich competition assay (see, e.g., Stahli et al. (1983) *Meth. Enzymol.,* 9: 242); solid phase direct biotin-avidin EIA (see Kirkland et al., (1986) *J. Immunol.* 137: 3614); solid phase direct labeled assay, solid phase direct labeled sandwich assay (see, e.g., Harlow and Lane (1988) *Antibodies: A Laboratory Manual*, Cold Spring Harbor Press); solid phase direct label RIA using, e.g., $^{125}$I label (see, e.g., Morel et al., (1988) *Mol. Immunol.* 25(1): 7); solid phase direct biotin-avidin EIA (Cheung et al. (1990) *Virology* 176: 546); and direct labeled RIA. (Moldenhauer et al. (1990) *Scand J. Immunol.* 32: 77). Typically, such an assay involves the use of purified antigen (e.g., CD46 domain 1 and/or domain 2) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

As used herein, the terms "specific binding," "specifically binds," "selective binding," and "selectively binds," mean that an antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least (KD equal to or less than) $10^{-6}$ M, $10^{-7}$M, $10^{-8}$M, $10^{-9}$M, $10^{-10}$ M, or $10^{-11}$M. Affinities greater than $10^{-9}$M, preferably greater than $10^{-10}$ M are more preferred. Values intermediate of those set forth herein are also intended to be within the scope of the present invention and a preferred binding affinity can be indicated as a range of affinities, for example, $10^{-6}$ M to $10^{-11}$ M, preferably $10^{-7}$ M or $10^{-8}$M to $10^{-10}$ M. An antibody that "does not exhibit significant cross-reactivity" is one that will not appreciably bind to an undesirable entity (e.g., an undesirable proteinaceous entity). For example, in one embodiment, an antibody or antigen-binding portion thereof that specifically binds to CD46 (e.g., domain 1 and/or domain 2) protein but will not significantly react with other molecules and non-CD46 proteins or peptides. Specific or selective binding can be determined according to any art-recognized means for determining such binding, including, for example, according to Scatchard analysis and/or competitive binding assays.

The term "$K_D$," as used herein, is intended to refer to the dissociation equilibrium constant of a particular antibody-antigen interaction or the affinity of an antibody for an antigen. In one embodiment, the antibody or antigen binding portion thereof according to the present invention binds an antigen (e.g., CD46 domain 1 and/or domain 2) with an affinity ($K_D$) of 5 nM or better (i.e., or less) (e.g., 40 nM or 30 nM or 20 nM or 10 nM or less), as measured using a surface plasmon resonance assay or a cell binding assay. In a particular embodiment, an antibody or antigen binding portion thereof according to the present invention binds CD46 with an affinity ($K_D$) of 5 nM or better (e.g., 4 nM, 2 nM, 1.5 nM, 1.4 nM, 1.3 nM, 1 nM or less), as measured by a surface plasmon resonance assay or a cell binding assay. In other embodiments, an antibody or antigen binding portion thereof binds an antigen (e.g., CD46) with an affinity ($K_D$) of approximately less than $10^{-10}$ M, or $100 \times 10^{-11}$M, or $10 \times 10^{-11}$M, or even lower using live prostate tumor cells by FACS.

The term "$K_{off}$," as used herein, is intended to refer to the off rate constant for the dissociation of an antibody from the antibody/antigen complex.

The term "EC50," as used herein, refers to the concentration of an antibody or an antigen-binding portion thereof or an immunoconjugate described herein, that induces a response, either in an in vitro or an in vivo assay, which is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "modifying," or "modification," as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis. For example, in some embodiments, an antibody or an antigen-binding portion thereof identified' using the methods of the invention can be modified, to thereby modify the binding affinity of the antibody or antigen-binding portion thereof to CD46.

In certain embodiments "conservative amino acid substitutions" in the sequences of the anti-CD46 antibodies described herein, i.e., nucleotide and amino acid sequence modifications that do not abrogate the binding of the antibody encoded by the nucleotide sequence or containing the amino acid sequence, to the antigen, e.g., CD46 are contemplated. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-CD46 antibody is preferably replaced with another amino acid residue from the same class. Methods of identifying nucleotide and amino acid conservative substitutions that do not eliminate antigen binding are well-known in the art (see, e.g., Brummell et al. (1993) *Biochem.* 32: 1180-1187; Kobayashi et al. (1999) *Protein Eng.* 12(10): 879-884; and Burks et al. (1997) *Proc. Natl. Acad. Sci. USA* 94: 412-417).

The term "non-conservative amino acid substitution" refers to the substitution of an amino acid in one class with an amino acid from another class; for example, substitution of an Ala, a class II residue, with a class III residue such as Asp, Asn, Glu, or Gln.

In another embodiment, mutations (conservative or non-conservative) can be introduced randomly along all or part of an anti-CD46 antibody coding sequence, such as by saturation mutagenesis, and the resulting modified antibodies can be screened for binding activity.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

Similarly, the consensus sequence for the CDRs of can be derived by optimal alignment of the CDR amino acid sequences of anti-CD46 antibodies described herein.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions.times.100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of Meyers and Miller (1989) *CABIOS,* 4: 11-17, which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) *J. Mol. Biol.* 48: 444-453 algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the contemplated herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

The nucleic acid compositions described herein (e.g., nucleic acids encoding all or a portion of an anti-CD46 antibody or immunoconjugate) while often in a native sequence (except for modified restriction sites and the like), from either cDNA, genomic or mixtures thereof may be mutated, in accordance with standard techniques to provide variant sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), that serve equivalent functions.

The term "recombinant host cell" (or simply "host cell"), as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject (e.g., a subject in need thereof), an anti-CD46 antibody or antigen binding portion or an immunoconjugate comprising such an antibody or antigen binding portion described herein. In certain embodiments the subject is a subject diagnosed with and/or under treatment for a CD46 positive cancer (e.g., prostate cancer) in order to prevent, cure, delay, reduce the severity of, or ameliorate one or more symptoms of the disease or disorder or recurring disease or disorder, or in order to prolong the survival of a subject beyond that expected in the absence of such treatment.

The terms "cancer" and "cancerous" refer to or describe the physiological condition in mammals that is typically characterized by unregulated cell growth. A CD46 positive cancer refers to a cancer characterized by cells that express or overexpress CD46. Illustrative CD46 cancers include, but are not limited to, ovarian cancer, breast cancer, lung cancer, prostate cancer, colon cancer, kidney cancer, and pancreatic cancer.

The term "effective amount," as used herein, refers to that amount of an anti-CD46 antibody or an antigen binding portion thereof and/or an immunoconjugate thereof, that is sufficient to effect treatment, prognosis or diagnosis of a disease associated with the growth and/or proliferation of CD46 positive cells (e.g., a CD46 positive cancer), as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an anti-CD46 antibody described herein and/or antigen binding portion thereof, and/or immunoconjugate thereof as described herein. Dosage regiments may be adjusted to provide the optimum therapeutic response. An effective amount is also one in which any toxic or detrimental effects (i.e., side effects) of an antibody or antigen binding portion thereof are minimized and/or outweighed by the beneficial effects.

The term "patient" includes human and other mammalian subjects that receive either prophylactic or therapeutic treatment.

As used herein, the term "subject" includes any human or non-human animal. For example, the methods and compositions of the present invention can be used to treat a subject having cancer. In a particular embodiment, the subject is a human. The term "non-human animal" includes all vertebrates, e.g., mammals and non-mammals, such as non-human primates, sheep, dog, cow, chickens, amphibians, reptiles, etc.

An "effector" refers to any molecule or combination of molecules whose activity it is desired to deliver/into and/or localize at cell. Effectors include, but are not limited to labels, cytotoxins, enzymes, growth factors, transcription factors, antibodies, drugs, etc.

The phrase "inhibiting the growth and/or proliferation", e.g. of cancer cells includes inter alia inducing cellular apoptosis or other cell killing mechanisms, reducing the invasiveness of the cells, stalling the cells at a point in the cell cycle, and the like.

The term "immunoconjugate" refers to an antibody attached to one or more effectors or to a plurality of antibodies attached to one or more effectors. The term "immunoconjugate" is intended to include effectors chemically conjugated to the antibodies as well as antibodies expresses as a fusion protein where the antibody (or a portion thereof) is directly attached or attached through a linker to a peptide effector or to an effector comprising a peptide.

BRIEF DESCRIPTION OF THE DRAWINGS

FIG. 1A shows VH framework and CDR regions for YS5 (SEQ ID NO:1), YS5F (SEQ ID NO:2), YS5vlD (SEQ ID NO:3), SB1HGNY (SEQ ID NO:4), YS12 (SEQ ID NO:5), 3G7RY (aka 3G8) (SEQ ID NO:6), YS6 (SEQ ID NO:7), YS1 (SEQ ID NO:8), YS3 (SEQ ID NO:9), YS4 (SEQ ID NO:10), YS8 (SEQ ID NO:11), YS7 (SEQ ID NO:12), YS9 (SEQ ID NO:13), YS10 (SEQ ID NO:14), YS11 (SEQ ID NO:15), 3G7HY (SEQ ID NO:16), 3G7NY (SEQ ID NO:17), 3G7 (SEQ ID NO:18), SB2 (SEQ ID NO:19), 2C8 (SEQ ID NO:20), and UA8kappa (SEQ ID NO:21). FIG. 1B shows VL framework and CDR regions for YS5 (SEQ ID NO:22), YS5F (SEQ ID NO:23), YS5vlD (SEQ ID NO:24), SB1HGNY (SEQ ID NO:25), YS12 (SEQ ID NO:26), 3G7RY (aka3G8) (SEQ ID NO:27), YS6 (SEQ ID NO:28), YS1 (SEQ ID NO:29), YS3 (SEQ ID NO:30), YS4 (SEQ ID NO:31), YS8 (SEQ ID NO:32), YS7 (SEQ ID NO:33), YS9 (SEQ ID NO:34), YS10 (SEQ ID NO:35), YS11 (SEQ ID NO:36), 3G7HY (SEQ ID NO:37), 3G7NY (SEQ ID NO:38), 3G7 (SEQ ID NO:39), SB2 (SEQ ID NO:40), 2C8 (SEQ ID NO:41), and UA8kappa (SEQ ID NO:42).

FIG. 10. Immunohistochemistry study of anti-CD46 antibodies on FDA standard panel of frozen tissues for therapeutic antibody evaluation. Shading indicates levels of positive staining with placental trophoblasts being the strongest. Signals in non-shaded ones are either weak or non-detectable.

FIG. 34 illustrates bone metastasis of mCRPC. Arrows indicate tumor cells (only selective tumor regions are indicated). The H-294 rabbit anti-human CD46 antibody (Santa Cruz Biotechnology) was used for staining, followed by detection with the Envision+ system (Dako North America).

FIG. 37 shows that CD46 is highly expressed by prostate cancer neuroendocrine cell line H660. Left panel: FACS analysis. Ctr: non-binding mAb. Right panel: Western blot analysis confirms CD46 expression, and the expression of neuroendocrine marker NSE by H660 cells.

FIG. 38 shows internalization of anti-CD46 antibody by prostate cancer neuroendocrine cell line H660. YS5 IgG1 was incubated with H660 cells overnight. The cells were fixed, permeated, stained, and imaged by confocal microscopy. A single confocal slice is shown. The anti-CD46 antibody is internalized and co-localize with LAMP1, the lysosome marker.

DETAILED DESCRIPTION

Figure 2:
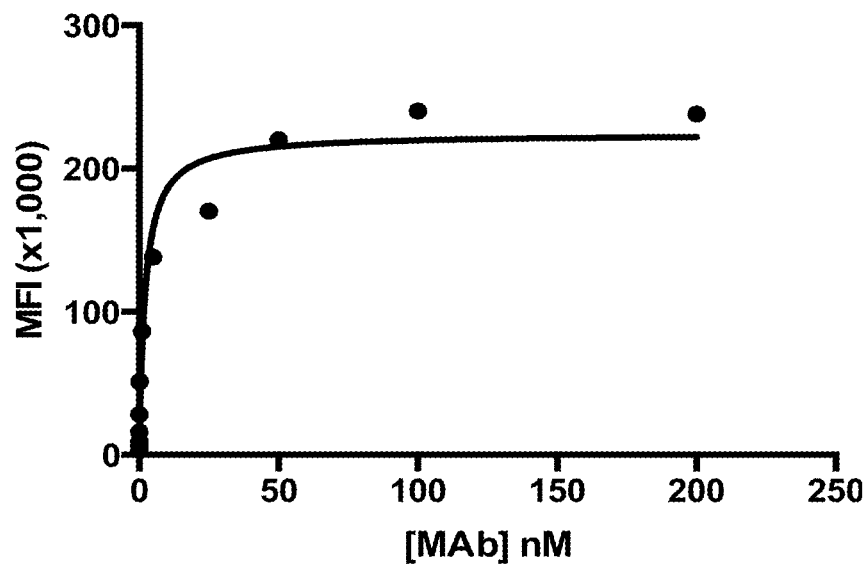
FIG. 2. YS5 IgG1 $K_D$ measurement on Du-145 cells. YS5 was incubated with Du-145 cells at 4° C. overnight and binding analyzed by FACS. Mean fluorescence intensity (MFI) values were curve-fit using Prism (GraphPad) to generate an estimated KD value of 2.19+/−0.73 nM.

In various embodiments, a number of new anti-CD46 antibodies are provided. The prototypical antibodies described herein were identified by a combination of selections on cell surface and recombinant CD46 using both phage and yeast display techniques. These antibodies are internalized by the tumor-selective macropinocytosis pathway, without the need of crosslinking, and localize to the lysosomes, which makes them well suited for the development of antibody drug conjugates (ADCs) and other targeted therapeutics that utilize intracellular payload release.

The antibodies described herein antibodies bind to domain 1 and 2 of the CD46 molecule, not the main complement binding domains 3 and 4, and thus do not block directly the normal complement cascade.

Fine epitope mapping also showed differences in antigen contact sites between the anti-CD46 antibodies described herein and the UA20 and 2B10 antibodies described in PCT Application No: PCT/US2008/076704, and copending U.S. application Ser. No. 14/205,101, respectively. Tested on CHO cells transfected with cynomolgus monkey CD46 cDNA, we found that our anti-CD46 antibodies bind to an epitope conserved between human and cynomolgus monkey, thus identifying an appropriate species for regulatory toxicology study.

Using FDA-approved frozen human tissue panel for therapeutic antibody evaluation, it was found that the CD46 epitopes bound by antibodies the antibodies described herein are expressed at low levels in virtually no tissues except for placental trophoblasts and, to a lesser degree, prostate epithelium. Conversely, it was determined that CD46 is overexpressed by a variety of tumors including but not limited to, prostate cancer, multiple myeloma, colorectal cancer, pancreatic cancer, mesothelioma, lung cancer, breast cancer, ovarian cancer, liver cancer, glioma, neuroblastoma, etc.

Given that CD46 is located in chromosome 1q32.2, and 1q gain has been observed in a broad spectrum of human cancers, it is likely to be an excellent target for antibody therapy development for various malignancies. Antibody drug conjugates (ADCs) utilizing the anti-CD46 antibodies described herein were constructed and it was found that they kill CD46-overexpressing cancer cell lines in vitro including but not limited to metastatic castration resistant prostate cancer, multiple myeloma, colorectal cancer, mesothelioma, ovarian cancer, etc. Most importantly, the anti-CD46 ADCs described herein showed potent in vivo anti-tumor activity, greatly reducing tumor burdens in xenograft models of castration resistant prostate cancer and multiple myeloma. This potent anti-tumor activity is believed to be applicable to other CD46-overexpressing tumor models as well. The studies described herein thus validate CD46 as a useful tumor cell surface antigen for targeted therapy development. Additionally, the anti-CD46 antibodies described herein can be used in companion diagnostics for patient stratification and treatment outcome monitoring.

In view of these discoveries, it is believed that the anti-CD46 antibodies described herein specifically bind and be internalized into cells that express or overexpress CD46. As CD46 is expressed/overexpressed by a number of cancers including, but not limited to ovarian cancer, breast cancer, lung cancer, prostate cancer, colon cancer, kidney cancer, pancreatic cancer mesothelioma, lymphoma, liver cancer, urothelial cancer, stomach cancer, and cervical cancer, these antibodies can be used to specifically target and internalize into these and other CD46 positive cancer cells.

In certain embodiments these antibodies can be used without attached effectors for their intrinsic cytotoxic and/or cytostatic and/or antiproliferative activity on cells (particularly cancer cells). In certain embodiments these antibodies can be attached to one or more effectors (e.g., second antibody, a detectable label, a cytotoxin, a liposome containing a drug, a radionuclide, a drug, a prodrug, a viral particle, a cytokine, a chelate, etc.) to thereby form an immunoconjugate that will specifically bind and internalize into cancer cells expressing or overexpressing CD46. In certain embodiments multiple effectors will be attached to a single antibody, or in certain embodiments, multiple antibodies will be attached to a single effector, or in certain embodiments, a single antibody will be attached to a single antibody.

In various embodiments methods of use of these antibodies and/or immunoconjugates are provided. In certain embodiments the methods involve contacting a cell that expresses or overexpresses CD46 (e.g., a cancer cell such as an ovarian cancer cell, a breast cancer cell, a lung cancer cell, a prostate cancer cell, a colon cancer cell, a kidney cancer cell, a pancreatic cancer cell, etc.) with the construct resulting in internalization of the construct (or a portion thereof) into the cell and thereby delivering the effector to the target cell. In certain embodiments the "contacting" comprises administering the antibody or the construct to a subject (e.g., a human or a non-human mammal) in need thereof.

Antibodies that Bind CD46

Antibodies were discovered that specifically bind CD46, in particular domains 1 and/or 2, and that are internalized by prostate (and other CD46 positive cancer cells) in situ, e.g., when the cancer cell is in the tissue microenvironment. As indicated above, such antibodies are useful for targeting cancers when used alone, or when attached to an effector to form a "targeted effector".

Accordingly in certain embodiments, an isolated antibody is provided that that specifically binds CD46 and that is internalized into a cell that expresses or overexpresses CD46 (e.g., a prostate cancer cell) via macropinocytosis. In various embodiments, the antibody binds domain 1 and/or domain 2 of CD46. In various embodiments, the antibody does not bind domain 3 and/or domain 4 of CD46.

The antibodies designated herein as YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and UA8kappa (see, e.g., Table 1) are illustrative prototypical antibodies. In certain embodiments antibodies that comprise VL CDR1 and/or VL CDR2, and/or VL CDR3, and/or VH CDR1 and/or VH CDR2, and/or VH CDR3 of one or more of these antibodies are contemplated. In certain embodiments antibodies that comprise the VH domain and/or the VL domain of one or more of theses antibodies are contemplated. Also contemplated are antibodies that compete for binding at CD46 with one or more of as YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa.

The amino acid sequences of the VH and VL domains of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibodies are shown in Table 1 (see Example 1).

TABLE 1

Novel human anti-CD46 antibody sequences. YS5 and YS5F differ by one amino acid in VH CDR1 (L vs. F). YS5 and YS5vlD have identical VH but one amino acid difference in the VL CDR2 (N vs. D). 3G7HY, 3G7NY, 3G7RY (aka 3G8), and 3G7 have one residue difference in VH CDR3, but entirely different VLs. YS6 and 3G17 have identical VH but different VL.

| | VH | VL |
|---|---|---|
| YS5 | QVQLVQSGGGVVQPGRSLRLACAASGLTV NNYAMHWVRQAPGKGLEWVAVISYDGNNK YYADSVKGRFTISRDNSKNTLYLQMNSLR AEDTAVYYCAKGGGYFDLWGRGTLVTSS (SEQ ID NO: 1) | QSVLTQPPSVSGAPGQRVTISCTGSSSNIGA GYDVHWYQQLPGTAPKLLIYGNNNRPSGVPD RFSGSKSGTSASLAITGLQAEDEADYYCSSY TSGTWLFGGGTKLTVL (SEQ ID NO: 22) |
| YS5F | QVQLVQSGGGVVQPGRSLRLACAASGFTV NNYAMHWVRQAPGKGLEWVAVISYDGNNK YYADSVKGRFTISRDNSKNTLYLQMNSLR AEDTAVYYCAKGGGYFDLWGRGTLVTSS (SEQ ID NO: 2) | QSVLTQPPSVSGAPGQRVTISCTGSSSNIGA GYDVHWYQQLPGTAPKLLIYGNNNRPSGVPD RFSGSKSGTSASLAITGLQAEDEADYYCSSY TSGTWLFGGGTKLTVL (SEQ ID NO: 23) |
| YS5vlD | QVQLVQSGGGVVQPGRSLRLACAASGFTV NNYAMHWVRQAPGKGLEWVAVISYDGNNK YYADSVKGRFTISRDNSKNTLYLQMNSLR AEDTAVYYCAKGGGYFDLWGRGTLVTSS (SEQ ID NO: 3) | QSVLTQPPSVSGAPGQRVTISCTGSSSNIGA GYDVHWYQQLPGTAPKLLIYGDNNRPSGVPD RFSGSKSGTSASLAITGLQAEDEADYYCSSY TSGTWLFGGGTKLTVL (SEQ ID NO: 24) |
| SB1HGNY | QVQLQQSGGGVVQPGRSLRLSCAASGFTF SSYAMHWVRQAPGKGLEWVAFIRSDGSKK YYADSVKGRFTISRDNSKNTLYLQMNSLR AEDTAVYYCARHGNYFDSWGQGTLVTVSS (SEQ ID NO: 4) | DIQMTQSPSFLSASVGDRVTITCRASQGISS YLAWYQQKPGKAPKLLIYAASTLQSGVPSSF SGSGSGTEFTLTISSLQPEDFATYYCQQLAS YPLTFGGGTKVDIK (SEQ ID NO: 25) |
| YS12 | QVQLVESGGGVVQPGRSLRLSCAASGFTF STYGMHWVRQAPGKGLEWLSFISYDGDEK YYADSVKGRFTISRDNSKNTLYLQMNSLR AEDTAVYWCAKASGYGMGILDYWGQGTLV TVSS (SEQ ID NO: 5) | SSELTQDPAVSVALGQTVRITCQGDSLRSYY VSWFQQKPGQAPVFVMYGQNNRPSGISERFS GSSSGNTASLIITGAQAEDEADYYCHSRDSS GTHLRVFGGGTKLTVL (SEQ ID NO: 26) |
| 3G7RY aka 3G8 | EVQLVESGGGLVQPGGSLRLSCAASGFTF SDYYMSWIRQAPGKGLEWVSYISSSGSTI YYADSVKGRFTISRDNSKNTLYLQMNSLR AEDTAVYYCARDYGRIAAAGRRYWGQGTL VTVSS (SEQ ID NO: 6) | QSALTQPPSASATPGQRVTISCSGRTSNIGS NHVYWYQQLPGTAPKLLIYRNNQRPSGVPDR FSGSKSGTSASLAISGLRSEDEADYYCATWD DSLSGEVFGGGTKLTVL (SEQ ID NO: 27) |
| YS6 | QVQLQESGGGVVRPGGSLRLSCAASGFTF SDYYMSWIRQAPGKGLEWVSYISSSGSTI YYADSVKGRFTISRDNSKNTLYLQMNSLR AEDTAVYYCARDYGRIAAAGRHYWGQGTL VTVSS (SEQ ID NO: 7) | SSELTQDPAVSVALGQTVRITCQGDSLRSYY ASWYQQKPGQAPVLVIYGKNNRPSGIPDRFS GSSSGNTASLTITGAQAEDEADYYCNSRDSS GTHLEVFGGGTKVTVL (SEQ ID NO: 28) |
| YS1 | EVQLVESGGGLVQPGGSLRLSCAASGFTF SDYYMSWIRQAPGKGLEWVSYISSSGSTI YYADSVKGRFTISRDNSKNTLYLQMNSLR AEDTAVYYCARDYGRIAAAGRHYWGQGTL VTVSS (SEQ ID NO: 8) | SSELTQDPAVSVALGQTVRITCQGDTLSTYY ANWYQQKPGQAPVLVIYGKNNRPSGIPDRFS GSSSGNTASLTITGAQAEDEADYYCHSRDIS GNYLFASGTKLTVL (SEQ ID NO: 29) |
| YS3 | QVQLQESGGGLVQPGGSLRLSCAASGFTF SSYWMSWVRQAPGKGLEWVADIKQDGSEK YYVDSVKGRFTISGDNAKNSLYLQMNSLR AEDTAVYYCAKDVGSTAINYVRAYTWFDP WGQGTLVTVSS (SEQ ID NO: 9) | QSVLTQPPSASGTPGQRVTISCSGSSSNIGS NTVNWSRQLPGTAPKLLIYSNNQRPSGVPDR FSGSKSGTSASLAISGLQSEDEADYYCAAWD DSLNVYVFGTGTKVTVL (SEQ ID NO: 30) |
| YS4 | QVQLQESGGGLVQPGGSLRLSCAASGFTF SNYAMSWVRQAPGKGLEWVSTISGSGSST FYVDSVKGRFTISRDNSKNTLYLQMNSLR AEDTAVYYCAQGLYSSGWANWFDPRGQGT LVTVSS (SEQ ID NO: 10) | KIVLTQSPSSLSASVGDTVTIACRASRDIRN DLAWYQQKPGKAPKLLIYGASSLQSGVPSRF SGSGSGTEFILTISSLQPEDFATYYCHRLNS YPLTFGGGTKVDIK (SEQ ID NO: 31) |
| YS8 | QVQLQESGGGVVQPGRSLRLSCAASGFTF SSYGMHWVRQAPGKGLEWVAVISYDGSNK YYADSVKGRFTISRDNSKNTLYLQMNSLR AEDTAVYYCAKVMGLAAAGLDAFDIWGQG TTVTVSS (SEQ ID NO: 11) | NFMLTQPASLSGSPGQSITISCTGTSSDVGG YNYVSWYQQHPGYAPKLMIYDVSNRPSGVSN RFSGSKSGNTASLTISGLQAEDEADYYCSSY TSSSTPWVFGGGTKLTVL (SEQ ID NO: 32) |

TABLE 1-continued

Novel human anti-CD46 antibody sequences. YS5 and YS5F differ by one amino acid in VH CDR1 (L vs. F). YS5 and YS5vlD have identical VH but one amino acid difference in the VL CDR2 (N vs. D). 3G7HY, 3G7NY, 3G7RY (aka 3G8), and 3G7 have one residue difference in VH CDR3, but entirely different VLs. YS6 and 3(17 have idenfical VH but different VL.

| | VH | VL |
|---|---|---|
| YS7 | QVQLVQSGGGVVQPGRSLRLSCAASGFTFSSYAMHWVRQAPGKGLEWVAVISYDGSNKYYADSVKGRFTISRDTSTNTLYLQMNSLRADDTAVYYCGRESSGSPGVWGQGTTVTVSS (SEQ ID NO: 12) | SYVLTQDPAVSVALGQTVRITCQGDSLRSYYASWYQQKPGQAPVLVIYGKNNRPSGIPDRFSGSSSGNTASLTITGAQAEDEADYYCNSRDSSGNQFGGGTKLTVL (SEQ ID NO: 33) |
| YS9 | QVQLVESGGGLIQPGGSLRLSCAASGFTVSSNYMSWVRQAPGKGLEWVSVIYTDGSTYYADSVKGRFTISRDNSKNTLYLQMNSLRAEDTAIYYCARDRGTSGYDWAWFDLWGQGTLVTVSS (SEQ ID NO: 13) | SSELTQDPAVSVALGQTVRITCQGDSLRTYYASWYQQRPGQAPILVLYGKNNRPSGIPDRFSGSSSGNTASLTITGAQAEDEADYYCNSRDSSGNHVVFGGGTKLTVL (SEQ ID NO: 34) |
| YS10 | QVQLQESGGGLVQPGGSLRLSCAASGFTFSSYAMSWVRQAPGKGLEWVSAISGSGGSTYYADSVKGRFTISRDNSKNTLYMQMNSLRAEDTAVYYCAKDRYYYGSGKDAFDIWGRGTMVTVSS (SEQ ID NO: 14) | QSVLTQPASVSGSPGQSITISCTGTGSDVGSYNYVSWYQQNPGKAPKLMIYEVSNRPSGVSNRFSGSKSGNTASLTISGLQAEDEADYYCSSYTTSSTLVFGGGTKVTVL (SEQ ID NO: 35) |
| YS11 | QVQLVESGGGLVQPGGSLGLSCAASGFTFSNYWMSWVRQAPGKGLEWVANVRQDGGQKYYVDSVKGRFTISRDNAKNSLYLQMNSLRTEDTAVYFCVSQRNSGEHDYWGQGTLVTVSS (SEQ ID NO: 15) | SELTQDPAVSVALGQTVRITCQGDSLRSYYASWYQQKPGQAPVLVIYGENSRPSGIPDRFSGSSSGNTASLTITGAQAEDEADYYCNSWDSSGNHVVFGGGTKLTVL (SEQ ID NO: 36) |
| 3G7HY | EVQLVESGGGLVQPGGSLRLSCAASGFTFSDYYMSWIRQAPGKGLEWVSYISSSGSTIYYADSVKGRFTISRDNSKNTLYLQMNSLRAEDTAVYYCARDYGRIAAAGRHYWGQGTLVTVSS (SEQ ID NO:1 6) | AIRMTQSPSSLSASVGDRVTITCRASQSISSYLNWYQQKPGKAPKLLIYAASSLQSGVPSRFSGSGSGTDFTLTISSLQPEDFATYYCQQSYSTPRTFGQGTKLEIK (SEQ ID NO: 37) |
| 3G7NY | EVQLVESGGGLVQPGGSLRLSCAASGFTFSDYYMSWIRQAPGKGLEWVSYISSSGSTIYYADSVKGRFTISRDNSKNTLYLQMNSLRAEDTAVYYCARDYGRIAAAGRNYWGQGTLVTVSS (SEQ ID NO: 17) | DIVMTQSPLSLPVTPGEPASISCRSSQSLLHSNGYDYLDWYLQKPGQSPQLLIYLGSNRASGVPDRFSGSGSGTDFTLKISRVETEDVGIYYCMQGLQTPSFGQGTKLEIK (SEQ ID NO: 38) |
| 3G7 | QVQLQESGGGVVRPGGSLRLSCAASGFTFSDYYMSWIRQAPGKGLEWVSYISSSGSTIYYADSVKGRFTISRDNSKNTLYLQMNSLRAEDTAVYYCARDYGRIAAAGRHYWGQGTLVTVSS (SEQ ID NO: 18) | SSELTQDPAVSVALGQTVRITCQGDSLRSYYASWYQQKPGQAPVPVIYGKNNRPSGIPDRFSGSSSGNTASLTITGAQAEDEADYYCNSRDSSSTHRGVFGGGTKLTVL (SEQ ID NO: 39) |
| SB2 | EVQLVESGGGLVKPGGSLRLSCAASGFTFSDYYMSWIRQAPGKGLEWVSYISSSGSSIYYADSVKGRFTISRDNAKNSLYLQMNSLKAEDTAVYYCARDITDVVGVSFDYWGQGTLVTVSS (SEQ ID NO: 19) | DIQLTQSPSSLSASVGDRVTITCRASRSISTYLSWYQQKPGKAPKLLIYDASRLQNGVPSRFSGSGSDTDFTLTISSLQPEDFATYFCQQSYNPPWTFGQGTKLEIK (SEQ ID NO: 40) |
| 2C8 | EVQLVESGGGVVQPGRSLRLSCAASGFTFSSYGMHWVRQAPGKGLEWVAVISYDGSNKYYADSVKGRFTISRDNSKNTLYLQMNSLRAEDTAEYYCAKVMGLAAAGLDAFDIWGQGTLVTVSS (SEQ ID NO: 20) | QSALTQPASVSGSPGQSITISCTGTSSDVGGYNYVSWYQQHPGKAPKLMIYDVSNRPSGVSNRFSGSKSGNTASLTISGLQAEDEAYYYCSSYTSSSDPWVFGGGTQLTVL (SEQ ID NO: 41) |
| UA8kappa | EVQLVESGGGVVQPGRSLRLSCAASGFTFSSFGMHWVRRAPGKGLEWVAVISYDGSNQYYADSVKGRFTISRDNSKNTLYLQMNSLRAEDTAVYYCGSRPGGGYASGSTVAYWGQGTLVTVSS (SEQ ID NO: 21) | NIQMTQSPSSLSASVGDRVTITCRAGQPISTYVNWYQHPGKAPKLLIYGASNLQSGVPSRFSGGGSATDFTLTISSLQPEDFATYYCQQSYSSLLTFGDGTKVEIK (SEQ ID NO: 42) |

In various embodiments the antibodies contemplated herein expressly exclude antibodies composing the three VH CDRs and/or the three VL CDRs of antibodies 3051.1, G12FC3, M6c42b, 4F3YW, M40pr146, UA20, UAB, 5851141, 5851141.1, 5851156, 3076, 3051, M49R, RCI-14, II79_4, II79_3, T5II-4B.1, T5II-4B.2, RCI-11, RCI-20, CI-11A, CI-14A, S95-2 that are described in PCT/US2008/076704 (WO 2009/039192) and/or the mPA7 antibody. The amino acid sequences of the VH and VL chains of these antibodies and the CDRs comprising these domains are shown in PCT/US2008/076704 and the amino acid sequences of these domains are reproduced below in Table 2.

TABLE 2

Excluded antibodies. The sequence shown below are scFv antibodies (the VL and VH regions are joined by a (Gly$_4$Ser)$_3$ (SEQ ID NO: 43) linker, however it will be recognized that other antibody forms comprising the CDRs (or the VH and/or VL domains) are similarly excluded.

| Clone | Amino Acid Sequence | SEQ ID No |
|---|---|---|
| 3051.1 | QVQLQESGGGLVKPGGPLRLSCAASGFTFSSYGMYWVRQAPGKGLEWV STLSRSGSGTYYADSVKGRFTISRDNSKNTLYLQMNSLRAEDTAVYYC ASIAVAGNYFDYWGQGTLVTVSSGGGGSGGGGSGGGGSSYVLTQDPAV SVALGQTVRITCQGDSLRSYYASWYQERPGQAPLLVIYGKNNRPSGIP DRFSGSNSGSTATLTISRVEAGDEGDYYCQVWDSINEQVVFGGGTKVT VL | 4 |
| G12FC3 | QVQLVQSGGGVVQPGRSLRLSCAATGIPFSGSGMHWVRQAPGKGLEWV TMIWYDGSNKFYADSVKGRFTISRDNSKNTLYLQMDSLRAEDTAVYFC ARDKGVRSMDVWGLGTTVTVSSGGGGSGGGGSGGGGSNFMLTQPPSVS VAPGQTAKITCDGYSIRTKSVHWYQQKPGQAPVVVVHDDSDRPSGIPE RFSGSNSGTTATLTISRVEAGDEADYYCQAWDSISEEVVFGGGTKLTV L | 5 |
| M6c42b | QVQLQESGGGLVQPGGSLRLSCSASGFTFGTYAMRWVRQTSGKGLEWV SGIGVSGDAYYTDSVRGRFTISRDNSKNTLYLQMNTLRAEDTATYYCT RKSSTTSNDYWGRGTLVTVSSGGGGSGGGGSGGGGSSYVLTQDPAVSV ALGQTVRITCQGDNIGSKSVHWYQQKPGQAPVLVVYDDSDRPSGIPER FSGSNSGTTATLTISSVEAGDEADYYCQAWDSISEHVIFGGGTKVTVL | 6 |
| 4F3YW | QVQLQESGGGLVQPGGSLRLSCAASGFTFSSYAMHWVRQAPGKGLEWV AVISYDGSNKYYADSVKGRFTISRDNSKNTLYLQMNSLRAEDTAVYYC ARFSSGWYYFDYWGQGTLVTVSSGGGGSGGGGSGGGGSDIQMTQSPSF LSASVGDRITITCRASHDISSYFAWYQQKPGKAPKPLIYAASTLQSGV PSRFSGSGSGTEFTLTISSLQPEDFATYYCQQLGSYPLTFGGGTKLEI K | 7 |
| M40pr146 | QVQLLQSGGGLVQPGGSLRLSCAASGFTFSSYAMSWVRQAPGKGLEWV SAISGSGGSTYYTDSVKGRFTISRDNSKNTLYLQMNSLRAEDTAVYYC AKSHDYGDYAGFDYWGQGTLVTVSSGGGGSGGGGSGGGGSHVILTQDP AVSVALGQTVRITCQGDSLKSYYASWYQQKPGQAPVLVIYGKNNRPSG IPDRFSGSSSGTTASLTITGAQAEDEADYYCHSRDSSGTHLRVFGGGT KLTVL | 8 |
| UA20 | QVQLQESGGGLVKPGGSLRLSCAASGFTFSNAWMNWVRQAPGKGLEWV GRIKSKTDEGTTDYAAPVKGRFSISRDDSKNTLYLQMNSLKTEDTGVY YCTATKGLGGSKLGQGTLVTVSSGGGGSGGGGSGGGGSQSVLTQPPSA SGTPGQRVTISCSGSSSNIGNNTVNWSRQLPGTAPKLLIYSNDQRPSG VPDRFSGSKSGTSASLAITGLQPEDEADYYCGTWDSSLSAYVFGTGTK LTVL | 9 |
| UA8 | QVQLVESGGGVVQPGRSLRLSCAASGFTFSSFGMHWVRRAPGKGLEWV AVISYDGSNQYYADSVKGRFTISRDNSKNTLYLQMNSLRAEDTAVYYC GSRPGGGYASGSTVAYWGQGTPVTVSSGGGGSGGGGSGGGGSSSELTQ DPAVSVALGQTVRITCQGDSLRSYYASWYQQKPGQAPLLVIYGQNIRP SGIPDRFSGSSSGNSASLTITGAQAEDEADYYCHSRDSSGKYVFGVGT KVTVL | 0 |
| 5851141 | QVQLVESGGGLVQPGGSLRLSCAASGFTFSSYAMGWVRQAPGKGLEWV SAISGSGGSTYYADSVKGRFTISRDNSKDTLYLQMNSLRAEDTAVYYC ASRSLLDYWGQGTLVTVSSGGGGSGGGGSGGGGSNFMLTQDPAVSVAL GQTVRITCQGDSLRSYYASWYQQKPGQAPLLVIYGKNNRPSGIPDRFS GSSSGNTASLTITGAQAEDEADYYCNSRDSSGNPVFGGGTKVTVL | 1 |
| 5851141.1 | QVQLVESGGGLVQPGGSLRLSCAASGFTFSSYAMSWVRQAPGKGLEWV SAISGSGGSTYYADSVKGRFTISRDNSKDTLYLQMNSLRAEDTAVYYC ASRSLLDYWGQGTLVTVSSGGGGSGGGGSGGGGSNFMLTQDPAVSVAL GQTVRITCQGDSLRSYYASWYQQKPGQAPLLVIYGKNNRPSGIPDRFS GSSSGNTASLTITGAQAEDEADYYCNSRDSSGNPVFGGGTKVTVL | 2 |
| 5851156 | QVQLQESGGGLVQLGGSLRLSCAASGETFSSYAMSWVRQAPGKGLEWV SAISGSGGSTYYADSVKGRFTISRDNSKNTLYLQMSSLRAEDTAFYYC ANSAYTGGWYDYWGHGTLVTVSSGGGGSGGGGSGGGGSSSELTQDPAV | 3 |

TABLE 2-continued

Excluded antibodies. The sequence shown below are scFv antibodies (the VL and VH regions are joined by a (Gly4Ser)3 (SEQ ID NO: 43) linker, however it will be recognized that other antibody forms comprising the CDRs (or the VH and/or VL domains) are similarly excluded.

| Clone | Amino Acid Sequence | SEQ ID No |
|---|---|---|
| | SVALGQTVKITCQGDSLRTYYASWYQQRPGQAPVLVIYGENSRPSGIP DRFSGSSSGNTASLTITGAQAEDEADYYCNSRDSSGNHLRVFGGGTKL TVL | |
| 3076 | QVNLRESGGGLVQPGGFLRLSCAAFGFTFSGYWMSWVHPAPGKGLEWV ANIKQDGSEKFYVDSVKGRFTISRDNAKNSLFLQMNSLRAEDTAVYFC ARGLLSDYWGQGTLVPVSSGGGGSGGGGSGGGGSNFMLTQPPSVSVAP GKTASLTCGGYNIGTKSVHWYQQKPGQAPVVVVHDDSDRPSGIPERFS GSNSGTTATLTIIRVEAGDEADYYCQAWDSISEEVVFGGGTKLTVL | 4 |
| 3051 | QVQLQESGGGLVKPGGPLRLSCAASGFTFSSYGMYWVRQAPGKGLEWV STLSRSGSGTYYAESVKGRFTISRDNSKNTLYFQMNSLRAEDTAVYYC ASIAVAGNYFEYWGQGTLVTVSSGGGGSGGGGSGGGGSSYVLTQDPAV SVALGQTVRITCQGDSLRSYYASWYQERPGQAPLLVIYGKNNRPSGIP DRFSGSNSGSTATLTISRVEAGDEGDYYCQVWDSINEQVVFGGGTKVT VL | 5 |
| M49R | QVQLQESGGGLVKPGESLRLSCAASGFTFSDHYMDWVRQAPGKGLEWV AYIRYDGSTKYYADSVKGRFTISRDNSKNTLYLQMNSLRPEDTAFYYC ARLIAEAEGWFDPWGQGTLVTVSSGGGGSGGGGSGGGGSNFMLTQPPS VSVAPGKTARITCGGNNIGSKSVYWYQQKPGQAPVLVVYDDSDRPSGI PERFSGSNSGNTATLTISRVEAGDEADYYCQVWDSSSDHVVFGGGKV TVL | 6 |
| RCI-14 | QVQLLQSAGGLVQPGGSLRLSCAASGFTFSTYAMNWVRQAPGKGLEWV SGISGSGGSTNYADSVKGRFTISRDSSKNTLFLQMNSLRAEDTAVYYC AKDYGSGWYDYWGQGTLVTVSSGGGGSGGGGSGGGGSSSELTQDPAVS VALGQTVRITCQGDSLRSYYASWYQERPGQAPLLVIYGRNERPSGIPD RFSASSSGNTASLTITGAQAEDEADYYCQVWDSFNEQVVFGGGTKLTV L | 7 |
| II79_4 | QVQLVESGGGLVQPGGSLRLSCAASGFTFSSYAMSWVHQAPGKGLEWV SAISGSGGSTYYADSVKGRFTISRDNSKNTLYLQMNSLRAEDTAVYYC AKTYYGFWSGYYDYLGQGTLVTVSSGGGGSGGGGSGGGGSSSELTQDP AVSVGLGQTVTITCQGDSLRSYYANWYQQKPGQAPILVIYGENNRPSG IPDRFSGSSSGNTASLTITGAQAEDEADYYCHSRDSSGTHLRVFGGGT KLTVL | 8 |
| II79_3 | QVQLLESGGGVVQPGTSLRLSCAASGFTFSNYAINWVRQAAGKGLEWV SGISGSGVSTSYADSVKGRFTVSRDNSKNTLYLQMNSLRVEDTALYYC AKNGGGPEYLQHWGQGTLVTVSSGGGGSGGGGSGGGGSQSVLTQPPSA SGTPGQRVTISCSGSSSNIGNNTVNWSRQLPGTAPKLLIYSNDQRPSG VPDRFSGSKSGTSASLAITGLQPEDEADYYCGTWDSSLSAYVFGTGTK LTVL | 9 |
| T5II-4B.1 | QVQLQESGGTLVQPGGSLRLSCAASGFTFSSYAMSWVRQAPGRGLEWV STISGSGGSTYYADSVKGRFTISRDNSKNTLYLQMNSLRAEDTAVYYC AKGAYSGSYWGQGTLVTVSSGGGGSGGGGSGGGGSSSELTQDPAVSVA LGQTVRITCQGDSLRSYYASWYQQKPGQAPSLVIYGENSRPSGIPDRF SGSSSGNTASLTITGAQAENEADYYCQAWDSSTAVVFGGGTKLTVL | 0 |
| T5II-4B.2 | QVQLQESGGTLVQPGGSLRLSCAASGFTFSSYAMSWVRQAPGRGLEWV STISGSGGSTYYADSVKGRFTISRDNSKNTLYLQMNSLRAEDTAVYYC AKGAYSGSHWGQGTLVTVSSGGGGSGGGGSGGGGSSSELTQDPAVSVA LGQTVRITCQGDSLRSYYASWYQQKPGQAPSLVIYGENSRPSGIPDRF SGSSSGNTASLTITGAQAENEADYYCQAWDSSTAVVFGGGTKLTVL | 1 |
| RCI-11 | QVQLVESGAEVKKPGASVKVSCKASGYTFTSYGISWVRQAPGQGLEWM GWISAYNGNTNYAQKLQGRVTMTDTSTSTAYMELRSLRSDDTAVYYC ARPIYDSSGYDAFDIWGQGTMVTVSSGGGGSGGGGSGGGGSDIVMTQS PSTLSASIGDRVTITCRASEGIYHWLAWYQQKPGKAPKLLIYKASSLA SGAPSRFSGSGSGTDFTLTISSLQPDDFATYYCQQYHTISRTFGPGTK VDIK | 2 |
| RCI-20 | QVQLVESGGGLVKPGGSLRLSCAASGFTFSSYAMHWVRQAPGKGLEWV AVISYDGSNKYYADSVKGRFTISRDNSKNTLYLQMNSLRAEDTAVYFC VRPSDSGWSFEHWGQGTLVPVSSGGGGSGGGGSGGGGSQSVLTQPPSA SGTPGQRVTISCSGSSSNIGNNTVNWSRQLPGTAPKLLIYSNDQRPSG VPDRFSGSKSGTSASLAITGLQPEDEADYYCGTWDSSLSAYVFGTGTK LTVL | 3 |

TABLE 2-continued

Excluded antibodies. The sequence shown below are scFv antibodies (the VL and VH regions are joined by a (Gly4Ser)3 (SEQ ID NO: 43) linker, however it will be recognized that other antibody forms comprising the CDRs (or the VH and/or VL domains) are similarly excluded.

| Clone | Amino Acid Sequence | SEQ ID No |
|---|---|---|
| CI-11A | QVQLQESGGGLVQPGGSLRLSCAASGFTFSSYAMSWVRQAPGKGLEWV AVISYDGSNKYYADSVKGRFTISRDNSKNTLYLQMNSLRAEDTAVYYC VRGDRSYGAEYFQHWGQGTLVTVSSGGGGSGGGGSGGGGSSELTQDP AVSVASGQTVRITCQGDSLRSYYASWYQQKPGQAPLLVIYGKNIRPSG IPDRFSGSTSGNSASLTITGAQAEDEADYYCNSRDSSGNRNWVFGGGT KLTVL | 4 |
| CI-14A | QVQLQESGGGLVKPGGSLRLSCAASGFTSSSYAMHWVRQAPGKGLEYV SAIGGNGGTYYADSVKGRFTISRDNSKNTLYLQMNSLRAEDTAVYYCA KEGEQWLEYRYYYGMDVWGQGTTVTVSSGGGGSGGGGSGGGGSSSELT QDPAVSVALGQTVRITCQGDSLRSYYASWYQQKPGQAPSLVIYGENSR PSGIPDRFSGSSSGNTASLTITGAQAENEADYYCQAWDSSTAVVFGGG TKLTVL | 5 |
| S95-2 | QVQLVESGGGVVQPGRSLRLSCTASGFTFSSYGMHWVRQAPGKGLEWV AVISYDGSNKYYADSVKGRFTISRDNSKNTLYLQMNSLRAEDTAVYYC ARGGRYSSNWFSYYYYGMDVWGQGTTVTVSSGGGGSGGGGSGGGGSNF MLTQPPSVSVAPGKTARITCGGNNIGSKSVYWYQQKPGQAPVLVVYDD SDRPSGIPERESGSNSGNTATLTISRVEAGDEADYYCQVWDSSSDHVV FGGGTKVTVL | 6 |

Using the amino acid sequences provided for the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and UA8kappa antibodies, numerous antibody forms can be prepared, e.g., as described below. Such forms include, but are not limited to a substantially intact (e.g., full length) immunoglobulin (e.g., an IgA, IgE, IgG, and the like), an antibody fragment (e.g., Fv, Fab, (Fab')$_2$, (Fab')$_3$, IgGΔCH$_2$, a minibody, and the like), a single chain antibody (e.g., scFv), a diabody, a unibody, an affibody, and the like.

It will be recognized, that where the antibodies are single chain antibodies, the VH and VL domains comprising such antibody can be joined directly together or by a peptide linker. Illustrative peptide linkers include, but are not limited to GGGGS GGGGS GGGGS (SEQ ID NO: 43), GGGGS GGGGS (SEQ ID NO: 67), GGGGS (SEQ ID NO: 68), GS GGGGS GGGGS GGS GGGGS (SEQ ID NO: 69), SGGGGS (SEQ ID NO: 70), GGGS (SEQ ID NO: 71), VPGV (SEQ ID NO: 72), VPGVG (SEQ ID NO: 73), GVPGVG (SEQ ID NO: 74), GVG VP GVG (SEQ ID NO: 75), VP GVG VP GVG (SEQ ID NO: 76), GGSSRSS (SEQ ID NO: 77), and GGSSRSSSSGGGGSGGGG (SEQ ID NO: 78), and the like.

As indicated above, in various embodiments, the antibody binds (e.g., specifically binds CD46 (e.g., domains 1 and/or 2). Typically antibodies contemplated herein will specifically bind prostate cancer cells including, but not limited to cells of a cell line selected from the group consisting of DU145 cells, PC3 cells, and LnCaP cells. In certain embodiments the antibody binds to a prostate tumor cell with an affinity greater than (K$_D$ less than) about 5 nM when measured on live prostate tumor cells by FACS. In certain embodiments the affinity is greater than (K$_D$ less than) about 1 nM, or at about 100 pM, or about 50 pM, or about 10 pM, or about 1 pM.

Using the sequence information provided herein antibodies comprising one or more of the CDRs comprising, e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and UA8kappa, or antibodies comprising the VH and/or VL domain(s) of these antibodies can readily be prepared using standard methods (e.g. chemical synthesis methods and/or recombinant expression methods) well known to those of skill in the art, e.g., as described below.

In addition, other "related" prostate cancer specific antibodies can be identified by screening for antibodies that bind to the same epitope (e.g. that compete with one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibodies for binding to CD446 and/or to a cell expressing or overexpressing CD46, e.g., a prostate cancer cell) and/or by modification of the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibodies identified herein to produce libraries of modified antibody and then rescreening antibodies in the library for improved binding to and/or internalization into cells expressing or overexpressing CD46, e.g., prostate cancer cells.

Identification of Other Antibodies Binding the Same CD46 Epitope(s) as YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa.

Having identified CD46, especially domains one and/or two as a useful antibody target and YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and UA8kappa antibodies as useful prototypical antibodies, other "related" antibodies that bind CD46 and preferably that are internalized via macropinocytosis can readily be identified by screening for antibodies that bind CD46 domains 1 and/or 2, e.g., by raising (e.g., monoclonal antibodies) that specifically bind CD46 domains 1 and/or 2. Additionally or alternatively, other antibodies that bind CD46 and that are internalized by macropinocytosis, can be identified by screening for antibodies that that cross-react with one or more of antibodies YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa, e.g., at the epitope bound by YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa, and/or for antibodies that cross-react with one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa for binding to a prostate cancer cell (e.g., CaP cells, PC3 cells, etc.), and/or with an idiotypic antibody raised against YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibody.

Monoclonal Antibodies.

Monoclonal antibodies that bind CD46 domains 1 and/or 2, preferably binding the epitope bound by one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa can be produced using a variety of known techniques, such as the standard somatic cell hybridization technique described by Kohler and Milstein (1975) Nature 256: 495, viral or oncogenic transformation of B lymphocytes or phage display technique using libraries of human antibody genes. In particular embodiments, the antibodies are fully human monoclonal antibodies.

Accordingly, in one embodiment, a hybridoma method is used for producing an antibody that binds CD46, preferably binding the domain 1 and/or domain 2 of CD46. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding (1986) Monoclonal Antibodies: Principles and Practice, pp. 59-103 (Academic Press)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Id.). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies and antibody portions that bind CD46 domains 1 and/or 2 can be isolated from antibody phage libraries generated using the techniques described in, for example, McCafferty et al. (1990) Nature, 348: 552-554, Clackson et al. (1991) Nature, 352:624-628, Marks et al. (1991) J. Mol. Biol., 222: 581-597, Hoet et al (2005) Nature Biotechnol., 23: 344-348; U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al. (1992) Bio/Technology, 10:779-783), as well as combinatorial infection and in vivo recombination as a strategy for constructing very large phage libraries (Waterhouse et al. (1993) Nucl. Acids. Res., 21: 2265-2266) may also be used.

In a particular embodiment, the monoclonal antibody or antigen binding portion thereof that binds CD46, preferably binding the epitope of bound by one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to CD46, preferably competing for binding with one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa.

In yet another embodiment, human monoclonal antibodies directed against CD46, preferably comprising the epitope bound by one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa can be generated using transgenic or transchromosomic mice carrying parts of the human immune system rather than the mouse system (see e.g., Lonberg, et al. (1994) Nature 368(6474): 856-859; Lonberg and Huszar, (1995) Intern. Rev. Immunol. 13: 65-93, Harding and Lonberg (1995) Ann. NY. Acad. Sci. 764: 536-546, and U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.).

In another embodiment, human antibodies directed against CD46 preferably binding the epitope bound by one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa can be raised using a mouse that carries human immunoglobulin sequences on transgenes and transchomosomes, such as a mouse that carries a human heavy chain transgene and a human light chain transchromosome (see e.g., PCT Publication WO 02/43478 to Ishida et al.).

Alternative transgenic animal systems expressing human immunoglobulin genes are available in the art and can be used to raise anti-CD46 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Alternative transchromosomic animal systems expressing human immunoglobulin genes are available in the art and can be used to raise anti-CD46 antibodies contemplated herein. For example, mice carrying both a human heavy chain transchromosome and a human light chain tranchromosome can be used; as described in Tomizuka et al. (2000)

*Proc. Natl. Acad. Sci. USA* 97: 722-727. Furthermore, cows carrying human heavy and light chain transchromosomes have been described in the art (see, e.g., Kuroiwa et al. (2002) *Nature Biotechnology* 20: 889-894) and can be used to raise anti-CD46 CCP1 antibodies.

In yet another embodiment, antibodies that specifically bind CD46, preferably binding the epitope bound by one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa can be prepared using a transgenic plant and/or cultured plant cells (such as, for example, tobacco, maize and duckweed) that produce such antibodies. For example, transgenic tobacco leaves expressing antibodies or antigen binding portions thereof can be used to produce such antibodies by, for example, using an inducible promoter (see, e.g., Cramer et al. (1999) *Curr. Top. Microbol. Immunol.* 240: 95-118). Also, transgenic maize can be used to express such antibodies and antigen binding portions thereof (see, e.g., Hood et al. (1999) *Adv. Exp. Med. Biol.* 464: 127-147). Antibodies can also be produced in large amounts from transgenic plant seeds including antibody portions, such as single chain antibodies (scFv's), for example, using tobacco seeds and potato tubers (see, e.g., Conrad et al. (1998) *Plant Mol. Biol.* 38: 101-109). Methods of producing antibodies or antigen binding portions in plants can also be found in, e.g., Fischer et al. (1999) *Biotechnol. Appl. Biochem.* 30: 99-108, Ma et al. (1995) *Trends Biotechnol.* 13: 522-527, Ma et al. (1995) *Plant Physiol.* 109: 341-346; Whitelam et al. (1994) *Biochem. Soc. Trans.* 22: 940-944, and U.S. Pat. Nos. 6,040,498 and 6,815,184.

The binding specificity of monoclonal antibodies or portions thereof that bind CD46, preferably comprising the preferably binding the epitope bound by one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa prepared using any technique including those disclosed here, can be determined by immunoprecipitation or by an in vitro binding assay, such as radioimmunoassay (MA) or enzyme-linked immunoabsorbent assay (ELISA). The binding affinity of a monoclonal antibody or portion thereof also can be determined by the Scatchard analysis of Munson et al. (1980) *Anal. Biochem.,* 107:220.

Cross-Reactivity with Anti-Idiotypic Antibodies.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of the antibodies identified herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa) using standard methods well known to those of skill in the art. Briefly, anti-idiotype antibodies can be made by injecting the antibodies of this invention, or fragments thereof (e.g., CDRs) into an animal thereby eliciting antisera against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine). In general, it is desirable to use a myeloma cell line which does not secrete an immunoglobulin. Several such lines are known in the art. One generally preferred cell line is P3X63Ag8.653. This cell line is on deposit at the American Type Culture Collection as CRL-1580.

Fusion can be carried out in the presence of polyethylene glycol according to established methods (see, e.g., Monoclonal Antibodies, R. Kennett, J. McKearn & K. Bechtol, eds. N.Y., Plenum Press, 1980, and *Current Topics in Microbiology & Immunology, Vol.* 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10-14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

Cross-Reactivity with the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa.

In another approach, antibodies that bind CD46 can be identified by the fact that they bind the same epitope as the "prototypic" antibodies of this invention (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa). To identify such antibodies, it s not necessary to isolate the subject epitope. In certain embodiments, one can screen, e.g. antibody libraries for antibodies that compete with the prototypic antibodies of this invention for binding and/or internalization by a prostate cancer cell (e.g. a CaP cell, a PC3 cell, etc.), and/or for binding to CD46.

Methods of screening libraries for epitope binding and/or cell binding and/or internalization are well known to those of skill in the art. In certain embodiments, cross-reactive prostate antibodies show at least 60%, preferably 80%, more preferably 90%, and most preferably at least 95% or at least 99% cross-reactivity with the one or more of the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibodies described herein.

Phage Display Methods to Select Other "Related" Anti-CD46 Antibodies.

Using the known sequences for the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa and/or other prostate specific antibodies, a variety of phage display (or yeast display) methods can be used to generate other antibodies that antibodies that specifically bind CD46, preferably binding the epitope bound by YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa, with the same or even greater affinity.

Chain Shuffling Methods.

One approach to creating antibody variants has been to replace the original $V_H$ or $V_L$ gene with a repertoire of V-genes to create new partners (chain shuffling) (Clackson et al. (1991) *Nature.* 352: 624-628) in a phage display or yeast display library. Using chain shuffling and phage display, the affinity of a human scFv antibody fragment that bound the hapten phenyloxazolone (phOx) was increased from 300 nM to 1 nM (300 fold) (Marks et al. (1992) *Bio/Technology* 10: 779-783).

Thus, for example, to alter the affinity of an anti-CD46 antibody described herein, a mutant scFv gene repertoire can be created containing a $V_H$ gene of the prototypic YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibody (e.g. as shown in FIG. 2) and a human $V_L$ gene repertoire (light chain shuffling). The scFv gene repertoire can be cloned into a phage display vector, e.g., pHEN-1 (Hoogenboom et al. (1991) *Nucleic Acids Res.,* 19: 4133-4137) or other vectors, and after transformation a library of transformants is obtained.

Similarly, for heavy chain shuffling, a mutant scFv gene repertoire can be created containing a $V_L$ gene of the prototypic YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibody (e.g. as shown in FIG. 2) and a human $V_H$ gene repertoire (heavy chain shuffling). The scFv gene repertoire can be cloned into a phage display vector, e.g., pHEN-1 (Hoogenboom et al. (1991) *Nucleic Acids Res.,* 19: 4133-4137) or other vectors, and after transformation a library of transformants is obtained.

The resulting libraries can be screened against the relevant target (e.g., CD46) and/or for cross-reactivity with YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa.

Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.,* 196: 901-917; Chothia et al. (1986) *Science,* 233: 755-8; Nhan et al. (1991) *J. Mol. Biol.,* 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.,* 234: 564-578; Wells (1990) *Biochemistry,* 29: 8509-8516). Site-directed mutagenesis of CDRs and screening against the prostate cancer cells, in particular for binding at CD46 e.g. as described herein in the examples, can produce antibodies having improved binding affinity.

CDR Randomization to Produce Higher Affinity Human scFv.

In an extension of simple site-directed mutagenesis, mutant antibody libraries can be created where partial or entire CDRs are randomized ($V_L$ CDR1 CDR2 and/or CDR3 and/or $V_H$ CDR1, CDR2 and/or CDR3). In one embodiment, each CDR is randomized in a separate library, using a known antibody (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$M (Lowman et al. (1993) *J. Mol. Biol.,* 234: 564-578).

$V_H$ CDR3 often occupies the center of the binding pocket, and thus mutations in this region are likely to result in an increase in affinity (Clackson et al. (1995) *Science,* 267: 383-386). In one embodiment, $V_H$ CDR3 residues are randomized (see, e.g., Schier et al. (1996) *Gene,* 169: 147-155; Schier and Marks (1996) *Human Antibodies and Hybridomas.* 7: 97-105, 1996; and Schier et al. (1996) *J. Mol. Biol.* 263: 551-567).

Other Antibody Modifications.

In one embodiment, partial antibody sequences derived from the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibody may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) *Nature* 332: 323-327; Jones et al., (1986) *Nature* 321: 522-525; and Queen et al. (1989) *Proc. Natl. Acad. Sci. USA*, 86: 10029-10033). Such framework sequences can be obtained from public DNA databases that include germline antibody gene sequences.

Thus, one or more structural features of an anti-CD46 antibody of the invention, such as the CDRs, can be used to create structurally related anti-CD46 antibodies that retain at least one functional property of, for example, the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibody, e.g., binding and internalizing into prostate cancer cells.

In a particular embodiment, one or more YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa CDR regions (e.g. VH CDR1, and/or CDR2, and/or CDR3, and/or VL CDR1, and/or CDR2, and/or CDR3) is combined recombinantly with known human framework regions and CDRs to create additional, recombinantly-engineered, anti-CD46 antibodies. The heavy and light chain variable framework regions can be derived from the same or different antibody sequences.

It is well known in the art that antibody heavy and light chain CDR3 domains play a particularly important role in the binding specificity/affinity of an antibody for an antigen (see, e.g., Hall et al. (1992) *J. Immunol.*, 149: 1605-1612; Polymenis et al. (1994) *J. Immunol.*, 152: 5318-5329; Jahn et al. (1995) *Immunobiol.*, 193:400-419; Klimka et al. (2000) *Brit. J. Cancer*, 83: 252-260; Beiboer et al. (2000) *J. Mol. Biol*, 296: 833-849; Rader et al. (1998) *Proc. Natl. Acad. Sci. USA*, 95: 8910-8915; Barbas et al. (1994) *J. Am. Chem. Soc.*, 116: 2161-2162; Ditzel et al. (1996) *J. Immunol.*, 157: 739-749). Accordingly, in certain embodiments, antibodies are generated that include the heavy and/or light chain CDR3s of the particular antibodies described herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa). Accordingly, in certain embodiments, antibodies are generated that include the heavy and/or light chain CDR1s of the particular antibodies described herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa). The antibodies can further include the other heavy and/or light chain CDRs of the antibodies of the present invention (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa).

In certain embodiments the CDR1, 2, and/or 3 regions of the engineered antibodies described above can comprise the exact amino acid sequence(s) as those disclosed herein (e.g., CDRs of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa). However, the ordinarily skilled artisan will appreciate that some deviation from the exact CDR sequences may be possible while still retaining the ability of the antibody to bind CD46 effectively (e.g., conservative amino acid substitutions). Accordingly, in another embodiment, the engineered antibody may be composed of one or more CDRs that are, for example, 90%, 95%, 98%, 99% or 99.5% identical to one or more CDRs of the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa antibody.

In another embodiment, one or more residues of a CDR may be altered to modify binding to achieve a more favored on-rate of binding. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to, or instead of, modifications within the CDRs, modifications can also be made within one or more of the framework regions, FR1, FR2, FR3 and FR4, of the heavy and/or the light chain variable regions of an antibody, so long as these modifications do not eliminate the binding affinity of the antibody.

In another embodiment, the antibody is further modified with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC) (see, e.g., Caron et al. (1992) *J. Exp Med.* 176: 1191-1195; Shopes (1992) *J. Immunol.* 148: 2918-2922). Homodimeric antibodies with enhanced anti-tumor activity may also be prepared using heterobifunctional cross-linkers (see, e.g., Wolff et al. (1993) *Cancer Res.* 53:2560-2565). Alternatively, an antibody can be engineered which has dual Fc regions and may thereby have enhanced complement lysis and ADCC capabilities (see, e.g., Stevenson et al. (1989) *Anti-Cancer Drug Design* 3: 219-230).

Antibody Production.

In various embodiments antibodies described herein can be produced by chemical synthesis or can be recombinantly expressed.

Chemical Synthesis.

Using the sequence information provided herein, the CD46 specific antibodies described herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, *Solid Phase Peptide Synthesis*; pp. 3-284 in *The Peptides: Analysis, Synthesis, Biology*. Vol. 2: *Special Methods in Peptide Synthesis*, Part A., Merrifield et al. (1963) *J. Am. Chem. Soc.*, 85: 2149-2156, and Stewart et al. (1984) *Solid Phase Peptide Synthesis*, 2nd *ed*. Pierce Chem. Co., Rockford, Ill.

Recombinant Expression of Prostate Cancer-Specific Antibodies.

In certain embodiments, the CD46 specific antibodies described herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa), or variants thereof, are recombinantly expressed using methods well known to those of skill in the art. For example, using the YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa sequence information provided herein, nucleic acids encoding the desired antibody can be prepared according to a number of standard methods known to those of skill in the art. The nucleic acids are transfected into host cells that then express the desired antibody or a chain thereof.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, CA (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl Acad. Sci. USA* 86: 10029-10033. In addition, detailed protocols for the expression of antibodies are also provided by Liu et al. (2004) *Cancer Res.* 64: 704-710, Poul et al. (2000) *J. Mol. Biol.* 301: 1149-1161, and the like.

Creation of Other Antibody Forms.

Using the known and/or identified sequences (e.g. $V_H$ and/or $V_L$ sequences) of the single chain antibodies provided herein other antibody forms can readily be created. Such forms include, but are not limited to multivalent antibodies, full antibodies, scFv, (scFv')$_2$, Fab, (Fab')$_2$, chimeric antibodies, and the like.

Creation of Homodimers.

For example, to create (scFv')$_2$ antibodies, two anti-CD46 antibodies are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM 3-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimer can be determined using standard methods, e.g. by BIAcore.

In one illustrative embodiment, the (scFv')$_2$ dimer is created by joining the scFv' fragments through a linker, e.g., through a peptide linker. This can be accomplished by a wide variety of means well known to those of skill in the art. For example, one approach is described by Holliger et al. (1993) *Proc. Natl. Acad. Sci. USA*, 90: 6444-6448 (see also WO 94/13804).

It is noted that using the $V_H$ and/or $V_L$ sequences provided herein Fabs and (Fab')$_2$ dimers can also readily be prepared. Fab is a light chain joined to $V_H$-$C_H$1 by a disulfide bond and can readily be created using standard methods known to those of skill in the art. The F(ab)'$_2$ can be produced by dimerizing the Fab, e.g. as described above for the (scFv')$_2$ dimer.

Chimeric Antibodies.

The antibodies contemplated herein also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851-6855, etc.).

While the prototypic antibodies provided herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa) are fully human antibodies, chimeric antibodies are contemplated, particularly when such antibodies are to be used in species other than humans (e.g., in veterinary applications). Chimeric antibodies are antibodies comprising portions from two different species (e.g. a human and non-human portion). Typically, the antigen combining region (or variable region) of a chimeric antibody is derived from a one species source and the constant region of the chimeric antibody (which confers biological effector function to the immunoglobulin) is derived from another source. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature*, 312: 643) and anti-tumor antigens (see, e.g., Sahagan et al. (1986) 1 *Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In certain embodiments, a recombinant DNA vector is used to transfect a cell line that produces an anti-CD46 (e.g., a prostate cancer specific) antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of a prostate cancer specific antibody of this invention and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification can be made to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

Intact Human Antibodies.

In another embodiment, this invention provides for intact, fully human anti-CD46 (e.g., prostate cancer specific) antibodies. Such antibodies can readily be produced in a manner analogous to making chimeric human antibodies. In this instance, instead of using a recognition function derived, e.g. from a murine, the fully human recognition function (e.g., VH and $V_L$) of the antibodies described herein is utilized.

Diabodies.

In certain embodiments, diabodies comprising one or more of the $V_H$ and $V_L$ domains described herein are contemplated. The term "diabodies" refers to antibody fragments typically having two antigen-binding sites. The fragments typically comprise a heavy chain variable domain ($V_H$) connected to a light chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Natl. Acad. Sci. USA* 90: 6444-6448.

Unibodies.

In certain embodiments using the sequence information provided herein, the anti-CD46 antibodies can be constructed as unibodies. UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule leaves only one area on the UniBody that can bind to a target. Methods of producing unibodies are described in detail in PCT Publication WO2007/059782, which is incorporated herein by reference in its entirety (see, also, Kolfschoten et al. (2007) *Science* 317: 1554-1557).

Affibodies.

In certain embodiments the sequence information provided herein is used to construct affibody molecules that bind CD46. Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) *Nat. Biotechnol.* 15: 772-777; Ronmark et al. (2002) *Eur. J. Biochem.*, 269: 2647-2655). Details of Affibodies and methods of production are known to those of skill (see, e.g., U.S. Pat. No. 5,831,012 which is incorporated herein by reference in its entirety).

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the antibody and/or immunoconjugate is to be used. In other words, for use in a human, it is desirable to use a human, humanized, or chimeric human antibody.

Measurement of Antibody/Polypeptide Binding Affinity.

As explained above, selection for increased avidity can involves measuring the affinity of the antibody for the target antigen (e.g., CD46, especially the epitope bound by one or more of YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa).

Methods of making such measurements are well known to those of skill in the art. Briefly, for example, the $K_d$ of the antibody is determined from the kinetics of binding to, e.g. the target cell in a BIAcore, a biosensor based on surface plasmon resonance. For this technique, the antigen or cell is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

Immunoconjguates Comprising YS5, YS5F, YS5vlD, SB1HGNY, YS12, 3G7RY (Aka 3G8), YS6, YS1, YS3, YS4, YS8, YS7, YS9, YS10, YS11, 3G7HY, 3G7NY, 3G7, SB2, 2C8, and/or UA8kappa or Other Anti-CD46 Antibodies.

The prototypical anti-CD46 antibodies (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa) described herein specifically bind to and are internalized by prostate cancer cells and by other CD46 positive cancer cells. The antibodies can be used alone as therapeutics (e.g., to inhibit growth and/or proliferation of a prostate cancer cell) or they can be coupled to an effector forming immunoconjugates that provide efficient and specific delivery of the effector (e.g. cytotoxins, labels, radionuclides, ligands, antibodies, drugs, liposomes, nanoparticles, viral particles, cytokines, and the like) to various cancer cells that express CD46 (e.g., isolated cells, metastatic cells, solid tumor cells, etc.).

Anti-CD46 immunoconjugates can be formed by conjugating the antibodies or antigen binding portions thereof described herein to an effector (e.g., a detectable label, another therapeutic agent, etc.). Suitable agents include, for example, a cytotoxic or cytostatic agent (e.g., a chemotherapeutic agent), a toxin (e.g. an enzymatically active toxin of bacterial, fungal, plant or animal origin, or fragments thereof), and/or a radioactive isotope (i.e., a radioconjugate).

In certain embodiments, the effector comprises a detectable label. Suitable detectable labels include, but are not limited to radio-opaque labels, nanoparticles, PET labels, MRI labels, radioactive labels, and the like. Among the radionuclides and useful in various embodiments of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing prostate cancer cells. Such detection/visualization can be useful in various contexts including, but not limited to pre-operative and intraoperative settings. Thus, in certain embodiment this invention relates to a method of intraoperatively detecting and prostate cancers in the body of a mammal. These methods typically involve administering to the mammal a composition comprising, in a quantity sufficient for detection by a detector (e.g. a gamma detecting probe), an prostate cancer specific antibody labeled with a detectable label (e.g. antibodies of this invention labeled with a radio-isotope, e.g. $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g. by using a gamma detecting probe.

In certain embodiments the label-bound antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place. In certain embodiments such methods are particularly useful in localizing and removing secondary cancers produced by metastatic cells from a primary tumor.

In addition to detectable labels, certain preferred effectors include, but are not limited to cytotoxins (e.g. *Pseudomonas* exotoxin, ricin, abrin, Diphtheria toxin, and the like), or cytotoxic drugs or prodrugs, in which case the chimeric molecule may act as a potent cell-killing agent specifically targeting the cytotoxin to prostate cancer cells.

In still other embodiments, the effector can include a liposome encapsulating a drug (e.g. an anti-cancer drug such as abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antigen that stimulates recognition of the bound cell by components of the immune system, an antibody that specifically binds immune system components and directs them to the prostate cancer, and the like.

Illustrative Effectors.
Imaging Compositions.

In certain embodiments, the anti-CD46 immunoconjugates can be used to direct detectable labels to a tumor site. This can facilitate tumor detection and/or localization. It can be effective for detecting primary tumors, or, in certain embodiments, secondary tumors produced by, e.g., prostate metastatic cells. In certain embodiments, the effector component of the immunoconjugate comprises a "radio-opaque" label, e.g. a label that can be easily visualized using x-rays. Radio-opaque materials are well known to those of skill in the art. The most common radio-opaque materials include iodide, bromide or barium salts. Other radiopaque materials are also known and include, but are not limited to, organic bismuth derivatives (see, e.g., U.S. Pat. No. 5,939,045), radio-opaque polyurethanes (see, e.g., U.S. Pat. No. 5,346, 981), organobismuth composites (see, e.g., U.S. Pat. No. 5,256,334), radio-opaque barium polymer complexes (see, e.g., U.S. Pat. No. 4,866,132), and the like.

The anti-CD46 antibodies described herein can be coupled directly to the radio-opaque moiety or they can be attached to a "package" (e.g., a chelate, a liposome, a polymer microbead, a nanoparticle, etc.) carrying, containing, or comprising the radio-opaque material, e.g., as described below.

In addition to radio-opaque labels, other labels are also suitable for use. Detectable labels suitable for use in immunoconjugates include any composition detectable by spectroscopic, photochemical, biochemical, immunochemical, electrical, optical or chemical means. Useful labels in the include magnetic beads (e.g., DYNABEADS™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads, nanoparticles, quantum dots, and the like.

In certain embodiments, suitable radiolabels include, but are not limited to, $^{99}$Tc, $^{203}$Pb, $^{67}$Ga, $^{68}$Ga, $^{72}$As, $^{111}$In, $^{113m}$In, $^{97}$Ru, $^{62}$Cu, 641Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{1535}$m, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, certain radiolabels may be detected using photographic film, scintillation detectors, PET imaging, MRI, and the like. Fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Radiosensitizers.

In another embodiment, the effector can comprise a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

Alpha Emitters.

In certain embodiments, the effector can include an alpha emitter, i.e. a radioactive isotope that emits alpha particles. Alpha-emitters have recently been shown to be effective in the treatment of cancer (see, e.g., McDevitt et al. (2001) *Science* 294:1537-1540; Ballangrud et al. (2001) *Cancer Res.* 61: 2008-2014; Borchardt et al. (2003) *Cancer Res.* 63: 5084-50). Suitable alpha emitters include, but are not limited to Bi, $^{213}$Bi, $^{211}$At, and the like.

Chelates

Many of the pharmaceuticals and/or radiolabels described herein can be provided as a chelate. The chelating molecule is typically coupled to a molecule (e.g. biotin, avidin, streptavidin, etc.) that specifically binds an epitope tag attached to an anti-CD46 antibody (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa) described herein.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N''',N''''-tetra-acetic acid (DOTA), hydroxyethyldiamine triacetic acid (HEDTA), 1,4,8,11-tetra-azacyclotetradecane-N,N',N'',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N, N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

In certain embodiments the chelating agent can be coupled, directly or through a linker, to an epitope tag or to a moiety that binds an epitope tag. Conjugates of DOTA and biotin have been described (see, e.g., Su (1995) *J. Nucl. Med.*, 36 (5 Suppl):154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239-244 discloses a synthesis of macrocylic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

Cytotoxins/Cytostatic Agents.

The anti-CD46 antibodies described herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa) can be used to deliver a variety of cytotoxic and/or cytostatic drugs including therapeutic drugs, a compound emitting radiation, cytotoxic molecules of plant, fungal, or bacterial origin, biological proteins, and mixtures thereof. In certain embodiments the cytotoxic drugs can comprise intracellularly acting cytotoxic drugs that are, e.g., small organic molecules, cytotoxic proteins or peptides, radiation emitters, including, for example, short-range, high-energy α-emitters as described above, and the like.

Accordingly, in certain embodiments, the anti-CD46 antibody is attached to a cytotoxic/cytostatic drug. In various embodiments the drugs being used to construct ADCs include, but are not limited to microtubule inhibitors and DNA-damaging agents, polymerase inhibitors (e.g., the polymerase II inhibitor, α-amanitin), and the like. In certain embodiments the antibody is conjugated to the drug directly or through a linker, while in other embodiments, the antibody is conjugated to a drug carrier (e.g., a liposome containing the drug, a polymeric drug carrier, a nanoparticle drug carrier, a lipid drug carrier, a dendrimeric drug carrier, and the like).

In certain embodiments the drug comprises a tubulin inhibitor, including, but not limited to auristatin, Dolastatin-10, synthetic derivatives of the natural product Dolastatin-10, and maytansine or a maytansine derivative.

In certain embodiments the drug comprises an auristatin. In certain embodiments the auristatin is selected from the group consisting of: Auristatin E (AE), Monomethylauristatin E (MMAE), Monomethylauristatin F (MMAF), vcM-MAE, and vcMMAF.

In certain embodiments the drug comprises a maytansine. Illustrative maytansines include, but are not limited to, Mertansine (DM1); and an analogue of maytansine such as DM3 or DM4.

In certain embodiments the drug comprises a DNA interacting agent. In certain embodiments the DNA interacting agent includes, but is not limited to calicheamicins, duocarmycins, pyrrolobenzodiazepines (PBDs), and the like.

In one illustrative, but non-limiting embodiment, the drug comprises a calicheamicin. Calicheamicins target DNA and cause strand scission. In certain embodiments the drug comprises calicheamicin or a calicheamicin analog. Calicheamicin analogs are described in U.S. Pat. No. 5,264,586, which is incorporated herein by reference for the calicheamicin analogs described therein.

In another illustrative, but non-limiting embodiment, the drug comprises a duocarmycin. Duocarmycins are DNA damaging agents able to exert their mode of action at any phase in the cellular cycle. Agents that are part of this class of duocarmycins typically have potency in the low picomolar range. Illustrative duocarmyhcins (e.g., duocarmycin analogues) that can be used as effectors in the chimeric constructs contemplated herein include, but are not limited to duocarmycin A, duocarmycin B1, duocarmycin B2, duocarmycin C1, duocarmycin C2, duocarmycin D, duocarmycin SA, Cyclopropylbenzoindole duocarmycin (CC-1065), Centanamycin, Rachelmycin, Adozelesin, Bizelesin, Carzelesin, and the like.

In another illustrative, but non-limiting embodiment, the drug comprises a pyrrolobenzodiazepine. In certain embodiments the drug comprises a synthetic derivative of two pyrrolobenzodiazepines linked by a flexible polymethylene tether. Pyrrolobenzodiazepines (PBDs) and PBD dimers are described in U.S. Pat. No. 7,528,126 B2, which is incorporated herein by reference for the Pyrrolobenzodiazepines and PBD dimers described therein. In certain embodiments the pyrrolobenzodiazepine is selected from the group consisting of: Anthramycin (and dimers thereof), Mazethramycin (and dimers thereof), Tomaymycin (and dimers thereof), Prothracarcin (and dimers thereof), Chicamycin (and dimers thereof), Neothramycin A (and dimers thereof), Neothramycin B (and dimers thereof), DC-81 (and dimers thereof), Sibiromycin (and dimers thereof), Porothramycin A (and dimers thereof), Porothramycin B (and dimers thereof), Sibanomycin (and dimers thereof), Abbeymycin (and dimers thereof), SG2000, and SG2285.

In certain embodiments the drug comprise a polymerase inhibitor, including, but not limited to polymerase II inhibitors such as α-amanitin, and poly(ADP-ribose) polymerase (PARP) inhibitors. Illustrative PARP inhibitors include, but are not limited to Iniparib (BSI 201), Talazoparib (BMN-673), Olaparib (AZD-2281), Olaparib, Rucaparib (AG014699, PF-01367338), Veliparib (ABT-888), CEP 9722, MK 4827, BGB-290, 3-aminobenzamide, and the like.

In certain embodiments the cytotoxic/cytostatic agent comprises a protein or peptide toxin or fragment thereof. Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, enomycin, and the tricothecenes, for example. A variety of radionuclides are available for the production of radioconjugated antibodies. Examples include, but are not limited to $^{212}$Bi, $^{131}$I, $^{131}$In, $^{90}$Y, $^{186}$Re, and the like.

In certain embodiments the cytotoxins can include, but are not limited to *Pseudomonas* exotoxins, Diphtheria toxins, ricin, abrin and derivatives thereof. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

In certain embodiments the antibody is attached to a preferred molecule in which domain Ia (amino acids 1 through 252) is deleted and amino acids 365 to 380 have been deleted from domain Ib. In certain embodiments all of domain Ib and a portion of domain II (amino acids 350 to 394) can be deleted, particularly if the deleted sequences are replaced with a linking peptide.

In addition, the PE and other cytotoxic proteins can be further modified using site-directed mutagenesis or other techniques known in the art, to alter the molecule for a particular desired application. For example, means to alter the PE molecule in a manner that does not substantially affect the functional advantages provided by the PE molecules described here can also be used and such resulting molecules are intended to be covered herein.

Methods of cloning genes encoding PE fused to various ligands are well known to those of skill in the art (see, e.g., Siegall et al. (1989) *FASEB* 1, 3: 2647-2652; and Chaudhary et al. (1987) *Proc. Natl. Acad. Sci. USA*, 84: 4538-4542).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science,* 175: 901-903; Uchida et al. (1973) *J. Biol. Chem.,* 248: 3838-3844).

In certain embodiments, the antibody-Diphtheria toxin immunoconjugates of this invention have the native receptor-binding domain removed by truncation of the Diphtheria toxin B chain. One illustrative modified Dipththeria toxin is DT388, a DT in which the carboxyl terminal sequence beginning at residue 389 is removed (see, e.g., Chaudhary et al. (1991) *Bioch. Biophys. Res. Comm.*, 180: 545-551). Like the PE chimeric cytotoxins, the DT molecules can be chemically conjugated to the prostate cancer specific antibody, but, in certain preferred embodiments, the antibody will be fused to the Diphtheria toxin by recombinant means (see, e.g., Williams et al. (1990) *J. Biol. Chem.* 265: 11885-11889).

Viral Particles.

In certain embodiments, the effector comprises a viral particle (e.g., a filamentous phage, an adeno-associated virus (AAV), a lentivirus, and the like). The antibody can be conjugated to the viral particle and/or can be expressed on the surface of the viral particle (e.g. a filamentous phage). The viral particle can additionally include a nucleic acid that is to be delivered to the target (e.g., prostate cancer) cell. The use of viral particles to deliver nucleic acids to cells is described in detail in WO 99/55720, U.S. Pat. Nos. 6,670, 188, 6,642,051, and 6,669,936.

Other Therapeutic Moieties.

Other suitable effector molecules include pharmacological agents or encapsulation systems containing various pharmacological agents. Thus, in various embodiments, it is recognized that the targeting molecule (e.g., the targeting antibody) can be attached directly or through a linker to a drug that is to be delivered directly to the tumor.

Such drugs are well known to those of skill in the art and include, but are not limited to, anti-cancer antibodies (e.g., HERCEPTIN®), antimetabolites, alkylating agents, topoisomerase inhibitors, microtubule targeting agents, kinase inhibitors, protein synthesis inhibitors, somatostatin analogs, glucocorticoids, aromatase inhibitors, mTOR inhibitors, protein Kinase B (PKB) inhibitors, phosphatidylinositol, 3-Kinase (PI3K) Inhibitors, cyclin dependent kinase inhibitors, anti-TRAIL molecules, MEK inhibitors, and the like. In certain embodiments the anti-cancer compounds include, but are not limited to flourouracil (5-FU), capecitabine/XELODA, 5-Trifluoromethyl-2'-deoxyuridine, methotrexate sodium, raltitrexed/Tomudex, pemetrexed/Alimta®, cytosine Arabinoside (Cytarabine, Ara-C)/Thioguanine, 6-mercaptopurine (Mercaptopurine, 6-MP), azathioprine/Azasan, 6-thioguanine (6-TG)/Purinethol (TEVA), pentostatin/Nipent, fludarabine phosphate/Fludara®, cladribine (2-CdA, 2-chlorodeoxyadenosine)/Leustatin, floxuridine (5-fluoro-2)/FUDR (Hospira, Inc.), ribonucleotide Reductase Inhibitor (RNR), cyclophosphamide/Cytoxan (BMS), neosar, ifosfamide/Mitoxana, thiotepa, BCNU 1,3-bis(2-chloroethyl)-1-nitrosourea, 1,-(2-chloroethyl)-3-cyclohexyl-lnitrosourea, methyl CCNU, hexamethylmelamine, busulfan/Myleran, procarbazine HCL/Matulane, dacarbazine (DTIC), chlorambucil/Leukaran melphalan/Alkeran, cisplatin (Cisplatinum, CDDP)/Platinol, carboplatin/Paraplatin, oxaliplatin/Eloxitan, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin HCL/Doxil, daunorubicin citrate/Daunoxome mitoxantrone HCL/Novantrone, actinomycin D, etoposide/Vepesid, topotecan HCL/Hycamtin, teniposide (VM-26), irinotecan HCL (CPT-11), camptosar camptothecin, Belotecan, rubitecan, vincristine, vinblastine sulfate, vinorelbine tartrate, vindesine sulphate, paclitaxel/Taxol, docetaxel/Taxotere, nanoparticle paclitaxel, abraxane, ixabepilone, larotaxel, ortataxel, tesetaxel, vinflunine, and the like. In certain embodiments the anti-cancer drug(s) comprise one or more drugs selected from the group consisting of carboplatin (e.g., PARAPLATIN®), Cisplatin (e.g., PLATINOL®, PLATINOL-AQ®), Cyclophosphamide (e.g., CYTOXAN®, NEOSAR®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafinib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an anti-sense molecule, an SiRNA, and the like.

Alternatively, the effector molecule can comprise an encapsulation system, such as a viral capsid, a liposome, or micelle that contains a therapeutic composition such as a drug, a nucleic acid (e.g. an antisense nucleic acid or another nucleic acid to be delivered to the cell), or another therapeutic moiety that is preferably shielded from direct exposure to the circulatory system. Means of preparing liposomes attached to antibodies are well known to those of skill in the art (see, e.g., U.S. Pat. No. 4,957,735, Connor et al. (1985) *Pharm. Ther.*, 28: 341-365, and the like).

B) Attachment of the Antibody to the Effector.

One of skill will appreciate that the anti-CD46 antibodies described herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa) and the effector molecule(s) can be joined together in any order. Thus, where antibody is a single chain polypeptide, the effector molecule can be joined to either the amino or carboxy termini of the targeting molecule. The antibody can also be joined to an internal region of the effector molecule, or conversely, the effector molecule can be joined to an internal location of the antibody, as long as the attachment does not interfere with the respective activities of the molecules.

The antibody and the effector can be attached by any of a number of means well known to those of skill in the art. Typically the effector is conjugated, either directly or through a linker (spacer), to the antibody. However, in certain embodiments, where both the effector molecule is or comprises a polypeptide it is preferable to recombinantly express the chimeric molecule as a single-chain fusion protein.

Conjugation of the Effector Molecule to the Antibody.

In one embodiment, the CD46 specific antibody is chemically conjugated to the effector molecule (e.g., a cytotoxin, a label, a ligand, a drug, a liposome, etc.). Means of chemically conjugating molecules are well known to those of skill.

The procedure for attaching an effector to an antibody will vary according to the chemical structure of the effector and/or antibody. Polypeptides typically contain variety of functional groups; e.g., carboxylic acid (COOH) or free amine (—NH$_2$) groups, that are available for reaction with a suitable functional group on an effector molecule to bind the effector thereto.

Alternatively, the antibody and/or the effector can be derivatized to expose or attach additional reactive functional groups. The derivatization can involve attachment of any of a number of linker molecules such as those available from Pierce Chemical Company, Rockford Illinois.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino or carboxyl groups of the terminal amino acids.

The immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an illustrative, but non-limiting, chelating agent for conjugation of, e.g., a radionucleotide to the antibody (see, e.g., WO1994/011026 (PCT/US1993/010953)).

In certain embodiments conjugation of effectors (e.g., drugs, liposomes, etc.), or linkers attached to effectors, to an antibody takes place at solvent accessible reactive amino acids such as lysines or cysteines that can be derived from the reduction of inter-chain disulfide bonds in the antibody. In certain embodiments cysteine conjugation can occur after reduction of four inter-chain disulfide bonds.

In certain embodiments site-specific conjugation, in which a known number of linker-drugs are consistently conjugated to defined sites in the antibody can be performed to produce a highly homogenous construct. Drug-to-antibody ratio (DAR) can precisely controlled and can be tailored to various linker-drugs, producing, for example, either 2- or 4-DAR site-specific ADCs.

A number of methods are known to achieve sites-specific conjugation. For example, the amino acid cysteine contains a reactive thiol group that serves essential roles in the structure and function of many proteins. Conjugation of thio-reactive probes to proteins through cysteine residues has long been a method for protein labeling, and it has also been applied to the generation of antibody drug conjugates (ADCs). In certain illustrative, but non-limiting embodiments, this process involves partial reduction of existing disulfide bonds (e.g., interchain disulfide bonds).

In certain embodiments to maintain disulfide bonds, cysteine residues can be engineered into proteins. The success of using introduced cysteine residues for site-specific conjugation relies on the ability to select proper sites in which cysteine-substitution does not alter protein structure or function. To accomplish this, the Phage Elisa for Selection of Reactive Thiols (PHESELECTOR) was developed by introducing reactive cysteine residues into an antibody-Fab (trastuzumab-Fab 4D5) at various sites, displaying the Fab on phage, and screening to identify reactive cysteines that do not interfere with antigen binding (see, e.g., Junutula et al. (2008) J. Immunol. Meth. 332: 41-52).

The PHESELECTOR approach has been demonstrated to be efficient and specific, especially compared with conventional cysteine conjugation. It has been demonstrated that the optimal sites for cysteine found using, e.g., an antibody fragment (e.g., Fab) and the PHESELECTOR method can also be applied to full-length antibodies, and data indicate that these sites work well for site-specific conjugation to other mAbs (see, e.g., Boswell et al. (2011) Bioconjug. Chem. 22: 1994-2004; Boswell et al. (2012) Soc. Nuclear Med. 53: 1454-1461; Shen et al. (2012) Nat. Biotechnol. 30:184-189).

Another illustrative, but non-limiting strategy for site-specific conjugation centers on the insertion of amino acids with bio-orthogonal reactive handles such as the amino acid selenocysteine and the unnatural amino acid, acetylphenylalanine (pAcPhe). Two methods have been developed to employ these amino acids and both utilize stop codons. However, one method incorporates selenocysteine (Sec) by pairing the opal stop codon, UGA, with a Sec insertion sequence and the other method incorporates acetylphenylalanine at the amber stop codon, UAG, using a tRNA/aminoacyltRNA synthetase pair. Selenocysteine, employed by the first method, is very similar to the amino acid, cysteine, but contains a selenium atom in place of the sulfur atom. The selenolate group is a more reactive nucleophile than the thiolate counterpart, rendering it amenable to conjugation with electrophilic compounds under conditions in which selenocysteine is selectively activated. There are approximately 25 known selenium-containing proteins in mammals, including proteins such as glutathione peroxidases and thioreductases (Kryukov et al. 92003) Science, 300: 1439-1443). Under normal conditions, UGA codes for transcriptional termination; however, in the presence of a Sec insertion sequence (SECIS) located in the 3' UTR of Sec containing proteins, termination is prevented by the formation of an mRNA secondary structure and Sec is inserted at the UGA codon (Caban and Copeland (2006) Cell Mol. Life Sci. 63: 73-81). Sec insertion can be engineered into non-Sec coding genes by insertion of the UGA codon and a SECIS at the 3' end of the gene. This technique has been used, inter alia, in the Sec labeling and subsequent site-specific conjugation of mAbs (see, e.g., Hofer et al. (2009) Biochem. 48: 12047-12057).

Still another illustrative method for site-specific conjugation utilizes the unnatural amino acid, p-acetylphenylalanine (pAcPhe). pAcPhe contains a keto group that can be selectively conjugated to a drug containing an alkoxy-amine through an oxime ligation. To incorporate pAcPhe into an antibody, the amber stop codon is substituted into the antibody at the desired location. The antibody cDNA is then co-expressed with an amber suppressor tRNA and the properly paired mutant tRNA sythetase. The tRNA sythetase loads pAcPhe onto the amber tRNA and thus pAcPhe is incorporated into the antibody at the amber site UAG (see, e.g., Liu et al. 92007) Nat. Meth. 4: 239-244; Wang et al. (2003) Proc. Natl. Acad. Sci. USA, 100: 56-61; Axup (2012) Proc. Natl. Acad. Sci. USA, 109: 16101-16116).

In addition to pAcPhe, other unnatural amino acids are exploited for use in site-specific conjugation using similar processes involving matching tRNA/aminoacyl-tRNA synthetase pairs (see, e.g., Young (2002) *J. Mol. Biol.* 395: 361-374; Kiick et al. (2002) *Proc. Natl. Acad. Sci. USA*, 99: 19-24).

In various embodiments the use of enzymes to catalyze bond formation can be exploited for use in site-specific conjugation. For example, the glycotransferase platform uses a mutant glycotransferase to attach a chemically active sugar moiety to a glycosylation site on an antibody. Molecules of choice can then be conjugated to the chemical handle on the sugar moiety. In another illustrative, but non-limiting approach transglutaminase is used to form a bond between an amine group on the linker/drug and an engineered glutamine residue on the antibody.

Glycotransferases are a large family of proteins involved in the synthesis of oligosaccharides and are responsible for the transfer of a sugar residue from an activated sugar nucleotide to a sugar acceptor or glycoprotein/lipid. The structures of several glycotransferases are known and reveal that sugar donor specificity is determined by a few amino acids in the catalytic pocket (Qasba et al. (2005) *Trends Biochem. Sci.* 30: 53-62), Using this knowledge, residues have been mutated in the pocket of the glycotransferase, e.g., B4Gal-T1, to broaden donor specificity and allow the transfer of the chemically reactive sugar residue, 2-keto-Gal (see, e.g., Ramakrishnan et al. (2002) *J. Biol. Chem.* 277: 20833-20839). This technology allows for the ability to transfer a chemically reactive sugar to any lipid or protein containing a glycosylation site. Human IgG antibodies contain an N-glycosylation site at the conserved Asn-297 of the Fc fragment. The glycans attached to this site are generally complex, but can be degalactosylated down to G0, onto which a mutant glycotransferase is capable of transferring C2-keto-Gal with high efficiency (see, e.g., Boeggeman et al. (2009) *Bioconjug. Chem.* 20: 1228-1236). The active chemical handle of C2-keto Gal can then be coupled to biomolecules with an orthogonal reactive group. This approach has been used successfully for the site-specific conjugation of the anti-Her2 antibody, trastuzumab, with Alexa Fluor 488 aminooxyacetamide and is a viable technique for sitespecific ADC generation (Id.).

The second platform utilizes transglutaminase to catalyze the formation of a covalent bond between a free amine group and a glutamine side chain. Transglutaminase from *Streptoverticillium mobaraense* (mTG) is commercially available and has been used extensively as a protein crosslinking agent (see, e.g., Yokoyama et al. (2004) *Appl. Microbiol. Biotechnol.* 64: 447-454). mTG does not recognize any of the natural occurring glutamine residues in the Fc region of glycosylated antibodies, but does recognize a "glutamine tag" that can be engineered into an antibody (see, e.g., Jeger et al. (2010) *Angew Chem. Int. Ed. Engl.* 49: 9995-9997). By way of illustration, the glutamine tag, LLQG, has been engineered into different sites in the constant domain of an antibody targeting the epidermal growth factor receptor. mTG was then used to conjugate these sites with fluorophores or monomethyl dolastatin 10 (MMAD) and several sites where found to have good biophysical properties and a high degree of conjugation. mTG was also able to conjugate to glutamine tags on anti-Her2 and anti-M1S1 antibodies. An antiM1S1-vc-MMAD conjugate displayed strong in vitro and in vivo activity, suggesting that conjugation using this method does not alter antibody binding or affinity and demonstrates the utility of this approach in the site-specific conjugation of ADCs (see, e.g., Strop et al. (2013) *Chem. Biol.* 20: 161-167).

In addition to glycotransferases and transglutaminases, other enzymes have been explored for use in protein labeling (Sunbul and Yin (2009) *Org. Biomol. Chem.* 7: 3361-3371). One such enzyme, formylglycine generating enzyme, recognizes the sequence CxPxR and oxidizes a cysteine residue to form formylglycine, thus generating a protein with an aldehyde tag. The aldehyde group can then be conjugated to molecule of choice through, e.g., hydrozino-Pictet-Spengler chemistry.'

Many other procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982), Waldmann (1991) *Science*, 252: 1657, U.S. Pat. Nos. 4,545,985 and 4,894,443.

In some circumstances, it is desirable to free the effector from the antibody when the immunoconjugate has reached its target site. Therefore, immunoconjugates comprising linkages that are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. Illustrative cleavable linkers include, but are not limited to, acid-labile linkers, protease cleavable linkers, disulfide linkers, and the like. Acid-labile linkers are designed to be stable at pH levels encountered in the blood, but become unstable and degrade when the low pH environment in lysosomes is encountered. Protease-cleavable linkers are also designed to be stable in blood/plasma, but rapidly release free drug inside lysosomes in cancer cells upon cleavage by lysosomal enzymes. They take advantage of the high levels of protease activity inside lysosomes and typically include a peptide sequence that is recognized and cleaved by these proteases, e.g., as occurs with a dipeptide Val-Cit linkage that is rapidly hydrolyzed by cathepsins. Disulfide linkers exploit the high level of intracellular reduced glutathione to release free drug inside the cell.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Conjugation of Chelates.

In certain embodiments, the effector comprises a chelate that is attached to an antibody or to an epitope tag. The anti-CD46 antibody bears a corresponding epitope tag or antibody so that simple contacting of the antibody to the chelate results in attachment of the antibody with the effector. The combining step can be performed before the moiety is used (targeting strategy) or the target tissue can be bound to the antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

Production of Fusion Proteins.

Where the antibody and/or the effector is relatively short (e.g., less than about 50 amino acids) they can be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part A*, Merrifield, et al. *J. Am. Chem. Soc.*, 85: 2149-2156 (1963), and Stewart et al., *Solid Phase Peptide Synthesis,* 2nd ed. Pierce Chem. Co., Rockford, Ill. (1984).

In certain embodiments, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention can be prepared by any suitable method, including, for example, cloning and restriction of appropriate sequences, or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, in certain embodiments subsequences can be cloned and the appropriate subsequences cleaved using appropriate restriction enzymes. The fragments can then be ligated to produce the desired DNA sequence.

In certain embodiments DNA encoding fusion proteins of the present invention can be cloned using PCR cloning methods.

While the antibody and the effector are, in certain embodiments, essentially joined directly together, one of skill will appreciate that the molecules can be separated by a spacer, e.g., a peptide spacer consisting of one or more amino acids (e.g., $(Gly_4Ser)_3$, SEQ ID NO:80). Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.,* 268: 14065-14070; Kreitman and Pastan (1993) *Bioconjug. Chem.,* 4: 581-585; and Buchner, et al. (1992) *Anal. Biochem.,* 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Pharmaceutical Compositions.

The anti-CD46 antibodies described herein (e.g., YS5, YS5F, YS5vlD, SB1HGNY, YS12, 3G7RY (aka 3G8), YS6, YS1, YS3, YS4, YS8, YS7, YS9, YS10, YS11, 3G7HY, 3G7NY, 3G7, SB2, 2C8, and/or UA8kappa) and/or immunoconjugates thereof are useful for parenteral, topical, oral, or local administration (e.g. injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the antibodies described herein and/or immunoconjugates thereof and pharmaceutical compositions comprising antibodies described herein and/or immunoconjugates thereof, when administered orally, are preferably protected from digestion. This can be accomplished by a number of means known to those of skill in the art, e.g., by complexing the protein with a composition to render it resistant to acidic and enzymatic hydrolysis or by packaging the protein in an appropriately resistant carrier such as a liposome. Means of protecting proteins from digestion are well known in the art.

In various embodiments a composition, e.g., a pharmaceutical composition, containing one or a combination of anti-CD46 antibodies, or antigen-binding portion(s) thereof, or immunoconjugates thereof, formulated together with a pharmaceutically acceptable carrier are provided.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, may be coated in a material to protect the compound from the action of acids and other natural conditions that may inactivate the compound.

In certain embodiments the antibody and/or immunoconjugate can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) Advanced Organic Chemistry; *Reactions, Mechanisms and Structure,* 4th Ed. N.Y. Wiley-Interscience, and as described above.

By way of illustration, a pharmaceutically acceptable salt can be prepared for any of the antibodies and/or immunoconjugates described herein having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the antibody and/or immunoconjugate. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

Pharmaceutical compositions comprising the antibodies and/or immunoconjugates described herein can be administered alone or in combination therapy, i.e., combined with other agents. For example, the combination therapy can include a an antibody or immunoconjugate with at least one or more additional therapeutic agents, such as the anticancer agents described infra. The pharmaceutical compositions can also be administered in conjunction with radiation therapy and/or surgery.

A composition comprising the antibodies and/or immunoconjugates described herein can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson, ed., Marcel Dekker, Inc., New York, 1978).

In certain embodiments administration of an anti-CD46 antibody or immunoconjugate may be facilitated by coating the antibody or immunoconjugate composition, or co-administering the antibody or immunoconjugate, a material to prevent its inactivation. For example, the compound may be administered to a subject in an appropriate carrier, for example, liposomes, or a diluent. Pharmaceutically acceptable diluents include, but are not limited to, saline and aqueous buffer solutions. Liposomes include, but are not limited to, water-in-oil-in-water CGF emulsions as well as conventional liposomes (Strej an et al. (1984) *J. Neuroimmunol,* 7: 27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of is contemplated. Supplementary active compounds can also be incorporated into the compositions.

In various embodiments the therapeutic compositions are typically sterile and stable under the conditions of manufacture and storage. The composition(s) can be formulated as a solution, a microemulsion, in a lipid or liposome, or other ordered structure suitable to contain high drug concentration(s). In certain embodiments the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound (e.g., antibodies and/or immunoconjugates described herein) in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, illustrative methods of preparation include vacuum drying, and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, in certain embodiments, the antibodies and/or immunoconjugates described herein may be administered once or twice daily, or once or twice weekly, or once or twice monthly by subcutaneous injection.

It is especially advantageous to formulate parenteral compositions in unit dosage form for ease of administration and uniformity of dosage. Unit dosage form as used herein refers to physically discrete units suited as unitary dosages for the subjects to be treated. Each unit contains a predetermined quantity of active compound calculated to produce the desired therapeutic effect in association with the required pharmaceutical carrier. The specifications for the unit dosage forms are dictated by and directly dependent on (a) the unique characteristics of the active compound and the particular therapeutic effect to be achieved, and (b) the limitations inherent in the art of compounding such an active compound for the treatment of individuals.

In certain embodiments the formulation comprises a pharmaceutically acceptable anti-oxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the antibodies and/or immunoconjugates described herein include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient that can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of antibodies and/or immunoconjugates described herein that are suitable for vaginal administration also include pessaries, tampons, creams, gels, pastes, foams or spray formulations containing such carriers as are known in the art to be appropriate. Dosage forms for the topical or transdermal administration of antibodies and/or immunoconjugates described herein include powders, sprays, ointments, pastes, creams, lotions, gels, solutions, patches and inhalants. In certain embodiments the active compound may be mixed under sterile conditions with a pharmaceutically acceptable carrier, and with any preservatives, buffers, or propellants that may be required.

The phrases "parenteral administration" and "administered parenterally" as used herein means modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection, and infusion.

Examples of suitable aqueous and nonaqueous carriers that may be employed in the pharmaceutical compositions comprising antibodies and/or immunoconjugates described herein include, but are not limited to water, ethanol, polyols (such as glycerol, propylene glycol, polyethylene glycol, and the like), and suitable mixtures thereof, vegetable oils, such as olive oil, and injectable organic esters, such as ethyl oleate, and the like. Proper fluidity can be maintained, for example, by the use of coating materials, such as lecithin, by the maintenance of the required particle size in the case of dispersions, and by the use of surfactants.

In various embodiments these compositions may also contain adjuvants such as preservatives, wetting agents, emulsifying agents and dispersing agents. Particular examples of adjuvants that are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes that contain a membrane-bound hemagglutinin and neuraminidase derived from the influenza virus).

Prevention of presence of microorganisms in formulations may be ensured both by sterilization procedures, and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

When the antibodies and/or immunoconjugates described herein are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the antibodies and/or immunoconjugates described herein, that may be used in a suitable hydrated form, and/or the pharmaceutical compositions, are formulated into pharmaceutically acceptable dosage forms by conventional methods known to those of skill in the art.

Actual dosage levels of the active ingredients (e.g., antibodies and/or immunoconjugates described herein) in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of antibodies and/or immunoconjugates described herein will be that amount of the compound which is the lowest dose effective to produce a therapeutic effect. Such an effective dose will generally depend upon the factors described above. In certain embodiments, it is preferred that administration be intravenous, intramuscular, intraperitoneal, or subcutaneous, preferably administered proximal to the site of the target. If desired, the effective daily dose of a therapeutic composition may be administered a single dosage, or as two, three, four, five, six or more sub-doses administered separately at appropriate intervals throughout the day, optionally, in unit dosage forms. While it is possible for antibodies and/or immunoconjugates described herein to be administered alone, it is typically preferable to administer the compound(s) as a pharmaceutical formulation (composition).

In certain embodiments the therapeutic compositions can be administered with medical devices known in the art. For example, in a illustrative embodiment, antibodies and/or immunoconjugates described herein can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of useful well-known implants and modules are described for example in U.S. Pat. No. 4,487,603, which discloses an implantable micro-infusion pump for dispensing medication at a controlled rate, in U.S. Pat. No. 4,486,194, which discloses a therapeutic device for administering medications through the skin, in U.S. Pat. No. 4,447,233, which discloses a medication infusion pump for delivering medication at a precise infusion rate, in U.S. Pat. No. 4,447,224, which discloses a variable flow implantable infusion apparatus for continuous drug delivery, in U.S. Pat. No. 4,439,196, which discloses an osmotic drug delivery system having multi-chamber compartments, and in U.S. Pat. No. 4,475,196, which discloses an osmotic drug delivery system. Many other such implants, delivery systems, and modules are known to those skilled in the art.

In certain embodiments, the anti-CD46 antibodies and/or immunoconjugates described herein can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade (1989) *J. Clin. Pharmacol.* 29: 685). Illustrative targeting moieties include, but are not limited to folate or biotin (see, e.g., U.S. Pat. No. 5,416,016); mannosides (Umezawa et al., (1988) *Biochem. Biophys. Res. Commun.* 153: 1038); antibodies (Bloeman et al. (1995) *FEBS Lett.* 357:140; Owais et al. (1995) *Antimicrob. Agents Chemother.* 39:180); surfactant protein A receptor (Briscoe et al. (1995) *Am. J. Physiol.* 1233:134).

Kits.

Where a radioactive, or other, effector is used as a diagnostic and/or therapeutic agent, it is frequently impossible to put the ready-for-use composition at the disposal of the user, because of the often poor shelf life of the radiolabeled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

In certain embodiments, such a kit comprises one or more antibodies or immumoconjugates described herein. The antibodies or immunoconjugates can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide, defined sub (ii) above, which solution has a limited shelf life, may be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the immunoconjugate can simply be produced by combining the components in a neutral medium and causing them to react. For that purpose the effector may be presented to the antibody, for example, in the form of a chelate.

When kit constituent(s) are used as component(s) for pharmaceutical administration (e.g. as an injection liquid) they are preferably sterile. When the constituent(s) are provided in a dry state, the user should preferably use a sterile physiological saline solution as a solvent. If desired, the constituent(s) may be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Novel Anti-CD46 Antibodies and Uses Thereof

To identify novel anti-human CD46 antibodies, a recombinant Fc fusion protein composed of the Sushi domain 1 and 2 of human CD46 was created. As complement elements bind predominantly to domain 3 and 4, the choice of domain 1 and 2 minimize selection of antibodies that could potently interfere with normal complement function. This CD46-Fc fusion was produced and purified from transfected HEK293 cells by protein A affinity chromatography. For human antibody selection, a $5 \times 10^9$ member phagemid display library was created using cDNAs pooled from peripheral blood mononuclear cells of 426 healthy human donors, and the library was selected the recombinant CD46-Fc fusion protein. Following three rounds of selection, binding phagemid were screened by FACS and sequenced. In parallel, an alternatively strategy was employed that involve first selecting the library on live tumor cells followed by transferring the output from round 1 phagemid selection into a yeast surface display vector, and then FACS-based selection using low concentration ligands to enrich high affinity binders to the recombinant CD46-Fc fusion protein. The resulting antibodies bind with high affinity to both live tumor cells and the recombinant human CD46 protein. All binding clones were sequenced and unique sequences are listed in Table 1.

Figure 3:
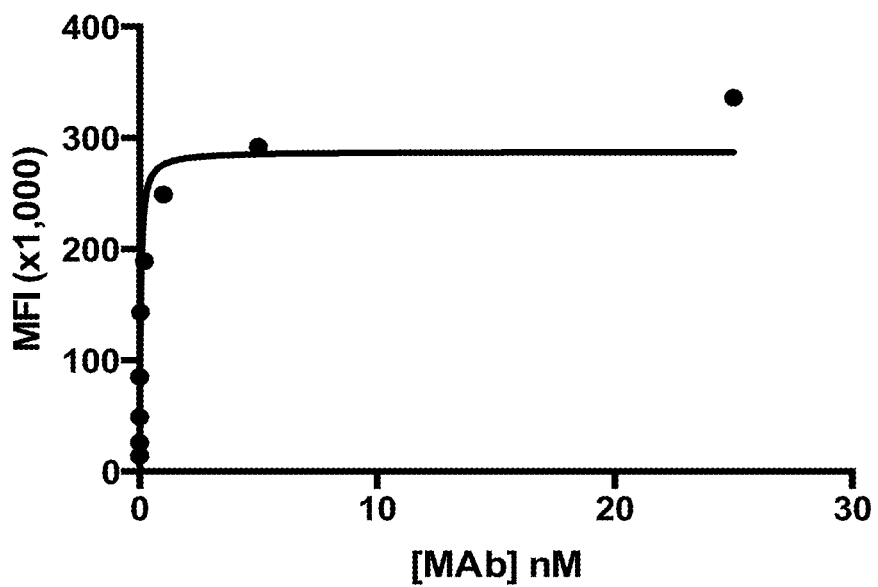
FIG. 3. YS12 IgG1 $K_D$ measurement on Du-145 cells. YS12 was incubated with Du-145 cells at 4° C. overnight and binding analyzed by FACS. MFI values were curve-fit using Prism (GraphPad) to generate an estimated KD value of 0.043+/−0.019 nM.

The scFvs were converted into full human IgG1s and binding affinities were measured on live tumor cells. FACS binding data were curved fit to generate KD values (FIG. 2 for YS5 on Du-145, and FIG. 3 for YS12 on Du-145). Affinities range from low to sub-nanomolar (nM) for the antibodies studied.

Figure 4:
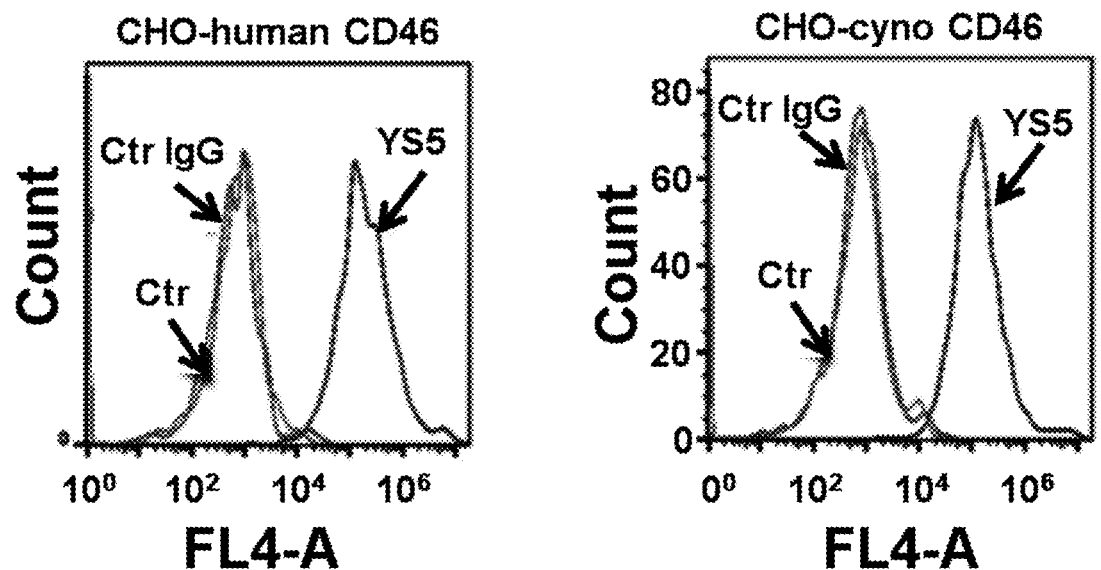
FIG. 4. Our anti-CD46 antibodies bind to both human and cynomolgus monkey CD46. FACS analysis were performed on CHO cells transfected with either human (left panel) and cyno monkey CD46 (right panel). The result for YS5 is shown but all our antibodies bind to both human and cynomolgus CD46. Ctr IgG: a non-binding human IgG1. Ctr: CHO stained with secondary antibodies only.
Figure 5:
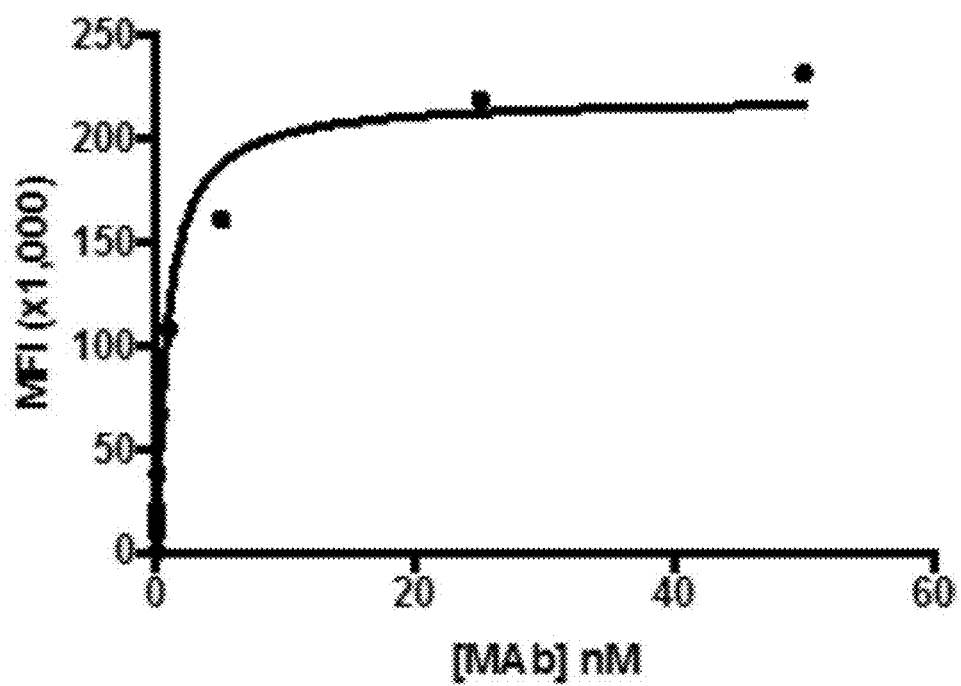
FIG. 5. YS5 $K_D$ measurement on CHO cells transfected with human CD46. YS5 was incubated with CHO-huCD46 cells at 4° C. overnight and binding analyzed by FACS. MFI values were curve-fit using Prism (GraphPad) to generate an estimated $K_D$ value of 0.867+/−0.299 nM.
Figure 6:
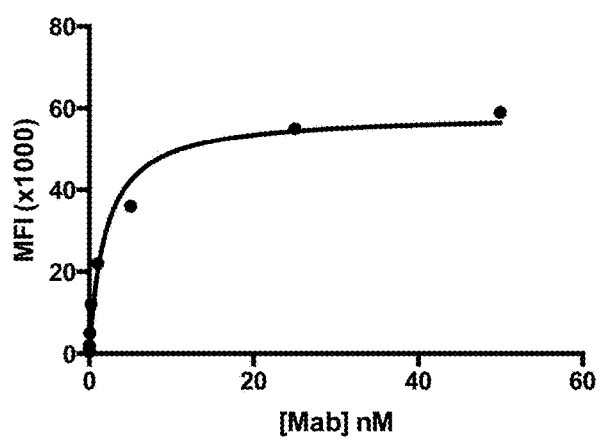
FIG. 6. YS5 $K_D$ measurement on CHO cells transfected with cynomolgus monkey CD46. YS5 was incubated with CHO-cynoCD46 cells at 4° C. overnight and binding analyzed by FACS. MFI values were curve-fit using Prism (GraphPad) to generate an estimated KD value of 1.952+/−0.508 nM.

In addition to human CD46, the antibodies described herein bind to the cynomolgus monkey CD46 (FIG. 4) with similar affinities (FIG. 5 for YS5 on CHO-huCD46 and FIG. 6 YS5 on CHO-cynoCD46), thus identifying an appropriate species for regulatory toxicology studies.

Figure 7:
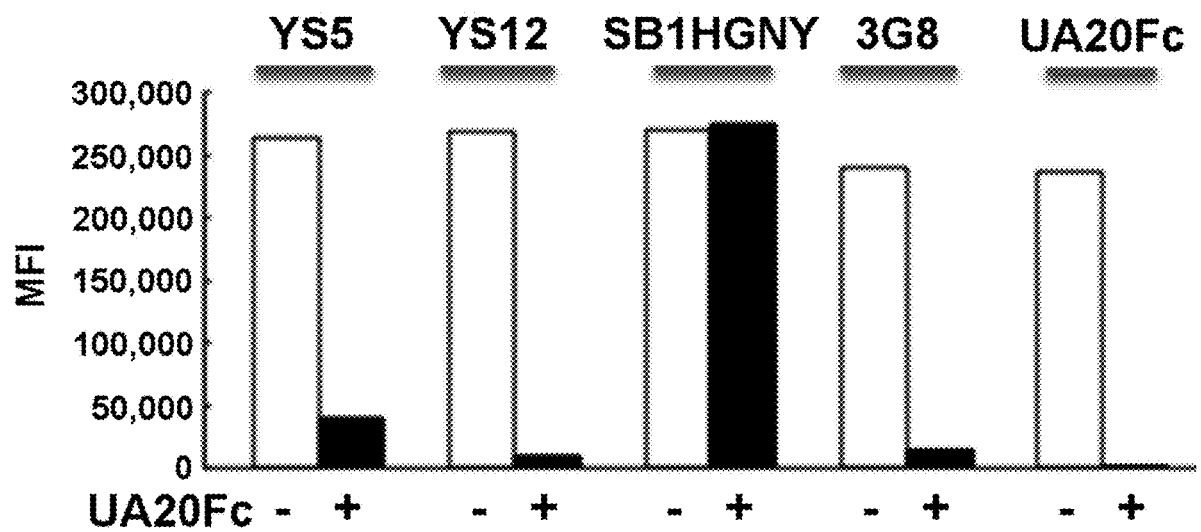
FIG. 7. Epitope mapping by competition assay. FACS binding on Du145 cells with or without UA20Fc as a competitor. UA20Fc vs. UA20Fc serves as a control for complete competition. YS5, YS12 and 3G8 (i.e., 3G7 aka 3G8) showed a different competition pattern than that of SB1HGNY, thus defining two groups with non-overlapping epitopes.
Figure 8:
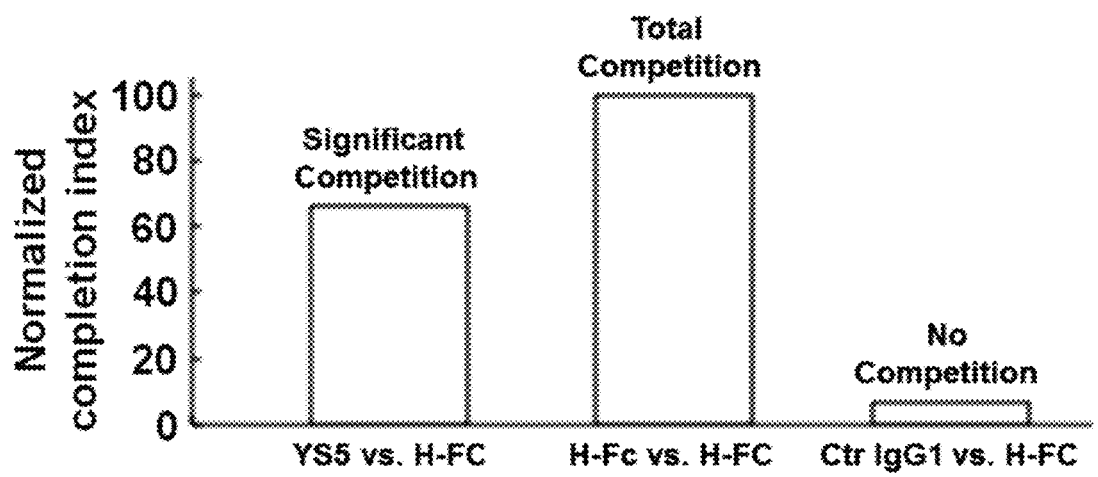
FIG. 8. Competition with Edmonston strain measles virus H protein. Antibody binding to Du-145 cells in the presence or absence of excess recombinant H protein-Fc fusion was measured by FACS. H protein-Fc vs. H protein-Fc was done as a positive control (total competition), against which the MFI values were normalized to generate the normalized competition index. A non-CD46 binding, Du-145 cell binding antibody was used as a negative control (lack of competition).
Figure 9:
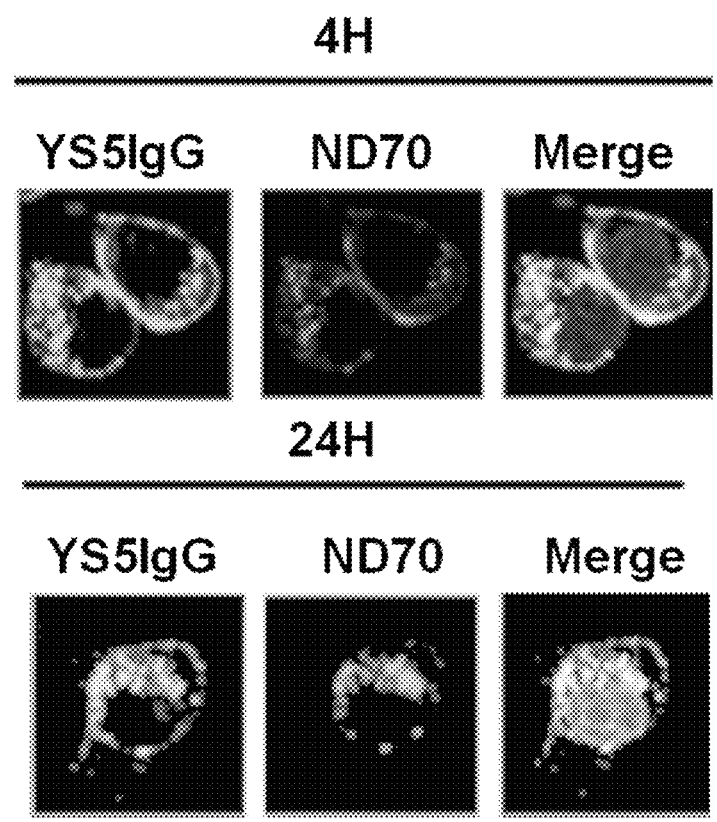
FIG. 9. Internalization by macropinocytosis. YS5 IgG1 was incubated with metastatic castration resistant prostate cancer cell line Du-145 along with the macropinocytosis indicator ND70-TRITC (Life Technologies) for 4 h and 24 h respectively. Co-localization was analyzed by an Olympus fluorescence confocal microscopy.
Figure 11:
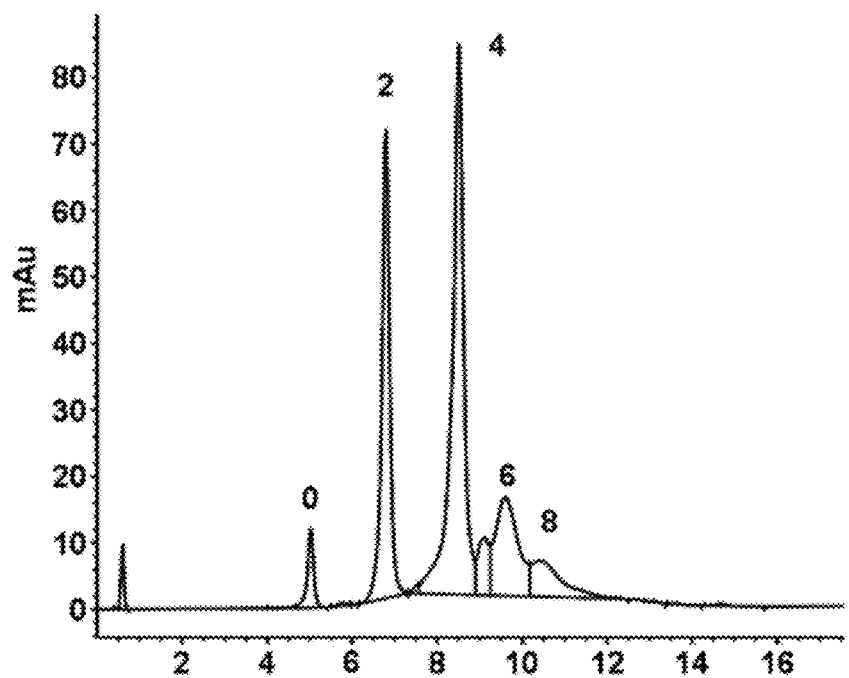
FIG. 11. HPLC analysis of anti-CD46 antibody drug conjugates. YS5 IgG1 was conjugated to monomethyl auristatin (MMAF) via the mc-vc-pab linker and analyzed by HIC. The number above peaks indicate the number of drug molecules. On average, about three drug molecules were conjugated to an IgG molecule.
Figure 12:
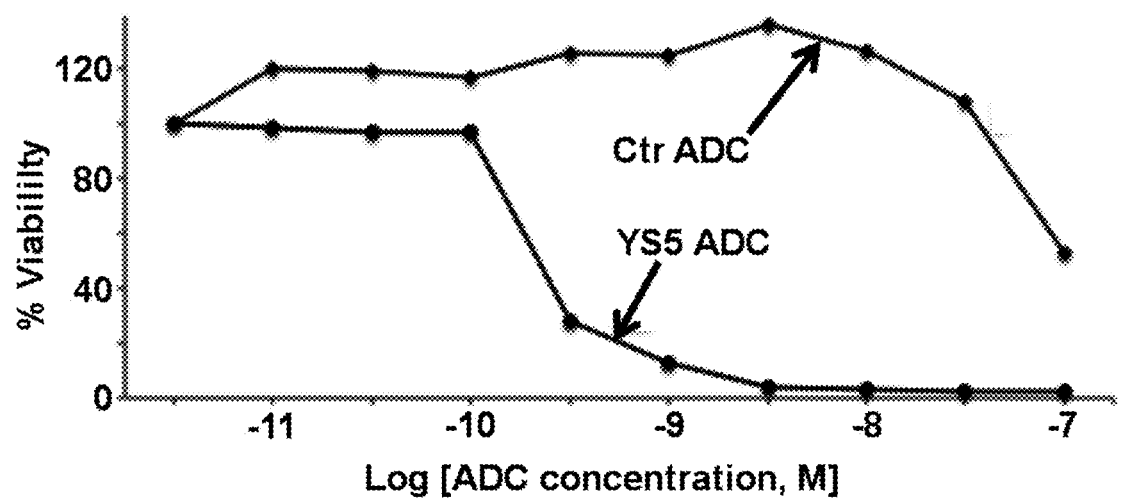
FIG. 12. Kill curve for prostate cancer cell lines LNCaP-C4-2b.
Figure 13:
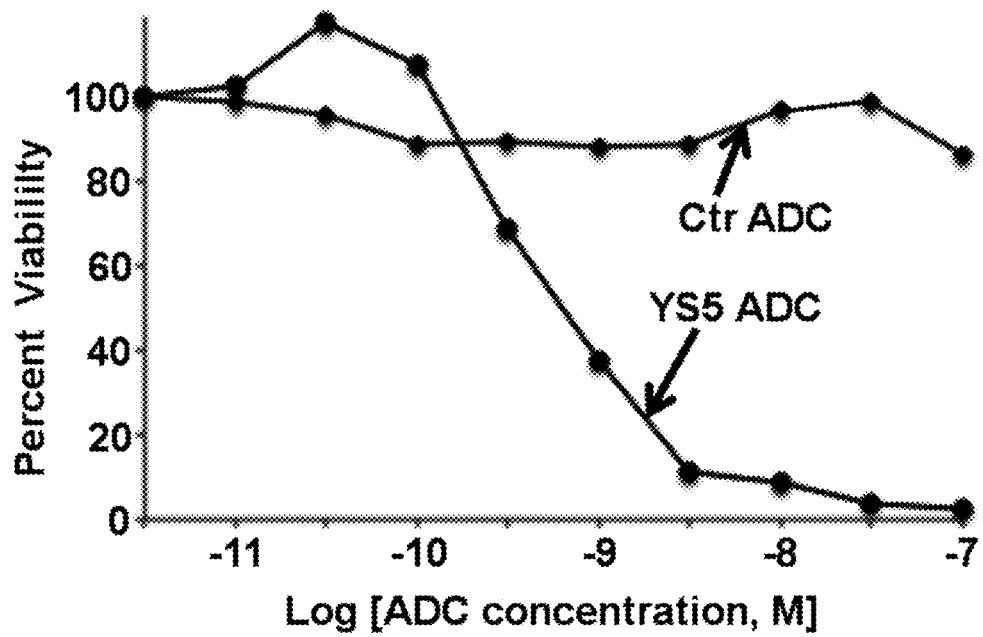
FIG. 13. Kill curve of anti-CD46 ADC (YS5) on metastatic castration resistant prostate cancer cell line Du-145.
Figure 14:
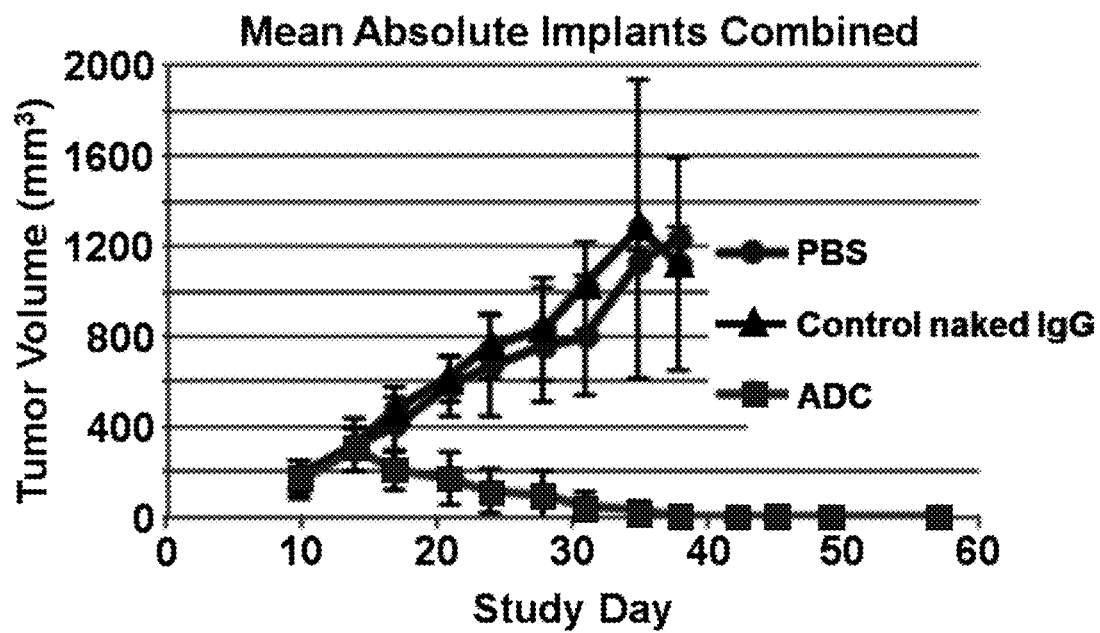
FIG. 14. In vivo tumor killing by anti-CD46 (YS5) ADC using subcutaneous prostate cancer xenograft models. LNCaP-C4-2B cells were implanted subcutaneously in SCID mice. Injection started at day-12 at 5 mg/kg ADC and four injections were administered (every 4-5 days). Mice in the anti-CD46 ADC group are being monitored for extended period post-treatment. N=6.
Figure 15:
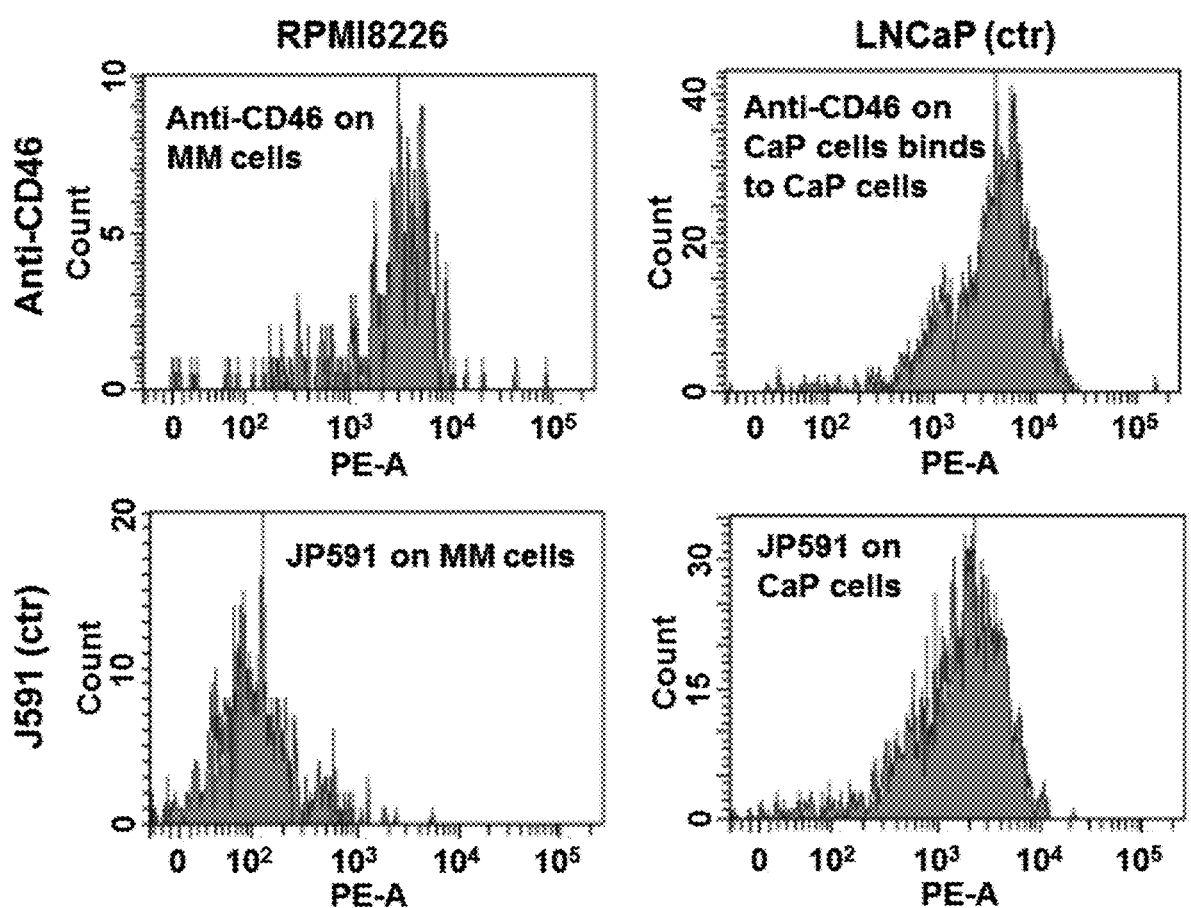
FIG. 15. CD46 is highly expressed on multiple myeloma cell line RPMI8226. Anti-CD46 antibody binds to both prostate cancer (LNCaP) and multiple myeloma cells while the anti-PSMA antibody J591 binds only to prostate cancer cells.
Figure 16:
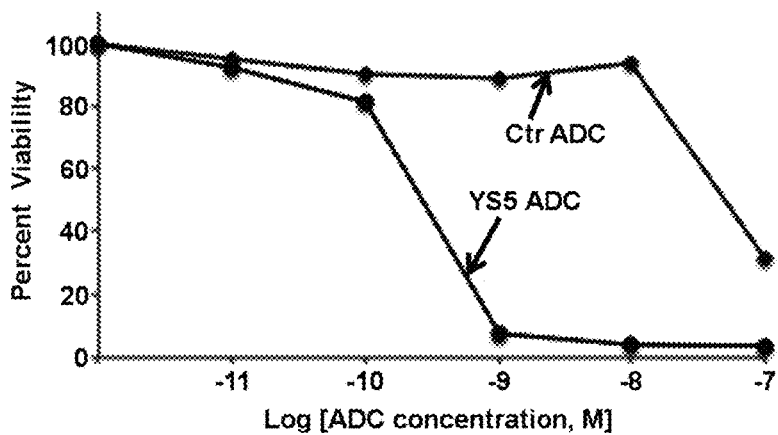
FIG. 16. Anti-CD46 ADC (YS5) kills RPMI8226 cells in vitro. Ctr ADC: a non-binding human IgG1 conjugated to MMAF.
Figure 17:
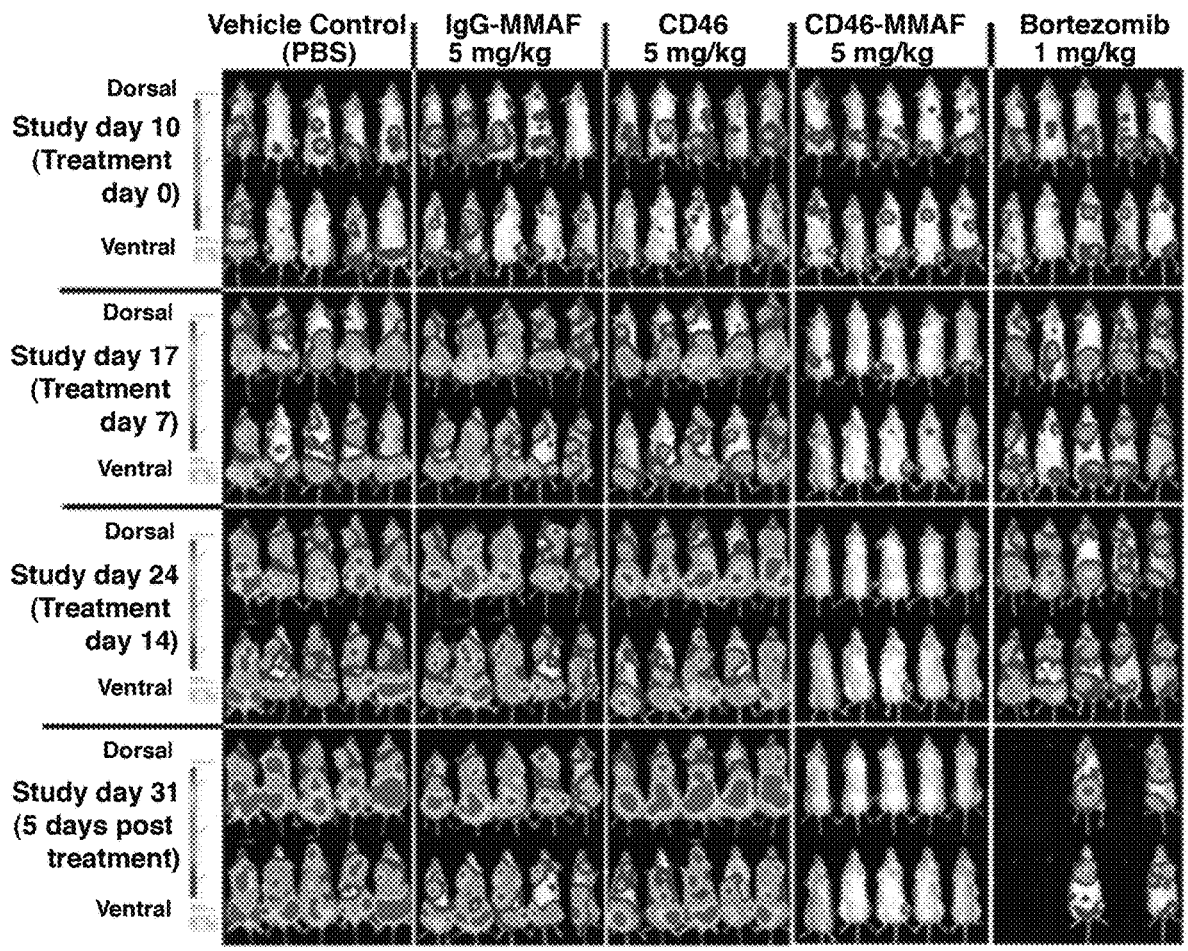
FIG. 17. In vivo anti-CD46 (YS5) ADC activity. RPMI8226-Luc cells were i.v. injected to NSG mice to create disseminated tumor xenograft. CD46-MMAF: YS5 ADC; IgG-MMAF: control ADC. A total of 4 injections were given every 4 days. Treatment started on day 10. Three mice in bortezomib-treated group did not last to day 31.
Figure 18:
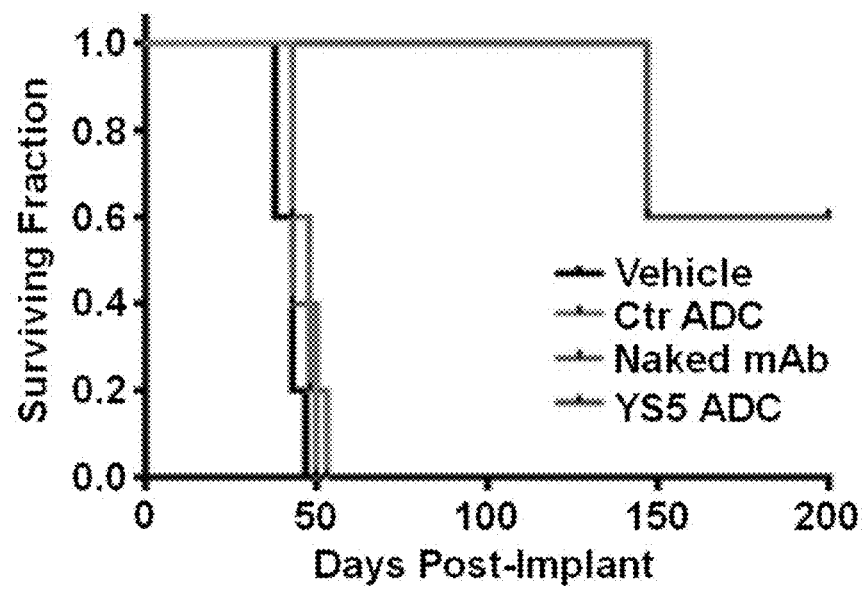
FIG. 18. Kaplan-Meier analysis of survival data for mice carrying RPMI8226 xenograft post YS5 ADC treatment.

All of the anti-CD46 antibodies, along with the previously identified UA20 and 2B10, bind to CD46 Sushi domains 1 and 2. This region was further analyzed to reveal epitope differences. We first performed FACS-based competition experiments on live tumor cells and found that our antibodies either compete or do not compete with UA20-Fc: Group 1 consists of YS5 and others, and Group 1 consists of SB1HGNY (FIG. 7). For antibodies in Group 1, there are additional epitope differences as evidenced by selective effect of antibody binding to various CD46 mutants (Table 3). For example, YS5 differs from other antibodies as mutation in position 39 uniquely affects its binding (Table 3), suggesting that the position 39, along with the position 40 that impacts binding for all antibodies, is part of the epitope for YS5 binding to CD46.

TABLE 3

Figure 20:
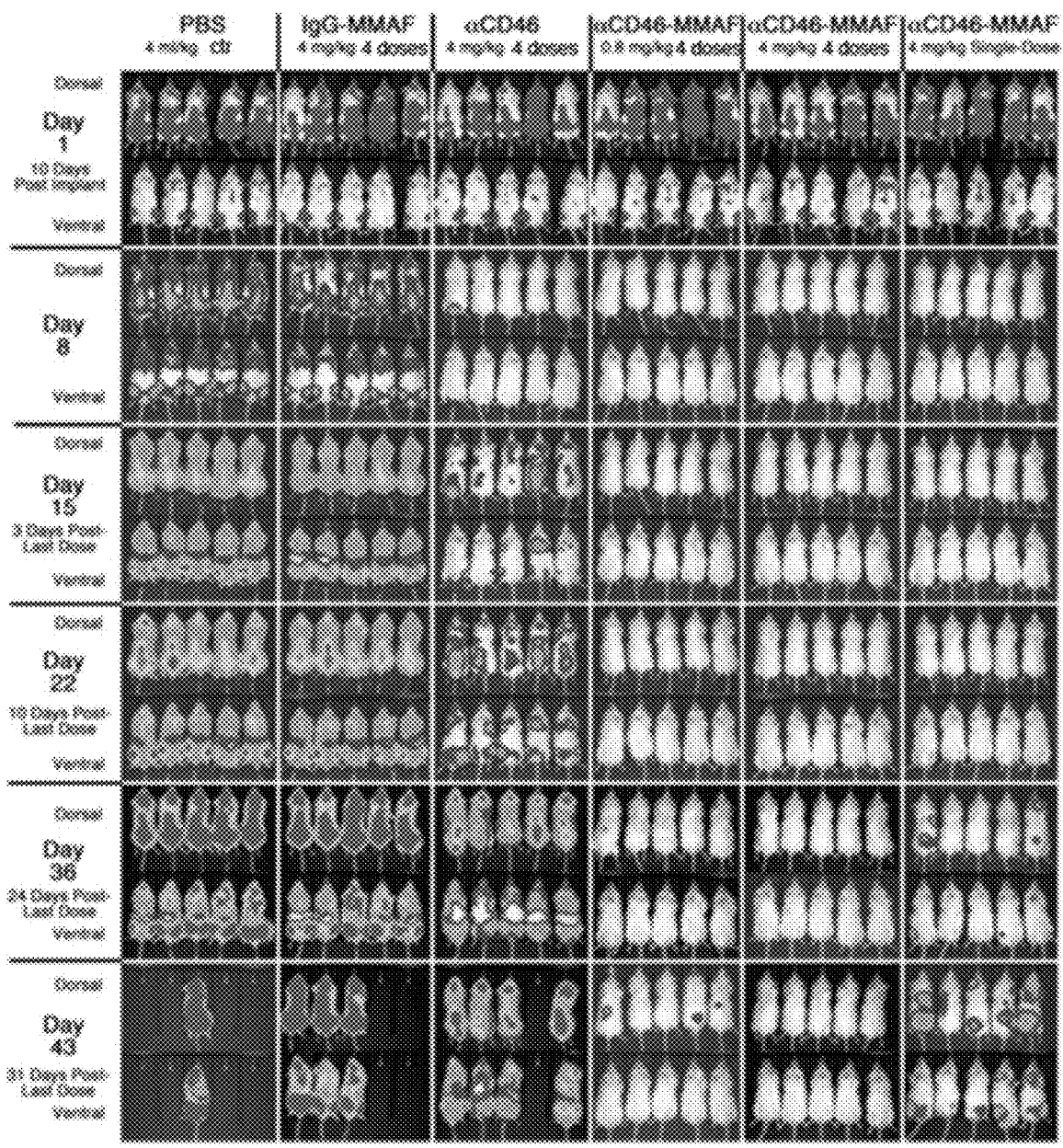
FIG. 20. Anti-CD46 ADC (YS5) on MM1S xenograft.

Alanine scan reveals epitope differences. CD46 residue changes are as indicated (top row, E13A, position 13 changed from E to A, etc). Binding to CHO cells transfected with various mutant constructed were quantified by FACS with MFI normalized against wild type CD46-transfected cells. A significant loss of binding is shown. R40A reduced binding for all antibodies, indicating that position 40 is a critical contact site for all. D39A uniquely affects YS5 binding, indicating the position 39 is a unique contact site that contributes to YS5 (and YS6) binding but not other antibodies listed in the table. YS6 differs from YS5 as it is selectively affected by position 31 mutation (P31A).

| | E13A | E16A | P31A | T36A | D39A | R40A |
|---|---|---|---|---|---|---|
| YS5 | 120 | 124 | 111 | 104 | 76 | 56 |
| YS12 | 96 | 157 | 89 | 88 | 121 | 77 |
| UA20FC | 133 | 123 | 113 | 136 | 120 | 73 |
| 3G8 | 212 | 132 | 117 | 83 | 129 | 70 |
| YS6 | 90 | 96 | 57 | 111 | 81 | 65 |
| 2B10 | 81 | 113 | 86 | 104 | 107 | 76 |

All the antibodies compete with the laboratory strain (Edmonston) measles virus H protein. Measles virus enters target cells by macropinocytosis (Crimeen-Irwin et al. (2003) *J. Biol. Chem.* 278: 46927-46937). The H protein is responsive for binding and crosslinking cell surface CD46, which is required for viral entry (Id.). To determine if our antibodies compete with H protein binding to CD46, a recombinant H protein-Fc fusion was created, and tested by FACS for competition with the anti-CD46 antibodies. It was found that the antibodies tested compete with H protein (FIG. 8), suggesting overlapping binding sites.

As measles virus enters target cells through macropinocytosis, it was next determined if the anti-CD46 antibodies are also internalized by tumor cells via maicropinocytosis. Using a 70 kDa neutral density dextran (ND70) as an indicator for macropinocytosis (Ha et al. (2014) *Mol. Cell Proteomics.* 13(12): 3320-3331), it was found that the anti-CD46 antibodies are indeed internalized by the macropinocytosis pathway (FIG. 9). Macropinocytosis is inherently tumor selective (Commisso et al. (2013) *Nature,* 497: 633-637; Ha et al. (2014) *Mol. Cell Proteomics.* 13(12): 3320-3331; Reyes-Reyes et al. (2010) *Cancer Res.* 70: 8617-8629), thus imparting the anti-CD46 antibodies with an additional selectivity for tumor cells.

To validate CD46 as a target for targeted therapeutic development, tissue specificity of the CD46 epitope was determined by immunohistochemistry. CD46 epitope expression in tumor was first studied. Immunohistochemistry studies were performed on both frozen and formalin fixed paraffin embedded (FFPE) prostate cancer tissues. On frozen tissues, 18/18 cases (100%) showed strong staining signals, indicating overexpression in all cases. On FFPE tissues, strong CD46 staining was found in 63/87, moderate staining in 23/87, and weak staining in 1/87 cases, supporting the conclusion that CD46 is overexpressed by a vast majority of prostate tumors. A summary of the immunohistochemistry results is shown in Table 4 and FIG. 10.

TABLE 4

Immunohistochemistry results of CD46 expression in prostate cancer tissues. Positive vs. total cases studied are indicated. FFPE: formalin fixed paraffin embedded (tissues). Biotin-labeled anti-human CD46 antibodies were used for this study.

| Tissue type | Strong | Moderate | Weak | Negative |
|---|---|---|---|---|
| Frozen | 18/18 | 0 | 0 | 0 |
| FFPE | 63/87 | 23/87 | 1/87 | 0 |

The aforementioned studies strongly support the development of a CD46-targeted monoclonal antibody therapeutic against human cancer. To this end, antibody drug conjugates (ADCs) were developed using the panel of novel anti-CD46 antibodies. Monomethyl auristatin F (MMAF) was conjugated via the MC-vc-PAB linker (McDonagh et al. (2008) *Mol. Canc. Therap.* 7: 2913-2923; Sutherland et al. (2006) *J. Biol. Chem.* 281: 10540-10547) to YS5 IgG1. By hydrophobic interaction chromatography (HIC), it was determined that, on average, about 3 drugs were conjugated per antibody molecule (FIG. 11). Tumor-killing activities in vitro were then tested using a panel of metastatic castration resistant prostate cancer cell lines (LNCaP-C4-2B and Du145). Potent tumor cell killing was observed with EC50 values ranging from low to sub nM (FIGS. 12 and 13).

In vivo anti-tumor activity of the anti-CD46 ADCs was tested using the LNCaP-C4-2B subcutaneous xenograft model. Potent inhibition of tumor growth and survival was observed, with tumor volume reduced to non-detectable levels following 5 doses at 5 mg/kg (FIG. 14). No tumor recurred during the indicated period post ADC injection (FIG. 14).

In addition to prostate cancer, it was found that the anti-CD46 ADCs potently kill various other cancers that express CD46. For example, it was found that in addition to prostate cancer, CD46 is also highly expressed on multiple myeloma cell surface (FIG. 15). Moreover, the anti-CD46 ADC potently kills the multiple myeloma cell line RPMI8226 (FIG. 16) with EC50 in the sub nM range. Finally it was shown that the anti-CD46 ADC greatly reduced multiple myeloma burdens in vivo. A reporter-expressing line (RPMI8226-Luc that expressed the firefly luciferase gene) was injected via the tail vein to immune-compromised mice and the disseminated tumor cells were allowed to establish in the bone and joints. Four doses of anti-CD46 ADCs were then injected at 5 mg/kg (every 4 days) and tumor status was monitored by bioluminescence. It was found that the anti-CD46 ADCs are highly effective in reducing tumor burdens in vivo (FIG. 17). Survival data were collected following ADC treatment (FIG. 18), showing "cure" for 60% of the treated mice and greatly delayed onset of death for the remaining 40% through the duration of the experiment.

To broaden applicability, the anti-CD46 ADC was studied using a second multiple myeloma cell line MM1.S that expresses the luciferase reporter. Potent tumor killing activity of the anti-CD46 ADC was observed in vivo. Four doses at 4 mg/kg completely eliminated MM1.S tumor cells (FIG. 20). In contrast, the control ADC (MMAF conjugated to a non-binding antibody) had no effect at all at the same dose and dosing frequency. Moreover, even a single dose of anti-CD46 ADC at 4 mg/kg greatly reduced tumor burden, causing a profound inhibition of tumor development (FIG. 20). Four doses of anti-CD46 ADC at 0.8 mg/kg also caused a lasting inhibition of MM1.S xenograft development (FIG. 20). Finally, even naked antibody (YS5 IgG1) caused significant tumor inhibition in this xenograft model (FIG. 20), suggesting an interesting possibility of a potential naked antibody-based therapy for certain subtypes of multiple myeloma.

Figure 21:
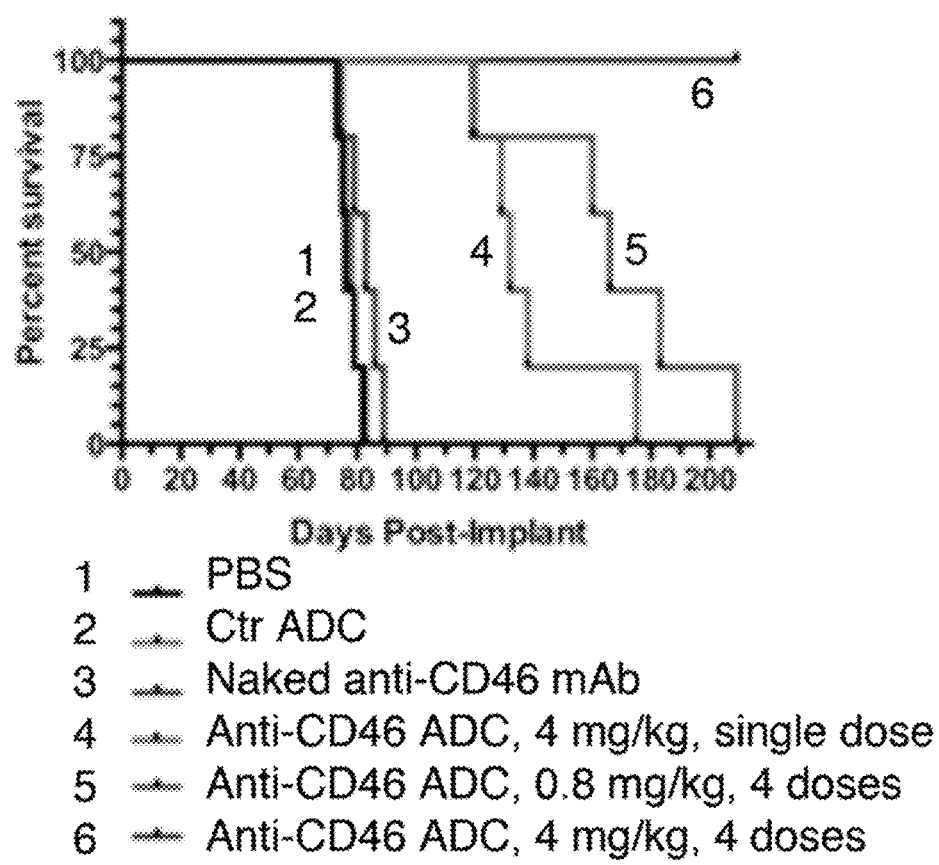
FIG. 21. Kaplan-Meier analysis of mice bearing orthometastatic xenografts post ADC treatment. 100% of mice treated with 4 mg/kg anti-CD46 ADC survived til the end of the experiment (day-212). Injection started on day-10 post implant. Anti-CD46 was injected at either a single dose of 4 mg/kg or 4 times at two dosing levels (0.8 mg/kg and 4 mg/kg). The control ADC (Ctr ADC) was injected 4 times at 4 mg/kg.

Kaplan-Meier analysis was performed to determine survival post-treatment. CD46 ADC treated groups showed a significant survival advantage over control groups (FIG. 21). For mice that received 4 doses of 4 mg/kg CD46 ADC, all survived until the end of the experiment (day 212).

Figure 19:
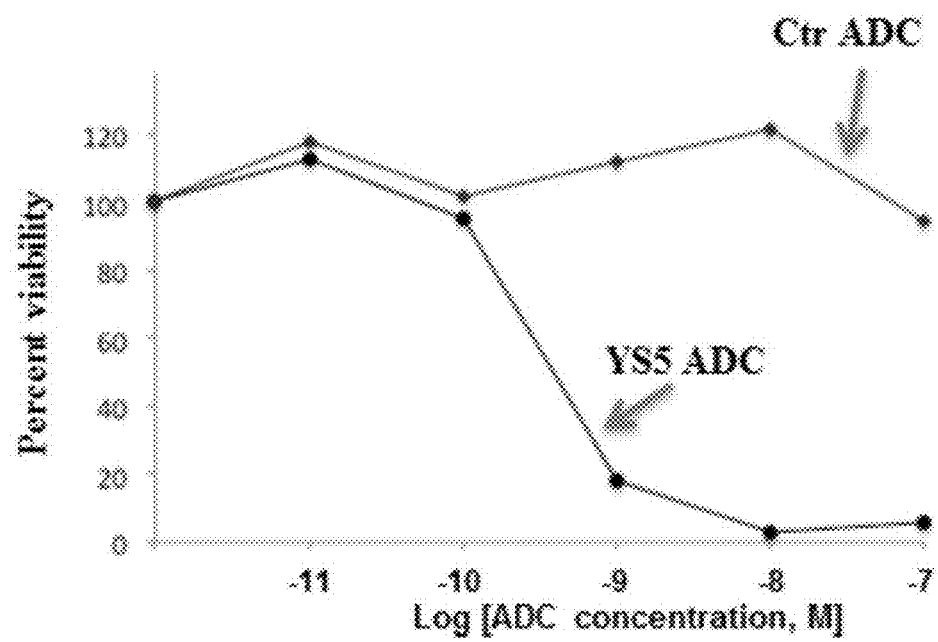
FIG. 19. Kill curve of anti-CD46 (YS5) ADC on colorectal cancer cell line HT29.
Figure 22:
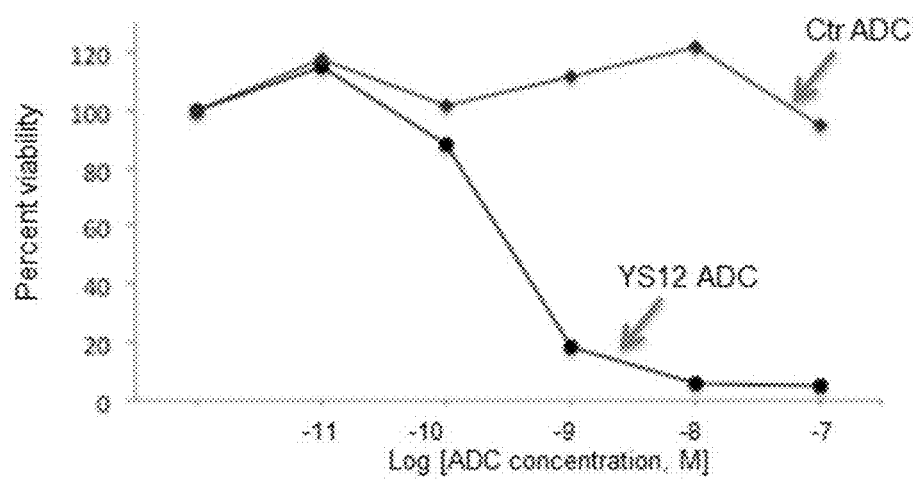
FIG. 22. Kill curve of anti-CD46 (YS12) ADC on colorectal cancer cell line HT29.
Figure 23:
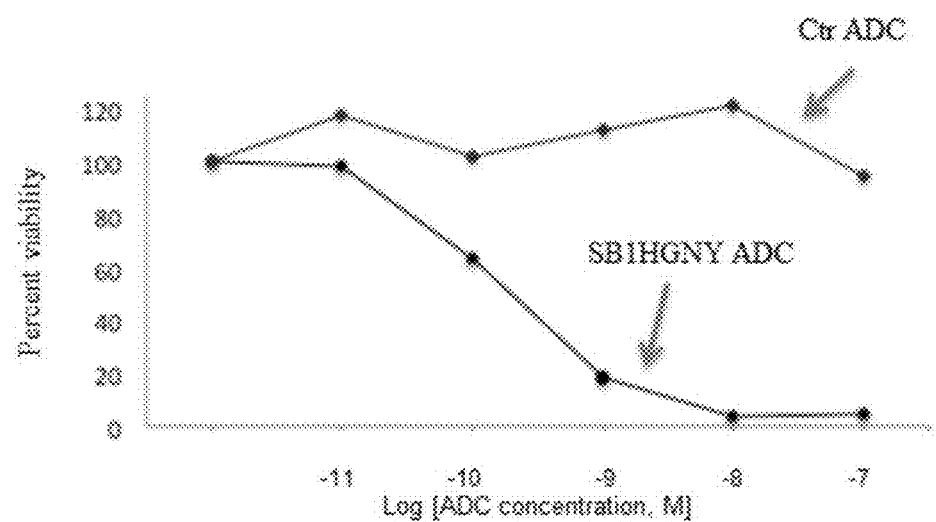
FIG. 23. Kill curve of anti-CD46 (SB1HGNY) ADC on colorectal cancer cell line HT29.
Figure 24:
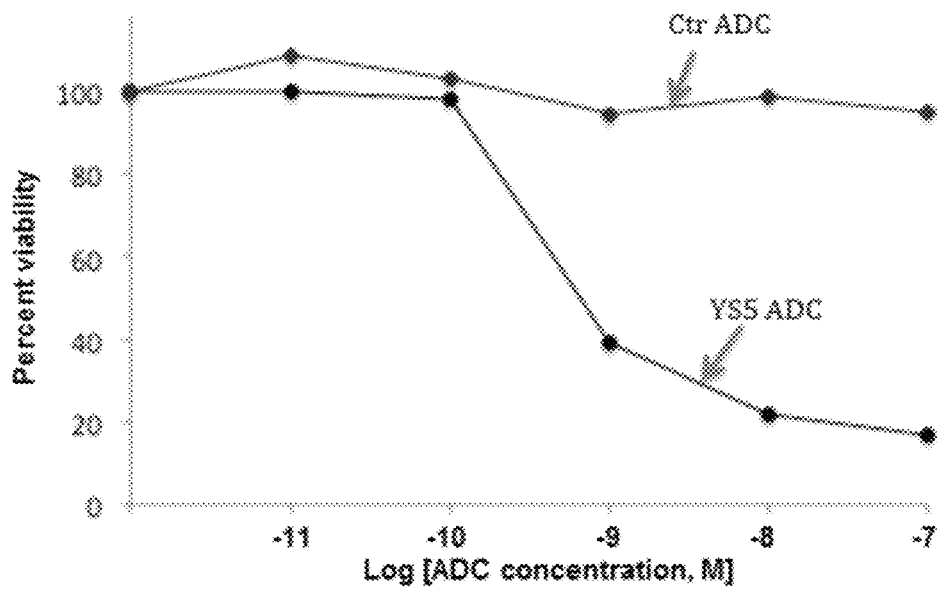
FIG. 24. Kill curve of anti-CD46 YS5 ADC on pancreatic cancer cell line MiaCaPa2.
Figure 25:
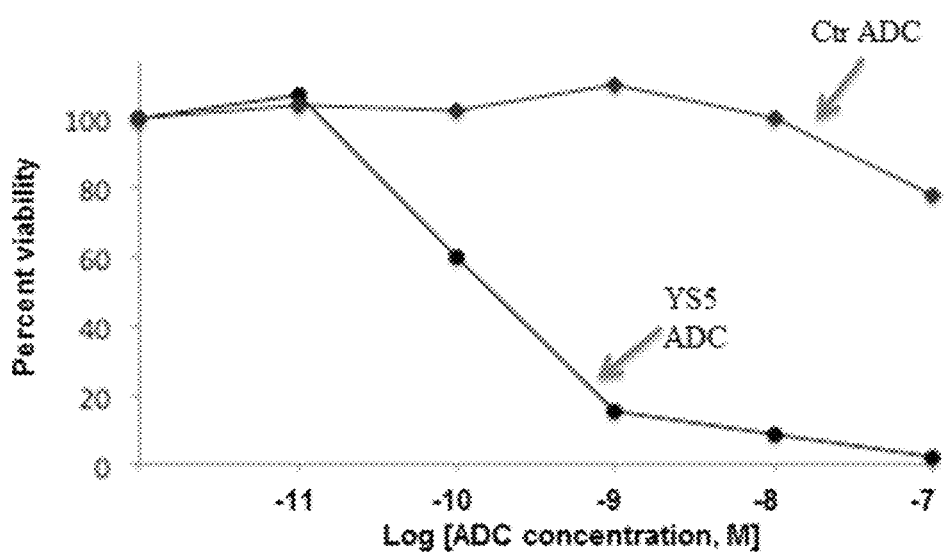
FIG. 25. Kill curve of anti-CD46 YS5 ADC on mesothelioma cell line M28.
Figure 26:
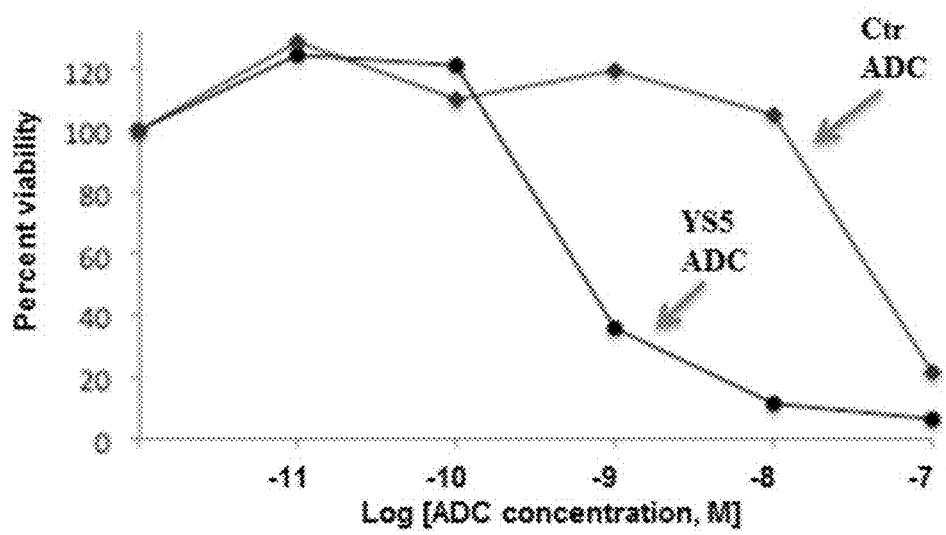
FIG. 26. Kill curve of anti-CD46 YS5 ADC on ovarian cancer cell line OVCAR3.

Besides the aforementioned prostate cancer and multiple myeloma, it was found that CD46 is highly expressed in a broad panel of cancer cell lines including, but not limited to, colorectal cancer, pancreatic cancer, mesothelioma, lung cancer, breast cancer, ovarian cancer, bladder cancer, liver cancer, glioma, and neuroblastoma. Moreover, the anti-CD46 ADCs potently killed those cells in vitro. For example, the anti-CD46 ADC is highly effective in killing colorectal cancer cells (FIG. 19 for YS5, FIG. 22 for YS12 on HT29, and FIG. 23 for SB1HGNY on HT29), pancreatic cancer cells (FIG. 24), mesothelioma cells (FIG. 25), and ovarian cancer cells (FIG. 26).

Figure 27:
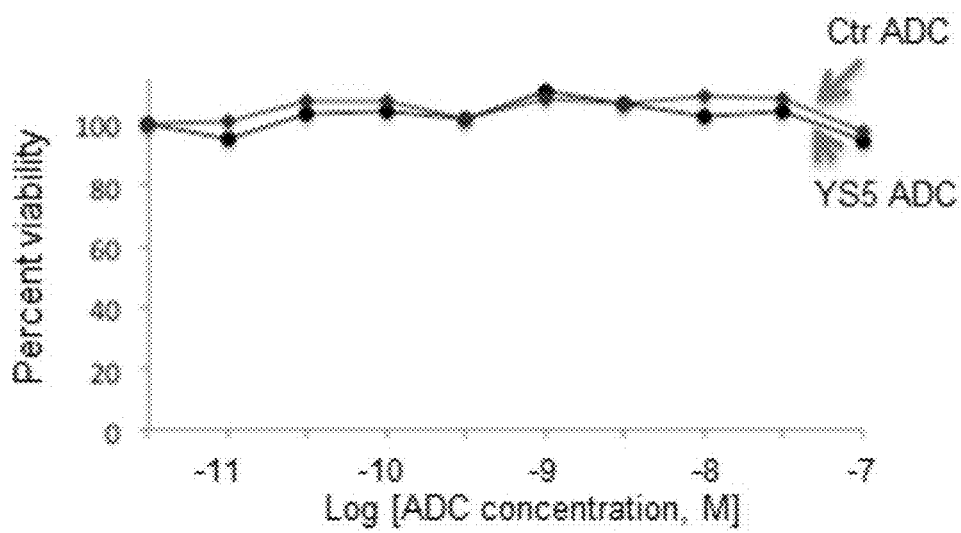
FIG. 27. Anti-CD46 ADC has no effect on BPH-1 cells. BPH-1 cells express very low levels of CD46 and is not affected by YS5 ADC.
Figure 28:
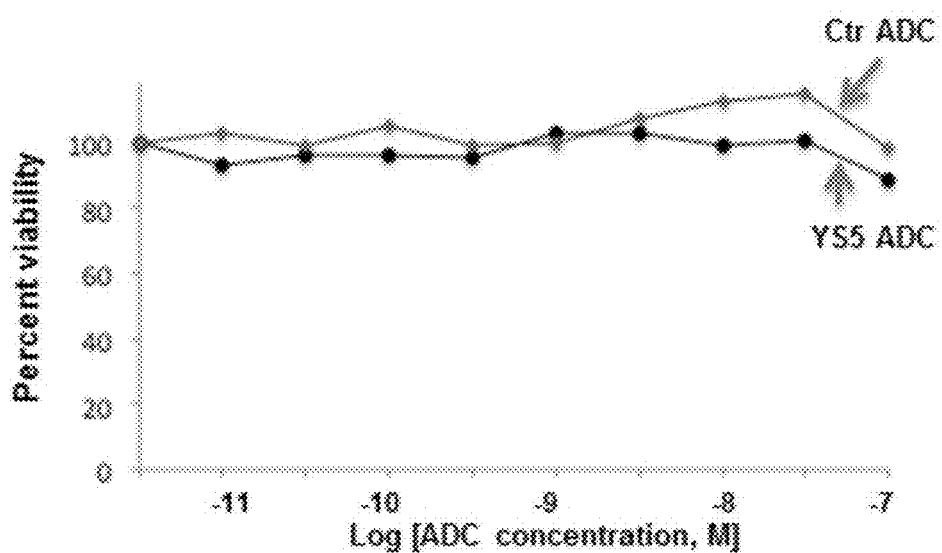
FIG. 28. Anti-CD46 (YS5) ADC on HS27 cells. Hs27 cells were seeded at 3,000 cells per well.
Figure 29:
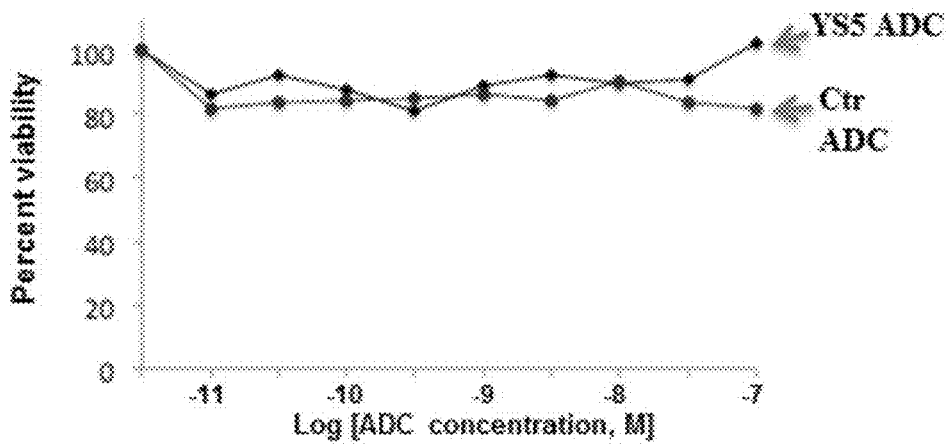
FIG. 29. Anti-CD46 ADC (YS5) show little toxicity on normal CD3+ T cells. 10,000 CD3+ T cells were seeded in 96-well plates and incubated with varying concentrations of YS5 ADCs at 37° C. for 96 h. Cell viability was assessed by the CCK-8 (Cell Counting Kit-8) (Dojindo).
Figure 30:
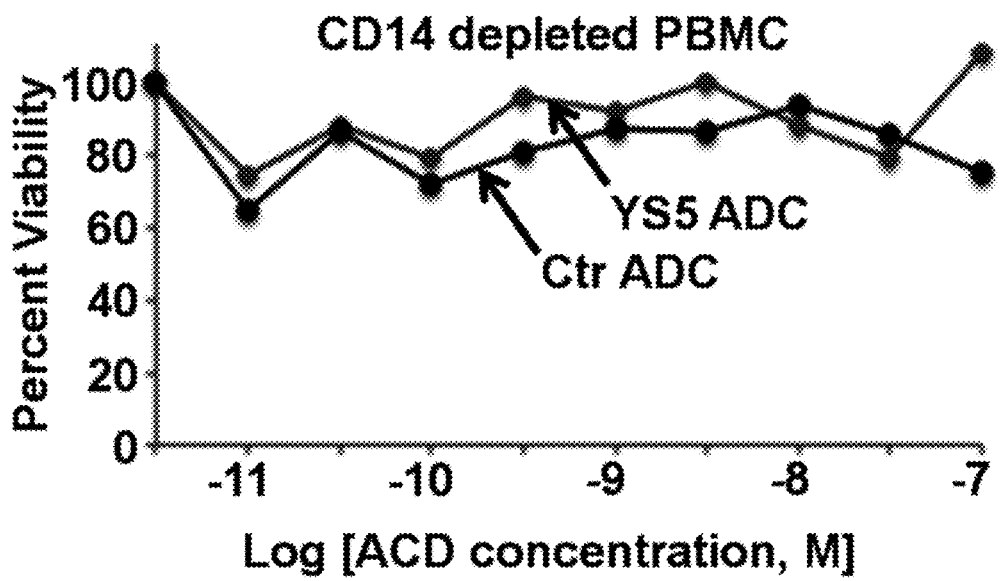
FIG. 30. Anti-CD46 ADC has no effect on normal CD14-depleted PBMCs. 10,000 cells were seeded in 96 well plates, and incubated with varying concentrations of ADC at 37° C. for 98h. Cell viability was determined by the CCK8 counting kit.

To evaluate potential toxicity, YS5 ADC was tested on a panel of control cells that either do not express CD46 (BPH-1) or that express it at moderate levels (e.g., HS27). Much reduced cytotoxicity was observed on those cells (FIG. 27 for YS5 ADC on BPH-1, FIG. 28 for YS5 ADC on HS27, FIG. 29 for YS5 ADC on normal T cells, and FIG. 30 for YS5 ADC on CD14-depleted peripheral blood mononuclear cells (PBMC)), suggesting that they do not take up readily the ADCs. Differential internalization via macropinocytosis is a likely mechanism that enhances selectivity of anti-CD46 ADCs.

Figure 31:
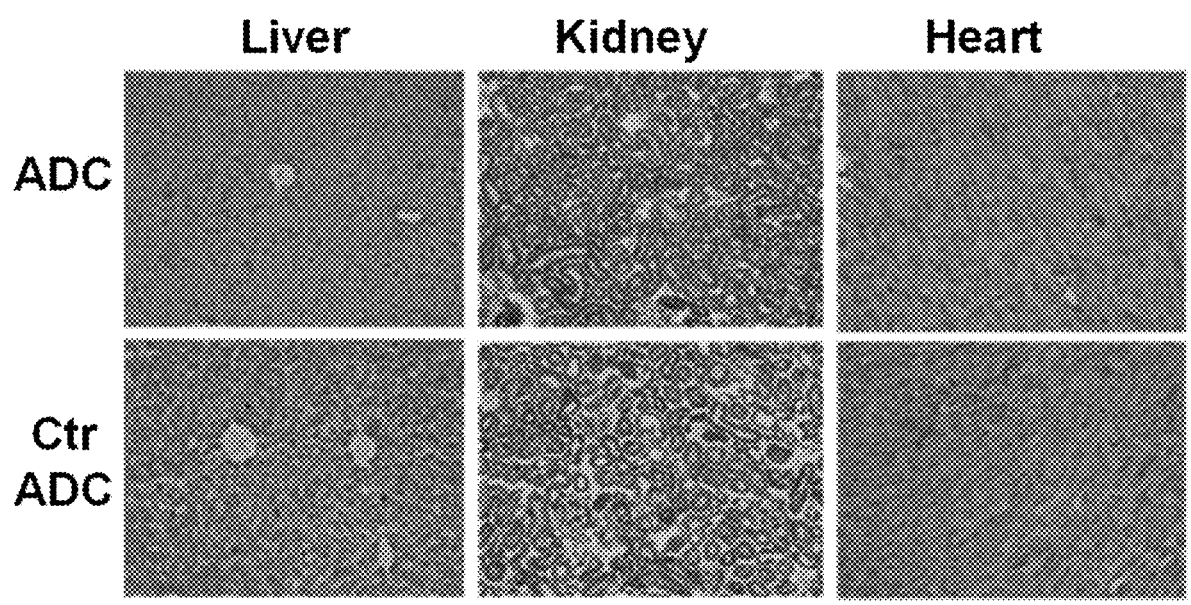
FIG. 31. Anti-CD46 ADC toxicity evaluation in transgenic mice expressing human CD46. Following i.v. injection of 6 mg/kg anti-CD46 and control ADCs, mice were followed for 14 days, sacrificed and major organs harvested for histological examinations.

ADC toxicity was studied in vivo using transgenic mice that express human CD46. There is not a true murine ortholog for human CD46 and murine CD46 performs a quite different physiological role than that of human CD46. The antibodies did not bind to murine CD46. Thus there is no good small animal model for evaluation of potential anti-CD46 ADC toxicity except for the transgenic model. Anti-CD46 ADC was injected at 6 mg/kg into human CD46-expressing transgenic mice, and the animals were monitored for overt sign of toxicity daily. The animals were sacrificed at day 14 and the vital organs were harvested for histological examination of tissue damages. As shown in FIG. 31, there is no notable difference between the anti-CD46 ADC-treated and the control ADC-treated mice. No overt sign of toxicity was observed during the duration of this experiment at this dose of ADC tested. It is understood that regulatory toxicology studies need to be performed in non-human primates such as the cynomolgus monkey whose CD46 is recognized by the anti-CD46 antibodies as shown above.

Given that human CD46 gene is located at the short arm of chromosome 1 (1q32.2), and given that 1q gain has been frequently observed in a variety of cancers especially those with poor prognosis, it is likely that anti-CD46 antibody therapeutics including but not limited to ADCs are applicable to a broad spectrum of malignancies at advanced stages with dire therapeutic need. For example, in prostate cancer, the region spanning 1q32.2 has been shown to gain in disseminated metastatic form of the disease where current therapies have failed to make an impact, (Hanamura et al. (2006) *Blood*, 108: 1724-1732), making metastatic castration resistant prostate cancer an excellent candidate for our anti-CD46 ADC treatment. In multiple myeloma, 1q gain is also frequently observed in recurrent patients (Id.), thus identifying an important patient population that our anti-CD46 ADCs could potentially help. The correlation between 1q gain (and specifically 1q32.2) and poor prognosis has been seen for other cancers as well, making 1q a potential biomarker for our anti-CD46 ADCs for patient stratification and outcome monitoring for those malignancies. FISH probe detecting 1q32.2 could be used to assess 1q status. Circulating DNA could also be used to detect 1q gain as a minimally invasive biomarker (Fan et al. (2008) *Proc. Natl. Acad. Sci. USA,* 105: 16266-16271) for CD46-expressing cancers with poor prognosis.

The anti-CD46 antibodies described herein can be used to in an imaging probe to monitor tumor status in vivo, either as a standalone imaging agent or a companion diagnostic for the anti-CD46 ADCs. We have previously labeled our original anti-CD46 antibody UA20 and demonstrated its excellent imaging property in vivo for prostate cancer targeting (He et al. (2010) *J. Nucl. Med.* 51: 427-432). Besides imaging, the anti-CD46 antibodies can in immunohistochemistry-based biomarkers to assess CD46 expression in biopsies and archived patient samples, capture ELISA assays to assess serum CD46 levels, and FACS or chip-based assays to assess CD46 cell surface expression in disseminated and/or circulating tumor cells.

Example 2

CD46 ADC is Highly Active in Intra-Femoral mCRPC Xenograft Model.

Figure 32:
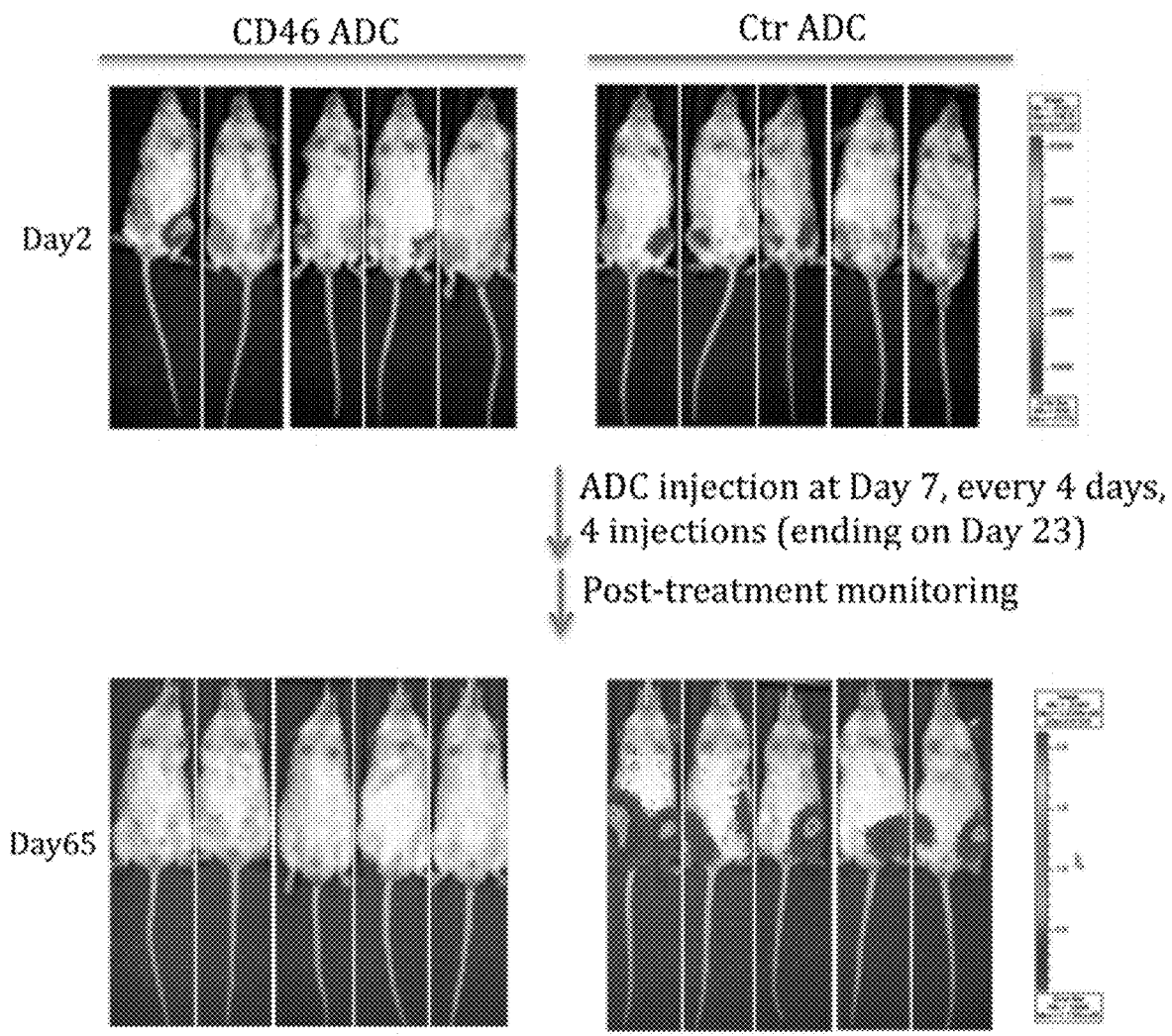
FIG. 32 shows that CD46 ADC is effective in intra femoral prostate cancer xenograft model. The mCRPC cell line LnCaP-C4-2B that carried a firefly luciferase reporter was injected into the femur of mice. CD46 ADC (YS5-mcvcpab-MMAF) was injected on day 7 every 4 days for a total of 4 injections. The mice were monitored post-treatment until day 65. Ctr ADC: a non-binding IgG1 conjugated to MMAF (ctr IgG-mcvcpab-MMAF).

As over 95% of prostate cancer metastasis is to the site of the bone, we further studied efficacy of our anti-CD46 ADC in a bone xenograft model. We injected the metastatic castration resistant prostate cancer (mCRPC) cell line LNCaP C4-2B that carries a firefly luciferase reporter into the femur of NSG mice to create the intra-bone mCRPC xenograft model. The CD46 ADC (YS5-mcvcpab-MMAF) was injected 7 days post grafting every 4 days for a total of 4 times. Tumor status was monitored by bioluminescence imaging during and post treatment. As shown in FIG. 32, CD46 ADC treated mice showed profound tumor inhibition that last through the post-treatment period til the end of the experiment (day 65), suggesting that our CD46 ADC is highly efficacious in this intra-femoral mCRPC xenograft model.

CD46 is Highly Expressed in CRPC and mCRPC Tissues.

Figure 33:
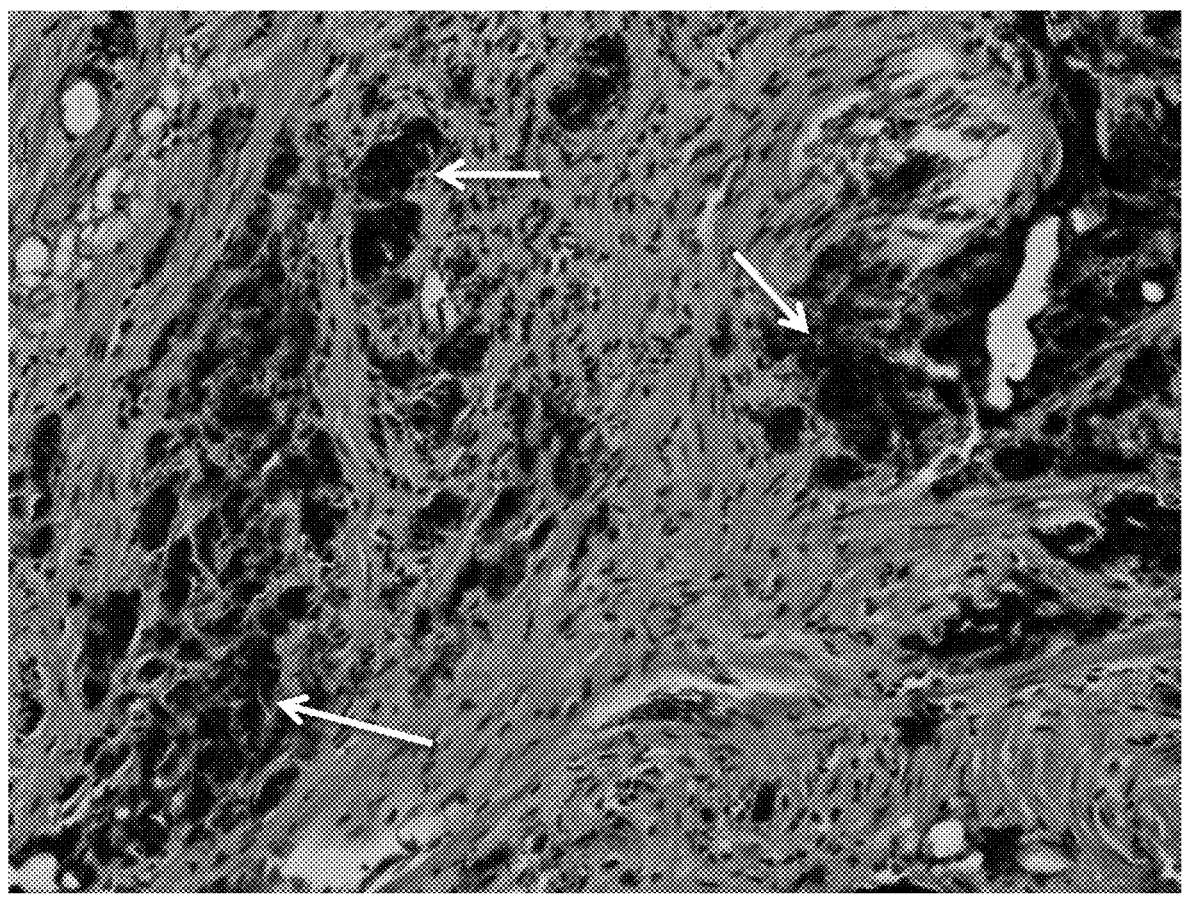
FIG. 33 illustrates CD46 expression in castration resistant prostate cancer (CRPC). Prostate tissue specimens were taken from patients who became resistant to hormone blockage. Arrows indicate tumor cells (only selective tumor regions are indicated). The H-294 rabbit anti-human CD46 antibody (Santa Cruz Biotechnology) was used for staining, followed by detection with the Envision+ system (Dako North America).
Figure 35:
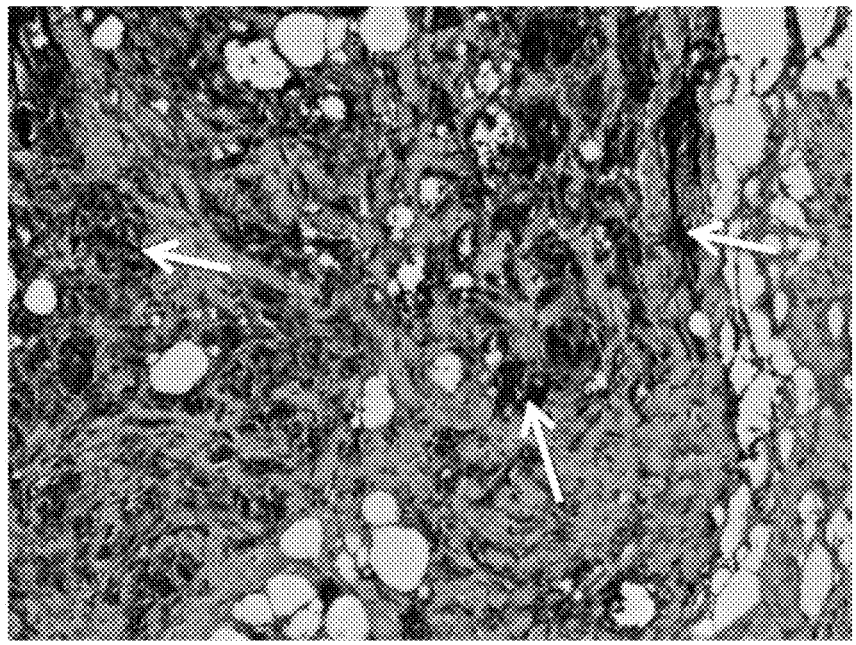
FIG. 35 illustrates lymph node metastasis of mCRPC. Arrows indicate tumor cells (only selective tumor regions are indicated). The H-294 rabbit anti-human CD46 antibody (Santa Cruz Biotechnology) was used for staining, followed by detection with the Envision+ system (Dako North America).
Figure 36:
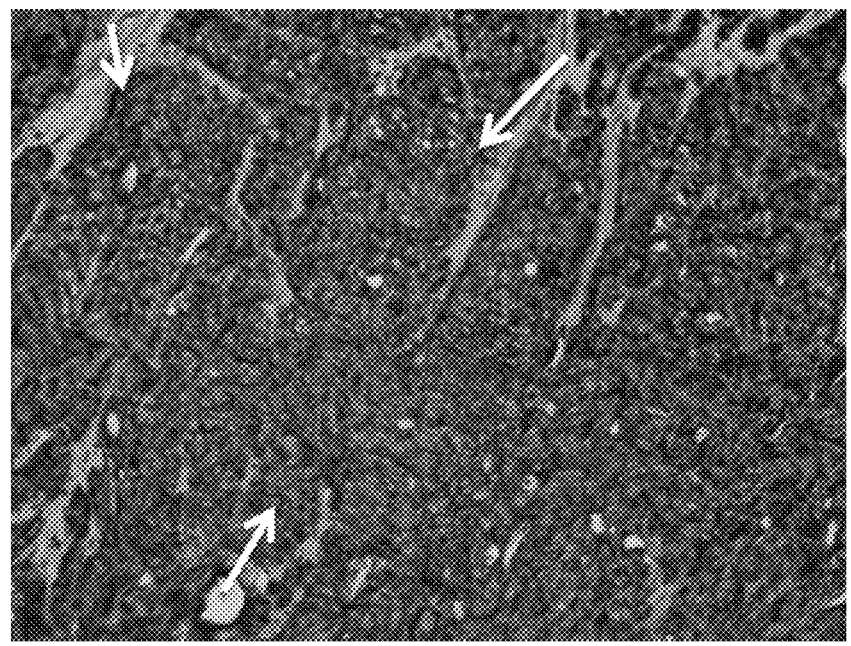
FIG. 36 illustrates bladder metastasis of mCRPC. Arrows indicate tumor cells (only selective tumor regions are indicated). The H-294 rabbit anti-human CD46 antibody (Santa Cruz Biotechnology) was used for staining, followed by detection with the Envision+ system (Dako North America).

In addition to primary tumors, we performed immunohistochemistry studies on tissue specimens from castration resistant prostate cancer (CRPC) and metastatic castration resistant prostate cancer (mCRPC). As shown in FIG. 33, CD46 is highly expressed in CRPC specimens. We further studied mCRPC specimens and found widespread (100% of cases studied, or 12/12) and strong expression of CD46 in bone metastasis (FIG. 34), lymph node metastasis (FIG. 35), and bladder metastasis (FIG. 36).

CD46 is Overexpressed by Neuroendocrine Subtype of Prostate Cancer.

Figure 39:
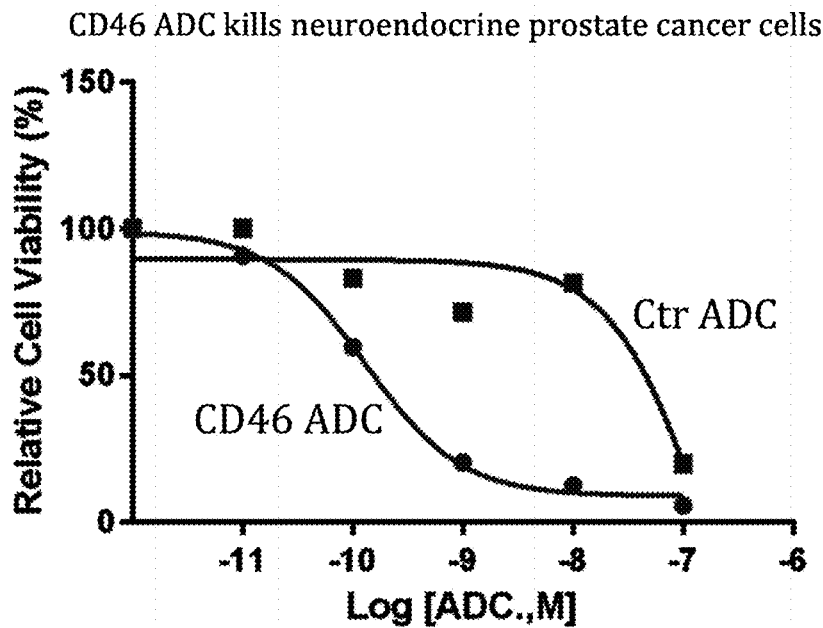
FIG. 39 shows that CD46 ADC kills H660 cells. Varying concentrations of CD46 ADC (YS5-mcvcpab-MMAF) were incubated with the neuroendocrine cell line H660 at 37° C. for 7 days. Calcein AM assay was used to assess viability. Ctr ADC: a non-binding IgG1-mcvcpab-MMAF.

About 30% patients are resistant to abiraterone and enzalutamide treatment. Emergence of small cell/neuroendocrine type of prostate cancer may be a frequent event (~30-40% of cases). Unlike adenocarcinoma, neuroendocrine prostate cancer often do not express common markers such as prostate specific antigen (PSA) and prostate specific membrane antigen (PSMA). Therefore we sought to study by FACS CD46 expression by a neuroendocrine prostate cancer cell line H660. As shown in FIG. 37, left panel, CD46 is highly expressed by H660 cells. Western blot analysis confirmed that H660 cells express CD46 and the neuroendocrine marker neuron-specific enolase (NSE) (FIG. 37, right panel). Our anti-CD46 antibody (YS5) is internalized by H660 cells and co-localized with the lysosomal marker LAMP1 (FIG. 38). When incubated with H660 cells, our anti-CD46 ADC showed potent cytotoxic activities in vitro with EC50<1 nM (FIG. 39).

CD46 is Further Upregulated by Prostate Cancer Cells Following Treatment with Abiraterone or Enzalutamide, Rendering them Susceptible to CD46 ADC.

Figure 40:
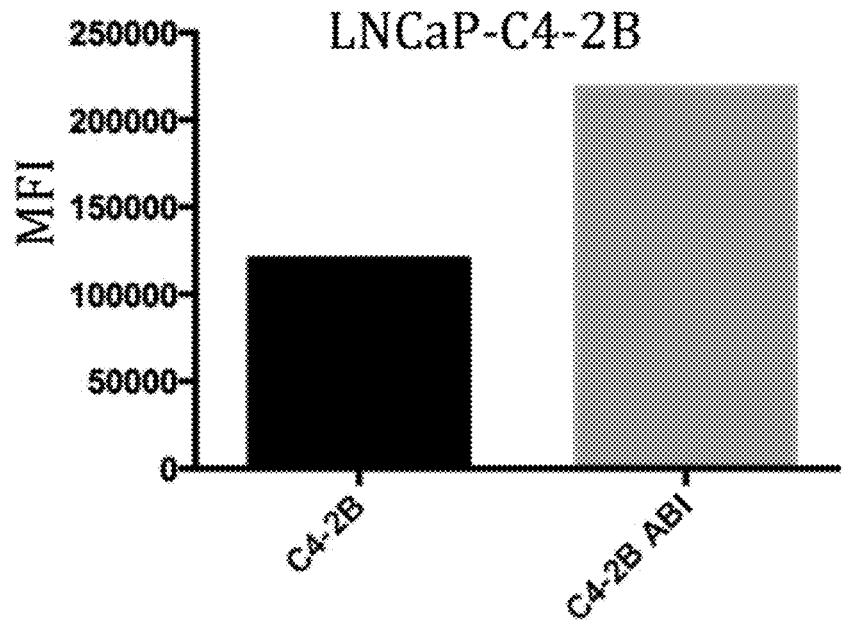
FIG. 40 shows that treatment of the metastatic castration resistant prostate cancer cell line LNCaP-C4-2B with 10 μM abiraterone (abi) for 7 days caused upregulation of cell surface CD46 expression as measured by FACS. MFI: mean fluorescence intensity.
Figure 41:
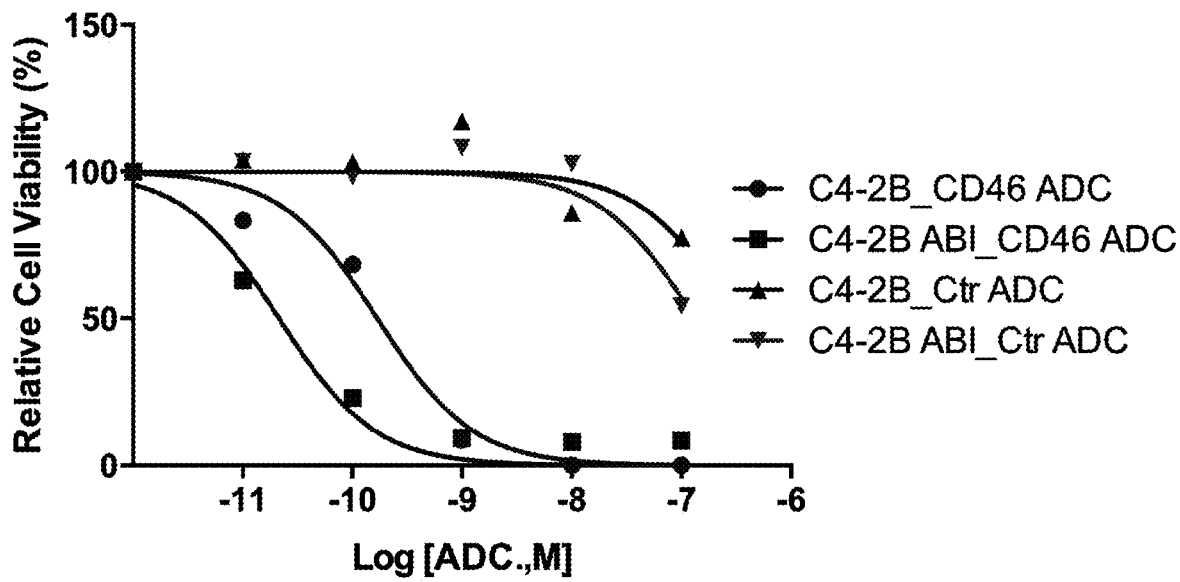
FIG. 41 shows that abiraterone (Abi)-treated LNCaP C4-2B cells are more sensitive to CD46 ADC. LNCaP-C4-2B cells were incubated with abiraterone for 7 days, washed and continued incubated with CD46 ADC in media containing no abiraterone for an additional 96 hours. C4-2B CD46 ADC: LNCaP C4-2B cells incubated with CD46 ADC (YS5-mcvcpab-MMAF) without prior exposure to abiraterone (EC50=169 pM). C4-2B ABI CD46 ADC: LNCaP C4-2B cells with prior exposure to abiraterone incubated with CD46 ADC (EC50=21 pM). Ctr ADC: a non-binding IgG1 conjugated to MMAF.
Figure 42:
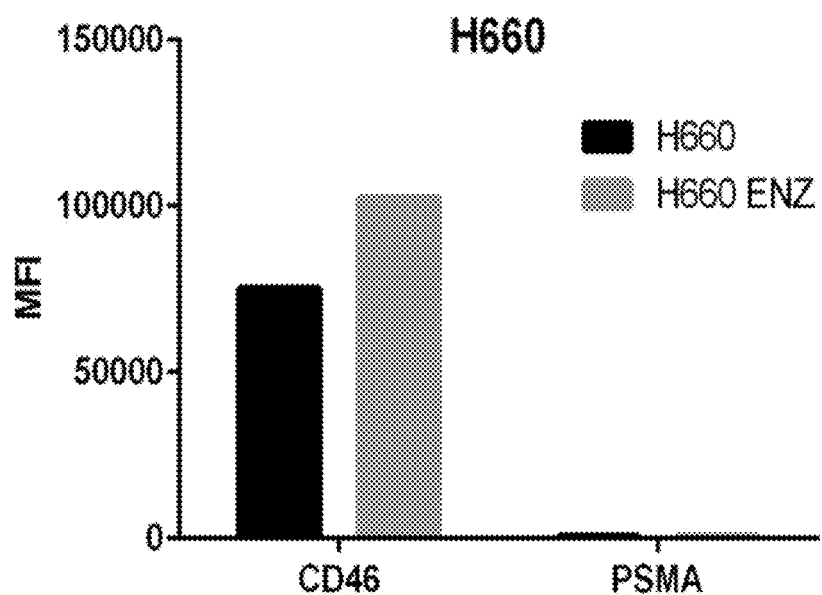
FIG. 42 illustrates upregulation of cell surface CD46 on neuroendocrine cell line H660 post enzalutamide (ENZ) treatment. H660 cells were treated with 10 μM enzalutamide for 7 days, and analyzed by FACS for cell surface antigen expression. CD46 is highly expressed by H660, while prostate specific membrane antigen (PSMA) is barely detectable. Moreover, exposure to enzalutamide caused an upregulation of CD46 expression on tumor cell surface. MFI: median fluorescence intensity.

We found that treating the mCRPC line LNCaP-C4-2B with 10 µM abiraterone for 7 days caused a significant upregulation of surface CD46 expression (FIG. 40). Interestingly, this upregulation correlates with an enhanced killing of tumor cells (FIG. 41) with EC50 values dropping from 169 pM to 21 pM. Similarly, when the neuroendocrine prostate cancer cell line H660 was incubated with 10 µM enzalutamide for 7 days, a significant upregulation of cell surface CD46 was observed (FIG. 42). Like what was observed in LNCaP-C4-2B cells, H660 cells became more sensitive to CD46 ADC post enzalutamide treatment with EC50 dropping by 4-5 fold.

CD46 Expression on Additional Tumors.

Figure 43:
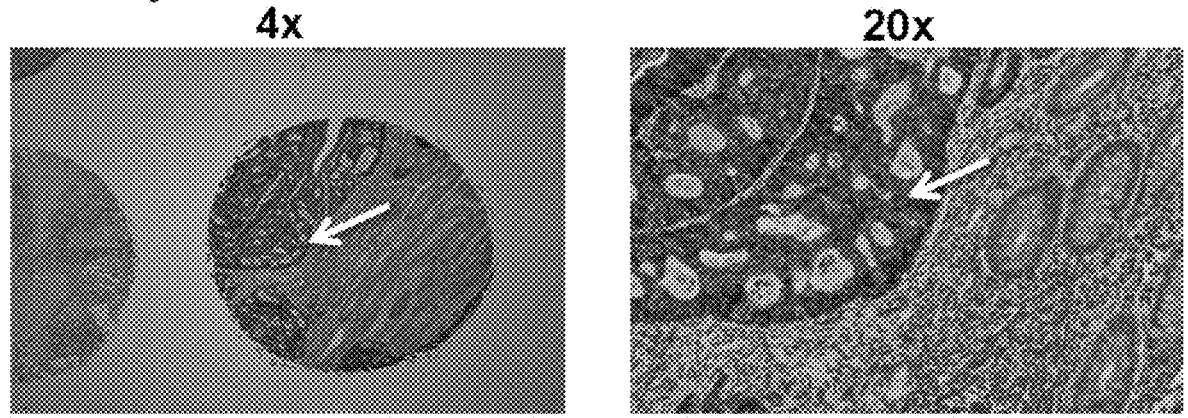
FIG. 43 shows that CD46 is highly expressed in primary colorectal cancer. Arrows indicate tumor cells (only selective tumor regions are indicated). The H-294 rabbit anti-human CD46 antibody (Santa Cruz Biotechnology) was used for staining, followed by detection with the Envision+ system (Dako North America). Images were taken using a digital microscope at two levels of amplification (4× and 20×).
Figure 44:
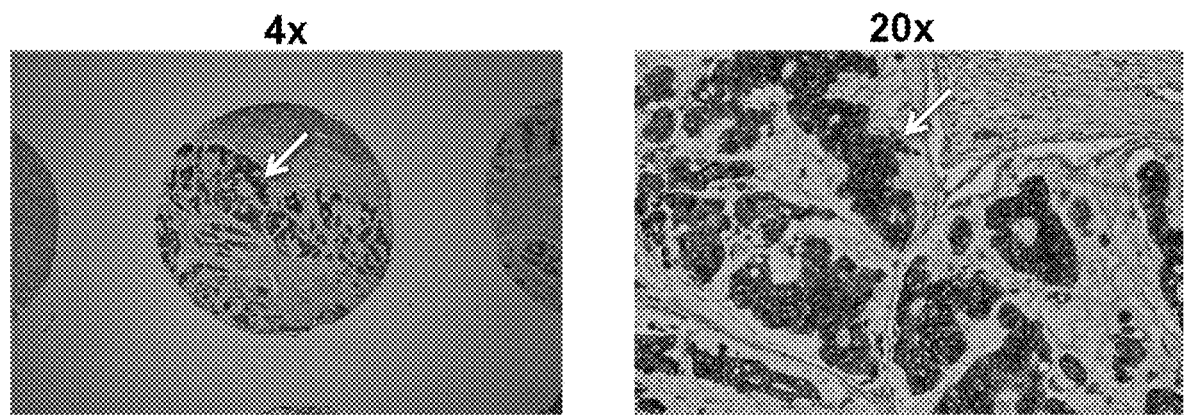
FIG. 44 shows that CD46 is highly expressed in colorectal cancer metastasized into the liver. Arrows indicate tumor cells (only selective tumor regions are indicated). The H-294 rabbit anti-human CD46 antibody (Santa Cruz Biotechnology) was used for staining, followed by detection with the Envision+ system (Dako North America). Images were taken using a digital microscope at two levels of amplification (4× and 20×).
Figure 45:
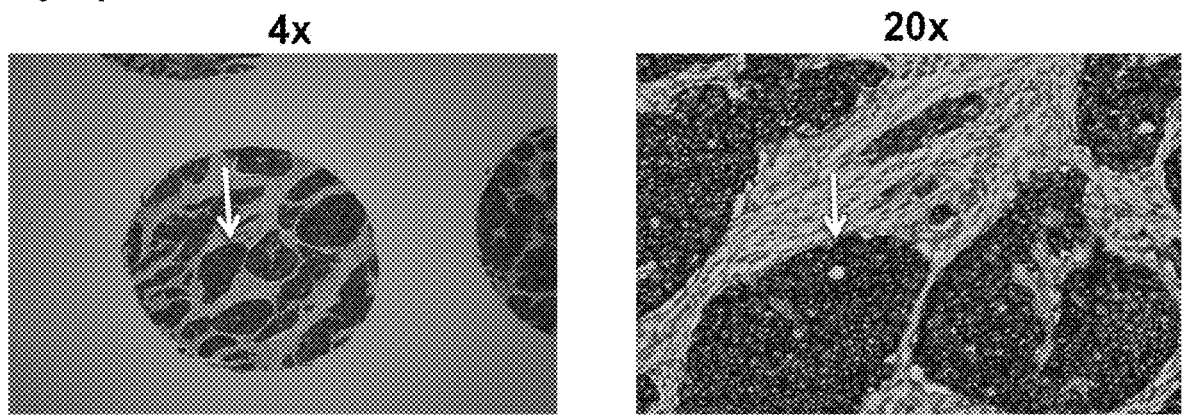
FIG. 45 shows that CD46 is highly expressed in colorectal cancer metastasized into the lymph node. Arrows indicate tumor cells (only selective tumor regions are indicated). The H-294 rabbit anti-human CD46 antibody (Santa Cruz Biotechnology) was used for staining, followed by detection with the Envision+ system (Dako North America). Images were taken using a digital microscope at two levels of amplification (4× and 20×).
Figure 46:
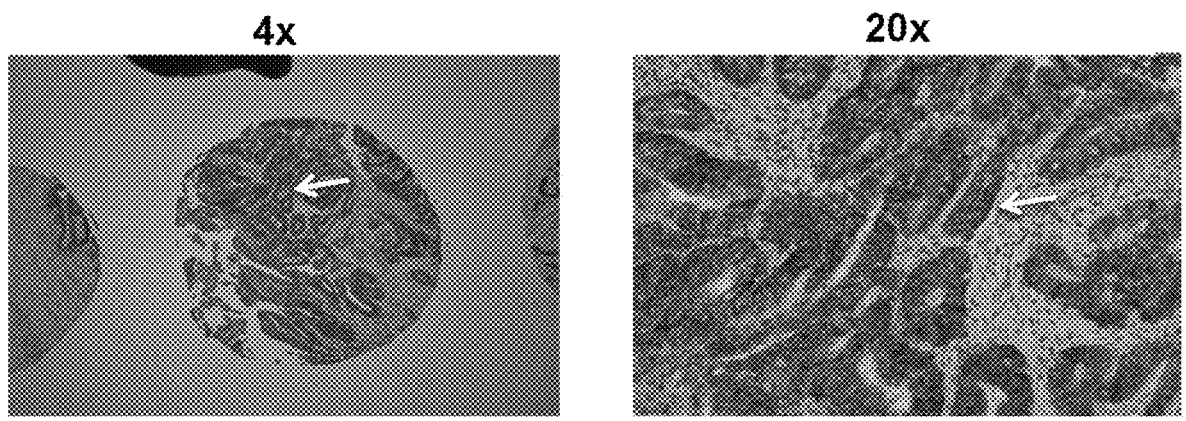
FIG. 46 shows that CD46 is highly expressed in colorectal cancer metastasized to the bladder. Arrows indicate tumor cells (only selective tumor regions are indicated). The H-294 rabbit anti-human CD46 antibody (Santa Cruz Biotechnology) was used for staining, followed by detection with the Envision+ system (Dako North America). Images were taken using a digital microscope at two levels of amplification (4× and 20×).

In addition to prostate cancer and multiple myeloma, we found that CD46 is overexpressed in a wide range of human cancers. By immunohistochemistry analysis, we found positive CD46 staining in 82% of colorectal cancer (81/99 cases) with 70/99 showing strong staining (71%) (FIG. 43). Interestingly, nearly 100% of metastatic colorectal cancers express CD46 (liver metastasis in FIG. 44, lymph node metastasis in FIG. 45, and bladder metastasis in FIG. 46).

Figure 47:
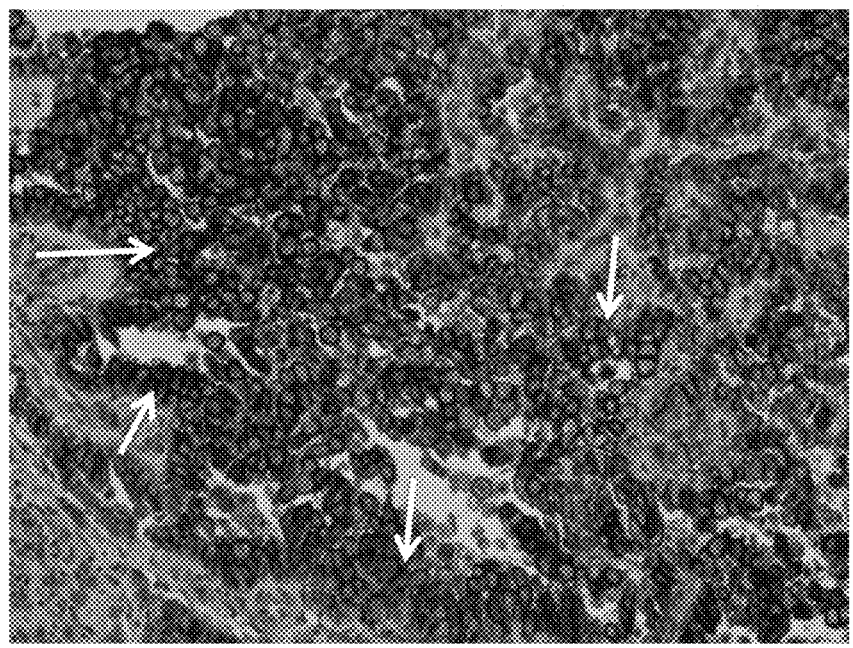
FIG. 47 shows that CD46 is highly expressed in mesothelioma as demonstrated by immunohistochemistry of CD46 staining in mesothelioma. Arrows indicate tumor cells (only selective tumor regions are indicated). The H-294 rabbit anti-human CD46 antibody (Santa Cruz Biotechnology) was used for staining, followed by detection with the Envision+ system (Dako North America).
Figure 48:
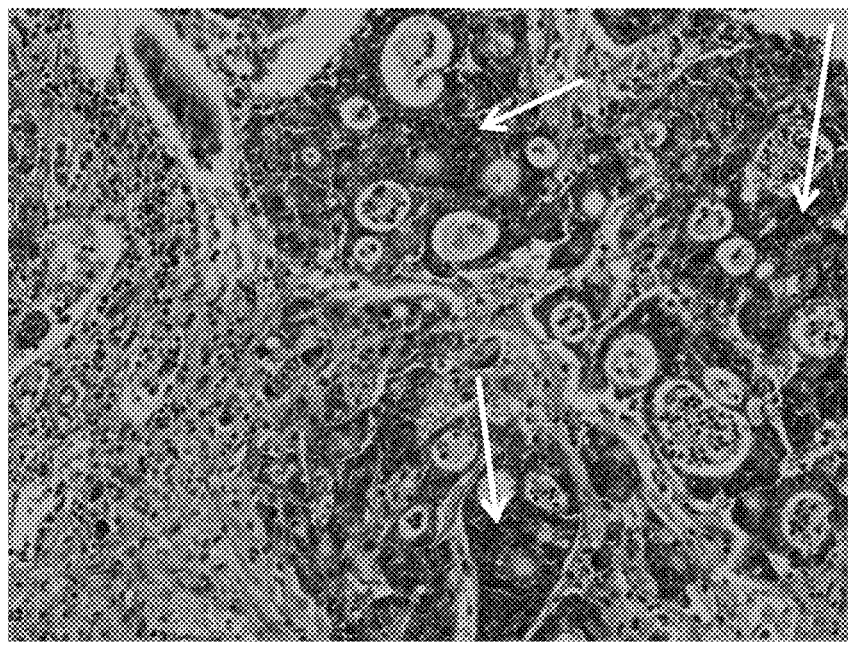
FIG. 48 shows that CD46 is highly expressed in pancreatic cancer. Arrows indicate tumor cells (only selective tumor regions are indicated). The H-294 rabbit anti-human CD46 antibody (Santa Cruz Biotechnology) was used for staining, followed by detection with the Envision+ system (Dako North America).
Figure 49:
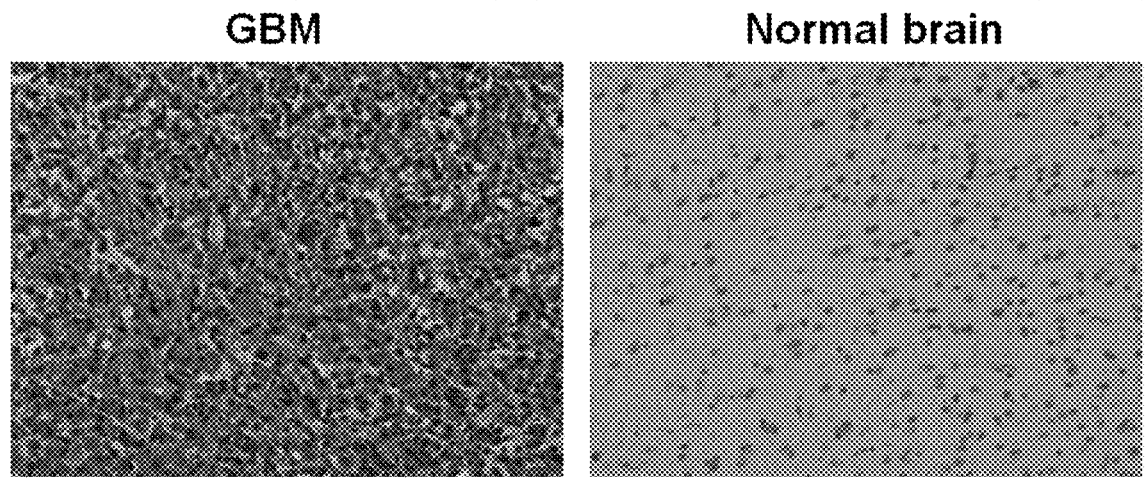
FIG. 49 shows that CD46 is overexpressed by glioblastoma multiforme (GBM) as illustrated by immunohistochemistry analysis of CD46 staining in GBM and normal brain. No CD46 staining was observed in normal human brain but strong staining was observed in GBM specimens. The H-294 rabbit anti-human CD46 antibody (Santa Cruz Biotechnology) was used for staining, followed by detection with the Envision+ system (Dako North America).

Positive CD46 staining was also observed for 41/50 cases (82%) of mesothelioma with 31/50 showing strong staining (62%) (FIG. 47). In pancreatic cancer, positive CD46 staining was observed in 28/50 cases (56%) (FIG. 48). In glioblastoma multiforme (GBM), positive staining was observed in 30/40 (75%) cases (FIG. 49).

Positive staining was also observed in other tumors including but are not limited to bladder cancer, ovarian cancer, stomach cancer, lung cancer, liver cancer, breast cancer, and lymphoma.

CD46 ADC is Effective Against Other Tumors.

Figure 50:
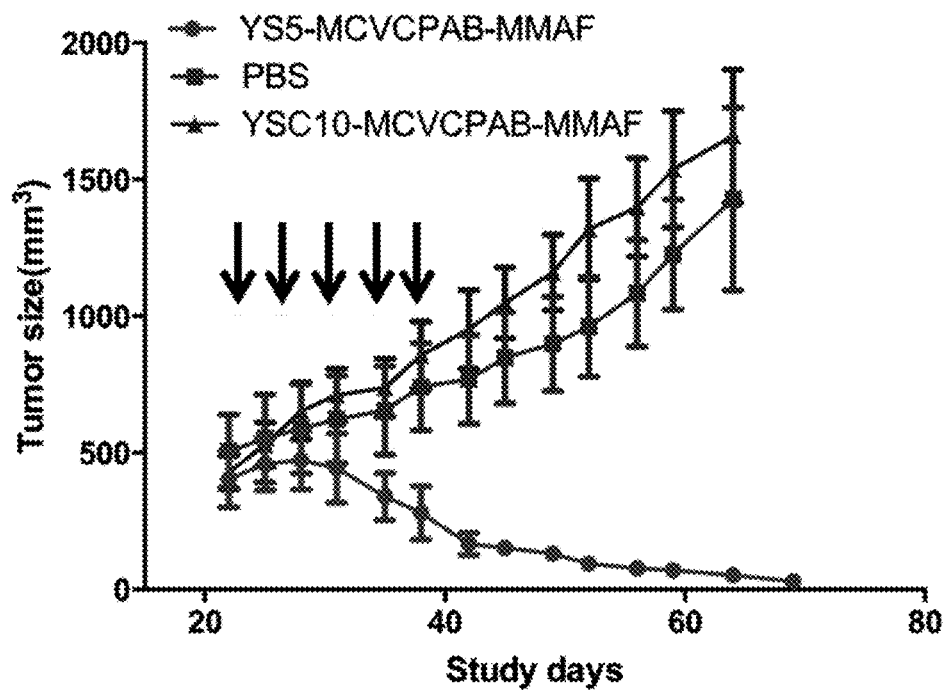
FIG. 50 illustrates in vivo inhibition of mesothelioma (M28) xenograft growth by CD46 ADC. YS5-mcvcpab-MMAF was injected every 3-4 days at 5 mg/kg for a total of 5 times (indicated by arrows). Tumor volumes were measured by caliper. YSC10 is a control non-binding human IgG1.

In addition to in vitro studies, we performed an in vivo study of CD46 ADC on mesothelioma xenografts carried in NSG mice. As shown in FIG. 50, YS5-mcvcpab-MMAF is highly effective in inhibiting tumor xenograft development.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated recombinant human antibody that specifically binds CD46 comprising VH CDR1 comprising the amino acid sequence of SEQ ID NO. 80, VH CDR2 comprising the amino acid sequence of SEQ ID NO. 82, VH CDR3 comprising the amino acid sequence of SEQ ID NO. 84, VL CDR1 comprising the amino acid sequence of SEQ ID NO. 227, VL CDR2 comprising the amino acid sequence of SEQ ID NO. 229, and VL CDR3 comprising the amino acid sequence of SEQ ID NO. 231.

2. The antibody of claim 1, wherein said isolated recombinant human antibody is an intact immunoglobulin selected from the group consisting of IgA, IgE, and IgG.

3. The antibody of claim 2, wherein said isolated recombinant human antibody comprises an IgG1.

4. The antibody of claim 1, wherein said isolated recombinant human antibody is an antibody fragment that specifically binds the cells that express or overexpress CD46 and wherein the antibody fragment is selected from the group consisting of Fv, Fab, (Fab')2, (Fab')3, IgGΔCH2, a minibody, and a single chain antibody.

5. An immunoconjugate comprising an antibody according to claim 1 and one or more than one effector wherein each effector is independently selected from the group consisting of a second antibody, a detectable label, a cytotoxic agent, a cytostatic agent, a liposome containing a drug, a radionuclide, a drug, a prodrug, a viral particle, a cytokine, and a chelate.

6. The immunoconjugate of claim 5, wherein said antibody is attached to the one or more than one effector, wherein each effector is selected from the group consisting of the cytotoxic agent, the cytostatic agent, and combinations thereof.

7. An immunoconjugate comprising an antibody according to claim 1, one or more than one linker, and one or more than one drug.

8. The immunoconjugate of claim 7, wherein said one or more than one drug is selected from the group consisting of an anti-cancer drug, a microtubule inhibitor, a tubulin inhibitor, a DNA-damaging agent, a polymerase inhibitor, and combinations thereof.

9. The immunoconjugate of claim 7, wherein said drug is selected from the group consisting of an auristatin, Dolastatin-10, synthetic derivatives of a natural product Dolastatin-10, maytansine, a maytansine derivative, Monomethylauristatin F (MMAF), Auristatin E (AE), Monomethylauristatin E (MMAE), vcMMAE, vcMMAF, Mertansine (DM1), DM3, and DM4.

10. The immunoconjugate of claim 7, wherein the drug comprises a calicheamicin, a calicheamicin analog, a duocarmycin, a pyrrolobenzodiazepine, or a pyrrolobenzodiazepine dimer.

11. The immunoconjugate of claim 7, wherein the one or more than one drug comprises duocarmycin A, duocarmycin B1, duocarmycin B2, duocarmycin C1, duocarmycin C2, duocarmycin D, duocarmycin SA, Centanamycin, Rachelmycin, Adozelesin, Bizelesin, Carzelesin, or combinations thereof.

12. The immunoconjugate of claim 7, wherein the drug comprises anthramycin, dimers of anthramyin, mazethramycin, dimers of mazethramycin, tomaymycin, dimers of tomaymycin, prothracarcin, dimers of prothracarcin, chicamycin, dimers of chicamycin, neothramycin A, dimers of neothramycin A, neothramycin B, dimers of neothramycin B, DC-81, dimers of DC-81, sibiromycin, dimers of sibiromycin, porothramycin A, dimers of porothramycin A, porothramycin B, dimers of porothramycin B, sibanomycin, dimers of sibanomycin, abbeymycin, dimers of abbeymycin, SG2000, or SG2285.

13. The immunoconjugate of claim 7, wherein said drug is selected from the group consisting of auristatin, dolastatin, colchicine, combretastatin, mTOR/PI3K inhibitors fluorouracil, capecitabine, 5-trifluoromethy 1-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitosourea (BCNU), 1-(2-chloroethyl)-3-cyclohexy 1-1-nitrosourea (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, vinflunine, retinoic acid, a retinoic acid derivative, vinblastine, a camptothecin derivative, interferon, tamoxifen, and taxol.

14. The immunoconjugate of claim 5, wherein said antibody is an antibody fragment that specifically binds the cells that express or overexpress CD46 and wherein the antibody fragment is selected from the group consisting of Fv, Fab, (Fab')2, (Fab')3, IgGΔCH2, a minibody, and a single chain antibody.

15. The immunoconjugate of claim 7, wherein said antibody is an antibody fragment that specifically binds the cells that express or overexpress CD46 and wherein the antibody fragment is selected from the group consisting of Fv, Fab, (Fab')2, (Fab')3, IgGΔCH2, a minibody, and a single chain antibody.

16. The antibody of claim 1, wherein the isolated recombinant human antibody comprises a variable light (VL) chain of a YS5 antibody comprising the amino acid sequence of SEQ ID NO:22 and a variable heavy (VH) chain of a YS5 antibody comprising the amino acid sequence of SEQ ID NO:1.

17. The immunoconjugate of claim 5, wherein the antibody comprises a variable light (VL) chain of a YS5 antibody comprising the amino acid sequence of SEQ ID NO:22 and a variable heavy (VH) chain of a YS5 antibody comprising the amino acid sequence of SEQ ID NO:1.

18. The immunoconjugate of claim 7, wherein said antibody comprises a variable light (VL) chain of a YS5 antibody comprising the amino acid sequence of SEQ ID NO:22 and a variable heavy (VH) chain of a YS5 antibody comprising the amino acid sequence of SEQ ID NO:1.

19. A pharmaceutical formulation said formulation comprising: a pharmaceutically acceptable excipient and the antibody according to claim 1.

20. The formulation according to claim 19, wherein said formulation is formulated for nasal administration, rectal administration, intraperitoneal injection, intravascular injection, subcutaneous injection, transcutaneous administration, or intramuscular injection.

21. The formulation of claim 19, wherein said antibody is an antibody fragment that specifically binds the cells that express or overexpress CD46 and wherein the antibody fragment is selected from the group consisting of Fv, Fab, (Fab')2, (Fab')3, IgGΔCH2, a minibody, and a single chain antibody.

22. The formulation of claim 19, wherein the antibody comprises a variable light (VL) chain of a YS5 antibody comprising the amino acid sequence of SEQ ID NO:22 and a variable heavy (VH) chain of a YS5 antibody comprising the amino acid sequence of SEQ ID NO: 1.

23. A method of inhibiting growth and/or proliferation of a cancer cell that expresses or overexpresses CD46, said method comprising:
contacting the cancer cell with immunoconjugate comprising the antibody according to claim 1 and an effector
wherein the effector has cytostatic or cytotoxic activity.

24. The method of claim 23, wherein the cancer cell that expresses or overexpresses CD46 is a metastatic castration resistant prostate cancer cell.

25. The method of claim 23, wherein said antibody is an antibody fragment that specifically binds the cancer cells that express or overexpress CD46 and wherein the antibody fragment is selected from the group consisting of Fv, Fab, (Fab')2, (Fab')3, IgGΔCH2, a minibody, and a single chain antibody.

26. The method of claim 23, wherein the antibody comprises a variable light (VL) chain of a YS5 antibody comprising the amino acid sequence of SEQ ID NO:22 and a variable heavy (VH) chain of a YS5 antibody comprising the amino acid sequence of SEQ ID NO:1.

27. An immunoconjugate comprising:
an isolated recombinant human antibody that specifically binds CD46 comprising VH CDR1 comprising the amino acid sequence of SEQ ID NO. 80, VH CDR2 comprising the amino acid sequence of SEQ ID NO. 82, VH CDR3 comprising the amino acid sequence of SEQ ID NO. 84, VL CDR1 comprising the amino acid sequence of SEQ ID NO. 227, VL CDR2 SEQ ID NO. 229, and VL CDR3 comprising the amino acid sequence of SEQ ID NO. 231; and
one or more than one effector comprising a drug selected from Monomethylauristatin F (MMAF), Auristatin E (AE), Monomethylauristatin E (MMAE), vcMMAE, vcMMAF, and combinations thereof.

28. The immunoconjugate of claim 27, wherein the isolated recombinant human antibody is covalently coupled to each effector through a MC-vc-PAB linker.

29. The immunoconjugate of claim 27, wherein the immunoconjugate comprises two effectors.

30. The immunoconjugate of claim 27, wherein the immunoconjugate comprises four effectors.

31. The immunoconjugate of claim 27, wherein said isolated human antibody comprises an IgG1.

32. The immunoconjugate of claim 27, wherein the isolated recombinant human antibody comprises a variable light (VL) chain of a YS5 antibody comprising the amino acid sequence of SEQ ID NO:22 and a variable heavy (VH) chain of a YS5 antibody comprising the amino acid sequence of SEQ ID NO:1.

33. The immunoconjugate of claim 27, wherein said effector is Monomethylauristatin E (MMAE).

34. The immunoconjugate of claim 33, wherein the isolated recombinant human antibody is covalently coupled to each effector through a MC-vc-PAB linker.

35. The immunoconjugate of claim 33, wherein the isolated recombinant human antibody comprises a variable light (VL) chain of a YS5 antibody comprising the amino acid sequence of SEQ ID NO:22 and a variable heavy (VH) chain of a YS5 antibody comprising the amino acid sequence of SEQ ID NO:1.

36. The immunoconjugate of claim 35, wherein the isolated recombinant human antibody is covalently coupled to each effector through a MC-vc-PAB linker.

37. The immunoconjugate of claim 27, wherein said isolated recombinant human antibody is an antibody fragment that specifically binds cancer cells that express or overexpress CD46 and wherein the antibody fragment is selected from the group consisting of Fv, Fab, (Fab')2, (Fab')3, IgGΔCH2, a minibody, and a single chain antibody.

38. An immunoconjugate comprising:
an isolated recombinant human antibody that specifically binds CD46 comprising VH CDR1 comprising the amino acid sequence of SEQ ID NO. 80, VH CDR2 comprising the amino acid sequence of SEQ ID NO. 82, VH CDR3 comprising the amino acid sequence of SEQ ID NO. 84, VL CDR1 comprising the amino acid sequence of SEQ ID NO. 227, VL CDR2 comprising the amino acid sequence of SEQ ID NO. 229, and VL CDR3 comprising the amino acid sequence of SEQ ID NO. 231; and
an effector comprising Monomethylauristatin E (MMAE) or Monomethylauristatin F (MMAF);
wherein said isolated recombinant human antibody is an intact IgG immunoglobulin.

39. The immunoconjugate of claim 38, wherein the isolated recombinant human antibody is covalently coupled to the effector through a MC-vc-PAB linker.

40. The immunoconjugate of claim 38, wherein the immunoconjugate comprises two effectors.

41. The immunoconjugate of claim 38, wherein said isolated human antibody comprises an IgG1.

42. The immunoconjugate of claim 38, wherein the isolated recombinant human antibody comprises a variable light (VL) chain of a YS5 antibody comprising the amino acid sequence of SEQ ID NO:22 and a variable heavy (VH) chain of a YS5 antibody comprising the amino acid sequence of SEQ ID NO:1.

43. The immunoconjugate of claim 38, wherein said isolated recombinant human antibody is an antibody fragment that specifically binds cells that express or overexpress CD46 and wherein the antibody fragment is selected from the group consisting of Fv, Fab, (Fab')2, (Fab')3, IgGΔCH2, a minibody, and a single chain antibody.

* * * * *

SEQUENCE LISTING

```
<160> NUMBER OF SEQ ID NOS: 370

<210> SEQ ID NO 1
<211> LENGTH: 116
<212> TYPE: PRT
<213> ORGANISM: Artificial Sequence
<220> FEATURE:
<223> OTHER INFORMATION: Synthetic antibody VH domain

<400> SEQUENCE: 1

Gln Val Gln Leu Val Gln Ser Gly Gly Gly Val Val Gln Pro Gly Arg
1               5                   10                  15

Ser Leu Arg Leu Ala Cys Ala Ala Ser Gly Leu Thr Val Asn Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gly Tyr Phe Asp Leu Trp Gly Arg Gly Thr Leu Val
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: Synthetic antibody VH domain
```

<400> SEQUENCE: 2

```
Gln Val Gln Leu Val Gln Ser Gly Gly Gly Val Val Gln Pro Gly Arg
1               5                   10                  15

Ser Leu Arg Leu Ala Cys Ala Ala Ser Gly Phe Thr Val Asn Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gly Tyr Phe Asp Leu Trp Gly Arg Gly Thr Leu Val
            100                 105                 110

Thr Val Ser Ser
            115
```

<210> SEQ ID NO 3
<211> LENGTH: 116
<212> TYPE: PRT
<213> ORGANISM: Artificial Sequence
<220> FEATURE:
<223> OTHER INFORMATION: Synthetic antibody VH domain

<400> SEQUENCE: 3

```
Gln Val Gln Leu Val Gln Ser Gly Gly Gly Val Val Gln Pro Gly Arg
1               5                   10                  15

Ser Leu Arg Leu Ala Cys Ala Ala Ser Gly Phe Thr Val Asn Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gly Tyr Phe Asp Leu Trp Gly Arg Gly Thr Leu Val
            100                 105                 110

Thr Val Ser Ser
            115
```

<210> SEQ ID NO 4
<211> LENGTH: 116
<212> TYPE: PRT
<213> ORGANISM: Artificial Sequence
<220> FEATURE:
<223> OTHER INFORMATION: Synthetic antibody VH domain

<400> SEQUENCE: 4

```
Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45
```

Ala Phe Ile Arg Ser Asp Gly Ser Lys Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Asn Tyr Phe Asp Ser Trp Gly Gln Gly Thr Leu Val
                100                 105                 110

Thr Val Ser Ser
        115

<210> SEQ ID NO 5
<211> LENGTH: 120
<212> TYPE: PRT
<213> ORGANISM: Artificial Sequence
<220> FEATURE:
<223> OTHER INFORMATION: Synthetic antibody VH domain

<400> SEQUENCE: 5

Gln Val Gln Leu Val Glu Ser Gly Gly Gly Val Val Gln Pro Gly Arg
 1                5                  10                  15

Ser Leu Arg Leu Ser Cys Ala Ala Ser Gly Phe Thr Phe Ser Thr Tyr
                 20                  25                  30

Gly Met His Trp Val Arg Gln Ala Pro Gly Lys Gly Leu Glu Trp Leu
             35                  40                  45

Ser Phe Ile Ser Tyr Asp Gly Asp Glu Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Trp Cys
                 85                  90                  95

Ala Lys Ala Ser Gly Tyr Gly Met Gly Ile Leu Asp Tyr Trp Gly Gln
                100                 105                 110

Gly Thr Leu Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: Synthetic antibody VH domain

<400> SEQUENCE: 6

Glu Val Gln Leu Val Glu Ser Gly Gly Gly Leu Val Gln Pro Gly Gly
 1                5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
             35                  40                  45

Ser Tyr Ile Ser Ser Ser Gly Ser Thr Ile Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Gly Arg Ile Ala Ala Gly Arg Arg Tyr Trp Gly
            100                 105                 110

Gln Gly Thr Leu Val Thr Val Ser Ser
        115                 120

<210> SEQ ID NO 7
<211> LENGTH: 121
<212> TYPE: PRT
<213> ORGANISM: Artificial Sequence
<220> FEATURE:
<223> OTHER INFORMATION: Synthetic antibody VH domain

<400> SEQUENCE: 7

Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Ile Ala Ala Ala Gly Arg His Tyr Trp Gly
            100                 105                 110

Gln Gly Thr Leu Val Thr Val Ser Ser
        115                 120

<210> SEQ ID NO 8
<211> LENGTH: 121
<212> TYPE: PRT
<213> ORGANISM: Artificial Sequence
<220> FEATURE:
<223> OTHER INFORMATION: Synthetic antibody VH domain

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Ile Ala Ala Ala Gly Arg His Tyr Trp Gly
            100                 105                 110

Gln Gly Thr Leu Val Thr Val Ser Ser
        115                 120

<210> SEQ ID NO 9
<211> LENGTH: 127
<212> TYPE: PRT

-continued

<213> ORGANISM: Artificial Sequence
<220> FEATURE:
<223> OTHER INFORMATION: Synthetic antibody VH domain

<400> SEQUENCE: 9

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asp Ile Lys Gln Asp Gly Ser Glu Lys Tyr Tyr Val Asp Ser Val
    50                  55                  60

Lys Gly Arg Phe Thr Ile Ser Gly Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Val Gly Ser Thr Ala Ile Asn Tyr Val Arg Ala Tyr Thr
            100                 105                 110

Trp Phe Asp Pro Trp Gly Gln Gly Thr Leu Val Thr Val Ser Ser
        115                 120                 125

<210> SEQ ID NO 10
<211> LENGTH: 122
<212> TYPE: PRT
<213> ORGANISM: Artificial Sequence
<220> FEATURE:
<223> OTHER INFORMATION: Synthetic antibody VH domain

<400> SEQUENCE: 10

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Ser Thr Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gln Gly Leu Tyr Ser Ser Gly Trp Ala Asn Trp Phe Asp Pro Arg
            100                 105                 110

Gly Gln Gly Thr Leu Val Thr Val Ser Ser
        115                 120

<210> SEQ ID NO 11
<211> LENGTH: 123
<212> TYPE: PRT
<213> ORGANISM: Artificial Sequence
<220> FEATURE:
<223> OTHER INFORMATION: Synthetic antibody VH domain

<400> SEQUENCE: 11

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

```
Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Met Gly Leu Ala Ala Gly Leu Asp Ala Phe Asp Ile
            100                 105                 110

Trp Gly Gln Gly Thr Thr Val Thr Val Ser Ser
        115                 120

<210> SEQ ID NO 12
<211> LENGTH: 117
<212> TYPE: PRT
<213> ORGANISM: Artificial Sequence
<220> FEATURE:
<223> OTHER INFORMATION: Synthetic antibody VH domain

<400> SEQUENCE: 12

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Thr Ser Thr Asn Thr Leu Tyr
65                  70                  75                  80

Leu Gln Met Asn Ser Leu Arg Ala Asp Asp Thr Ala Val Tyr Tyr Cys
                85                  90                  95

Gly Arg Glu Ser Ser Gly Ser Pro Gly Val Trp Gly Gln Gly Thr Thr
            100                 105                 110

Val Thr Val Ser Ser
        115

<210> SEQ ID NO 13
<211> LENGTH: 122
<212> TYPE: PRT
<213> ORGANISM: Artificial Sequence
<220> FEATURE:
<223> OTHER INFORMATION: Synthetic antibody VH domain

<400> SEQUENCE: 13

Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Thr Asp Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Ile Tyr Tyr Cys Ala
                85                  90                  95

Arg Asp Arg Gly Thr Ser Gly Tyr Asp Trp Ala Trp Phe Asp Leu Trp
            100                 105                 110

Gly Gln Gly Thr Leu Val Thr Val Ser Ser
            115                 120

<210> SEQ ID NO 14
<211> LENGTH: 123
<212> TYPE: PRT
<213> ORGANISM: Artificial Sequence
<220> FEATURE:
<223> OTHER INFORMATION: Synthetic antibody VH domain

<400> SEQUENCE: 14

Gln Val Gln Leu Gln Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Met Gln Met Asn Ser Leu Arg Ala Glu Asp Thr Ala Val Tyr Tyr Cys
                85                  90                  95

Ala Lys Asp Arg Tyr Tyr Tyr Gly Ser Gly Lys Asp Ala Phe Asp Ile
            100                 105                 110

Trp Gly Arg Gly Thr Met Val Thr Val Ser Ser
            115                 120

<210> SEQ ID NO 15
<211> LENGTH: 118
<212> TYPE: PRT
<213> ORGANISM: Artificial Sequence
<220> FEATURE:
<223> OTHER INFORMATION: Synthetic antibody VH domain

<400> SEQUENCE: 15

Gln Val Gln Leu Val Glu Ser Gly Gly Gly Leu Val Gln Pro Gly Gly
1               5                   10                  15

Ser Leu Gly Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
            35                  40                  45

Ala Asn Val Arg Gln Asp Gly Gly Gln Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Val Tyr Phe Cys
                85                  90                  95

Val Ser Gln Arg Asn Ser Gly Glu His Asp Tyr Trp Gly Gln Gly Thr
            100                 105                 110

Leu Val Thr Val Ser Ser
            115
```

```
<210> SEQ ID NO 16
<211> LENGTH: 121
<212> TYPE: PRT
<213> ORGANISM: Artificial Sequence
<220> FEATURE:
<223> OTHER INFORMATION: Synthetic antibody VH domain

<400> SEQUENCE: 16
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Ile Ala Ala Ala Gly Arg His Tyr Trp Gly
            100                 105                 110

Gln Gly Thr Leu Val Thr Val Ser Ser
        115                 120

```
<210> SEQ ID NO 17
<211> LENGTH: 121
<212> TYPE: PRT
<213> ORGANISM: Artificial Sequence
<220> FEATURE:
<223> OTHER INFORMATION: Synthetic antibody VH domain

<400> SEQUENCE: 17
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Ile Ala Ala Ala Gly Arg Asn Tyr Trp Gly
            100                 105                 110

Gln Gly Thr Leu Val Thr Val Ser Ser
        115                 120

```
<210> SEQ ID NO 18
<211> LENGTH: 121
<212> TYPE: PRT
<213> ORGANISM: Artificial Sequence
<220> FEATURE:
<223> OTHER INFORMATION: Synthetic antibody VH domain

<400> SEQUENCE: 18
```

Gln Val Gln Leu Gln Glu Ser Gly Gly Gly Val Val Arg Pro Gly Gly
1               5                   10                  15

```
Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Gly Arg Ile Ala Ala Gly Arg His Tyr Trp Gly
                100                 105                 110

Gln Gly Thr Leu Val Thr Val Ser Ser
            115                 120

<210> SEQ ID NO 19
<211> LENGTH: 121
<212> TYPE: PRT
<213> ORGANISM: Artificial Sequence
<220> FEATURE:
<223> OTHER INFORMATION: Synthetic antibody VH domain

<400> SEQUENCE: 19

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Ser Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Lys Ala Glu Asp Thr Ala Val Tyr Tyr Cys
                 85                  90                  95

Ala Arg Asp Ile Thr Asp Val Val Gly Val Ser Phe Asp Tyr Trp Gly
                100                 105                 110

Gln Gly Thr Leu Val Thr Val Ser Ser
            115                 120

<210> SEQ ID NO 20
<211> LENGTH: 123
<212> TYPE: PRT
<213> ORGANISM: Artificial Sequence
<220> FEATURE:
<223> OTHER INFORMATION: Synthetic antibody VH domain

<400> SEQUENCE: 20

Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Glu Tyr Tyr Cys
                 85                  90                  95

Ala Lys Val Met Gly Leu Ala Ala Gly Leu Asp Ala Phe Asp Ile
            100                 105                 110

Trp Gly Gln Gly Thr Leu Val Thr Val Ser Ser
            115                 120

<210> SEQ ID NO 21
<211> LENGTH: 123
<212> TYPE: PRT
<213> ORGANISM: Artificial Sequence
<220> FEATURE:
<223> OTHER INFORMATION: Synthetic antibody VH domain

<400> SEQUENCE: 21

Glu Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Phe
                 20                  25                  30

Gly Met His Trp Val Arg Arg Ala Pro Gly Lys Gly Leu Glu Trp Val
             35                  40                  45

Ala Val Ile Ser Tyr Asp Gly Ser Asn Gln Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Ser Arg Pro Gly Gly Gly Tyr Ala Ser Gly Ser Thr Val Ala Tyr
            100                 105                 110

Trp Gly Gln Gly Thr Leu Val Thr Val Ser Ser
            115                 120

<210> SEQ ID NO 22
<211> LENGTH: 109
<212> TYPE: PRT
<213> ORGANISM: Artificial Sequence
<220> FEATURE:
<223> OTHER INFORMATION: Synthetic antibody VL domain

<400> SEQUENCE: 22

Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
             35                  40                  45

Leu Ile Tyr Gly Asn Asn Asn Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Ser Ser Tyr Thr Ser Gly
                 85                  90                  95

Thr Trp Leu Phe Gly Gly Gly Thr Lys Leu Thr Val Leu
            100                 105
```

```
<210> SEQ ID NO 23
<211> LENGTH: 109
<212> TYPE: PRT
<213> ORGANISM: Artificial Sequence
<220> FEATURE:
<223> OTHER INFORMATION: Synthetic antibody VL domain

<400> SEQUENCE: 23

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Thr Ser Gly
                85                  90                  95

Thr Trp Leu Phe Gly Gly Gly Thr Lys Leu Thr Val Leu
            100                 105

<210> SEQ ID NO 24
<211> LENGTH: 109
<212> TYPE: PRT
<213> ORGANISM: Artificial Sequence
<220> FEATURE:
<223> OTHER INFORMATION: Synthetic antibody VL domain

<400> SEQUENCE: 24

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Thr Ser Gly
                85                  90                  95

Thr Trp Leu Phe Gly Gly Gly Thr Lys Leu Thr Val Leu
            100                 105

<210> SEQ ID NO 25
<211> LENGTH: 107
<212> TYPE: PRT
<213> ORGANISM: Artificial Sequence
<220> FEATURE:
<223> OTHER INFORMATION: Synthetic antibody VL domain

<400> SEQUENCE: 25

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Gln Ser Gly Val Pro Ser Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Ala Ser Tyr Pro Leu
                 85                  90                  95

Thr Phe Gly Gly Gly Thr Lys Val Asp Ile Lys
                100                 105

<210> SEQ ID NO 26
<211> LENGTH: 109
<212> TYPE: PRT
<213> ORGANISM: Artificial Sequence
<220> FEATURE:
<223> OTHER INFORMATION: Synthetic antibody VL domain

<400> SEQUENCE: 26

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Val
                 20                  25                  30

Ser Trp Phe Gln Gln Lys Pro Gly Gln Ala Pro Val Phe Val Met Tyr
             35                  40                  45

Gly Gln Asn Asn Arg Pro Ser Gly Ile Ser Glu Arg Phe Ser Gly Ser
 50                  55                  60

Ser Ser Gly Asn Thr Ala Ser Leu Ile Ile Thr Gly Ala Gln Ala Glu
 65                  70                  75                  80

Asp Glu Ala Asp Tyr Tyr Cys His Ser Arg Asp Ser Ser Gly Thr His
                 85                  90                  95

Leu Arg Val Phe Gly Gly Gly Thr Lys Leu Thr Val Leu
                100                 105

<210> SEQ ID NO 27
<211> LENGTH: 110
<212> TYPE: PRT
<213> ORGANISM: Artificial Sequence
<220> FEATURE:
<223> OTHER INFORMATION: Synthetic antibody VL domain

<400> SEQUENCE: 27

Gln Ser Ala Leu Thr Gln Pro Pro Ser Ala Ser Ala Thr Pro Gly Gln
 1               5                  10                  15

Arg Val Thr Ile Ser Cys Ser Arg Thr Ser Asn Ile Gly Ser Asn
                 20                  25                  30

His Val Tyr Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Asp Ser Leu
                 85                  90                  95

Ser Gly Glu Val Phe Gly Gly Gly Thr Lys Leu Thr Val Leu
                100                 105                 110

<210> SEQ ID NO 28
<211> LENGTH: 109
<212> TYPE: PRT
```

<213> ORGANISM: Artificial Sequence
<220> FEATURE:
<223> OTHER INFORMATION: Synthetic antibody VL domain

<400> SEQUENCE: 28

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Thr His
                85                  90                  95

Leu Glu Val Phe Gly Gly Gly Thr Lys Val Thr Val Leu
            100                 105

<210> SEQ ID NO 29
<211> LENGTH: 107
<212> TYPE: PRT
<213> ORGANISM: Artificial Sequence
<220> FEATURE:
<223> OTHER INFORMATION: Synthetic antibody VL domain

<400> SEQUENCE: 29

Ser Ser Glu Leu Thr Gln Asp Pro Ala Val Ser Val Ala Leu Gly Gln
1               5                   10                  15

Thr Val Arg Ile Thr Cys Gln Gly Asp Thr Leu Ser Thr Tyr Tyr Ala
            20                  25                  30

Asn Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys His Ser Arg Asp Ile Ser Gly Asn Tyr
                85                  90                  95

Leu Phe Ala Ser Gly Thr Lys Leu Thr Val Leu
            100                 105

<210> SEQ ID NO 30
<211> LENGTH: 110
<212> TYPE: PRT
<213> ORGANISM: Artificial Sequence
<220> FEATURE:
<223> OTHER INFORMATION: Synthetic antibody VL domain

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Ser Arg Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

```
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Tyr Val Phe Gly Thr Gly Thr Lys Val Thr Val Leu
                100                 105                 110
```

<210> SEQ ID NO 31
<211> LENGTH: 107
<212> TYPE: PRT
<213> ORGANISM: Artificial Sequence
<220> FEATURE:
<223> OTHER INFORMATION: Synthetic antibody VL domain

<400> SEQUENCE: 31

```
Lys Ile Val Leu Thr Gln Ser Pro Ser Ser Leu Ser Ala Ser Val Gly
1               5                   10                  15

Asp Thr Val Thr Ile Ala Cys Arg Ala Ser Arg Asp Ile Arg Asn Asp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Glu Phe Ile Leu Thr Ile Ser Ser Leu Gln Pro
65                  70                  75                  80

Glu Asp Phe Ala Thr Tyr Tyr Cys His Arg Leu Asn Ser Tyr Pro Leu
                85                  90                  95

Thr Phe Gly Gly Gly Thr Lys Val Asp Ile Lys
                100                 105
```

<210> SEQ ID NO 32
<211> LENGTH: 111
<212> TYPE: PRT
<213> ORGANISM: Artificial Sequence
<220> FEATURE:
<223> OTHER INFORMATION: Synthetic antibody VL domain

<400> SEQUENCE: 32

```
Asn Phe Met Leu Thr Gln Pro Ala Ser Leu Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Tyr Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Pro Trp Val Phe Gly Gly Gly Thr Lys Leu Thr Val Leu
                100                 105                 110
```

<210> SEQ ID NO 33
<211> LENGTH: 106
<212> TYPE: PRT
<213> ORGANISM: Artificial Sequence
<220> FEATURE:
<223> OTHER INFORMATION: Synthetic antibody VL domain

<400> SEQUENCE: 33

Ser Tyr Val Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Gln
                85                  90                  95

Phe Gly Gly Gly Thr Lys Leu Thr Val Leu
            100                 105

<210> SEQ ID NO 34
<211> LENGTH: 108
<212> TYPE: PRT
<213> ORGANISM: Artificial Sequence
<220> FEATURE:
<223> OTHER INFORMATION: Synthetic antibody VL domain

<400> SEQUENCE: 34

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Arg Pro Gly Gln Ala Pro Ile Leu Val Leu Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 35
<211> LENGTH: 110
<212> TYPE: PRT
<213> ORGANISM: Artificial Sequence
<220> FEATURE:
<223> OTHER INFORMATION: Synthetic antibody VL domain

<400> SEQUENCE: 35

Gln Ser Val Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Tyr Val Ser Trp Tyr Gln Gln Asn Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Thr Leu Val Phe Gly Gly Gly Thr Lys Val Thr Val Leu
            100                 105                 110

<210> SEQ ID NO 36
<211> LENGTH: 107
<212> TYPE: PRT
<213> ORGANISM: Artificial Sequence
<220> FEATURE:
<223> OTHER INFORMATION: Synthetic antibody VL domain

<400> SEQUENCE: 36

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
            35                  40                  45

Glu Asn Ser Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Trp Asp Ser Ser Gly Asn His Val
                85                  90                  95

Val Phe Gly Gly Gly Thr Lys Leu Thr Val Leu
            100                 105

<210> SEQ ID NO 37
<211> LENGTH: 107
<212> TYPE: PRT
<213> ORGANISM: Artificial Sequence
<220> FEATURE:
<223> OTHER INFORMATION: Synthetic antibody VL domain

<400> SEQUENCE: 37

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Leu Glu Ile Lys
            100                 105

<210> SEQ ID NO 38
<211> LENGTH: 111
<212> TYPE: PRT
<213> ORGANISM: Artificial Sequence
<220> FEATURE:
<223> OTHER INFORMATION: Synthetic antibody VL domain

```
<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asp Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Ile Tyr Tyr Cys Met Gln Gly
                85                  90                  95

Leu Gln Thr Pro Ser Phe Gly Gln Gly Thr Lys Leu Glu Ile Lys
            100                 105                 110

<210> SEQ ID NO 39
<211> LENGTH: 109
<212> TYPE: PRT
<213> ORGANISM: Artificial Sequence
<220> FEATURE:
<223> OTHER INFORMATION: Synthetic antibody VL domain

<400> SEQUENCE: 39

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Pro Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Thr His
                85                  90                  95

Arg Gly Val Phe Gly Gly Gly Thr Lys Leu Thr Val Leu
            100                 105

<210> SEQ ID NO 40
<211> LENGTH: 107
<212> TYPE: PRT
<213> ORGANISM: Artificial Sequence
<220> FEATURE:
<223> OTHER INFORMATION: Synthetic antibody VL domain

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Ser Ile Ser Thr Tyr
            20                  25                  30

Leu Ser Trp Tyr Gln Gln Lys Pro Gly Lys Ala Pro Lys Leu Leu Ile
            35                  40                  45

Tyr Asp Ala Ser Arg Leu Gln Asn Gly Val Pro Ser Arg Phe Ser Gly
        50                  55                  60

Ser Gly Ser Asp Thr Asp Phe Thr Leu Thr Ile Ser Ser Leu Gln Pro
65                  70                  75                  80
```

Glu Asp Phe Ala Thr Tyr Phe Cys Gln Gln Ser Tyr Asn Pro Pro Trp
                85                  90                  95

Thr Phe Gly Gln Gly Thr Lys Leu Glu Ile Lys
            100                 105

<210> SEQ ID NO 41
<211> LENGTH: 111
<212> TYPE: PRT
<213> ORGANISM: Artificial Sequence
<220> FEATURE:
<223> OTHER INFORMATION: Synthetic antibody VL domain

<400> SEQUENCE: 41

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Tyr Tyr Tyr Cys Ser Ser Tyr Thr Ser Ser
                85                  90                  95

Ser Asp Pro Trp Val Phe Gly Gly Gly Thr Gln Leu Thr Val Leu
            100                 105                 110

<210> SEQ ID NO 42
<211> LENGTH: 107
<212> TYPE: PRT
<213> ORGANISM: Artificial Sequence
<220> FEATURE:
<223> OTHER INFORMATION: Synthetic antibody VL domain

<400> SEQUENCE: 42

Asn Ile Gln Met Thr Gln Ser Pro Ser Ser Leu Ser Ala Ser Val Gly
1               5                   10                  15

Asp Arg Val Thr Ile Thr Cys Arg Ala Gly Gln Pro Ile Ser Thr Tyr
                20                  25                  30

Val Asn Trp Tyr Gln His Lys Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Gly Gly Ser Ala Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Leu Leu
                85                  90                  95

Thr Phe Gly Asp Gly Thr Lys Val Glu Ile Lys
            100                 105

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide linker

<400> SEQUENCE: 43

Gly Gly Gly Gly Ser Gly Gly Gly Ser Gly Gly Gly Ser
1               5                   10                  15

<210> SEQ ID NO 44
<211> LENGTH: 242
<212> TYPE: PRT
<213> ORGANISM: Artificial Sequence
<220> FEATURE:
<223> OTHER INFORMATION: Synthetic antibody

<400> SEQUENCE: 44

Gln Val Gln Leu Gln Glu Ser Gly Gly Gly Leu Val Lys Pro Gly Gly
1               5                   10                  15

Pro Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ser Thr Leu Ser Arg Ser Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ile Ala Val Ala Gly Asn Tyr Phe Asp Tyr Trp Gly Gln Gly
            100                 105                 110

Thr Leu Val Thr Val Ser Ser Gly Gly Gly Ser Gly Gly Gly
        115                 120                 125

Ser Gly Gly Gly Ser Ser Tyr Val Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Glu Arg Pro Gly Gln Ala
                165                 170                 175

Pro Leu Leu Val Ile Tyr Gly Lys Asn Asn Arg Pro Ser Gly Ile Pro
            180                 185                 190

Asp Arg Phe Ser Gly Ser Asn Ser Gly Ser Thr Ala Thr Leu Thr Ile
        195                 200                 205

Ser Arg Val Glu Ala Gly Asp Glu Asp Tyr Tyr Cys Gln Val Trp
    210                 215                 220

Asp Ser Ile Asn Glu Gln Val Val Phe Gly Gly Thr Lys Val Thr
225                 230                 235                 240

Val Leu

<210> SEQ ID NO 45
<211> LENGTH: 241
<212> TYPE: PRT
<213> ORGANISM: Artificial Sequence
<220> FEATURE:
<223> OTHER INFORMATION: Synthetic antibody

<400> SEQUENCE: 45

Gln Val Gln Leu Val Gln Ser Gly Gly Gly Val Val Gln Pro Gly Arg
1               5                   10                  15

Ser Leu Arg Leu Ser Cys Ala Ala Thr Gly Ile Pro Phe Ser Gly Ser
            20                  25                  30

Gly Met His Trp Val Arg Gln Ala Pro Gly Lys Gly Leu Glu Trp Val
         35                  40                  45

Thr Met Ile Trp Tyr Asp Gly Ser Asn Lys Phe Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Phe Cys
                 85                  90                  95

Ala Arg Asp Lys Gly Val Arg Ser Met Asp Val Trp Gly Leu Gly Thr
             100                 105                 110

Thr Val Thr Val Ser Ser Gly Gly Gly Ser Gly Gly Gly Gly Ser
         115                 120                 125

Gly Gly Gly Gly Ser Asn Phe Met Leu Thr Gln Pro Pro Ser Val Ser
130                 135                 140

Val Ala Pro Gly Gln Thr Ala Lys Ile Thr Cys Asp Gly Tyr Ser Ile
145                 150                 155                 160

Arg Thr Lys Ser Val His Trp Tyr Gln Gln Lys Pro Gly Gln Ala Pro
                165                 170                 175

Val Val Val His Asp Asp Ser Asp Arg Pro Ser Gly Ile Pro Glu
             180                 185                 190

Arg Phe Ser Gly Ser Asn Ser Gly Thr Thr Ala Thr Leu Thr Ile Ser
            195                 200                 205

Arg Val Glu Ala Gly Asp Glu Ala Asp Tyr Tyr Cys Gln Ala Trp Asp
        210                 215                 220

Ser Ile Ser Glu Glu Val Val Phe Gly Gly Thr Lys Leu Thr Val
225                 230                 235                 240

Leu

<210> SEQ ID NO 46
<211> LENGTH: 240
<212> TYPE: PRT
<213> ORGANISM: Artificial Sequence
<220> FEATURE:
<223> OTHER INFORMATION: Synthetic antibody

<400> SEQUENCE: 46

Gln Val Gln Leu Gln Glu Ser Gly Gly Gly Leu Val Gln Pro Gly Gly
1               5                   10                  15

Ser Leu Arg Leu Ser Cys Ser Ala Ser Gly Phe Thr Phe Gly Thr Tyr
             20                  25                  30

Ala Met Arg Trp Val Arg Gln Thr Ser Gly Lys Gly Leu Glu Trp Val
         35                  40                  45

Ser Gly Ile Gly Val Ser Gly Asp Ala Tyr Tyr Thr Asp Ser Val Arg
 50                      55                  60

Gly Arg Phe Thr Ile Ser Arg Asp Asn Ser Lys Asn Thr Leu Tyr Leu
 65                  70                  75                  80

Gln Met Asn Thr Leu Arg Ala Glu Asp Thr Ala Thr Tyr Tyr Cys Thr
                 85                  90                  95

Arg Lys Ser Ser Thr Thr Ser Asn Asp Tyr Trp Gly Arg Gly Thr Leu
            100                 105                 110

Val Thr Val Ser Ser Gly Gly Gly Ser Gly Gly Gly Gly Ser Gly
        115                 120                 125

Gly Gly Gly Ser Ser Tyr Val Leu Thr Gln Asp Pro Ala Val Ser Val
130                 135                 140

```
Ala Leu Gly Gln Thr Val Arg Ile Thr Cys Gln Gly Asp Asn Ile Gly
145                 150                 155                 160

Ser Lys Ser Val His Trp Tyr Gln Gln Lys Pro Gly Gln Ala Pro Val
                165                 170                 175

Leu Val Val Tyr Asp Asp Ser Asp Arg Pro Ser Gly Ile Pro Glu Arg
            180                 185                 190

Phe Ser Gly Ser Asn Ser Gly Thr Thr Ala Thr Leu Thr Ile Ser Ser
        195                 200                 205

Val Glu Ala Gly Asp Glu Ala Asp Tyr Tyr Cys Gln Ala Trp Asp Ser
    210                 215                 220

Ile Ser Glu His Val Ile Phe Gly Gly Gly Thr Lys Val Thr Val Leu
225                 230                 235                 240
```

<210> SEQ ID NO 47
<211> LENGTH: 241
<212> TYPE: PRT
<213> ORGANISM: Artificial Sequence
<220> FEATURE:
<223> OTHER INFORMATION: Synthetic antibody

<400> SEQUENCE: 47

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Ser Ser Gly Trp Tyr Tyr Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Ser Asp Ile Gln Met Thr Gln Ser Pro Ser Phe
    130                 135                 140

Leu Ser Ala Ser Val Gly Asp Arg Ile Thr Ile Thr Cys Arg Ala Ser
145                 150                 155                 160

His Asp Ile Ser Ser Tyr Phe Ala Trp Tyr Gln Gln Lys Pro Gly Lys
                165                 170                 175

Ala Pro Lys Pro Leu Ile Tyr Ala Ala Ser Thr Leu Gln Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Glu Asp Phe Ala Thr Tyr Tyr Cys Gln Gln
    210                 215                 220

Leu Gly Ser Tyr Pro Leu Thr Phe Gly Gly Gly Thr Lys Leu Glu Ile
225                 230                 235                 240

Lys
```

<210> SEQ ID NO 48
<211> LENGTH: 245

```
<212> TYPE: PRT
<213> ORGANISM: Artificial Sequence
<220> FEATURE:
<223> OTHER INFORMATION: Synthetic antibody

<400> SEQUENCE: 48

Gln Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Asp Tyr Gly Asp Tyr Ala Gly Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser His Val Ile Leu Thr Gln Asp Pro
130                 135                 140

Ala Val Ser Val Ala Leu Gly Gln Thr Val Arg Ile Thr Cys Gln Gly
145                 150                 155                 160

Asp Ser Leu Lys Ser Tyr Tyr Ala Ser Trp Tyr Gln Gln Lys Pro Gly
            165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Gly Thr Thr Ala Ser Leu
            195                 200                 205

Thr Ile Thr Gly Ala Gln Ala Glu Asp Glu Ala Asp Tyr Tyr Cys His
    210                 215                 220

Ser Arg Asp Ser Ser Gly Thr His Leu Arg Val Phe Gly Gly Gly Thr
225                 230                 235                 240

Lys Leu Thr Val Leu
                245

<210> SEQ ID NO 49
<211> LENGTH: 244
<212> TYPE: PRT
<213> ORGANISM: Artificial Sequence
<220> FEATURE:
<223> OTHER INFORMATION: Synthetic antibody

<400> SEQUENCE: 49

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Glu Gly Thr Thr Asp Tyr Ala Ala
    50                  55                  60

Pro Val Lys Gly Arg Phe Ser Ile Ser Arg Asp Asp Ser Lys Asn Thr
65                  70                  75                  80
```

```
Leu Tyr Leu Gln Met Asn Ser Leu Lys Thr Glu Asp Thr Gly Val Tyr
                85                  90                  95

Tyr Cys Thr Ala Thr Lys Gly Leu Gly Gly Ser Lys Leu Gly Gln Gly
                100                 105                 110

Thr Leu Val Thr Val Ser Ser Gly Gly Gly Ser Gly Gly Gly
            115                 120                 125

Ser Gly Gly Gly Ser Gln Ser Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
                165                 170                 175

Thr Ala Pro Lys Leu Leu Ile Tyr Ser Asn Asp Gln Arg Pro Ser Gly
                180                 185                 190

Val Pro Asp Arg Phe Ser Gly Ser Lys Ser Gly Thr Ser Ala Ser Leu
                195                 200                 205

Ala Ile Thr Gly Leu Gln Pro Glu Asp Glu Ala Asp Tyr Tyr Cys Gly
                210                 215                 220

Thr Trp Asp Ser Ser Leu Ser Ala Tyr Val Phe Gly Thr Gly Thr Lys
225                 230                 235                 240

Leu Thr Val Leu

<210> SEQ ID NO 50
<211> LENGTH: 245
<212> TYPE: PRT
<213> ORGANISM: Artificial Sequence
<220> FEATURE:
<223> OTHER INFORMATION: Synthetic antibody

<400> SEQUENCE: 50

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
                20                  25                  30

Gly Met His Trp Val Arg Arg Ala Pro Gly Lys Gly Leu Glu Trp Val
                35                  40                  45

Ala Val Ile Ser Tyr Asp Gly Ser Asn Gln Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Ser Arg Pro Gly Gly Gly Tyr Ala Ser Gly Ser Thr Val Ala Tyr
                100                 105                 110

Trp Gly Gln Gly Thr Pro Val Thr Val Ser Ser Gly Gly Gly Gly Ser
            115                 120                 125

Gly Gly Gly Gly Ser Gly Gly Gly Ser Ser Glu Leu Thr Gln
    130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Leu Leu Val Ile Tyr Gly Gln Asn Ile Arg Pro
                180                 185                 190
```

```
Ser Gly Ile Pro Asp Arg Phe Ser Gly Ser Ser Gly Asn Ser Ala
        195                 200                 205

Ser Leu Thr Ile Thr Gly Ala Gln Ala Glu Asp Glu Ala Asp Tyr Tyr
    210                 215                 220

Cys His Ser Arg Asp Ser Ser Gly Lys Tyr Val Phe Gly Val Gly Thr
225                 230                 235                 240

Lys Val Thr Val Leu
            245
```

<210> SEQ ID NO 51
<211> LENGTH: 237
<212> TYPE: PRT
<213> ORGANISM: Artificial Sequence
<220> FEATURE:
<223> OTHER INFORMATION: Synthetic antibody

<400> SEQUENCE: 51

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asn Phe Met Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Arg Asp Ser Ser Gly
    210                 215                 220

Asn Pro Val Phe Gly Gly Gly Thr Lys Val Thr Val Leu
225                 230                 235
```

<210> SEQ ID NO 52
<211> LENGTH: 237
<212> TYPE: PRT
<213> ORGANISM: Artificial Sequence
<220> FEATURE:
<223> OTHER INFORMATION: Synthetic antibody

<400> SEQUENCE: 52

```
Gln Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                 85                  90                  95

Ala Ser Arg Ser Leu Leu Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asn Phe Met Leu Thr Gln Asp Pro Ala Val Ser Val Ala Leu
130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Arg Asp Ser Ser Gly
    210                 215                 220

Asn Pro Val Phe Gly Gly Gly Thr Lys Val Thr Val Leu
225                 230                 235

<210> SEQ ID NO 53
<211> LENGTH: 243
<212> TYPE: PRT
<213> ORGANISM: Artificial Sequence
<220> FEATURE:
<223> OTHER INFORMATION: Synthetic antibody

<400> SEQUENCE: 53

Gln Val Gln Leu Gln Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser Gly Gly Gly Gly Ser Gly Gly Gly Gly
        115                 120                 125

Ser Gly Gly Gly Gly Ser Ser Ser Glu Leu Thr Gln Asp Pro Ala Val
    130                 135                 140

```
Ser Val Ala Leu Gly Gln Thr Val Lys Ile Thr Cys Gln Gly Asp Ser
145                 150                 155                 160

Leu Arg Thr Tyr Tyr Ala Ser Trp Tyr Gln Gln Arg Pro Gly Gln Ala
            165                 170                 175

Pro Val Leu Val Ile Tyr Gly Glu Asn Ser Arg Pro Ser Gly Ile Pro
            180                 185                 190

Asp Arg Phe Ser Gly Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
            210                 215                 220

Asp Ser Ser Gly Asn His Leu Arg Val Phe Gly Gly Gly Thr Lys Leu
225                 230                 235                 240

Thr Val Leu

<210> SEQ ID NO 54
<211> LENGTH: 238
<212> TYPE: PRT
<213> ORGANISM: Artificial Sequence
<220> FEATURE:
<223> OTHER INFORMATION: Synthetic antibody

<400> SEQUENCE: 54

Gln Val Asn Leu Arg Glu Ser Gly Gly Gly Leu Val Gln Pro Gly Gly
1               5                   10                  15

Phe Leu Arg Leu Ser Cys Ala Ala Phe Gly Phe Thr Phe Ser Gly Tyr
            20                  25                  30

Trp Met Ser Trp Val His Pro Ala Pro Gly Lys Gly Leu Glu Trp Val
            35                  40                  45

Ala Asn Ile Lys Gln Asp Gly Ser Glu Lys Phe Tyr Val Asp Ser Val
50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Phe Cys
            85                  90                  95

Ala Arg Gly Leu Leu Ser Asp Tyr Trp Gly Gln Gly Thr Leu Val Pro
            100                 105                 110

Val Ser Ser Gly Gly Gly Gly Ser Gly Gly Gly Ser Gly Gly Gly
            115                 120                 125

Gly Ser Asn Phe Met Leu Thr Gln Pro Pro Ser Val Ser Val Ala Pro
130                 135                 140

Gly Lys Thr Ala Ser Leu Thr Cys Gly Gly Tyr Asn Ile Gly Thr Lys
145                 150                 155                 160

Ser Val His Trp Tyr Gln Gln Lys Pro Gly Gln Ala Pro Val Val Val
            165                 170                 175

Val His Asp Asp Ser Asp Arg Pro Ser Gly Ile Pro Glu Arg Phe Ser
            180                 185                 190

Gly Ser Asn Ser Gly Thr Thr Ala Thr Leu Thr Ile Ile Arg Val Glu
            195                 200                 205

Ala Gly Asp Glu Ala Asp Tyr Tyr Cys Gln Ala Trp Asp Ser Ile Ser
            210                 215                 220

Glu Glu Val Val Phe Gly Gly Gly Thr Lys Leu Thr Val Leu
225                 230                 235

<210> SEQ ID NO 55
<211> LENGTH: 242
```

```
<212> TYPE: PRT
<213> ORGANISM: Artificial Sequence
<220> FEATURE:
<223> OTHER INFORMATION: Synthetic antibody

<400> SEQUENCE: 55

Gln Val Gln Leu Gln Glu Ser Gly Gly Gly Leu Val Lys Pro Gly Gly
1               5                   10                  15

Pro Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ser Thr Leu Ser Arg Ser Gly Ser Gly Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Phe Gln Met Asn Ser Leu Arg Ala Glu Asp Thr Ala Val Tyr Tyr Cys
                85                  90                  95

Ala Ser Ile Ala Val Ala Gly Asn Tyr Phe Glu Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ser Tyr Val Leu Thr Gln Asp Pro Ala Val
130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Glu Arg Pro Gly Gln Ala
                165                 170                 175

Pro Leu Leu Val Ile Tyr Gly Lys Asn Asn Arg Pro Ser Gly Ile Pro
            180                 185                 190

Asp Arg Phe Ser Gly Ser Asn Ser Gly Ser Thr Ala Thr Leu Thr Ile
        195                 200                 205

Ser Arg Val Glu Ala Gly Asp Glu Gly Asp Tyr Tyr Cys Gln Val Trp
    210                 215                 220

Asp Ser Ile Asn Glu Gln Val Val Phe Gly Gly Gly Thr Lys Val Thr
225                 230                 235                 240

Val Leu

<210> SEQ ID NO 56
<211> LENGTH: 243
<212> TYPE: PRT
<213> ORGANISM: Artificial Sequence
<220> FEATURE:
<223> OTHER INFORMATION: Synthetic antibody

<400> SEQUENCE: 56

Gln Val Gln Leu Gln Glu Ser Gly Gly Gly Leu Val Lys Pro Gly Glu
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Ala Tyr Ile Arg Tyr Asp Gly Ser Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Pro Glu Asp Thr Ala Phe Tyr Tyr Cys
                    85                  90                  95

Ala Arg Leu Ile Ala Glu Ala Glu Gly Trp Phe Asp Pro Trp Gly Gln
                100                 105                 110

Gly Thr Leu Val Thr Val Ser Ser Gly Gly Gly Ser Gly Gly Gly
                115                 120                 125

Gly Ser Gly Gly Gly Gly Ser Asn Phe Met Leu Thr Gln Pro Pro Ser
        130                 135                 140

Val Ser Val Ala Pro Gly Lys Thr Ala Arg Ile Thr Cys Gly Gly Asn
145                 150                 155                 160

Asn Ile Gly Ser Lys Ser Val Tyr Trp Tyr Gln Gln Lys Pro Gly Gln
                165                 170                 175

Ala Pro Val Leu Val Val Tyr Asp Asp Ser Asp Arg Pro Ser Gly Ile
                180                 185                 190

Pro Glu Arg Phe Ser Gly Ser Asn Ser Gly Asn Thr Ala Thr Leu Thr
                195                 200                 205

Ile Ser Arg Val Glu Ala Gly Asp Glu Ala Asp Tyr Tyr Cys Gln Val
        210                 215                 220

Trp Asp Ser Ser Ser Asp His Val Val Phe Gly Gly Gly Thr Lys Val
225                 230                 235                 240

Thr Val Leu
```

<210> SEQ ID NO 57
<211> LENGTH: 241
<212> TYPE: PRT
<213> ORGANISM: Artificial Sequence
<220> FEATURE:
<223> OTHER INFORMATION: Synthetic antibody

<400> SEQUENCE: 57

```
Gln Val Gln Leu Leu Gln Ser Ala Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Ser Gly Ile Ser Gly Ser Gly Gly Ser Thr Asn Tyr Ala Asp Ser Val
        50                  55                  60

Lys Gly Arg Phe Thr Ile Ser Arg Asp Ser Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Asp Tyr Gly Ser Gly Trp Tyr Asp Tyr Trp Gly Gln Gly Thr
                100                 105                 110

Leu Val Thr Val Ser Ser Gly Gly Gly Gly Ser Gly Gly Gly Gly Ser
                115                 120                 125

Gly Gly Gly Gly Ser Ser Glu Leu Thr Gln Asp Pro Ala Val Ser
        130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Glu Arg Pro Gly Gln Ala Pro
                165                 170                 175

Leu Leu Val Ile Tyr Gly Arg Asn Glu Arg Pro Ser Gly Ile Pro Asp
                180                 185                 190
```

```
Arg Phe Ser Ala Ser Ser Gly Asn Thr Ala Ser Leu Thr Ile Thr
        195                 200                 205

Gly Ala Gln Ala Glu Asp Glu Ala Asp Tyr Tyr Cys Gln Val Trp Asp
    210                 215                 220

Ser Phe Asn Glu Gln Val Val Phe Gly Gly Thr Lys Leu Thr Val
225                 230                 235                 240

Leu

<210> SEQ ID NO 58
<211> LENGTH: 245
<212> TYPE: PRT
<213> ORGANISM: Artificial Sequence
<220> FEATURE:
<223> OTHER INFORMATION: Synthetic antibody

<400> SEQUENCE: 58

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val His Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Tyr Tyr Gly Phe Trp Ser Gly Tyr Tyr Asp Tyr Leu Gly
            100                 105                 110

Gln Gly Thr Leu Val Thr Val Ser Ser Gly Gly Gly Ser Gly Gly
        115                 120                 125

Gly Gly Ser Gly Gly Gly Ser Ser Glu Leu Thr Gln Asp Pro
    130                 135                 140

Ala Val Ser Val Gly Leu Gly Gln Thr Val Thr Ile Thr Cys Gln Gly
145                 150                 155                 160

Asp Ser Leu Arg Ser Tyr Tyr Ala Asn Trp Tyr Gln Gln Lys Pro Gly
                165                 170                 175

Gln Ala Pro Ile Leu Val Ile Tyr Gly Glu Asn Asn Arg Pro Ser Gly
            180                 185                 190

Ile Pro Asp Arg Phe Ser Gly Ser Ser Ser Gly Asn Thr Ala Ser Leu
        195                 200                 205

Thr Ile Thr Gly Ala Gln Ala Glu Asp Glu Ala Asp Tyr Tyr Cys His
    210                 215                 220

Ser Arg Asp Ser Ser Gly Thr His Leu Arg Val Phe Gly Gly Gly Thr
225                 230                 235                 240

Lys Leu Thr Val Leu
                245

<210> SEQ ID NO 59
<211> LENGTH: 244
<212> TYPE: PRT
<213> ORGANISM: Artificial Sequence
<220> FEATURE:
<223> OTHER INFORMATION: Synthetic antibody
```

-continued

<400> SEQUENCE: 59

```
Gln Val Gln Leu Leu Glu Ser Gly Gly Val Val Gln Pro Gly Thr
1               5                   10                  15

Ser Leu Arg Leu Ser Cys Ala Ala Ser Gly Phe Thr Phe Ser Asn Tyr
            20                  25                  30

Ala Ile Asn Trp Val Arg Gln Ala Ala Gly Lys Gly Leu Glu Trp Val
        35                  40                  45

Ser Gly Ile Ser Gly Ser Gly Val Ser Thr Ser Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asn Gly Gly Pro Glu Tyr Leu Gln His Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Gln Ser Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
                165                 170                 175

Thr Ala Pro Lys Leu Leu Ile Tyr Ser Asn Asp Gln Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Leu Gln Pro Glu Asp Glu Ala Asp Tyr Tyr Cys Gly
    210                 215                 220

Thr Trp Asp Ser Ser Leu Ser Ala Tyr Val Phe Gly Thr Gly Thr Lys
225                 230                 235                 240

Leu Thr Val Leu
```

<210> SEQ ID NO 60
<211> LENGTH: 238
<212> TYPE: PRT
<213> ORGANISM: Artificial Sequence
<220> FEATURE:
<223> OTHER INFORMATION: Synthetic antibody

<400> SEQUENCE: 60

```
Gln Val Gln Leu Gln Glu Ser Gly Gly Thr Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
        35                  40                  45

Ser Thr Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Gly Ala Tyr Ser Gly Ser Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Ser Glu Leu Thr Gln Asp Pro Ala Val Ser Val Ala
    130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Ser Leu
                165                 170                 175

Val Ile Tyr Gly Glu Asn Ser Arg Pro Ser Gly Ile Pro Asp Arg Phe
            180                 185                 190

Ser Gly Ser Ser Ser Gly Asn Thr Ala Ser Leu Thr Ile Thr Gly Ala
            195                 200                 205

Gln Ala Glu Asn Glu Ala Asp Tyr Tyr Cys Gln Ala Trp Asp Ser Ser
    210                 215                 220

Thr Ala Val Val Phe Gly Gly Gly Thr Lys Leu Thr Val Leu
225                 230                 235

<210> SEQ ID NO 61
<211> LENGTH: 238
<212> TYPE: PRT
<213> ORGANISM: Artificial Sequence
<220> FEATURE:
<223> OTHER INFORMATION: Synthetic antibody

<400> SEQUENCE: 61

Gln Val Gln Leu Gln Glu Ser Gly Gly Thr Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Tyr Ser Gly Ser His Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Ser Glu Leu Thr Gln Asp Pro Ala Val Ser Val Ala
    130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Ser Leu
                165                 170                 175

Val Ile Tyr Gly Glu Asn Ser Arg Pro Ser Gly Ile Pro Asp Arg Phe
            180                 185                 190

Ser Gly Ser Ser Ser Gly Asn Thr Ala Ser Leu Thr Ile Thr Gly Ala
            195                 200                 205

Gln Ala Glu Asn Glu Ala Asp Tyr Tyr Cys Gln Ala Trp Asp Ser Ser
    210                 215                 220

```
Thr Ala Val Val Phe Gly Gly Thr Lys Leu Thr Val Leu
225                 230                 235

<210> SEQ ID NO 62
<211> LENGTH: 244
<212> TYPE: PRT
<213> ORGANISM: Artificial Sequence
<220> FEATURE:
<223> OTHER INFORMATION: Synthetic antibody

<400> SEQUENCE: 62

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Pro Ile Tyr Asp Ser Ser Gly Tyr Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Ser Thr Leu Ser Ala Ser Ile Gly Asp Arg Val Thr Ile Thr Cys
145                 150                 155                 160

Arg Ala Ser Glu Gly Ile Tyr His Trp Leu Ala Trp Tyr Gln Gln Lys
                165                 170                 175

Pro Gly Lys Ala Pro Lys Leu Leu Ile Tyr Lys Ala Ser Ser Leu Ala
            180                 185                 190

Ser Gly Ala Pro Ser Arg Phe Ser Gly Ser Gly Ser Gly Thr Asp Phe
        195                 200                 205

Thr Leu Thr Ile Ser Ser Leu Gln Pro Asp Asp Phe Ala Thr Tyr Tyr
    210                 215                 220

Cys Gln Gln Tyr His Thr Ile Ser Arg Thr Phe Gly Pro Gly Thr Lys
225                 230                 235                 240

Val Asp Ile Lys

<210> SEQ ID NO 63
<211> LENGTH: 244
<212> TYPE: PRT
<213> ORGANISM: Artificial Sequence
<220> FEATURE:
<223> OTHER INFORMATION: Synthetic antibody

<400> SEQUENCE: 63

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45
```

```
Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                85                  90                  95

Val Arg Pro Ser Asp Ser Gly Trp Ser Phe Glu His Trp Gly Gln Gly
            100                 105                 110

Thr Leu Val Pro Val Ser Ser Gly Gly Gly Ser Gly Gly Gly Gly
            115                 120                 125

Ser Gly Gly Gly Ser Gln Ser Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
                165                 170                 175

Thr Ala Pro Lys Leu Leu Ile Tyr Ser Asn Asp Gln Arg Pro Ser Gly
                180                 185                 190

Val Pro Asp Arg Phe Ser Gly Ser Lys Ser Gly Thr Ser Ala Ser Leu
            195                 200                 205

Ala Ile Thr Gly Leu Gln Pro Glu Asp Glu Ala Asp Tyr Tyr Cys Gly
            210                 215                 220

Thr Trp Asp Ser Ser Leu Ser Ala Tyr Val Phe Gly Thr Gly Thr Lys
225                 230                 235                 240

Leu Thr Val Leu

<210> SEQ ID NO 64
<211> LENGTH: 245
<212> TYPE: PRT
<213> ORGANISM: Artificial Sequence
<220> FEATURE:
<223> OTHER INFORMATION: Synthetic antibody

<400> SEQUENCE: 64

Gln Val Gln Leu Gln Glu Ser Gly Gly Gly Leu Val Gln Pro Gly Gly
  1                   5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Val Arg Gly Asp Arg Ser Tyr Gly Ala Glu Tyr Phe Gln His Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Ser Glu Leu Thr Gln Asp Pro
    130                 135                 140

Ala Val Ser Val Ala Ser Gly Gln Thr Val Arg Ile Thr Cys Gln Gly
145                 150                 155                 160
```

```
Asp Ser Leu Arg Ser Tyr Tyr Ala Ser Trp Tyr Gln Gln Lys Pro Gly
                165                 170                 175

Gln Ala Pro Leu Leu Val Ile Tyr Gly Lys Asn Ile Arg Pro Ser Gly
            180                 185                 190

Ile Pro Asp Arg Phe Ser Gly Ser Thr Ser Gly Asn Ser Ala Ser Leu
        195                 200                 205

Thr Ile Thr Gly Ala Gln Ala Glu Asp Glu Ala Asp Tyr Tyr Cys Asn
    210                 215                 220

Ser Arg Asp Ser Ser Gly Asn Arg Asn Trp Val Phe Gly Gly Gly Thr
225                 230                 235                 240

Lys Leu Thr Val Leu
                245

<210> SEQ ID NO 65
<211> LENGTH: 246
<212> TYPE: PRT
<213> ORGANISM: Artificial Sequence
<220> FEATURE:
<223> OTHER INFORMATION: Synthetic antibody

<400> SEQUENCE: 65

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Ser Ser Ser Tyr
            20                  25                  30

Ala Met His Trp Val Arg Gln Ala Pro Gly Lys Gly Leu Glu Tyr Val
            35                  40                  45

Ser Ala Ile Gly Gly Asn Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Glu Gly Glu Gln Trp Leu Glu Tyr Arg Tyr Tyr Gly Met Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Ser Ser Ser Glu Leu Thr
        130                 135                 140

Gln Asp Pro Ala Val Ser Val Ala Leu Gly Gln Thr Val Arg Ile Thr
145                 150                 155                 160

Cys Gln Gly Asp Ser Leu Arg Ser Tyr Tyr Ala Ser Trp Tyr Gln Gln
                165                 170                 175

Lys Pro Gly Gln Ala Pro Ser Leu Val Ile Tyr Gly Glu Asn Ser Arg
            180                 185                 190

Pro Ser Gly Ile Pro Asp Arg Phe Ser Gly Ser Ser Ser Gly Asn Thr
        195                 200                 205

Ala Ser Leu Thr Ile Thr Gly Ala Gln Ala Glu Asn Glu Ala Asp Tyr
    210                 215                 220

Tyr Cys Gln Ala Trp Asp Ser Ser Thr Ala Val Val Phe Gly Gly Gly
225                 230                 235                 240

Thr Lys Leu Thr Val Leu
                245

<210> SEQ ID NO 66
<211> LENGTH: 250
```

```
<212> TYPE: PRT
<213> ORGANISM: Artificial Sequence
<220> FEATURE:
<223> OTHER INFORMATION: Synthetic antibody

<400> SEQUENCE: 66

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Tyr Ser Ser Asn Trp Phe Ser Tyr Tyr Tyr Tyr
            100                 105                 110

Gly Met Asp Val Trp Gly Gln Gly Thr Thr Val Thr Val Ser Ser Gly
        115                 120                 125

Gly Gly Gly Ser Gly Gly Gly Ser Gly Gly Gly Ser Asn Phe
    130                 135                 140

Met Leu Thr Gln Pro Pro Ser Val Ser Val Ala Pro Gly Lys Thr Ala
145                 150                 155                 160

Arg Ile Thr Cys Gly Gly Asn Asn Ile Gly Ser Lys Ser Val Tyr Trp
                165                 170                 175

Tyr Gln Gln Lys Pro Gly Gln Ala Pro Val Leu Val Tyr Asp Asp
            180                 185                 190

Ser Asp Arg Pro Ser Gly Ile Pro Glu Arg Phe Ser Gly Ser Asn Ser
        195                 200                 205

Gly Asn Thr Ala Thr Leu Thr Ile Ser Arg Val Glu Ala Gly Asp Glu
    210                 215                 220

Ala Asp Tyr Tyr Cys Gln Val Trp Asp Ser Ser Ser Asp His Val Val
225                 230                 235                 240

Phe Gly Gly Gly Thr Lys Val Thr Val Leu
                245                 250

<210> SEQ ID NO 67
<211> LENGTH: 10
<212> TYPE: PRT
<213> ORGANISM: Artificial Sequence
<220> FEATURE:
<223> OTHER INFORMATION: Synthetic peptide linker

<400> SEQUENCE: 67

Gly Gly Gly Gly Ser Gly Gly Gly Gly Ser
1               5                   10

<210> SEQ ID NO 68
<211> LENGTH: 5
<212> TYPE: PRT
<213> ORGANISM: Artificial Sequence
<220> FEATURE:
<223> OTHER INFORMATION: Synthetic peptide linker
```

<400> SEQUENCE: 68

Gly Gly Gly Gly Ser
1               5

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide linker

<400> SEQUENCE: 69

Gly Ser Gly Gly Gly Gly Ser Gly Gly Gly Ser Gly Gly Ser Gly
1               5                   10                  15

Gly Gly Gly Ser
            20

<210> SEQ ID NO 70
<211> LENGTH: 6
<212> TYPE: PRT
<213> ORGANISM: Artificial Sequence
<220> FEATURE:
<223> OTHER INFORMATION: Synthetic peptide linker

<400> SEQUENCE: 70

Ser Gly Gly Gly Gly Ser
1               5

<210> SEQ ID NO 71
<211> LENGTH: 4
<212> TYPE: PRT
<213> ORGANISM: Artificial Sequence
<220> FEATURE:
<223> OTHER INFORMATION: Synthetic peptide linker

<400> SEQUENCE: 71

Gly Gly Gly Ser
1

<210> SEQ ID NO 72
<211> LENGTH: 4
<212> TYPE: PRT
<213> ORGANISM: Artificial Sequence
<220> FEATURE:
<223> OTHER INFORMATION: Synthetic peptide linker

<400> SEQUENCE: 72

Val Pro Gly Val
1

<210> SEQ ID NO 73
<211> LENGTH: 5
<212> TYPE: PRT
<213> ORGANISM: Artificial Sequence
<220> FEATURE:
<223> OTHER INFORMATION: Synthetic peptide linker

<400> SEQUENCE: 73

Val Pro Gly Val Gly
1               5

<210> SEQ ID NO 74
<211> LENGTH: 6
<212> TYPE: PRT
<213> ORGANISM: Artificial Sequence

```
<220> FEATURE:
<223> OTHER INFORMATION: Synthetic peptide linker

<400> SEQUENCE: 74

Gly Val Pro Gly Val Gly
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic peptide linker

<400> SEQUENCE: 75

Gly Val Gly Val Pro Gly Val Gly
1               5

<210> SEQ ID NO 76
<211> LENGTH: 10
<212> TYPE: PRT
<213> ORGANISM: Artificial Sequence
<220> FEATURE:
<223> OTHER INFORMATION: Synthetic peptide linker

<400> SEQUENCE: 76

Val Pro Gly Val Gly Val Pro Gly Val Gly
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Synthetic peptide linker

<400> SEQUENCE: 77

Gly Gly Ser Ser Arg Ser Ser
1               5

<210> SEQ ID NO 78
<211> LENGTH: 18
<212> TYPE: PRT
<213> ORGANISM: Artificial Sequence
<220> FEATURE:
<223> OTHER INFORMATION: Synthetic peptide linker

<400> SEQUENCE: 78

Gly Gly Ser Ser Arg Ser Ser Ser Gly Gly Gly Gly Ser Gly Gly
1               5                   10                  15

Gly Gly

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Val Gln Leu Val Gln Ser Gly Gly Gly Val Val Gln Pro Gly Arg
1               5                   10                  15

Ser Leu Arg Leu Ala Cys Ala Ala Ser
            20                  25
```

```
<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Leu Thr Val Asn Asn Tyr Ala
1               5

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Met His Trp Val Arg Gln Ala Pro Gly Lys Gly Leu Glu Trp Val Ala
1               5                   10                  15

Val

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Ser Tyr Asp Gly Asn Asn Lys
1               5

<210> SEQ ID NO 83
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Lys Gly Gly Gly Tyr Phe Asp Leu
1               5
```

```
<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Gly Arg Gly Thr Leu Val Thr Val Ser Ser
1               5                   10

<210> SEQ ID NO 86
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Val Gln Leu Val Gln Ser Gly Gly Gly Val Val Gln Pro Gly Arg
1               5                   10                  15

Ser Leu Arg Leu Ala Cys Ala Ala Ser
            20                  25

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Phe Thr Val Asn Asn Tyr Ala
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Met His Trp Val Arg Gln Ala Pro Gly Lys Gly Leu Glu Trp Val Ala
1               5                   10                  15

Val

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Ser Tyr Asp Gly Asn Asn Lys
1               5

<210> SEQ ID NO 90
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 90

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
            35

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Lys Gly Gly Gly Tyr Phe Asp Leu
1               5

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Gly Arg Gly Thr Leu Val Thr Val Ser Ser
1               5                   10

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Val Gln Leu Val Gln Ser Gly Gly Val Val Gln Pro Gly Arg
1               5                   10                  15

Ser Leu Arg Leu Ala Cys Ala Ala Ser
            20                  25

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Phe Thr Val Asn Asn Tyr Ala
1               5

<210> SEQ ID NO 95
<211> LENGTH: 17
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 95

Met His Trp Val Arg Gln Ala Pro Gly Lys Gly Leu Glu Trp Val Ala
1               5                   10                  15

Val

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ile Ser Tyr Asp Gly Asn Asn Lys
1               5

<210> SEQ ID NO 97
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
            35

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Lys Gly Gly Gly Tyr Phe Asp Leu
1               5

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Trp Gly Arg Gly Thr Leu Val Thr Val Ser Ser
1               5                   10

<210> SEQ ID NO 100
<211> LENGTH: 25
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 100

Gln Val Gln Leu Gln Gln Ser Gly Gly Gly Val Val Gln Pro Gly Arg
1               5                   10                  15

Ser Leu Arg Leu Ser Cys Ala Ala Ser
            20                  25

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Thr Phe Ser Ser Tyr Ala
1               5

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Met His Trp Val Arg Gln Ala Pro Gly Lys Gly Leu Glu Trp Val Ala
1               5                   10                  15

Phe

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ile Arg Ser Asp Gly Ser Lys Lys
1               5

<210> SEQ ID NO 104
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
                35

<210> SEQ ID NO 105
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 105

Ala Arg His Gly Asn Tyr Phe Asp Ser
1               5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Trp Gly Gln Gly Thr Leu Val Thr Val Ser Ser
1               5                   10

<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Val Gln Leu Val Glu Ser Gly Gly Val Val Gln Pro Gly Arg
1               5                   10                  15

Ser Leu Arg Leu Ser Cys Ala Ala Ser
            20                  25

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Phe Thr Phe Ser Thr Tyr Gly
1               5

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Met His Trp Val Arg Gln Ala Pro Gly Lys Gly Leu Glu Trp Leu Ser
1               5                   10                  15

Phe

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 110

Ile Ser Tyr Asp Gly Asp Glu Lys
1               5

<210> SEQ ID NO 111
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Trp Cys
        35

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Lys Ala Ser Gly Tyr Gly Met Gly Ile Leu Asp Tyr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Gly Gln Gly Thr Leu Val Thr Val Ser Ser
1               5                   10

<210> SEQ ID NO 114
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 115

Gly Phe Thr Phe Ser Asp Tyr Tyr
1               5

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Met Ser Trp Ile Arg Gln Ala Pro Gly Lys Gly Leu Glu Trp Val Ser
1               5                   10                  15

Tyr

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ile Ser Ser Ser Gly Ser Thr Ile
1               5

<210> SEQ ID NO 118
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
                20                  25                  30

Thr Ala Val Tyr Tyr Cys
            35

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Arg Asp Tyr Gly Arg Ile Ala Ala Ala Gly Arg Arg Tyr
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 120

Trp Gly Gln Gly Thr Leu Val Thr Val Ser Ser
1               5                   10

<210> SEQ ID NO 121
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Val Gln Leu Gln Glu Ser Gly Gly Gly Val Val Arg Pro Gly Gly
1               5                   10                  15

Ser Leu Arg Leu Ser Cys Ala Ala Ser
            20                  25

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Phe Thr Phe Ser Asp Tyr Tyr
1               5

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Met Ser Trp Ile Arg Gln Ala Pro Gly Lys Gly Leu Glu Trp Val Ser
1               5                   10                  15

Tyr

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ile Ser Ser Ser Gly Ser Thr Ile
1               5

<210> SEQ ID NO 125
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Tyr Tyr Ala Asp Ser Val Lys Gly Arg Phe Thr Ile Ser Arg Asp Asn
1               5                   10                  15
```

```
Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Arg Asp Tyr Gly Arg Ile Ala Ala Ala Gly Arg His Tyr
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Trp Gly Gln Gly Thr Leu Val Thr Val Ser Ser
1               5                   10

<210> SEQ ID NO 128
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Phe Thr Phe Ser Asp Tyr Tyr
1               5

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Met Ser Trp Ile Arg Gln Ala Pro Gly Lys Gly Leu Glu Trp Val Ser
1               5                   10                  15
```

Tyr

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ile Ser Ser Ser Gly Ser Thr Ile
1               5

<210> SEQ ID NO 132
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Arg Asp Tyr Gly Arg Ile Ala Ala Ala Gly Arg His Tyr
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Gly Gln Gly Thr Leu Val Thr Val Ser Ser
1               5                   10

<210> SEQ ID NO 135
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Val Gln Leu Gln Glu Ser Gly Gly Gly Leu Val Gln Pro Gly Gly
1               5                   10                  15

```
Ser Leu Arg Leu Ser Cys Ala Ala Ser
            20                  25

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Phe Thr Phe Ser Ser Tyr Trp
1               5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Met Ser Trp Val Arg Gln Ala Pro Gly Lys Gly Leu Glu Trp Val Ala
1               5                   10                  15

Asp

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ile Lys Gln Asp Gly Ser Glu Lys
1               5

<210> SEQ ID NO 139
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Tyr Tyr Val Asp Ser Val Lys Gly Arg Phe Thr Ile Ser Gly Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 140
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 140

Ala Lys Asp Val Gly Ser Thr Ala Ile Asn Tyr Val Arg Ala Tyr Thr
1               5                   10                  15

Trp Phe Asp Pro
            20

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Trp Gly Gln Gly Thr Leu Val Thr Val Ser Ser
1               5                   10

<210> SEQ ID NO 142
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Phe Thr Phe Ser Asn Tyr Ala
1               5

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Met Ser Trp Val Arg Gln Ala Pro Gly Lys Gly Leu Glu Trp Val Ser
1               5                   10                  15

Thr

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 145

Ile Ser Gly Ser Gly Ser Ser Thr
1               5

<210> SEQ ID NO 146
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Phe Tyr Val Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Gln Gly Leu Tyr Ser Ser Gly Trp Ala Asn Trp Phe Asp Pro
1               5                   10                  15

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Gly Gln Gly Thr Leu Val Thr Val Ser Ser
1               5                   10

<210> SEQ ID NO 149
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Val Gln Leu Gln Glu Ser Gly Gly Gly Val Val Gln Pro Gly Arg
1               5                   10                  15

Ser Leu Arg Leu Ser Cys Ala Ala Ser
            20                  25

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 150

Gly Phe Thr Phe Ser Ser Tyr Gly
1               5

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Met His Trp Val Arg Gln Ala Pro Gly Lys Gly Leu Glu Trp Val Ala
1               5                   10                  15

Val

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ile Ser Tyr Asp Gly Ser Asn Lys
1               5

<210> SEQ ID NO 153
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Lys Val Met Gly Leu Ala Ala Ala Gly Leu Asp Ala Phe Asp Ile
1               5                   10                  15

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 155

Trp Gly Gln Gly Thr Thr Val Thr Val Ser Ser
1               5                   10

<210> SEQ ID NO 156
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Val Gln Leu Val Gln Ser Gly Gly Gly Val Val Gln Pro Gly Arg
1               5                   10                  15

Ser Leu Arg Leu Ser Cys Ala Ala Ser
            20                  25

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Phe Thr Phe Ser Ser Tyr Ala
1               5

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Met His Trp Val Arg Gln Ala Pro Gly Lys Gly Leu Glu Trp Val Ala
1               5                   10                  15

Val

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ile Ser Tyr Asp Gly Ser Asn Lys
1               5

<210> SEQ ID NO 160
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 160

Tyr Tyr Ala Asp Ser Val Lys Gly Arg Phe Thr Ile Ser Arg Asp Thr
1               5                   10                  15

Ser Thr Asn Thr Leu Tyr Leu Gln Met Asn Ser Leu Arg Ala Asp Asp
            20                  25                  30

Thr Ala Val Tyr Tyr Cys
            35

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Arg Glu Ser Ser Gly Ser Pro Gly Val
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp Gly Gln Gly Thr Thr Val Thr Val Ser Ser
1               5                   10

<210> SEQ ID NO 163
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Val Gln Leu Val Glu Ser Gly Gly Leu Ile Gln Pro Gly Gly
1               5                   10                  15

Ser Leu Arg Leu Ser Cys Ala Ala Ser
            20                  25

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Phe Thr Val Ser Ser Asn Tyr
1               5

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Met Ser Trp Val Arg Gln Ala Pro Gly Lys Gly Leu Glu Trp Val Ser
1               5                   10                  15

Val

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Tyr Thr Asp Gly Ser Thr
1               5

<210> SEQ ID NO 167
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Ile Tyr Tyr Cys
        35

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Arg Asp Arg Gly Thr Ser Gly Tyr Asp Trp Ala Trp Phe Asp Leu
1               5                   10                  15

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Trp Gly Gln Gly Thr Leu Val Thr Val Ser Ser
1               5                   10

<210> SEQ ID NO 170
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 170

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Phe Thr Phe Ser Ser Tyr Ala
1               5

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Met Ser Trp Val Arg Gln Ala Pro Gly Lys Gly Leu Glu Trp Val Ser
1               5                   10                  15

Ala

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ile Ser Gly Ser Gly Gly Ser Thr
1               5

<210> SEQ ID NO 174
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Tyr Tyr Ala Asp Ser Val Lys Gly Arg Phe Thr Ile Ser Arg Asp Asn
1               5                   10                  15

Ser Lys Asn Thr Leu Tyr Met Gln Met Asn Ser Leu Arg Ala Glu Asp
            20                  25                  30

Thr Ala Val Tyr Tyr Cys
                35

<210> SEQ ID NO 175
<211> LENGTH: 16
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 175

Ala Lys Asp Arg Tyr Tyr Tyr Gly Ser Gly Lys Asp Ala Phe Asp Ile
1               5                   10                  15

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Trp Gly Arg Gly Thr Met Val Thr Val Ser Ser
1               5                   10

<210> SEQ ID NO 177
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gln Val Gln Leu Val Glu Ser Gly Gly Gly Leu Val Gln Pro Gly Gly
1               5                   10                  15

Ser Leu Gly Leu Ser Cys Ala Ala Ser
            20                  25

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Phe Thr Phe Ser Asn Tyr Trp
1               5

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Met Ser Trp Val Arg Gln Ala Pro Gly Lys Gly Leu Glu Trp Val Ala
1               5                   10                  15

Asn

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 180

Val Arg Gln Asp Gly Gly Gln Lys
1               5

<210> SEQ ID NO 181
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Tyr Tyr Val Asp Ser Val Lys Gly Arg Phe Thr Ile Ser Arg Asp Asn
1               5                   10                  15

Ala Lys Asn Ser Leu Tyr Leu Gln Met Asn Ser Leu Arg Thr Glu Asp
            20                  25                  30

Thr Ala Val Tyr Phe Cys
        35

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Val Ser Gln Arg Asn Ser Gly Glu His Asp Tyr
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Trp Gly Gln Gly Thr Leu Val Thr Val Ser Ser
1               5                   10

<210> SEQ ID NO 184
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 185

Gly Phe Thr Phe Ser Asp Tyr Tyr
1               5

<210> SEQ ID NO 186
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Met Ser Trp Ile Arg Gln Ala Pro Gly Lys Gly Leu Glu Trp Val Ser
1               5                   10                  15

Tyr

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ile Ser Ser Ser Gly Ser Thr Ile
1               5

<210> SEQ ID NO 188
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Arg Asp Tyr Gly Arg Ile Ala Ala Ala Gly Arg His Tyr
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 190

Trp Gly Gln Gly Thr Leu Val Thr Val Ser Ser
1               5                   10

<210> SEQ ID NO 191
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Phe Thr Phe Ser Asp Tyr Tyr
1               5

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Met Ser Trp Ile Arg Gln Ala Pro Gly Lys Gly Leu Glu Trp Val Ser
1               5                   10                  15

Tyr

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ile Ser Ser Ser Gly Ser Thr Ile
1               5

<210> SEQ ID NO 195
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Tyr Tyr Ala Asp Ser Val Lys Gly Arg Phe Thr Ile Ser Arg Asp Asn
1               5                   10                  15
```

```
Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 196
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Arg Asp Tyr Gly Arg Ile Ala Ala Ala Gly Arg Asn Tyr
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Trp Gly Gln Gly Thr Leu Val Thr Val Ser Ser
1               5                   10

<210> SEQ ID NO 198
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gln Val Gln Leu Gln Glu Ser Gly Gly Gly Val Val Arg Pro Gly Gly
1               5                   10                  15

Ser Leu Arg Leu Ser Cys Ala Ala Ser
            20                  25

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Phe Thr Phe Ser Asp Tyr Tyr
1               5

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 200

Met Ser Trp Ile Arg Gln Ala Pro Gly Lys Gly Leu Glu Trp Val Ser
1               5                   10                  15

Tyr

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ile Ser Ser Ser Gly Ser Thr Ile
1               5

<210> SEQ ID NO 202
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 203
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Arg Asp Tyr Gly Arg Ile Ala Ala Ala Gly Arg His Tyr
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Trp Gly Gln Gly Thr Leu Val Thr Val Ser Ser
1               5                   10

<210> SEQ ID NO 205
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 205

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Phe Thr Phe Ser Asp Tyr Tyr
1               5

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Met Ser Trp Ile Arg Gln Ala Pro Gly Lys Gly Leu Glu Trp Val Ser
1               5                   10                  15

Tyr

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ile Ser Ser Ser Gly Ser Ser Ile
1               5

<210> SEQ ID NO 209
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Lys Ala Glu Asp
            20                  25                  30

Thr Ala Val Tyr Tyr Cys
        35

<210> SEQ ID NO 210
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 210

Ala Arg Asp Ile Thr Asp Val Val Gly Val Ser Phe Asp Tyr
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Trp Gly Gln Gly Thr Leu Val Thr Val Ser Ser
1               5                   10

<210> SEQ ID NO 212
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Glu Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Phe Thr Phe Ser Ser Tyr Gly
1               5

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Met His Trp Val Arg Gln Ala Pro Gly Lys Gly Leu Glu Trp Val Ala
1               5                   10                  15

Val

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 215

Ile Ser Tyr Asp Gly Ser Asn Lys
1               5

<210> SEQ ID NO 216
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Glu Tyr Tyr Cys
        35

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Lys Val Met Gly Leu Ala Ala Ala Gly Leu Asp Ala Phe Asp Ile
1               5                   10                  15

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Trp Gly Gln Gly Thr Leu Val Thr Val Ser Ser
1               5                   10

<210> SEQ ID NO 219
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Glu Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 220

Gly Phe Thr Phe Ser Ser Phe Gly
1               5

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Met His Trp Val Arg Arg Ala Pro Gly Lys Gly Leu Glu Trp Val Ala
1               5                   10                  15

Val

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ile Ser Tyr Asp Gly Ser Asn Gln
1               5

<210> SEQ ID NO 223
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Ser Arg Pro Gly Gly Gly Tyr Ala Ser Gly Ser Thr Val Ala Tyr
1               5                   10                  15

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 225

Trp Gly Gln Gly Thr Leu Val Thr Val Ser Ser
1               5                   10

<210> SEQ ID NO 226
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Ser Val Leu Thr Gln Pro Pro Ser Val Ser Gly Ala Pro Gly Gln
1               5                   10                  15

Arg Val Thr Ile Ser Cys Thr Gly Ser
            20                  25

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ser Ser Asn Ile Gly Ala Gly Tyr Asp
1               5

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Val His Trp Tyr Gln Gln Leu Pro Gly Thr Ala Pro Lys Leu Leu Ile
1               5                   10                  15

Tyr

<210> SEQ ID NO 229
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Asn Asn
1

<210> SEQ ID NO 230
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asn Arg Pro Ser Gly Val Pro Asp Arg Phe Ser Gly Ser Lys Ser Gly
1               5                   10                  15
```

-continued

```
Thr Ser Ala Ser Leu Ala Ile Thr Gly Leu Gln Ala Glu Asp Glu Ala
            20                  25                  30
Asp Tyr Tyr Cys
        35

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ser Ser Tyr Thr Ser Gly Thr Trp Leu
1               5

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Phe Gly Gly Gly Thr Lys Leu Thr Val Leu
1               5                   10

<210> SEQ ID NO 233
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gln Ser Val Leu Thr Gln Pro Pro Ser Val Ser Gly Ala Pro Gly Gln
1               5                   10                  15
Arg Val Thr Ile Ser Cys Thr Gly Ser
            20                  25

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Ser Asn Ile Gly Ala Gly Tyr Asp
1               5

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 235

Val His Trp Tyr Gln Gln Leu Pro Gly Thr Ala Pro Lys Leu Leu Ile
1               5                   10                  15

Tyr

<210> SEQ ID NO 236
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Asn Asn
1

<210> SEQ ID NO 237
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Ser Tyr Thr Ser Gly Thr Trp Leu
1               5

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Phe Gly Gly Gly Thr Lys Leu Thr Val Leu
1               5                   10

<210> SEQ ID NO 240
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 240

Gln Ser Val Leu Thr Gln Pro Pro Ser Val Ser Gly Ala Pro Gly Gln
1               5                   10                  15

Arg Val Thr Ile Ser Cys Thr Gly Ser
            20                  25

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Ser Asn Ile Gly Ala Gly Tyr Asp
1               5

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Val His Trp Tyr Gln Gln Leu Pro Gly Thr Ala Pro Lys Leu Leu Ile
1               5                   10                  15

Tyr

<210> SEQ ID NO 243
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Asp Asn
1

<210> SEQ ID NO 244
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Asp Tyr Tyr Cys
            35

<210> SEQ ID NO 245
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 245

Ser Ser Tyr Thr Ser Gly Thr Trp Leu
1               5

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Phe Gly Gly Gly Thr Lys Leu Thr Val Leu
1               5                   10

<210> SEQ ID NO 247
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Asp Ile Gln Met Thr Gln Ser Pro Ser Phe Leu Ser Ala Ser Val Gly
1               5                   10                  15

Asp Arg Val Thr Ile Thr Cys Arg Ala Ser
            20                  25

<210> SEQ ID NO 248
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Gly Ile Ser Ser Tyr
1               5

<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Leu Ala Trp Tyr Gln Gln Lys Pro Gly Lys Ala Pro Lys Leu Leu Ile
1               5                   10                  15

Tyr

<210> SEQ ID NO 250
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 250

Ala Ala Ser
1

<210> SEQ ID NO 251
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Thr Leu Gln Ser Gly Val Pro Ser Ser Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
            35

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gln Gln Leu Ala Ser Tyr Pro Leu Thr
1               5

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Phe Gly Gly Gly Thr Lys Val Asp Ile Lys
1               5                   10

<210> SEQ ID NO 254
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ser Ser Glu Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 255
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 255

Ser Leu Arg Ser Tyr Tyr
1               5

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Val Ser Trp Phe Gln Gln Lys Pro Gly Gln Ala Pro Val Phe Val Met
1               5                   10                  15

Tyr

<210> SEQ ID NO 257
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Gln Asn
1

<210> SEQ ID NO 258
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Asn Arg Pro Ser Gly Ile Ser Glu Arg Phe Ser Gly Ser Ser Ser Gly
1               5                   10                  15

Asn Thr Ala Ser Leu Ile Ile Thr Gly Ala Gln Ala Glu Asp Glu Ala
            20                  25                  30

Asp Tyr Tyr Cys
            35

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

His Ser Arg Asp Ser Ser Gly Thr His Leu Arg Val
1               5                   10

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 260

Phe Gly Gly Gly Thr Lys Leu Thr Val Leu
1               5                   10

<210> SEQ ID NO 261
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Ser Ala Leu Thr Gln Pro Pro Ser Ala Ser Ala Thr Pro Gly Gln
1               5                   10                  15

Arg Val Thr Ile Ser Cys Ser Gly Arg
            20                  25

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Thr Ser Asn Ile Gly Ser Asn His
1               5

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Val Tyr Trp Tyr Gln Gln Leu Pro Gly Thr Ala Pro Lys Leu Leu Ile
1               5                   10                  15

Tyr

<210> SEQ ID NO 264
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Arg Asn Asn
1

<210> SEQ ID NO 265
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gln Arg Pro Ser Gly Val Pro Asp Arg Phe Ser Gly Ser Lys Ser Gly
1               5                   10                  15
```

Thr Ser Ala Ser Leu Ala Ile Ser Gly Leu Arg Ser Glu Asp Glu Ala
            20                  25                  30
Asp Tyr Tyr Cys
        35

<210> SEQ ID NO 266
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Thr Trp Asp Asp Ser Leu Ser Gly Glu Val
1               5                   10

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Phe Gly Gly Gly Thr Lys Leu Thr Val Leu
1               5                   10

<210> SEQ ID NO 268
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ser Ser Glu Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ser Leu Arg Ser Tyr Tyr
1               5

<210> SEQ ID NO 270
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ala Ser Trp Tyr Gln Gln Lys Pro Gly Gln Ala Pro Val Leu Val Ile
1               5                   10                  15

Tyr

<210> SEQ ID NO 271
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gly Lys Asn
1

<210> SEQ ID NO 272
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Asn Arg Pro Ser Gly Ile Pro Asp Arg Phe Ser Gly Ser Ser Ser Gly
1               5                   10                  15

Asn Thr Ala Ser Leu Thr Ile Thr Gly Ala Gln Ala Glu Asp Glu Ala
            20                  25                  30

Asp Tyr Tyr Cys
        35

<210> SEQ ID NO 273
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Asn Ser Arg Asp Ser Ser Gly Thr His Leu Glu Val
1               5                   10

<210> SEQ ID NO 274
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Phe Gly Gly Gly Thr Lys Val Thr Val Leu
1               5                   10

<210> SEQ ID NO 275
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 275

Ser Ser Glu Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 276
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Thr Leu Ser Thr Tyr Tyr
1               5

<210> SEQ ID NO 277
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ala Asn Trp Tyr Gln Gln Lys Pro Gly Gln Ala Pro Val Leu Val Ile
1               5                   10                  15

Tyr

<210> SEQ ID NO 278
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gly Lys Asn
1

<210> SEQ ID NO 279
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Asn Arg Pro Ser Gly Ile Pro Asp Arg Phe Ser Gly Ser Ser Ser Gly
1               5                   10                  15

Asn Thr Ala Ser Leu Thr Ile Thr Gly Ala Gln Ala Glu Asp Glu Ala
            20                  25                  30

Asp Tyr Tyr Cys
            35

<210> SEQ ID NO 280
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 280

His Ser Arg Asp Ile Ser Gly Asn Tyr Leu
1               5                   10

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Phe Ala Ser Gly Thr Lys Leu Thr Val Leu
1               5                   10

<210> SEQ ID NO 282
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ser Ser Asn Ile Gly Ser Asn Thr
1               5

<210> SEQ ID NO 284
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Val Asn Trp Ser Arg Gln Leu Pro Gly Thr Ala Pro Lys Leu Leu Ile
1               5                   10                  15

Tyr

<210> SEQ ID NO 285
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 285

Ser Asn Asn
1

<210> SEQ ID NO 286
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 287
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Ala Trp Asp Asp Ser Leu Asn Val Tyr Val
1               5                   10

<210> SEQ ID NO 288
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Phe Gly Thr Gly Thr Lys Val Thr Val Leu
1               5                   10

<210> SEQ ID NO 289
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Lys Ile Val Leu Thr Gln Ser Pro Ser Ser Leu Ser Ala Ser Val Gly
1               5                   10                  15

Asp Thr Val Thr Ile Ala Cys Arg Ala Ser
            20                  25

<210> SEQ ID NO 290
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 290

Arg Asp Ile Arg Asn Asp
1               5

<210> SEQ ID NO 291
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Leu Ala Trp Tyr Gln Gln Lys Pro Gly Lys Ala Pro Lys Leu Leu Ile
1               5                   10                  15

Tyr

<210> SEQ ID NO 292
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gly Ala Ser
1

<210> SEQ ID NO 293
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Ser Leu Gln Ser Gly Val Pro Ser Arg Phe Ser Gly Ser Gly Ser Gly
1               5                   10                  15

Thr Glu Phe Ile Leu Thr Ile Ser Ser Leu Gln Pro Glu Asp Phe Ala
            20                  25                  30

Thr Tyr Tyr Cys
        35

<210> SEQ ID NO 294
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

His Arg Leu Asn Ser Tyr Pro Leu Thr Phe Gly Gly Gly Thr Lys Val
1               5                   10                  15

Asp Ile Lys

<210> SEQ ID NO 295
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 295

Asn Phe Met Leu Thr Gln Pro Ala Ser Leu Ser Gly Ser Pro Gly Gln
1               5                   10                  15

Ser Ile Thr Ile Ser Cys Thr Gly Thr
            20                  25

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ser Ser Asp Val Gly Gly Tyr Asn Tyr
1               5

<210> SEQ ID NO 297
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Val Ser Trp Tyr Gln Gln His Pro Gly Tyr Ala Pro Lys Leu Met Ile
1               5                   10                  15

Tyr

<210> SEQ ID NO 298
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asp Val Ser
1

<210> SEQ ID NO 299
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Asn Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 300
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ser Ser Tyr Thr Ser Ser Ser Thr Pro Trp Val
1               5                   10

<210> SEQ ID NO 301
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Phe Gly Gly Gly Thr Lys Leu Thr Val Leu
1               5                   10

<210> SEQ ID NO 302
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ser Tyr Val Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 303
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ser Leu Arg Ser Tyr Tyr
1               5

<210> SEQ ID NO 304
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ala Ser Trp Tyr Gln Gln Lys Pro Gly Gln Ala Pro Val Leu Val Ile
1               5                   10                  15

Tyr

<210> SEQ ID NO 305
<211> LENGTH: 3
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 305

Gly Lys Asn
1

<210> SEQ ID NO 306
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Asn Arg Pro Ser Gly Ile Pro Asp Arg Phe Ser Gly Ser Ser Ser Gly
1               5                   10                  15

Asn Thr Ala Ser Leu Thr Ile Thr Gly Ala Gln Ala Glu Asp Glu Ala
            20                  25                  30

Asp Tyr Tyr Cys
            35

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Asn Ser Arg Asp Ser Ser Gly Asn Gln
1               5

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Phe Gly Gly Gly Thr Lys Leu Thr Val Leu
1               5                   10

<210> SEQ ID NO 309
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Ser Glu Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 310
<211> LENGTH: 6
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 310

Ser Leu Arg Thr Tyr Tyr
1               5

<210> SEQ ID NO 311
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ala Ser Trp Tyr Gln Gln Arg Pro Gly Gln Ala Pro Ile Leu Val Leu
1               5                   10                  15

Tyr

<210> SEQ ID NO 312
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Lys Asn
1

<210> SEQ ID NO 313
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Asn Arg Pro Ser Gly Ile Pro Asp Arg Phe Ser Gly Ser Ser Ser Gly
1               5                   10                  15

Asn Thr Ala Ser Leu Thr Ile Thr Gly Ala Gln Ala Glu Asp Glu Ala
            20                  25                  30

Asp Tyr Tyr Cys
        35

<210> SEQ ID NO 314
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Asn Ser Arg Asp Ser Ser Gly Asn His Val Val
1               5                   10

<210> SEQ ID NO 315
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 315

Phe Gly Gly Gly Thr Lys Leu Thr Val Leu
1               5                   10

<210> SEQ ID NO 316
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Ser Val Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gly Ser Asp Val Gly Ser Tyr Asn Tyr
1               5

<210> SEQ ID NO 318
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Val Ser Trp Tyr Gln Gln Asn Pro Gly Lys Ala Pro Lys Leu Met Ile
1               5                   10                  15

Tyr

<210> SEQ ID NO 319
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Glu Val Ser
1

<210> SEQ ID NO 320
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 320

Asn Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 321
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ser Ser Tyr Thr Thr Ser Ser Thr Leu Val
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Phe Gly Gly Gly Thr Lys Val Thr Val Leu
1               5                   10

<210> SEQ ID NO 323
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Ser Glu Leu Thr Gln Asp Pro Ala Val Ser Val Ala Leu Gly Gln Thr
1               5                   10                  15

Val Arg Ile Thr Cys Gln Gly Asp
            20

<210> SEQ ID NO 324
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ser Leu Arg Ser Tyr Tyr
1               5

<210> SEQ ID NO 325
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ala Ser Trp Tyr Gln Gln Lys Pro Gly Gln Ala Pro Val Leu Val Ile
1               5                   10                  15

Tyr

<210> SEQ ID NO 326
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Glu Asn
1

<210> SEQ ID NO 327
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Ser Arg Pro Ser Gly Ile Pro Asp Arg Phe Ser Gly Ser Ser Ser Gly
1               5                   10                  15

Asn Thr Ala Ser Leu Thr Ile Thr Gly Ala Gln Ala Glu Asp Glu Ala
            20                  25                  30

Asp Tyr Tyr Cys
        35

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Asn Ser Trp Asp Ser Ser Gly Asn His Val Val
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Phe Gly Gly Gly Thr Lys Leu Thr Val Leu
1               5                   10

<210> SEQ ID NO 330
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 330

Ala Ile Arg Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 331
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln Ser Ile Ser Ser Tyr
1               5

<210> SEQ ID NO 332
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Leu Asn Trp Tyr Gln Gln Lys Pro Gly Lys Ala Pro Lys Leu Leu Ile
1               5                   10                  15

Tyr

<210> SEQ ID NO 333
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ala Ala Ser
1

<210> SEQ ID NO 334
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
            35

<210> SEQ ID NO 335
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 335

Gln Gln Ser Tyr Ser Thr Pro Arg Thr
1               5

<210> SEQ ID NO 336
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Phe Gly Gln Gly Thr Lys Leu Glu Ile Lys
1               5                   10

<210> SEQ ID NO 337
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Asp Ile Val Met Thr Gln Ser Pro Leu Ser Leu Pro Val Thr Pro Gly
1               5                   10                  15

Glu Pro Ala Ser Ile Ser Cys Arg Ser Ser
            20                  25

<210> SEQ ID NO 338
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gln Ser Leu Leu His Ser Asn Gly Tyr Asp Tyr
1               5                   10

<210> SEQ ID NO 339
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Leu Asp Trp Tyr Leu Gln Lys Pro Gly Gln Ser Pro Gln Leu Leu Ile
1               5                   10                  15

Tyr

<210> SEQ ID NO 340
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 340

Leu Gly Ser
1

<210> SEQ ID NO 341
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Asn Arg Ala Ser Gly Val Pro Asp Arg Phe Ser Gly Ser Gly Ser Gly
1               5                   10                  15

Thr Asp Phe Thr Leu Lys Ile Ser Arg Val Glu Thr Glu Asp Val Gly
            20                  25                  30

Ile Tyr Tyr Cys
        35

<210> SEQ ID NO 342
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Met Gln Gly Leu Gln Thr Pro Ser
1               5

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Phe Gly Gln Gly Thr Lys Leu Glu Ile Lys
1               5                   10

<210> SEQ ID NO 344
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ser Ser Glu Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 345
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 345

Ser Leu Arg Ser Tyr Tyr
1               5

<210> SEQ ID NO 346
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ala Ser Trp Tyr Gln Gln Lys Pro Gly Gln Ala Pro Val Pro Val Ile
1               5                   10                  15

Tyr

<210> SEQ ID NO 347
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gly Lys Asn
1

<210> SEQ ID NO 348
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Asn Arg Pro Ser Gly Ile Pro Asp Arg Phe Ser Gly Ser Ser Ser Gly
1               5                   10                  15

Asn Thr Ala Ser Leu Thr Ile Thr Gly Ala Gln Ala Glu Asp Glu Ala
            20                  25                  30

Asp Tyr Tyr Cys
            35

<210> SEQ ID NO 349
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Asn Ser Arg Asp Ser Ser Ser Thr His Arg Gly Val
1               5                   10

<210> SEQ ID NO 350
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 350

Phe Gly Gly Gly Thr Lys Leu Thr Val Leu
1               5                   10

<210> SEQ ID NO 351
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asp Ile Gln Leu Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 352
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Arg Ser Ile Ser Thr Tyr
1               5

<210> SEQ ID NO 353
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Leu Ser Trp Tyr Gln Gln Lys Pro Gly Lys Ala Pro Lys Leu Leu Ile
1               5                   10                  15

Tyr

<210> SEQ ID NO 354
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asp Ala Ser
1

<210> SEQ ID NO 355
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Arg Leu Gln Asn Gly Val Pro Ser Arg Phe Ser Gly Ser Gly Ser Asp
1               5                   10                  15
```

```
Thr Asp Phe Thr Leu Thr Ile Ser Ser Leu Gln Pro Glu Asp Phe Ala
            20                  25                  30

Thr Tyr Phe Cys
        35

<210> SEQ ID NO 356
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gln Gln Ser Tyr Asn Pro Pro Trp Thr
1               5

<210> SEQ ID NO 357
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Phe Gly Gln Gly Thr Lys Leu Glu Ile Lys
1               5                   10

<210> SEQ ID NO 358
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gln Ser Ala Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ser Ser Asp Val Gly Gly Tyr Asn Tyr
1               5

<210> SEQ ID NO 360
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 360

Val Ser Trp Tyr Gln Gln His Pro Gly Lys Ala Pro Lys Leu Met Ile
1               5                   10                  15

Tyr

<210> SEQ ID NO 361
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Asp Val Ser
1

<210> SEQ ID NO 362
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Asn Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Tyr Tyr Tyr Cys
        35

<210> SEQ ID NO 363
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ser Ser Tyr Thr Ser Ser Ser Asp Pro Trp Val
1               5                   10

<210> SEQ ID NO 364
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Phe Gly Gly Gly Thr Gln Leu Thr Val Leu
1               5                   10

<210> SEQ ID NO 365
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 365

Asn Ile Gln Met Thr Gln Ser Pro Ser Leu Ser Ala Ser Val Gly
1               5                   10                  15

Asp Arg Val Thr Ile Thr Cys Arg Ala Gly
            20                  25

<210> SEQ ID NO 366
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gln Pro Ile Ser Thr Tyr
1               5

<210> SEQ ID NO 367
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Val Asn Trp Tyr Gln His Lys Pro Gly Lys Ala Pro Lys Leu Leu Ile
1               5                   10                  15

Tyr

<210> SEQ ID NO 368
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Ala Ser
1

<210> SEQ ID NO 369
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Asn Leu Gln Ser Gly Val Pro Ser Arg Phe Ser Gly Gly Ser Ala
1               5                   10                  15

Thr Asp Phe Thr Leu Thr Ile Ser Ser Leu Gln Pro Glu Asp Phe Ala
            20                  25                  30

Thr Tyr Tyr Cys
            35

<210> SEQ ID NO 370
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 370

Gln Gln Ser Tyr Ser Ser Leu Leu Thr Phe Gly Asp Gly Thr Lys Val
1               5                   10                  15

Glu Ile Lys
```